United States Patent
Nomura et al.

(10) Patent No.: US 8,288,012 B2
(45) Date of Patent: *Oct. 16, 2012

(54) ANTHRACENE DERIVATIVES AND LIGHT-EMITTING DEVICES USING THE ANTHRACENE DERIVATIVES

(75) Inventors: Hiroko Nomura, Kanagawa (JP);
Sachiko Kawakami, Kanagawa (JP);
Nobuharu Ohsawa, Kanagawa (JP);
Tsunenori Suzuki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 879 days.

This patent is subject to a terminal disclaimer.

(21) Appl. No.: 11/962,509

(22) Filed: Dec. 21, 2007

(65) Prior Publication Data

US 2009/0004506 A1    Jan. 1, 2009

(30) Foreign Application Priority Data

Dec. 28, 2006    (JP) .................. 2006-355196

(51) Int. Cl.
*C07C 211/54* (2006.01)
*C07D 209/86* (2006.01)
*H01L 51/54* (2006.01)

(52) U.S. Cl. ........ 428/690; 428/917; 313/504; 313/506; 548/442; 564/427

(58) Field of Classification Search .................. None
See application file for complete search history.

(56) References Cited

U.S. PATENT DOCUMENTS

| | | | |
|---|---|---|---|
| 7,252,894 B2 | 8/2007 | Yu et al. | |
| 7,351,999 B2 | 4/2008 | Li | |

(Continued)

FOREIGN PATENT DOCUMENTS

EP    1 734 038 A1    12/2006

(Continued)

OTHER PUBLICATIONS

Machine-generated translation of JP 2004-095850, which was published Mar. 2004.*

(Continued)

*Primary Examiner* — Dawn L Garrett
(74) *Attorney, Agent, or Firm* — Husch Blackwell LLP

(57) ABSTRACT

The present invention provides novel anthracene derivatives. In particular, the present invention provides light-emitting elements with high luminous efficiency, and light-emitting elements with long lifetime. Further, the present invention provides light-emitting devices and electronic devices having long lifetime by using these light-emitting elements. An anthracene derivative represented by the general formula (1) is provided. In addition, since the anthracene derivative represented by the general formula (1) has high luminous efficiency, a light-emitting element using the anthracene derivative represented by the general formula (1) can also have high luminous efficiency. By using the anthracene derivative represented by the general formula (1), light-emitting elements with long lifetime can be provided.

26 Claims, 45 Drawing Sheets

U.S. PATENT DOCUMENTS

| | | |
|---|---|---|
| 7,674,914 B2 | 3/2010 | Egawa et al. |
| 7,842,945 B2 | 11/2010 | Egawa et al. |
| 7,965,032 B2 | 6/2011 | Bae et al. |
| 8,030,646 B2 | 10/2011 | Suzuki et al. |
| 8,106,392 B2 | 1/2012 | Egawa et al. |
| 8,110,980 B2 | 2/2012 | Egawa et al. |
| 2003/0189401 A1 | 10/2003 | Kido et al. |
| 2005/0211958 A1 | 9/2005 | Conley et al. |
| 2005/0260442 A1 | 11/2005 | Yu et al. |
| 2005/0271899 A1 | 12/2005 | Brown et al. |
| 2006/0019116 A1 | 1/2006 | Conley et al. |
| 2006/0043859 A1 | 3/2006 | Fukuoka et al. |
| 2006/0158102 A1 | 7/2006 | Kawamura et al. |
| 2006/0240278 A1 | 10/2006 | Hatwar et al. |
| 2007/0108892 A1 | 5/2007 | Bae et al. |
| 2007/0122656 A1 | 5/2007 | Klubek et al. |
| 2007/0200490 A1 | 8/2007 | Kawamura et al. |
| 2007/0205412 A1 | 9/2007 | Bae et al. |
| 2008/0006821 A1 | 1/2008 | Suzuki et al. |
| 2008/0017853 A1 | 1/2008 | Egawa et al. |
| 2008/0103315 A1 | 5/2008 | Egawa et al. |
| 2008/0130278 A1 | 6/2008 | Ushikubo et al. |
| 2009/0058278 A1 | 3/2009 | Ushikubo et al. |
| 2010/0164376 A1 | 7/2010 | Egawa et al. |
| 2011/0062428 A1 | 3/2011 | Egawa et al. |

FOREIGN PATENT DOCUMENTS

| | | |
|---|---|---|
| EP | 1 863 105 A2 | 12/2007 |
| EP | 1 918 350 A2 | 5/2008 |
| JP | 2000-68057 | 3/2000 |
| JP | 2003-146951 | 5/2003 |
| JP | 2003-267973 | 9/2003 |
| JP | 2003-313156 | 11/2003 |
| JP | 2003-313156 A | 11/2003 |
| JP | 2004-91334 | 3/2004 |
| JP | 2004-95850 | 3/2004 |
| JP | 2004-273163 | 9/2004 |
| WO | WO 2007/046658 A1 | 4/2007 |
| WO | WO 2007/102683 A1 | 9/2007 |

OTHER PUBLICATIONS

Kido, J. et al, "Multilayer White Light-Emitting Organic Electroluminescent Device," Science, vol. 267, No. 5202, Mar. 3, 1995, pp. 1332-1334.

Kido, J. et al, "Single-Layer White Light-Emitting Organic Electroluminescent Devices Based on Dye-Dispersed Poly(N-vinylcarbazole)," Applied Physics Letters, vol. 67, No. 16, Oct. 16, 1995, pp. 2281-2283.

International Search Report re application No. PCT/JP2007/058896, dated Aug. 14, 2007.

Written Opinion re application No. PCT/JP2007/058896, dated Aug. 14, 2007.

Search Report re European application No. EP 07742331.7, dated Feb. 14, 2012.

* cited by examiner

ANTHRACENE DERIVATIVES AND LIGHT-EMITTING DEVICES USING THE ANTHRACENE DERIVATIVES

BACKGROUND OF THE INVENTION

1. Field of the Invention

The present invention relates to anthracene derivatives, organic compounds, and light-emitting devices and electronic devices using the anthracene derivatives.

2. Description of the Related Art

There are more types of materials of organic compounds than those of inorganic compounds. Thus, organic compounds can take wider variety of structures compared with inorganic compounds, and it is possible to synthesize a material having various functions by appropriate molecular-design of an organic compound. Owing to these advantages, photo electronics and electronics, which employ a functional organic material, have been attracting attention in recent years.

Solar cells, light-emitting elements, organic transistors, and the like can be exemplified as electronic devices using an organic compound as a functional organic material. These devices take advantage of electrical properties and optical properties of the organic compound. Among them, in particular, light-emitting elements have been making remarkable progress.

It is considered that the light emission mechanism of a light-emitting element is as follows: when a voltage is applied between a pair of electrodes which interpose a light-emitting layer, electrons injected from a cathode and holes injected from an anode are recombined in the light-emitting layer to form a molecular exciton, and energy is released to emit light when the molecular exciton relaxes to the ground state. As excited states, a singlet excited state and a triplet excited state are known, and light emission is considered to be possible through either of these excited states.

In an attempt to improve the performances of such a light-emitting element, there are many problems which depend on materials, and in order to solve these problems, improvement of the element structure and development of a material have been carried out.

For example, in Patent Document 1: United States Patent Application Publication No. 2005-0260442, an anthracene derivative exhibiting green light emission is disclosed. However, in Patent Document 1, only the PL spectrum of the anthracene derivative is described, and the device performance of when the anthracene derivative was applied to a light-emitting element.

Also, in Patent Document 2: Japanese Published Patent Application No. 2004-91334, a light-emitting element using an anthracene derivative as a charge transporting layer is mentioned. However, in Patent Document 2, there is no description on the lifetime of the light-emitting element.

If commercialization is considered, extending the lifetime is an important issue. Further, the development of light-emitting elements with much higher performances is desired.

SUMMARY OF THE INVENTION

In view of the foregoing problems, an object of the present invention is to provide novel anthracene derivatives.

In addition, another object of the present invention is to provide light-emitting elements with high luminous efficiency. Further, another object of the present invention is to provide light-emitting elements with a long lifetime. Another object of the present invention is to provide light-emitting devices and electronic devices having a long lifetime by using these light-emitting elements.

An aspect of the present invention is an anthracene derivative represented by the general formula (1).

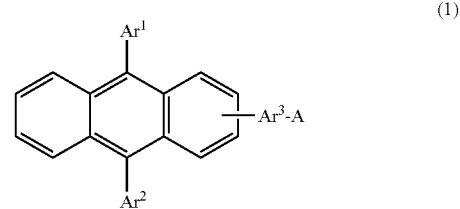

(1)

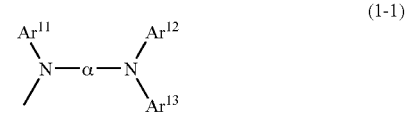

(1-1)

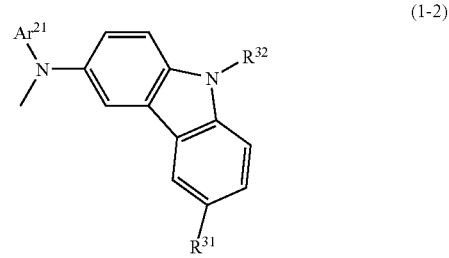

(1-2)

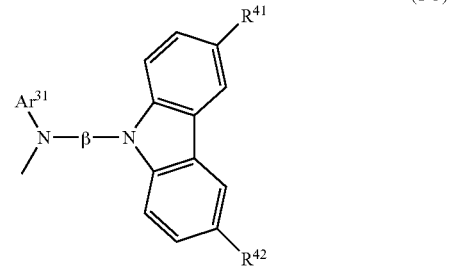

(1-3)

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (1-1) to (1-3). In the general formulae (1-1) to (1-3), $Ar^{11}$ to $Ar^{13}$ each represent an aryl group having 6 to 25 carbon atoms; α represents an arylene group having 6 to 25 carbon atoms; $Ar^{21}$ represents an aryl group having 6 to 25 carbon atoms; $R^{31}$ represents a hydrogen atom, an alkyl group having 1 to 4 carbon atoms, an aryl group having 6 to 25 carbon atoms, a halogen atom, or a haloalkyl group having 1 to 4 carbon atoms; $R^{32}$ represents an alkyl group having 1 to 4 carbon atoms, an aryl group having 6 to 25 carbon atoms, or a haloalkyl group having 1 to 4 carbon atoms; $Ar^{31}$ represents an aryl group having 6 to 25 carbon atoms; β represents an arylene group having 6 to 25 carbon atoms; $R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

An aspect of the present invention is an anthracene derivative represented by a general formula (2).

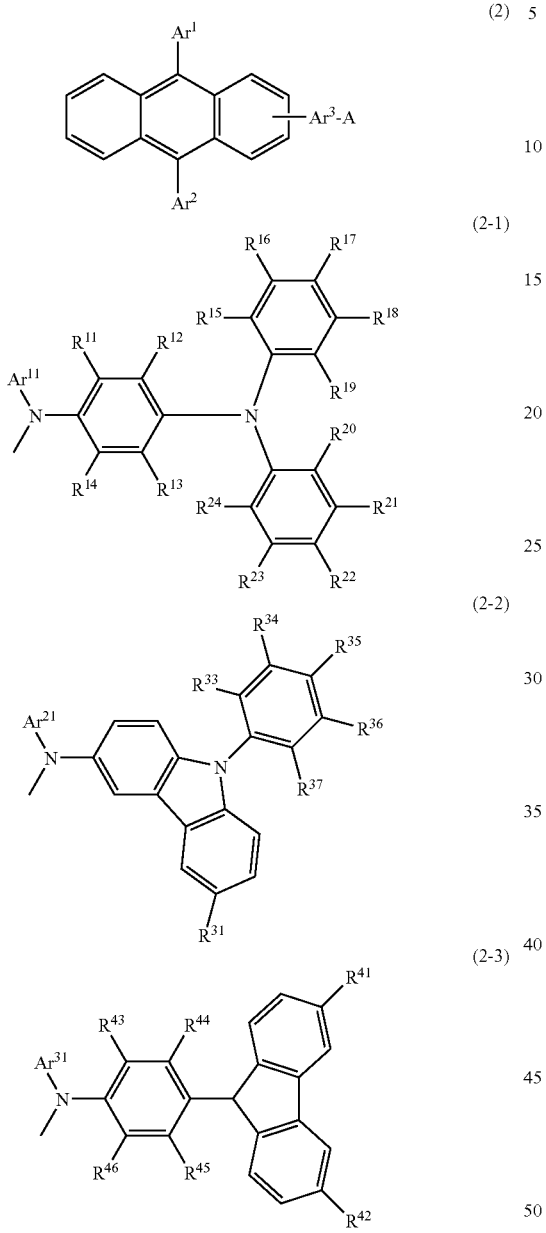

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (2-1) to (2-3). In the general formulae (2-1) to (2-3), $Ar^{11}$ represents an aryl group having 6 to 25 carbon atoms; $R^{11}$ to $R^{24}$ each represent a hydrogen atom, an alkyl group having 1 to 4 carbon atoms, an aryl group having 6 to 15 carbon atoms, a halogen atom, or a haloalkyl group having 1 to 4 carbon atoms; $Ar^{21}$ represents an aryl group having 6 to 25 carbon atoms; $R^{31}$ represents a hydrogen atom, an alkyl group having 1 to 4 carbon atoms, an aryl group having 6 to 25 carbon atoms, a halogen atom, or a haloalkyl group having 1 to 4 carbon atoms; $R^{33}$ to $R^{37}$ each represent a hydrogen atom, an alkyl group having 1 to 4 carbon atoms, an aryl group having 6 to 15 carbon atoms, a halogen atom, or a haloalkyl group having 1 to 4 carbon atoms; $Ar^{31}$ represents an aryl group having 6 to 25 carbon atoms; $R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms; $R^{43}$ to $R^{46}$ each represent a hydrogen atom, an alkyl group having 1 to 4 carbon atoms, an aryl group having 6 to 15 carbon atoms, a halogen atom, or a haloalkyl group having 1 to 4 carbon atoms.

An aspect of the present invention is an anthracene derivative represented by a general formula (3).

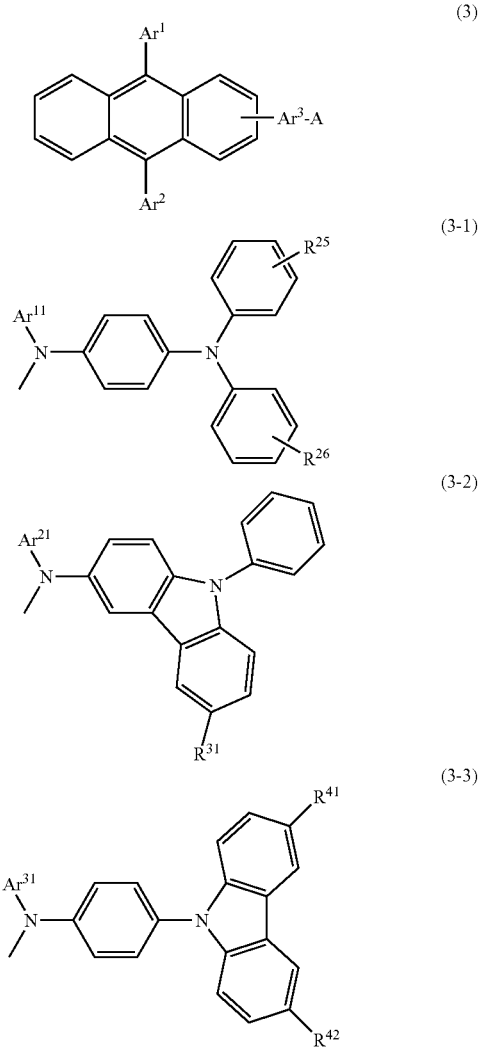

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (3-1) to (3-3). In the general formulae (3-1) to (3-3), $Ar^{11}$ represents an aryl group having 6 to 25 carbon atoms; $R^{25}$ and $R^{26}$ each represent a hydrogen atom, an alkyl group having 1 to 4 carbon atoms, an aryl group having 6 to 15 carbon atoms, a halogen atom, or a haloalkyl group having 1 to 4 carbon atoms; $Ar^{21}$ represents an aryl group having 6 to 25 carbon atoms; $R^{31}$ represents a hydrogen atom, an alkyl group having 1 to 4 carbon atoms, an aryl group having 6 to 25 carbon atoms, a halogen atom, or a haloalkyl group having 1 to 4 carbon atoms; $Ar^{31}$ represents an aryl group having 6 to 25 carbon atoms; and $R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

An aspect of the present invention is an anthracene derivative represented by a general formula (4).

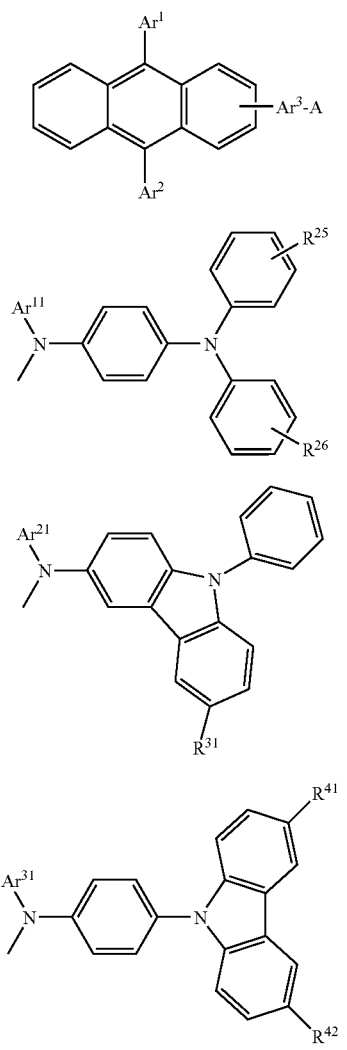

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (4-1) to (4-3). In the general formulae (4-1) to (4-3), $Ar^{11}$ represents a phenyl group, a 1-naphthyl group or a 2-naphthyl group; $R^{25}$ and $R^{26}$ each represent a hydrogen atom, an alkyl group having 1 to 4 carbon atoms, or an aryl group having 6 to 15 carbon atoms; $Ar^{21}$ represents a phenyl group, a 1-naphthyl group or a 2-naphthyl group; $R^{31}$ represents a hydrogen atom, an alkyl group having 1 to 4 carbon atoms, or an aryl group having 6 to 25 carbon atoms; $Ar^{31}$ represents a phenyl group, a 1-naphthyl group or a 2-naphthyl group; and $R^{41}$ and $R^{42}$ each represent a hydrogen atom, an alkyl group having 1 to 4 carbon atoms, or an aryl group having 6 to 25 carbon atoms.

An aspect of the present invention is an anthracene derivative represented by a general formula (5).

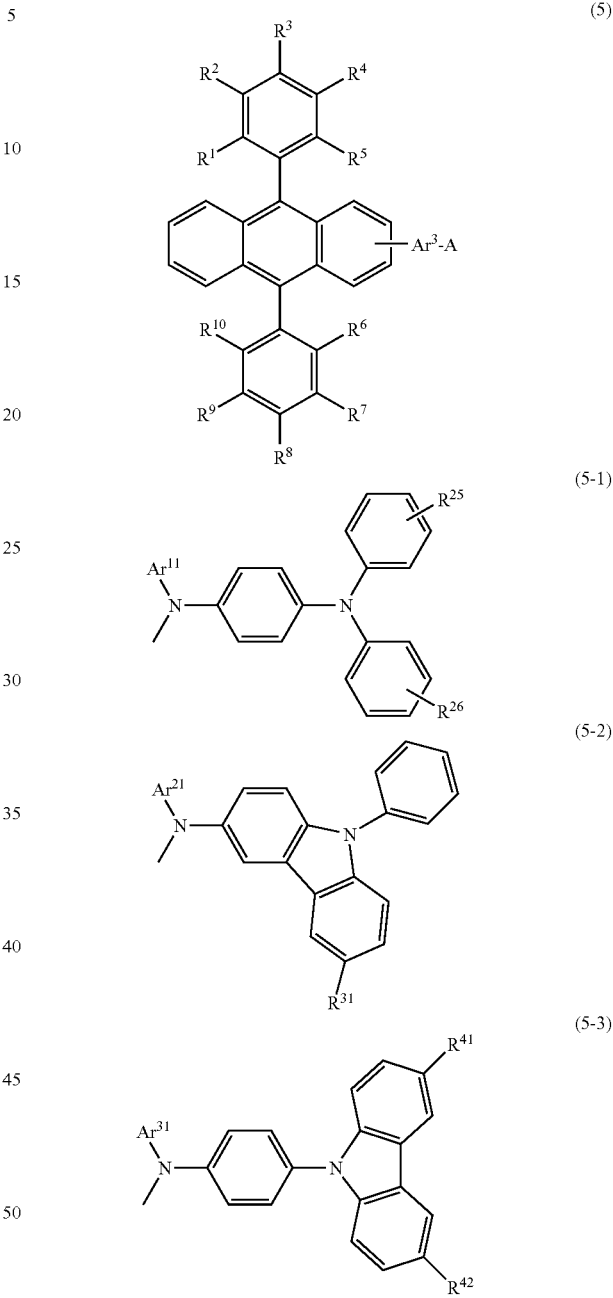

In the formula, $R^1$ to $R^{10}$ each represent a hydrogen atom, an alkyl group having 1 to 4 carbon atoms, an aryl group having 6 to 15 carbon atoms, a halogen atom, a haloalkyl group having 1 to 4 carbon atoms, $Ar^3$ represents an arylene group having 6 to 25 carbon atoms, and A represents any of substituents represented by general formulae (5-1) to (5-3). In the general formulae (5-1) to (5-3), $Ar^{11}$ represents a phenyl group, a 1-naphthyl group or a 2-naphthyl group; $R^{25}$ and $R^{26}$ each represent a hydrogen atom, an alkyl group having 1 to 4 carbon atoms, or an aryl group having 6 to 15 carbon atoms; $Ar^{21}$ represents a phenyl group, a 1-naphthyl group or a 2-naphthyl group; $R^{31}$ represents a hydrogen atom, an alkyl group having 1 to 4 carbon atoms, or an aryl group having 6 to 25 carbon atoms; $Ar^{31}$ represents a phenyl group, a 1-naphthyl group or a 2-naphthyl group; and $R^{41}$ and $R^{42}$ each represent a hydrogen atom, an alkyl group having 1 to 4 carbon atoms, or an aryl group having 6 to 25 carbon atoms.

In the above structures, $Ar^3$ is preferably any of substituents represented by general formulae (11-1) to (11-5).

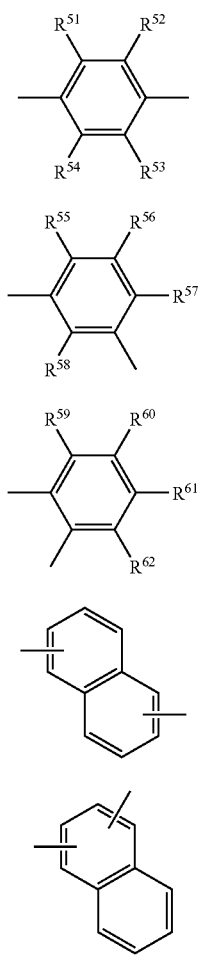

(11-1)

(11-2)

(11-3)

(11-4)

(11-5)

In the formula, $R^{51}$ to $R^{62}$ each represent a hydrogen atom, an alkyl group having 1 to 4 carbon atoms, an aryl group having 6 to 15 carbon atoms, a halogen atom, or a haloalkyl group having 1 to 4 carbon atoms.

In the above structures, $Ar^1$ and $Ar^2$ preferably have the same structure for the sake of easy synthesis.

An aspect of the present invention is an anthracene derivative represented by a general formula (6).

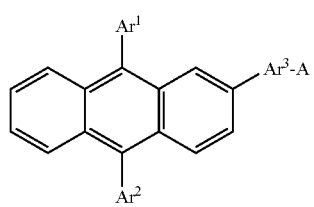

(6)

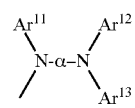

(6-1)

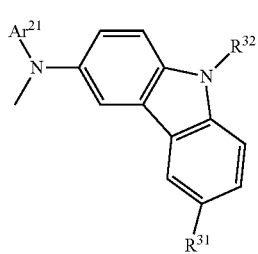

(6-2)

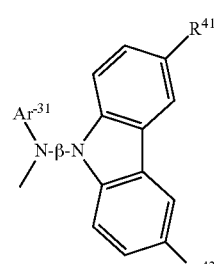

(6-3)

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (6-1) to (6-3). In the general formulae (6-1) to (6-3), $Ar^{11}$ to $Ar^{13}$ each represent an aryl group having 6 to 25 carbon atoms; a represents an arylene group having 6 to 25 carbon atoms; $Ar^{21}$ represents an aryl group having 6 to 25 carbon atoms; $R^{31}$ represents a hydrogen atom, an alkyl group having 1 to 4 carbon atoms, an aryl group having 6 to 25 carbon atoms, a halogen atom, or a haloalkyl group having 1 to 4 carbon atoms; $R^{32}$ represents an alkyl group having 1 to 4 carbon atoms, an aryl group having 6 to 25 carbon atoms, or a haloalkyl group having 1 to 4 carbon atoms; $Ar^{31}$ represents an aryl group having 6 to 25 carbon atoms; 6 represents an arylene group having 6 to 25 carbon atoms; and $R^{41}$ to $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

An aspect of the present invention is an anthracene derivative represented by a general formula (7).

(7)

-continued

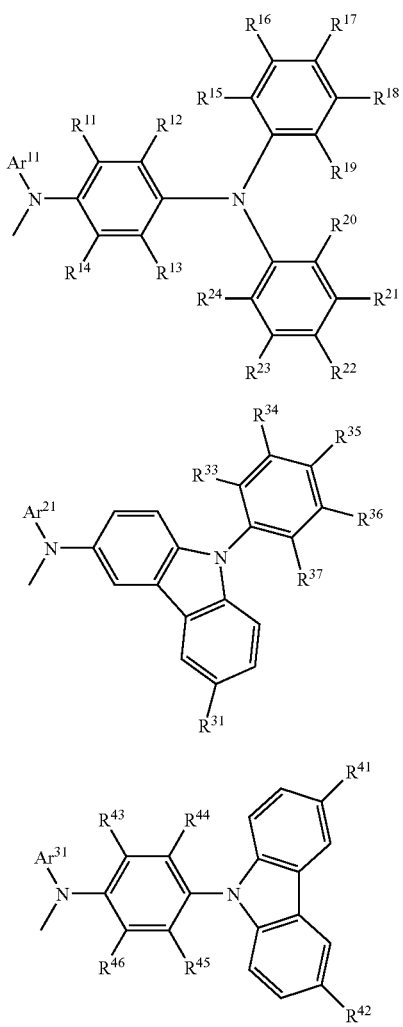

(7-1)

(7-2)

(7-3)

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (7-1) to (7-3). In the general formulae (7-1) to (7-3), $Ar^{11}$ represents an aryl group having 6 to 25 carbon atoms; $R^{11}$ to $R^{24}$ each represent a hydrogen atom, an alkyl group having 1 to 4 carbon atoms, an aryl group having 6 to 15 carbon atoms, a halogen atom, or a haloalkyl group having 1 to 4 carbon toms; $Ar^{21}$ represents an aryl group having 6 to 25 carbon atoms; $R^{31}$ represents a hydrogen atom, an alkyl group having 1 to 4 carbon atoms, an aryl group having 6 to 25 carbon atoms, a halogen atom, or a haloalkyl group having 1 to 4 carbon atoms; $R^{33}$ to $R^{37}$ each represent a hydrogen atom, an alkyl group having 1 to 4 carbon atoms, an aryl group having 6 to 15 carbon atoms, a halogen atom, or a haloalkyl group having 1 to 4 carbon toms; $Ar^{31}$ represents an aryl group having 6 to 25 carbon atoms; $R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms; and $R^{43}$ to $R^{46}$ each represent a hydrogen atom, an alkyl group having 1 to 4 carbon atoms, an aryl group having 6 to 15 carbon atoms, a halogen atom, or a haloalkyl group having 1 to 4 carbon atoms.

An aspect of the present invention is an anthracene derivative represented by a general formula (8).

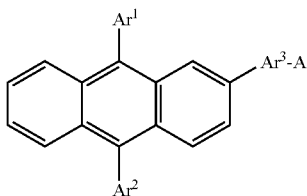

(8)

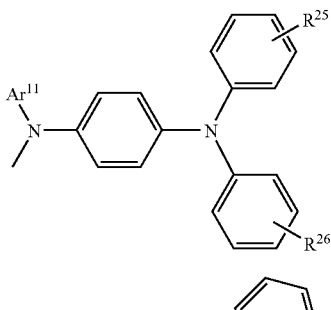

(8-1)

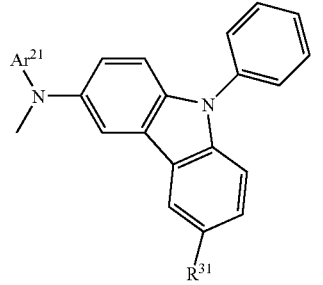

(8-2)

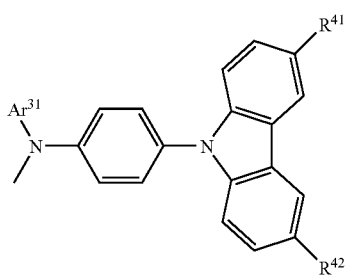

(8-3)

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (8-1) to (8-3). In the general formulae (8-1) to (8-3), $Ar^{11}$ represents an aryl group having 6 to 25 carbon atoms; $R^{25}$ and $R^{26}$ each represent a hydrogen atom, an alkyl group having 1 to 4 carbon atoms, an aryl group having 6 to 15 carbon atoms, a halogen atom, or a haloalkyl group having 1 to 4 carbon atoms; $Ar^{21}$ represents an aryl group having 6 to 25 carbon atoms; $R^{31}$ represents a hydrogen atom, an alkyl group having 1 to 4 carbon atoms, an aryl group having 6 to 25 carbon atoms, a halogen atom, or a haloalkyl group having 1 to 4 carbon atoms; $Ar^{31}$ represents an aryl group having 6 to 25 carbon atoms; and $R^{41}$ and $R^{42}$ each represent a: hydrogen atom, an alkyl group having 1 to 4 carbon atoms, an aryl group having 6 to 25 carbon atoms, a halogen atom, or a haloalkyl group having 1 to 4 carbon atoms.

An aspect of the present invention is an anthracene derivative represented by a general formula (9).

An aspect of the present invention is an anthracene derivative represented by a general formula (10).

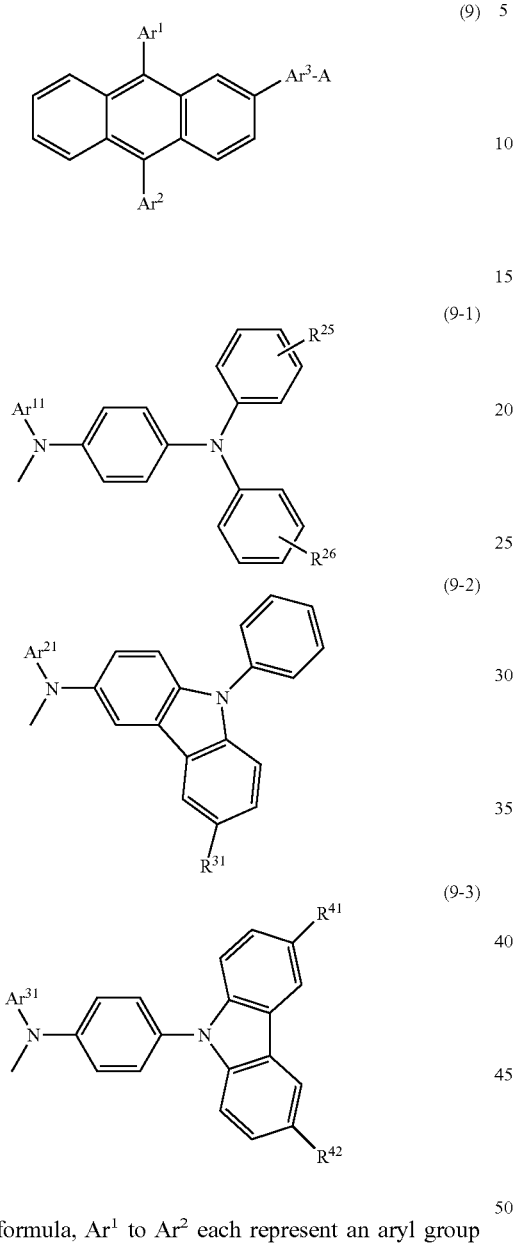

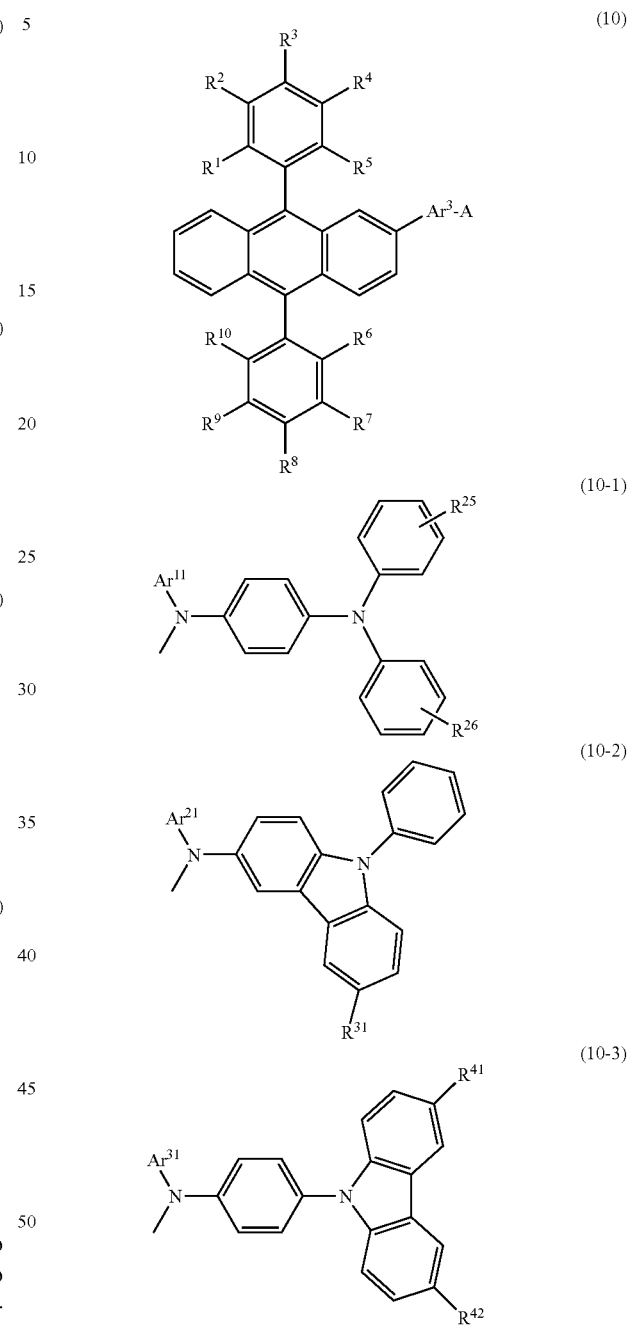

In the formula, $Ar^1$ to $Ar^2$ each represent an aryl group having 6 to 25 carbon atoms, $Ar^3$ represents an arylene group having 6 to 25 carbon atoms, and A represents any of substituents represented by general formulae (9-1) to (9-3). In the general formulae (9-1) to (9-3), $Ar^{11}$ represents a phenyl group, a 1-naphthyl group or a 2-naphthyl group; $R^{25}$ and $R^{26}$ each represent a hydrogen atom, an alkyl group having 1 to 4 carbon atoms, or an aryl group having 6 to 15 carbon atoms; $Ar^{21}$ represents a phenyl group, a 1-naphthyl group or a 2-naphthyl group; $R^{31}$ represents a hydrogen atom, an alkyl group having 1 to 4 carbon atoms, or an aryl group having 6 to 25 carbon atoms; $Ar^{31}$ represents a phenyl group, a 1-naphthyl group or a 2-naphthyl group; and $R^{41}$ and $R^{42}$ each represent a hydrogen atom, an alkyl group having 1 to 4 carbon atoms, or an aryl group having 6 to 25 carbon atoms.

In the formula, $R^1$ to $R^{10}$ each represent a hydrogen atom, an alkyl group having 1 to 4 carbon atoms, an aryl group having 6 to 15 carbon atoms, a halogen atom, a haloalkyl group having 1 to 4 carbon atoms; $Ar^3$ represents an arylene group having 6 to 25 carbon atoms; and A represents any of substituents represented by general formulae (10-1) to (10-3). In the general formulae (10-1) to (10-3), $Ar^{11}$ represents a phenyl group, a 1-naphthyl group or a 2-naphthyl group; $R^{25}$ and $R^{26}$ each represent a hydrogen atom, an alkyl group having 1 to 4 carbon atoms, or an aryl group having 6 to 15 carbon atoms; $Ar^{21}$ represents a phenyl group, a 1-naphthyl group or a 2-naphthyl group; $R^{31}$ represents a hydrogen atom, an alkyl group having 1 to 4 carbon atoms, or an aryl group having 6 to 25 carbon atoms; $Ar^{31}$ represents a phenyl group, a 1-naphthyl group or a 2-naphthyl group; and $R^{41}$ and $R^{42}$ each represent a hydrogen atom, an alkyl group having 1 to 4 carbon atoms, or an aryl group having 6 to 25 carbon atoms.

In the above structures, $Ar^3$ is preferably any of substituents represented by general formulae (11-1) to (11-5).

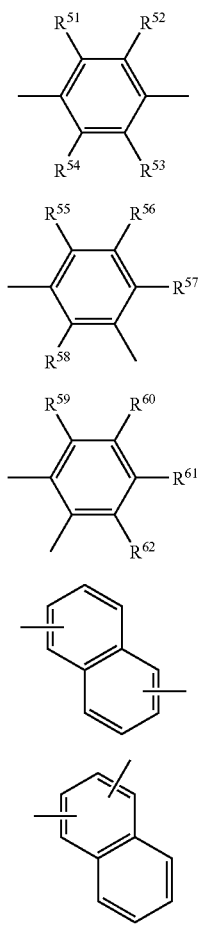

In the formula, $R^{51}$ to $R^{62}$ each represent a hydrogen atom, an alkyl group having 1 to 4 carbon atoms, an aryl group having 6 to 15 carbon atoms, a halogen atom, or a haloalkyl group having 1 to 4 carbon atoms.

In the above structures, $Ar^1$ and $Ar^2$ preferably have the same structure for the sake of easy synthesis.

An aspect of the present invention is a light-emitting element including any of the above anthracene derivatives. Specifically, the light-emitting element includes any of the above anthracene derivatives between a pair of electrodes.

An aspect of the present invention is a light-emitting element comprising a light-emitting layer between a pair of electrodes, and the light-emitting layer includes any of the above anthracene derivatives. In particular, the light-emitting element preferably uses any of the above anthracene derivatives as a light-emitting substance. In other words, the anthracene derivative preferably emits light.

A light-emitting device of the present invention includes a light-emitting element and a control means to control light emission from the light-emitting element. The light-emitting element includes an EL layer between a pair of electrodes and the EL layer includes any of the above described anthracene derivatives. The light-emitting device in this specification includes an image display device, a light-emitting device, and a light source (including a lighting device). Further, the light-emitting device also includes a module in which a connector such as an FPC (Flexible Printed Circuit), a TAB (Tape Automated Bonding) tape, or a TCP (Tape Carrier Package) is attached to a panel, a module in which a printed wiring board is provided at an end of a TAB tape or a TCP, and a module in which an IC (Integrated Circuit) is directly mounted on the light-emitting device by a COG (Chip On Glass) method.

Further, an electronic device using the light-emitting element of the present invention in its display portion is also included in the category of the present invention. Therefore, the electronic device of the present invention has a display portion, and the display portion is equipped with the above-described light-emitting element and a controller to control light emission from the light-emitting element.

An anthracene derivative of the present invention has high luminous efficiency. Therefore, by using the anthracene derivative of the present invention in light-emitting elements, such light-emitting elements can have high luminous efficiency. Also, by using the anthracene derivative of the present invention in light-emitting elements, such light-emitting element can have long lifetime.

Further, by using an anthracene derivative of the present invention, light-emitting devices and electronic devices each with a long lifetime can be obtained.

DETAILED DESCRIPTION OF THE INVENTION

Figure 1A:
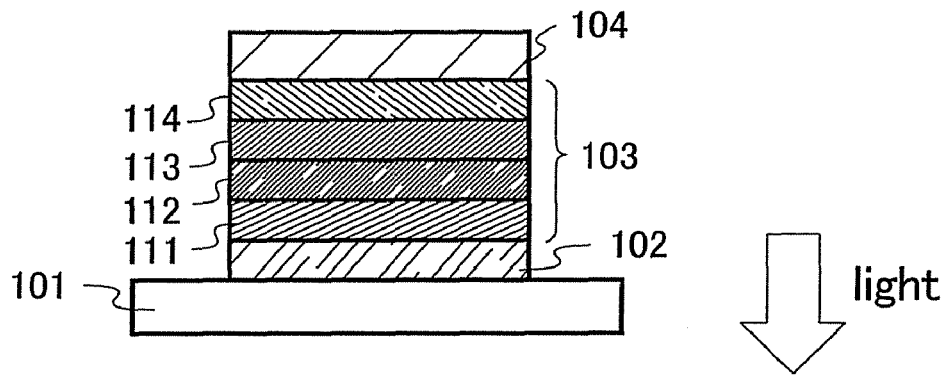
FIGS. 1A to 1C illustrate light-emitting elements according to an aspect of the present invention.

Hereinafter, embodiment modes of the present invention will be explained with reference to accompanied drawings. However, the present invention is not limited to the following description, and it is easily understood by those skilled in the art that the modes and details thereof can be changed in various ways without departing from the spirit and scope of the present invention. Therefore, the present invention is not interpreted, as being limited to the following description of embodiment modes.

Embodiment Mode 1

Embodiment Mode 1 will describe anthracene derivatives of the present invention.

An anthracene derivative of the present invention is represented by a general formula (1).

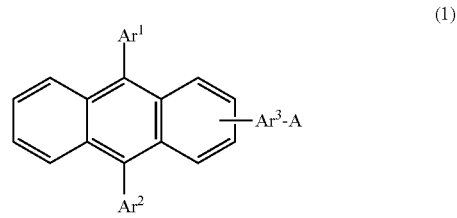

(1)

(1-1)

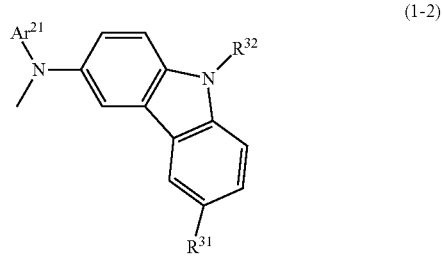

(1-2)

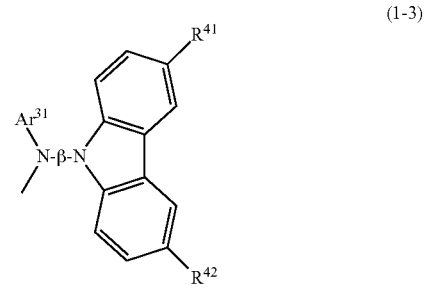

(1-3)

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (1-1) to (1-3). In the general formulae (1-1) to (1-3), $Ar^{11}$ to $Ar^{13}$ each represent an aryl group having 6 to 25 carbon atoms; a represents an arylene group having 6 to 25 carbon atoms; $Ar^{21}$ represents an aryl group having 6 to 25 carbon atoms; $R^{31}$ represents a hydrogen atom, an alkyl group having 1 to 4 carbon atoms, an aryl group having 6 to 25 carbon atoms, a halogen atom, or a haloalkyl group having 1 to 4 carbon atoms; $R^{32}$ represents an alkyl group having 1 to 4 carbon atoms, an aryl group having 6 to 25 carbon atoms, or a haloalkyl group having 1 to 4 carbon atoms; $Ar^{31}$ represents an aryl group having 6 to 25 carbon atoms; β represents an arylene group having 6 to 25 carbon atoms; $R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

In the general formula (1), as examples of the substituents represented by $Ar^1$ and $Ar^2$, substituents represented by structural formulae (12-1) to (12-9) are given.

(12-1)
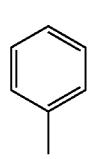

(12-2)
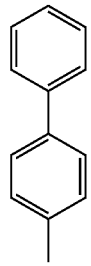

(12-3)
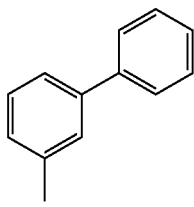

(12-4)
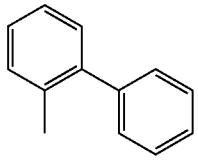

(12-5)
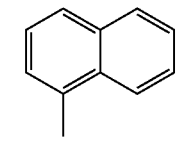

(12-6)
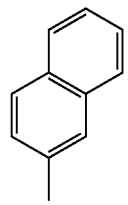

(12-7)
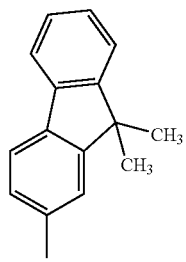

(12-8)
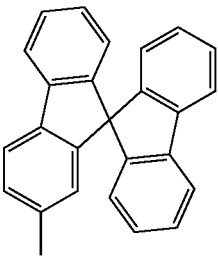

(12-9)
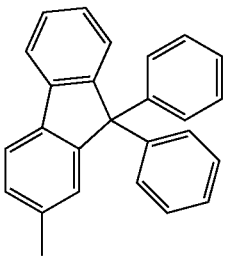

In the general formula (1), as examples of the substituent represented by $Ar^3$, substituents represented by structural formulae (13-1) to (13-9) are given.

(13-1)
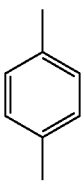

(13-2)
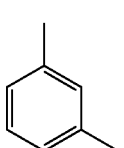

(13-3)
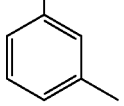

(13-4)
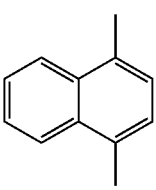

-continued
(13-5)
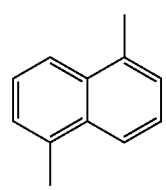
(13-6)
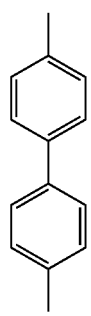
(13-7)
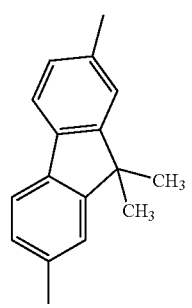
(13-8)
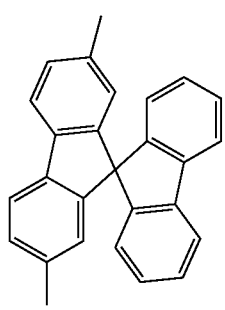
(13-9)
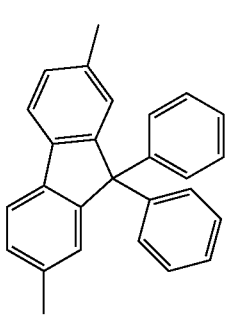
In the general formula (1-1), as examples of substituents represented by $Ar^{11}$ to $Ar^{13}$, substituents represented by structural formulae (21-1) to (21-9) are given.
(21-1)
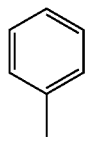
(21-2)
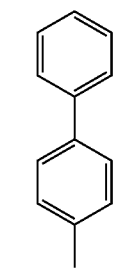
(21-3)
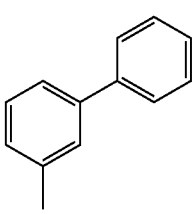
(21-4)
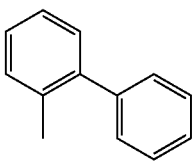
(21-5)
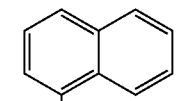
(21-6)
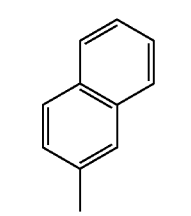
(21-7)
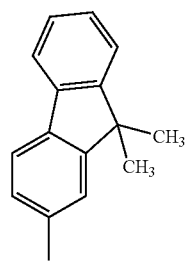

(21-8)
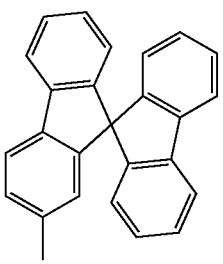
(21-9)
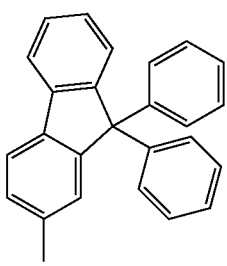
In the general formula (1-1), as examples of the substituent represented by α, substituents represented by structural formulae (22-1) to (22-9) are given.
(22-1)
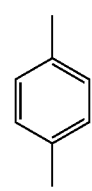
(22-2)
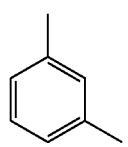
(22-3)
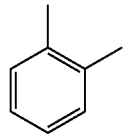
(22-4)
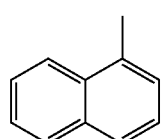
(22-5)
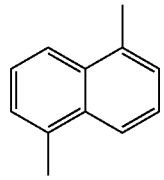
(22-6)
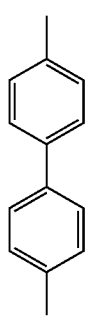
(22-7)
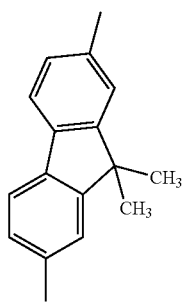
(22-8)
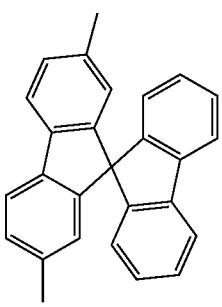
(22-9)
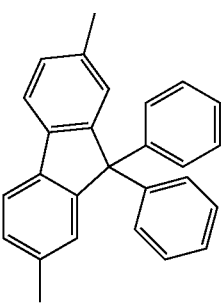
As examples of the substituent represented in the general formula (1-1), substituents represented by structural formulae (31-1) to (31-23) are given.

(31-1)
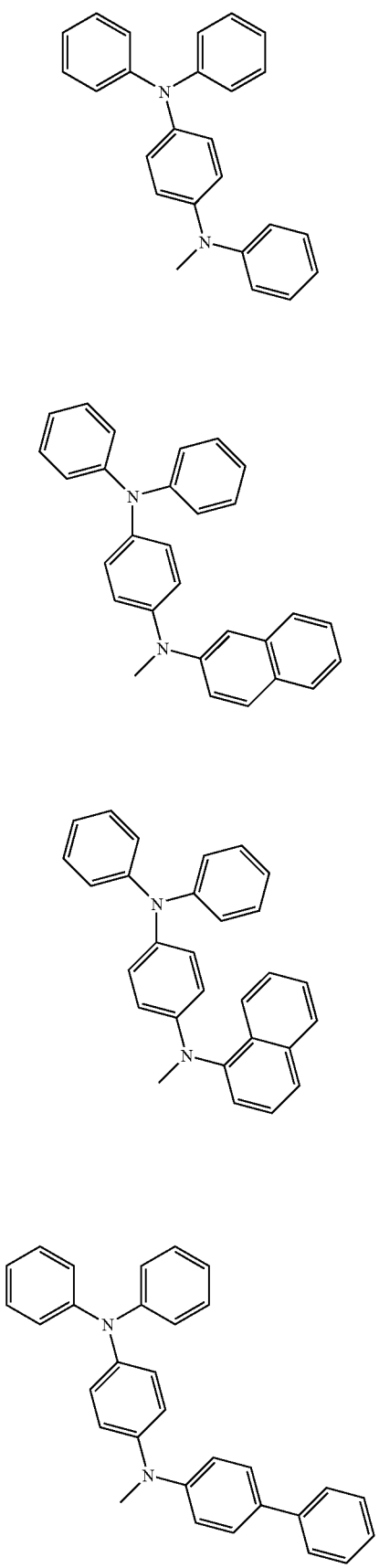
(31-2)
(31-3)
(31-4)
(31-5)
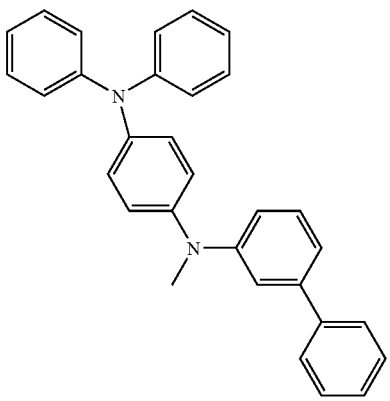
(31-6)
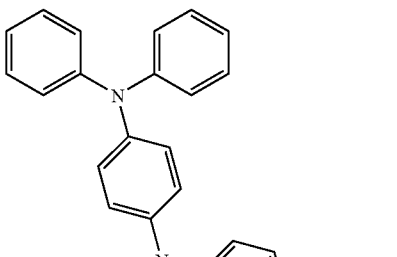
(31-7)
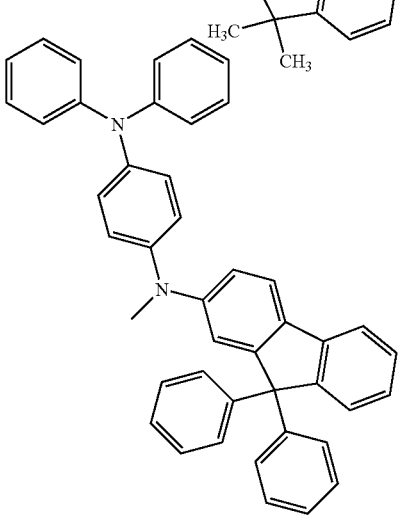
(31-8)

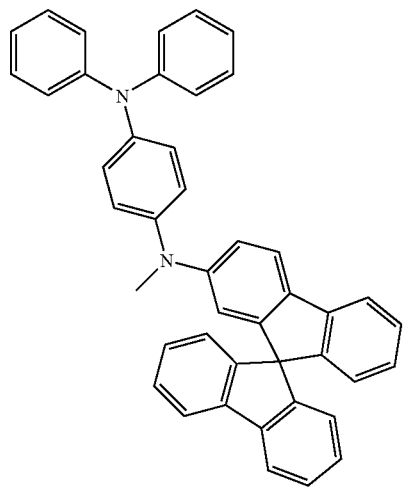
(31-9)
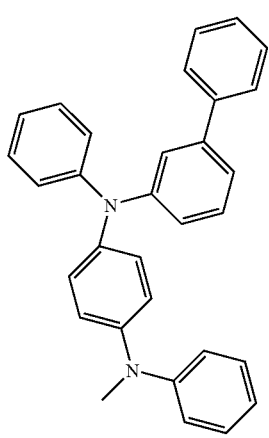
(31-13)
(31-10)
(31-14)
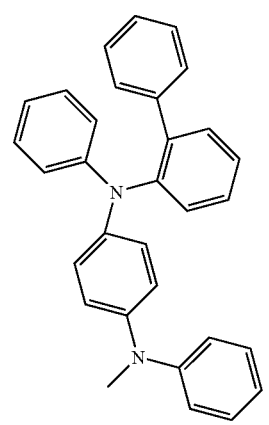
(31-11)
(31-12)
(31-15)
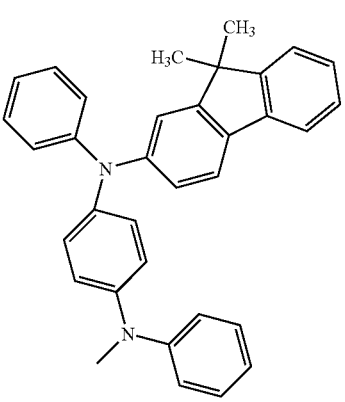

(31-16)
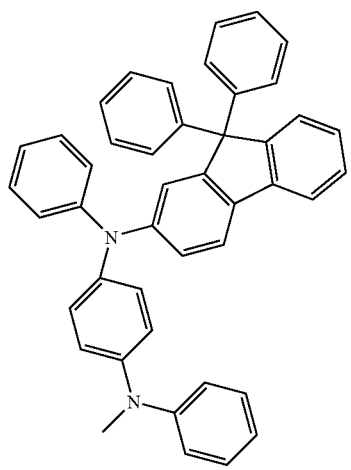
(31-17)
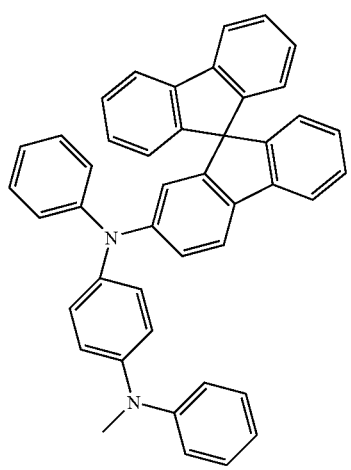
(31-18)
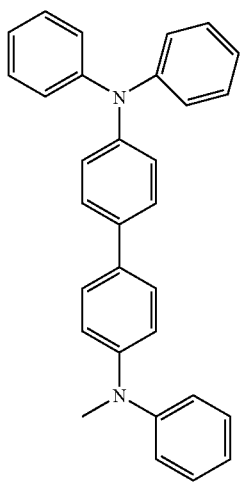
(31-19)
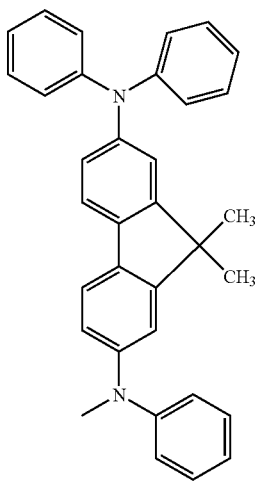
(31-20)
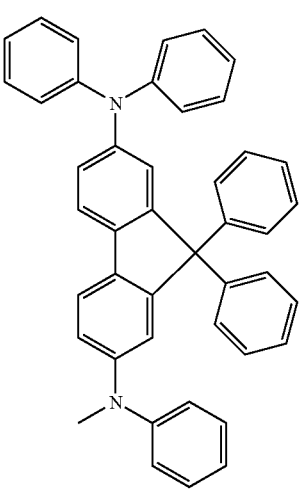
(31-21)
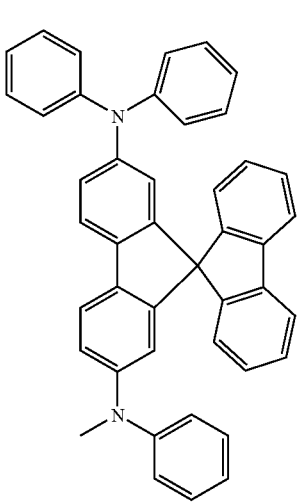

(31-22)
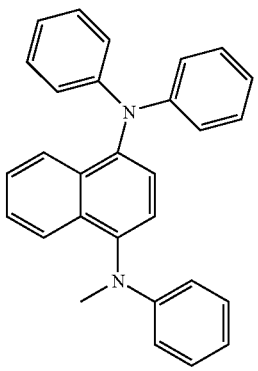
(31-23)
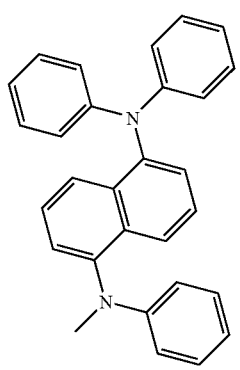
In the general formula (1-2), as examples of the substituent represented by $Ar^{21}$, substituents represented by structural formulae (23-1) to (23-9) are given.
(23-1)
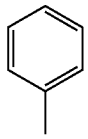
(23-2)
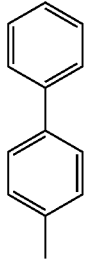
(23-3)
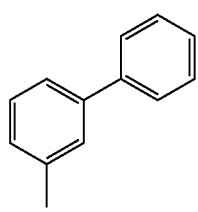
(23-4)
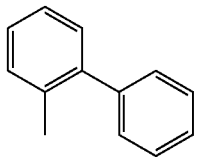
(23-5)
(23-6)
(23-7)
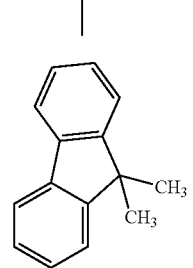
(23-8)
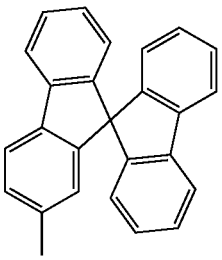
(23-9)
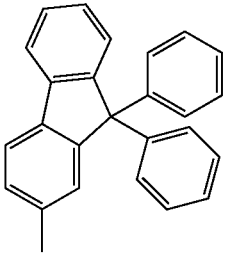
In the general formula (1-2), as examples of the substituent represented by $R^{31}$, substituents represented by structural formulae (24-1) to (24-18) are given.
(24-1)
H
(24-2)

In the general formula (1-2), as examples of the substituent represented by $R^{32}$, substituents represented by structural formulae (25-1) to (25-17) are given.

(25-4) 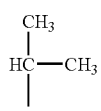
(25-5) 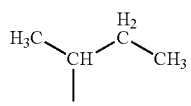
(25-6) 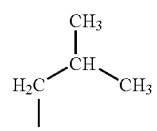
(25-7) 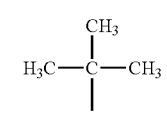
(25-8) 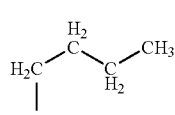
(25-9) 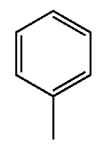
(25-10)
(25-11) 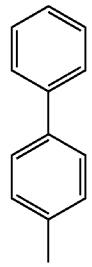
(25-12) 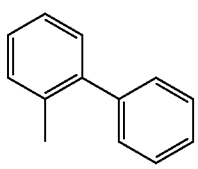
(25-13) 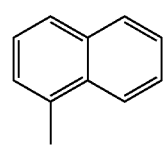
(25-14) 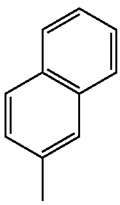
(25-15) 
(25-16) 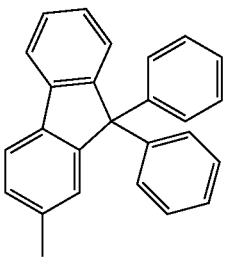
(25-17) 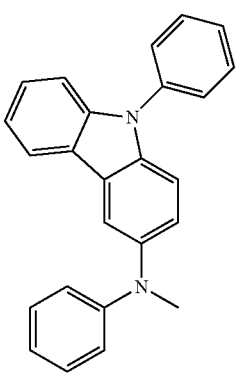
Therefore, as examples of the substituents represented in the general formula (1-2), substituents represented by structural formulae (32-1) to (32-42) are given.
(32-1)

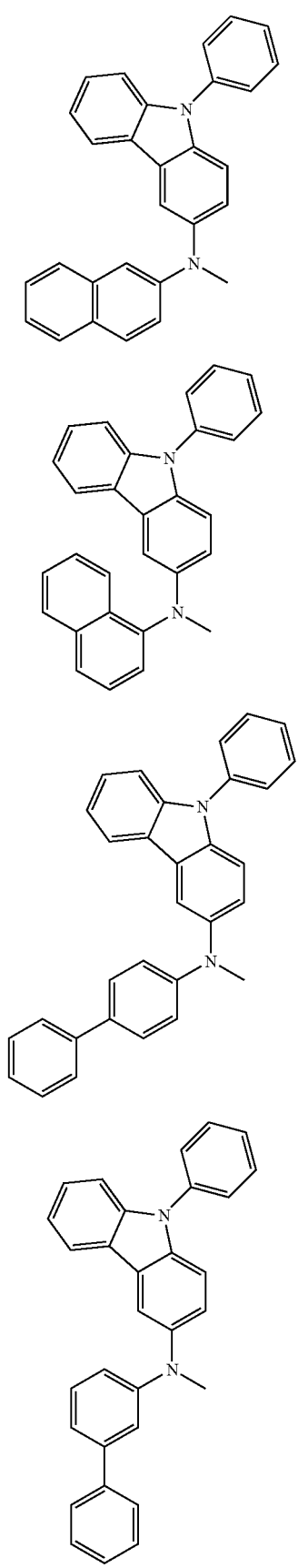
(32-2)
(32-3)
(32-4)
(32-5)
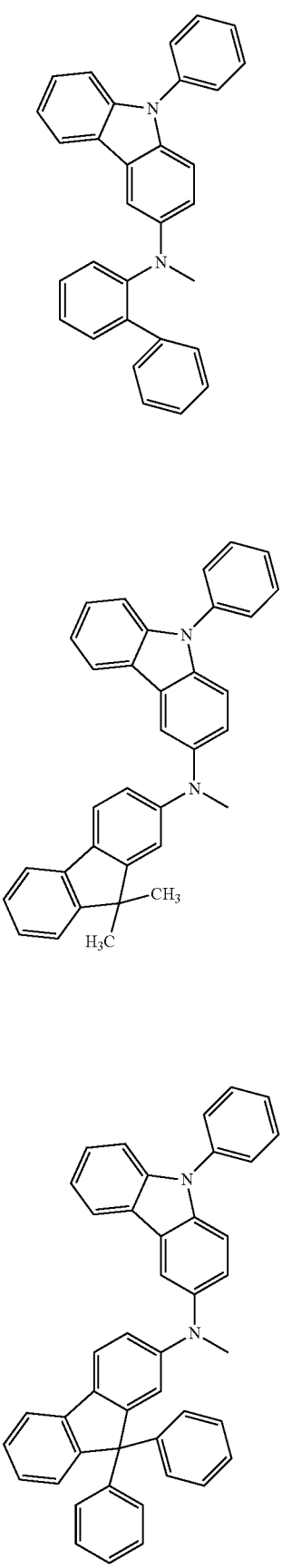
(32-6)
(32-7)
(32-8)

(32-9)
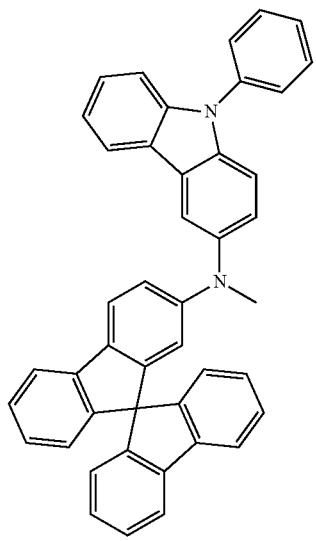
(32-10)
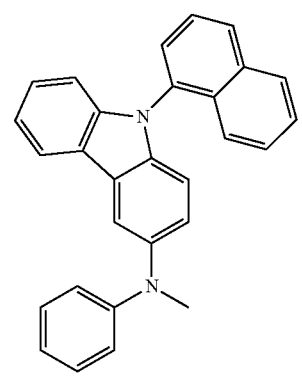
(32-11)
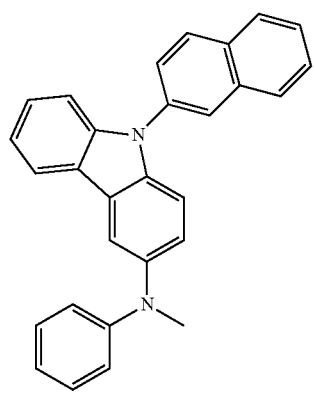
(32-12)
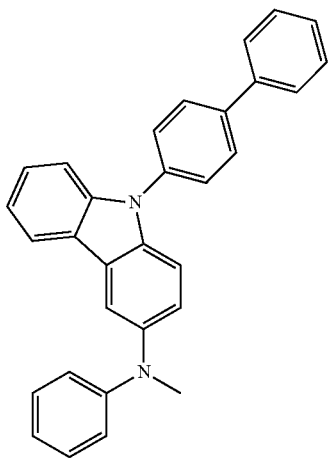
(32-13)
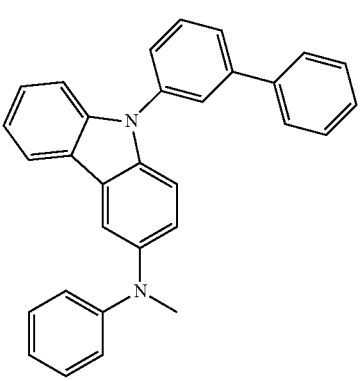
(32-14)
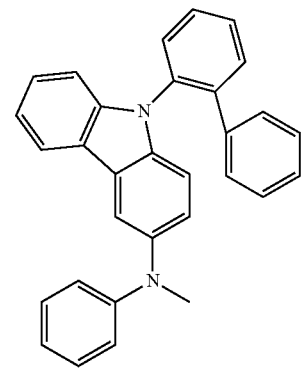
(32-15)
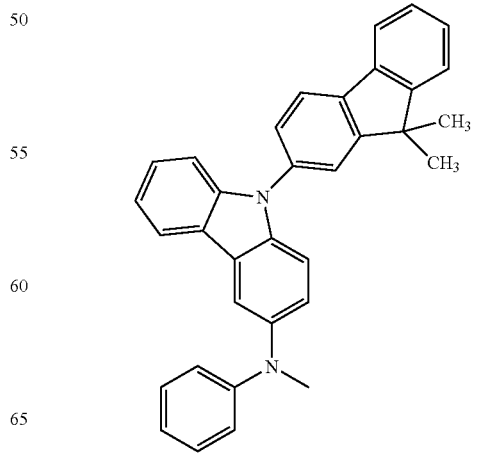

(32-16)
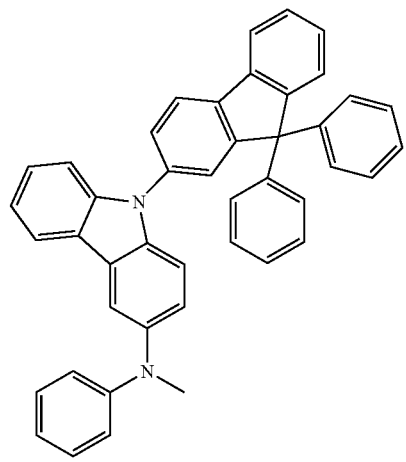
(32-17)
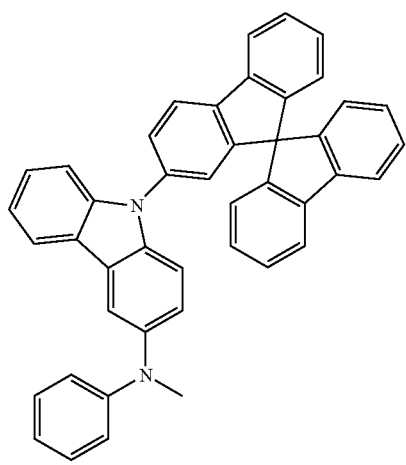
(32-18)
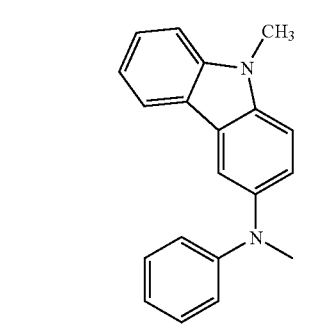
(32-19)
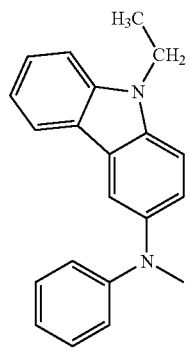
(32-20)
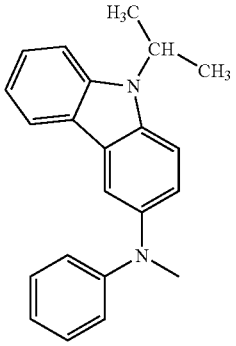
(32-21)
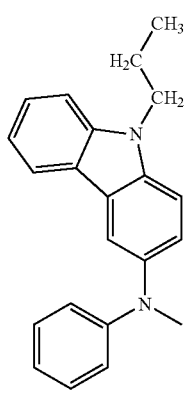
(32-22)
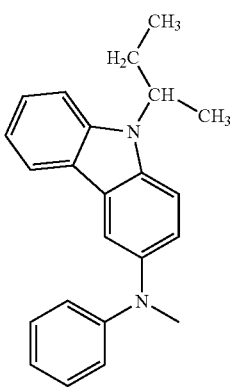
(32-23)
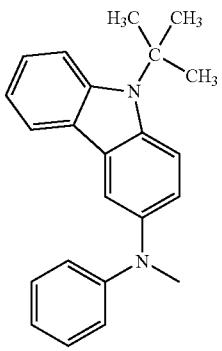

(32-24)
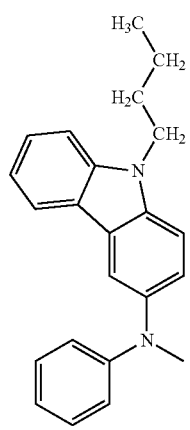
(32-25)
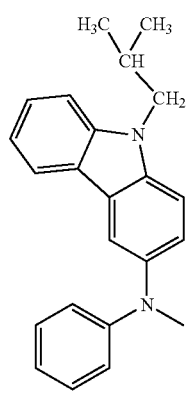
(32-26)
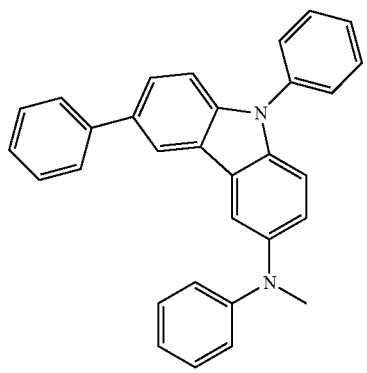
(32-27)
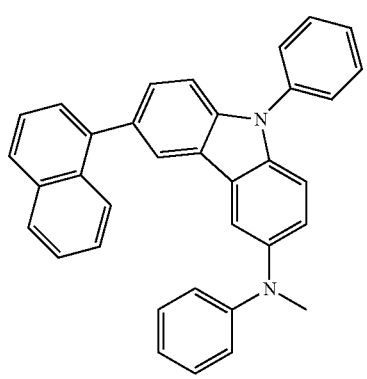
(32-28)
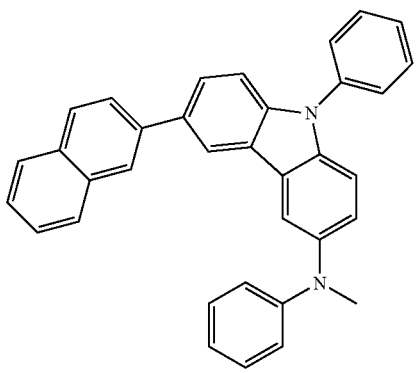
(32-29)
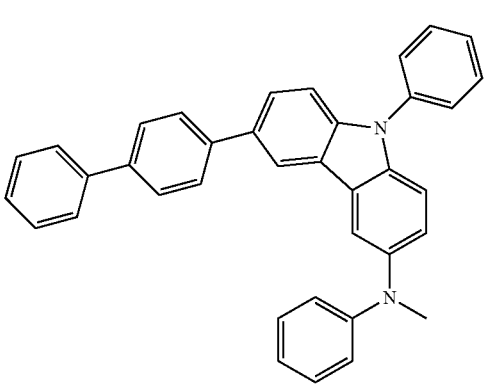
(32-30)
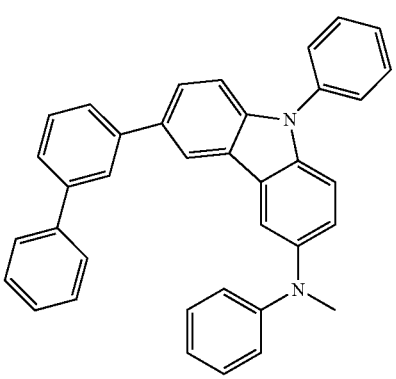
(32-31)
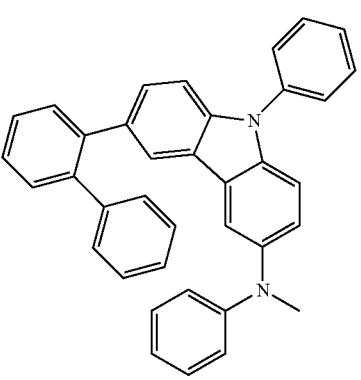

(32-32) 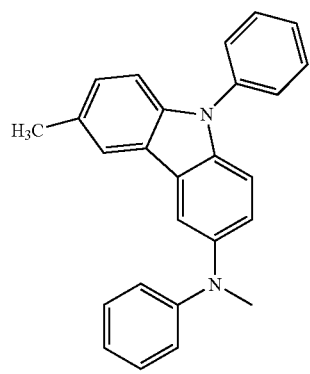
(32-36) 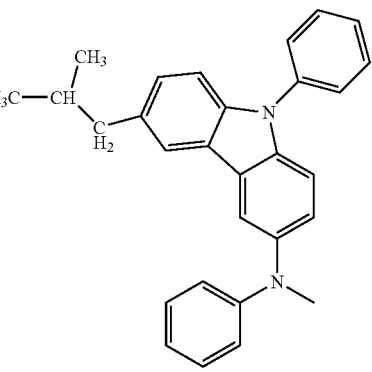
(32-33) 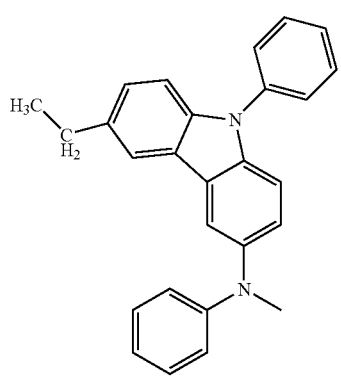
(32-37) 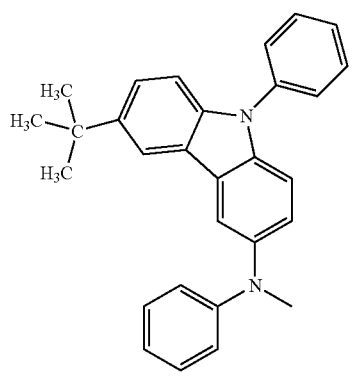
(32-34) 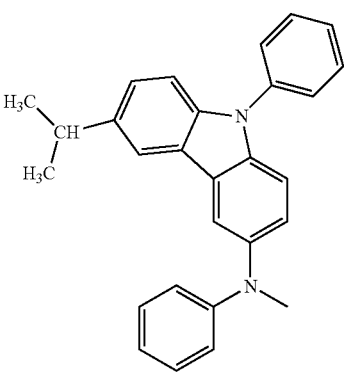
(32-38) 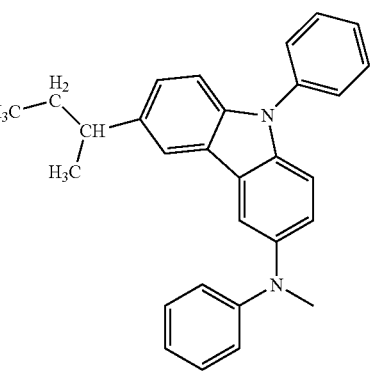
(32-35) 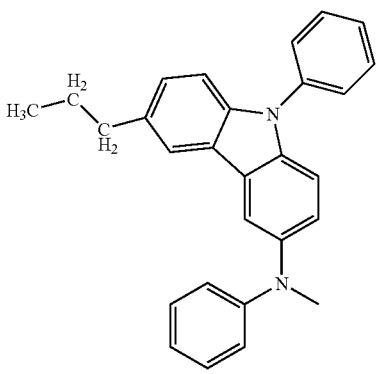
(32-39) 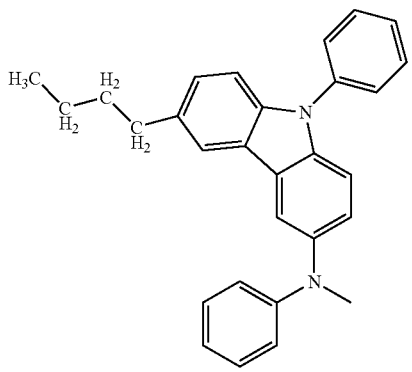

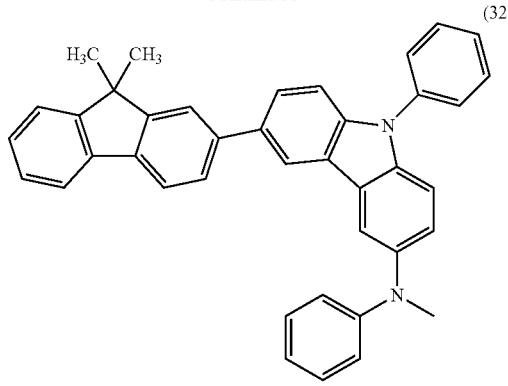 (32-40)
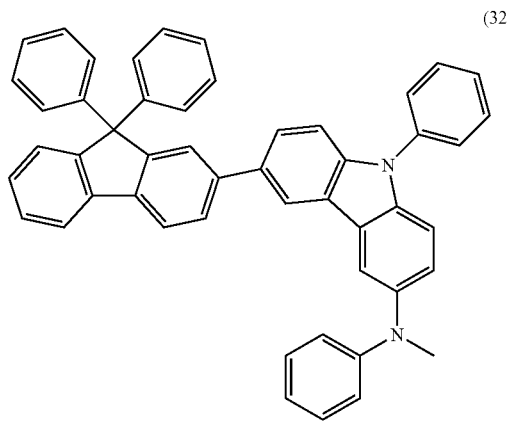 (32-41)
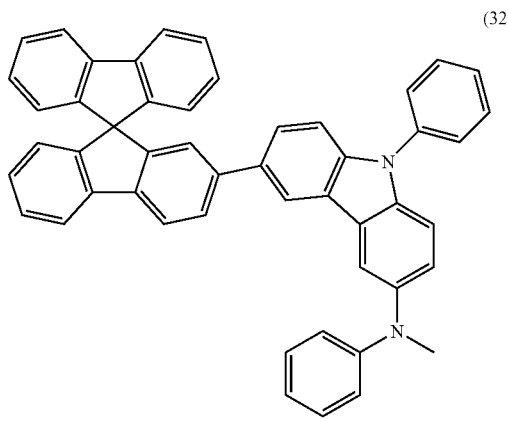 (32-42)
In the general formula (1-3), as examples of the substituent represented by $Ar^{31}$, substituents represented by structural formulae (26-1) to (26-9) are given.
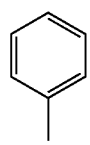 (26-1)
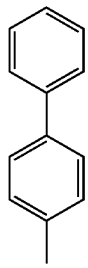 (26-2)
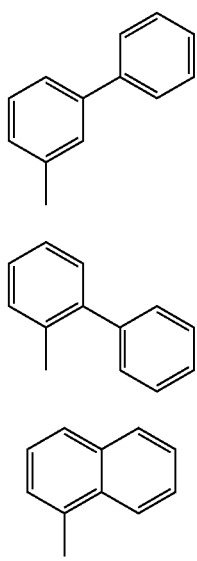 (26-3)
(26-4)
(26-5)
(26-6)
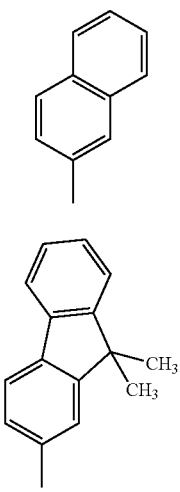 (26-7)
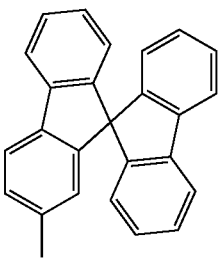 (26-8)

(26-9)
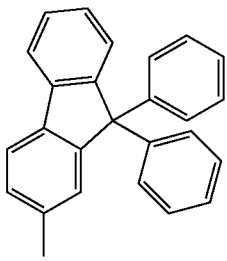
In the general formula (1-3), as examples of the substituent represented by β, substituents represented by structural formulae (27-1) to (27-9) are given.
(27-1)
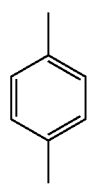
(27-2)
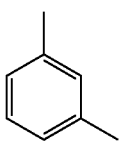
(27-3)
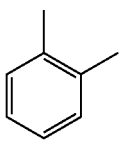
(27-4)
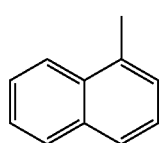
(27-5)
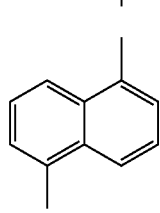
(27-6)
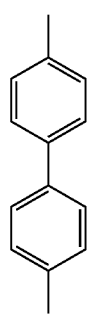
(27-7)
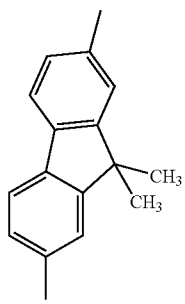
(27-8)
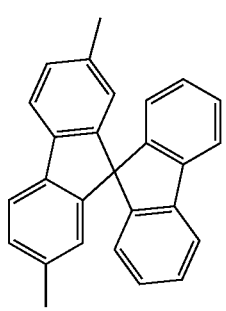
(27-9)
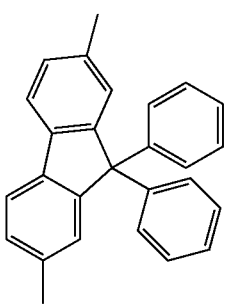
In the general formula (1-3), as examples of the substituents represented by $R^{41}$ to $R^{42}$, substituents represented by structural formulae (28-1) to (28-18) are given.
(28-1)
(28-2)
(28-3)
(28-4)
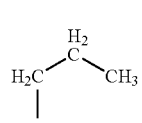
(28-5)
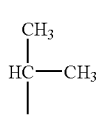

(28-6) 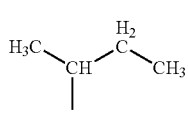
(28-7) 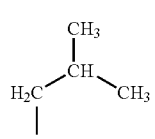
(28-8) 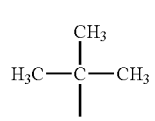
(28-9) 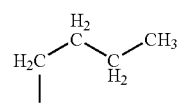
(28-10) 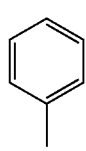
(28-11) 
(28-12) 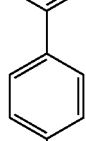
(28-13) 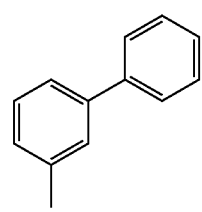
(28-14) 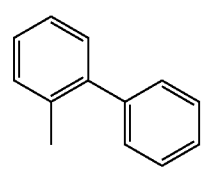
(28-15) 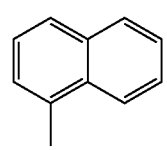
(28-16) 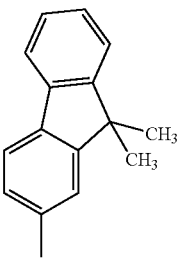
(28-17) 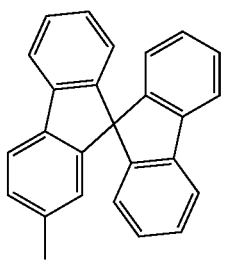
(28-18) 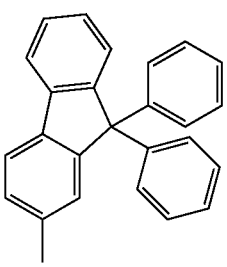
Therefore, as examples of the substituents represented in the general formula (1-3), substituents represented by structural formulae (33-1) to (33-34) are given.
(33-1) 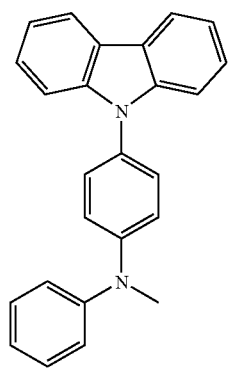

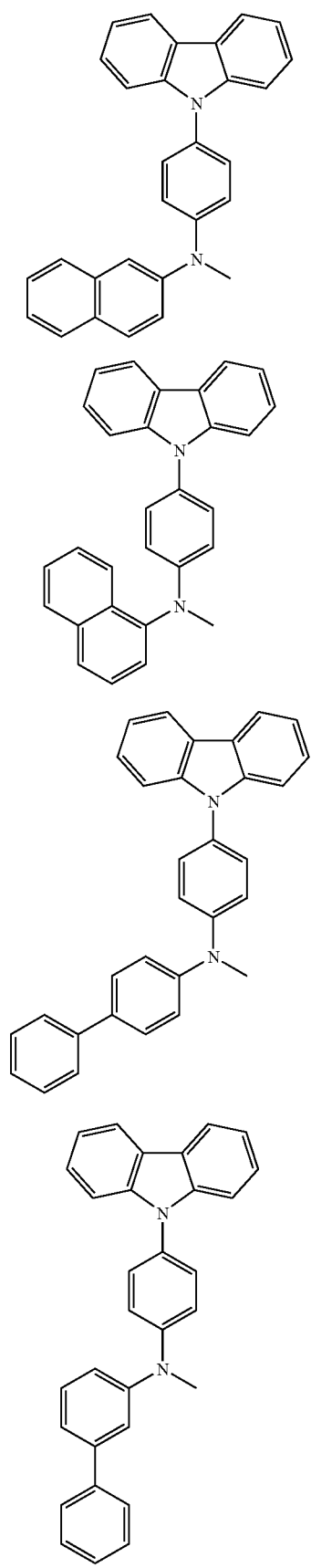
(33-2)
(33-3)
(33-4)
(33-5)
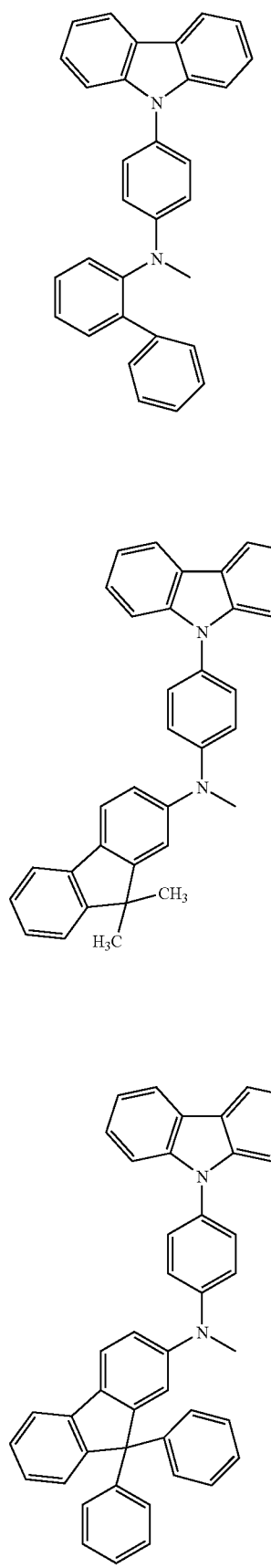
(33-6)
(33-7)
(33-8)

(33-9)
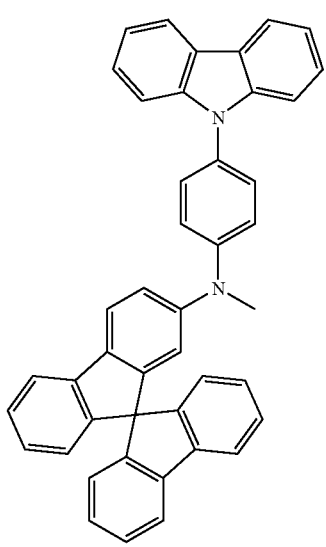
(33-10)
(33-11)
(33-12)
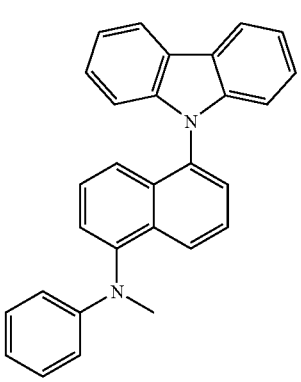
(33-13)
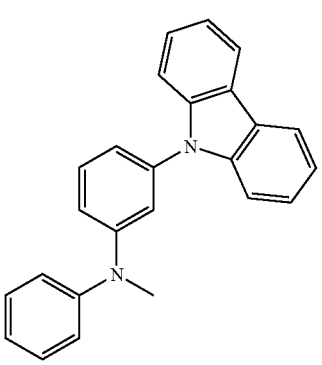
(33-14)
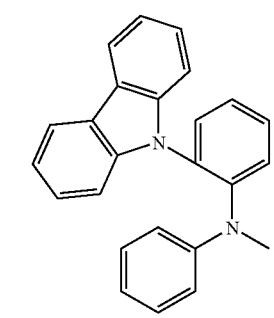
(33-15)
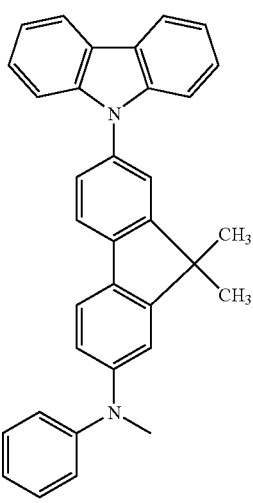

(33-16)
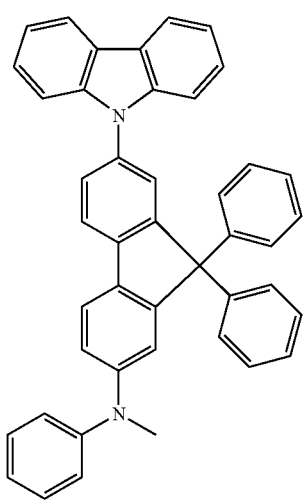
(33-19)
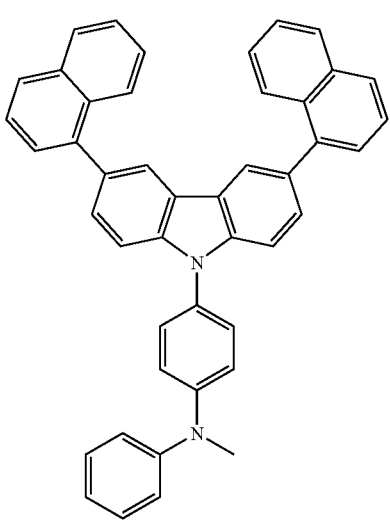
(33-17)
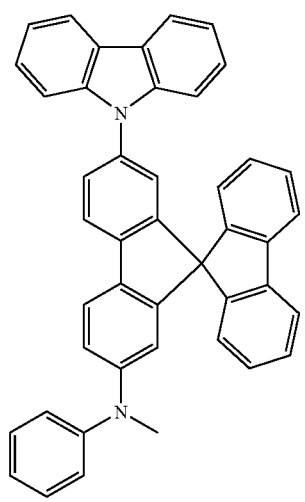
(33-20)
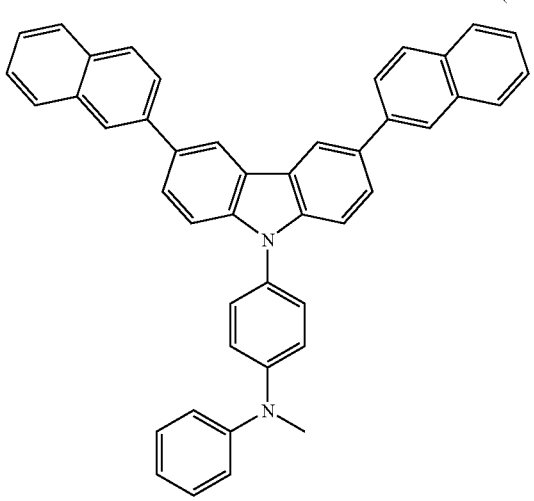
(33-18)
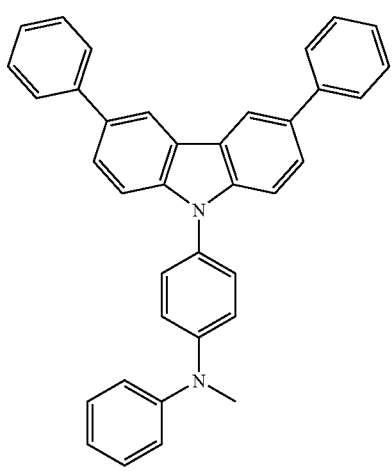
(33-21)
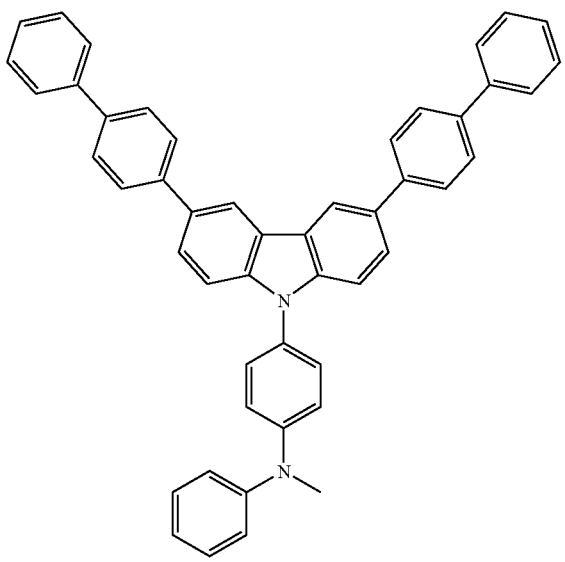

(33-22)
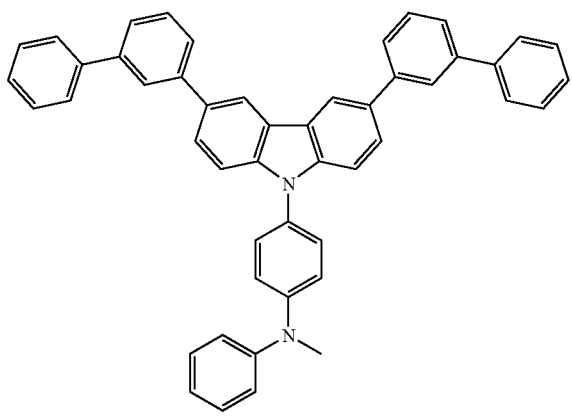
(33-25)
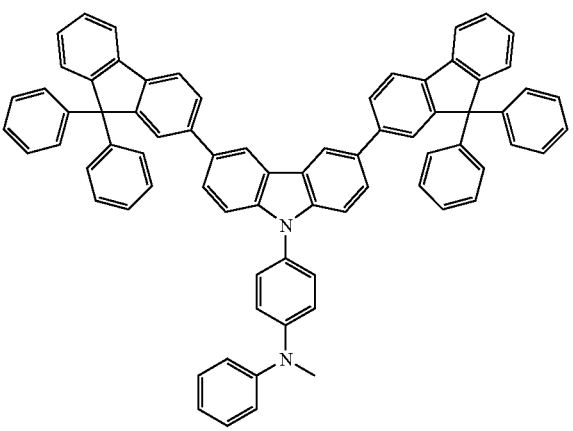
(33-23)
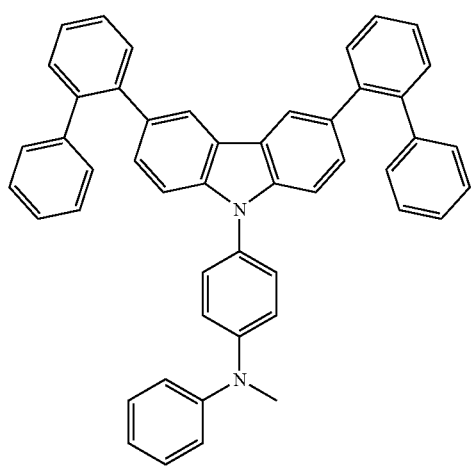
(33-26)
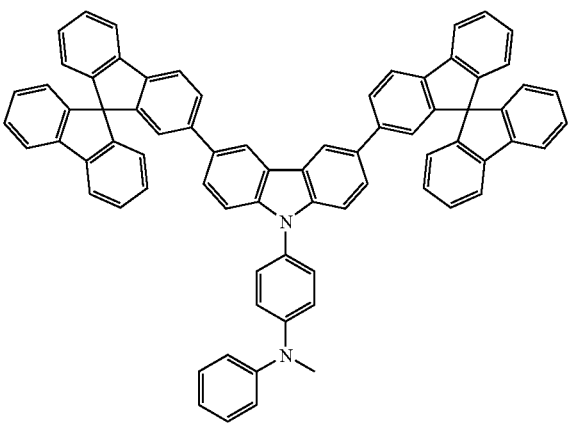
(33-24)
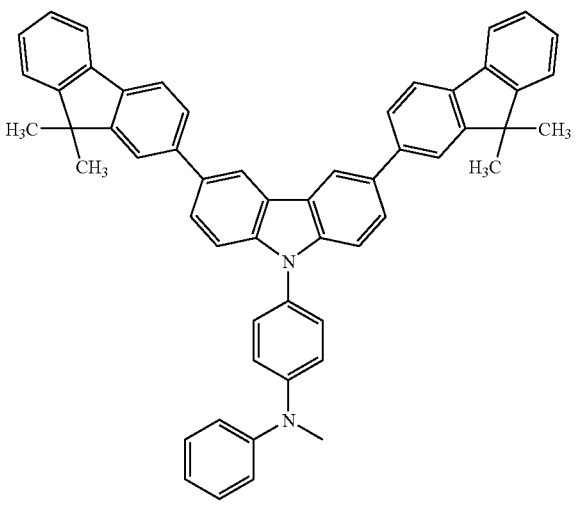
(33-27)
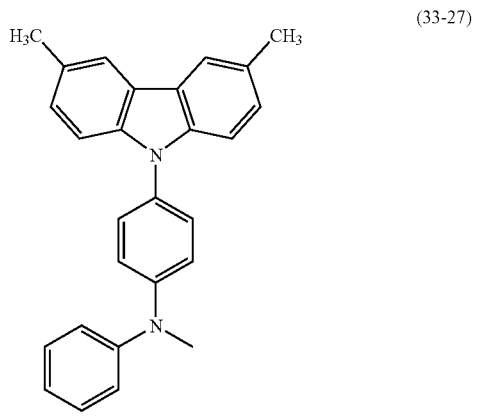

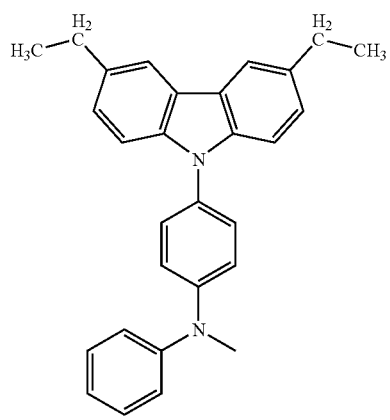
(33-28)
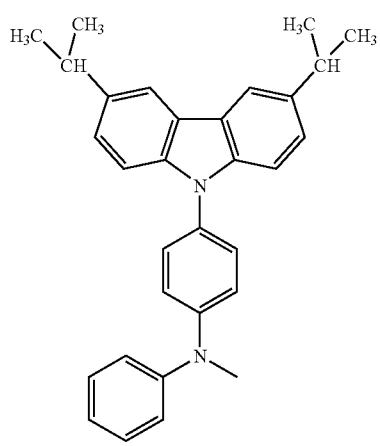
(33-29)
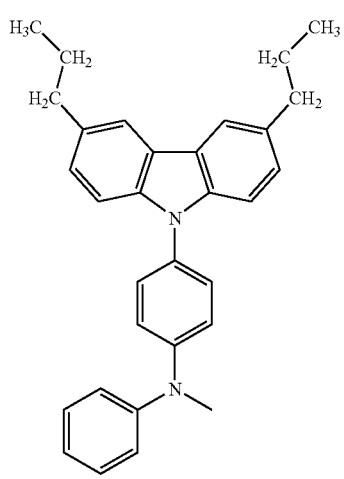
(33-30)
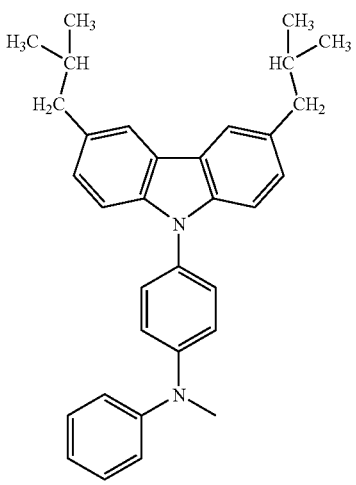
(33-31)
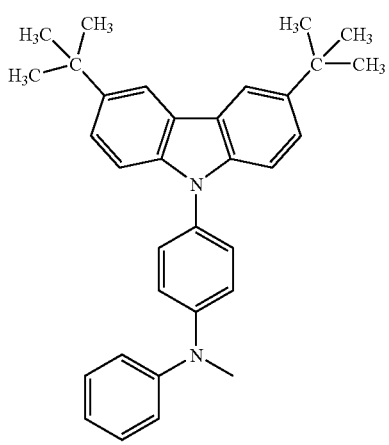
(33-32)
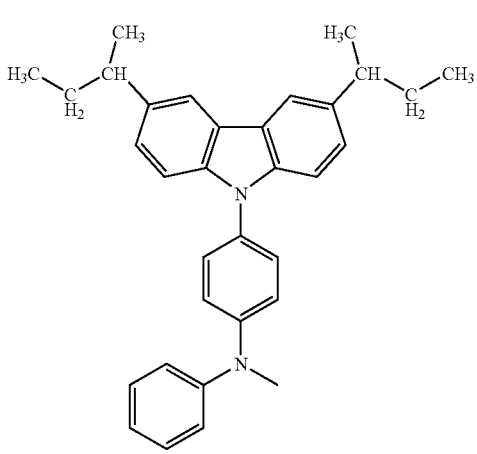
(33-33)

-continued (33-34)

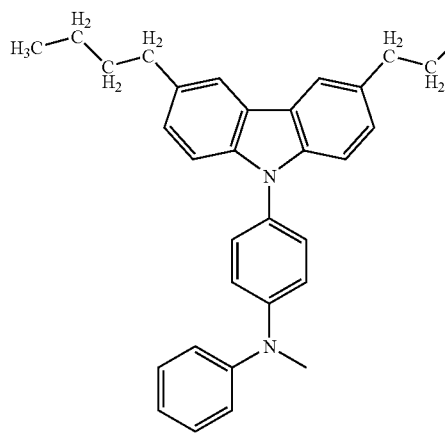

In addition, among anthracene derivatives represented by the general formula (1), an anthracene derivative represented by a general formula (2) is preferable.

(2)

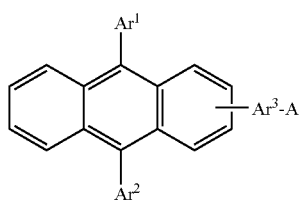

(2-1)

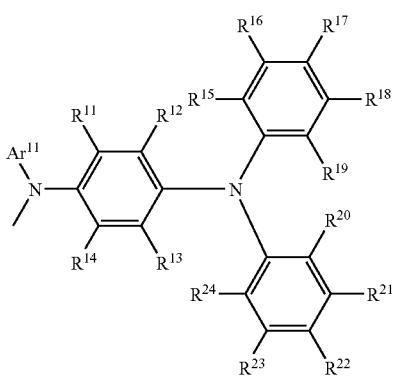

(2-2)

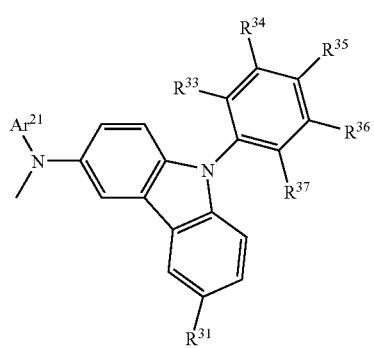

-continued (2-3)

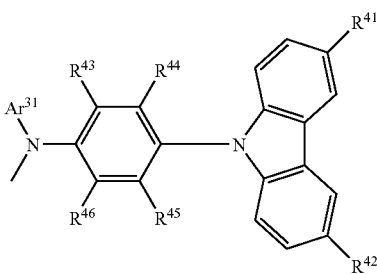

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (2-1) to (2-3). In the general formulae (2-1) to (2-3), $Ar^{11}$ represents an aryl group having 6 to 25 carbon atoms; $R^{11}$ to $R^{24}$ each represent a hydrogen atom, an alkyl group having 1 to 4 carbon atoms, an aryl group having 6 to 15 carbon atoms, a halogen atom, or a haloalkyl group having 1 to 4 carbon atoms; $Ar^{21}$ represents an aryl group having 6 to 25 carbon atoms; $R^{31}$ represents a hydrogen atom, an alkyl group having 1 to 4 carbon atoms, an aryl group having 6 to 25 carbon atoms, a halogen atom, or a haloalkyl group having 1 to 4 carbon atoms; $R^{33}$ to $R^{37}$ each represent a hydrogen atom, an alkyl group having 1 to 4 carbon atoms, an aryl group having 6 to 15 carbon atoms, a halogen atom, or a haloalkyl group having 1 to 4 carbon atoms; $Ar^{31}$ represents an aryl group having 6 to 25 carbon atoms; $R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms; $R^{43}$ to $R^{46}$ each represent a hydrogen atom, an alkyl group having 1 to 4 carbon atoms, an aryl group having 6 to 15 carbon atoms, a halogen atom, or a haloalkyl group having 1 to 4 carbon atoms.

In addition, among anthracene derivatives represented by the general formula (1), an anthracene derivative represented by a general formula (3) is preferable.

(3)

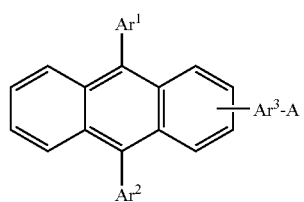

(3-1)

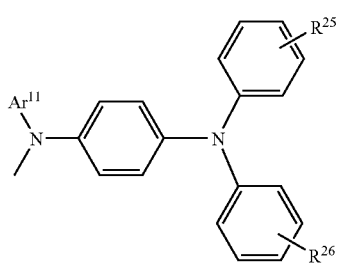

(3-2)

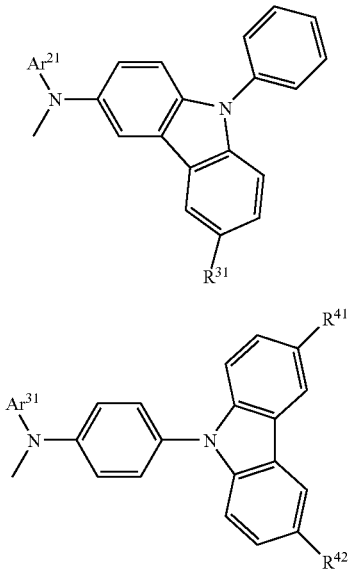

(3-3)

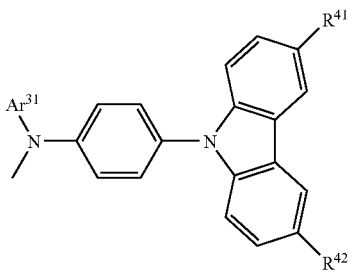

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (3-1) to (3-3). In the general formulae (3-1) to (3-3), $Ar^{11}$ represents an aryl group having 6 to 25 carbon atoms; $R^{25}$ and $R^{26}$ each represent a hydrogen atom, an alkyl group having 1 to 4 carbon atoms, an aryl group having 6 to 15 carbon atoms, a halogen atom, or a haloalkyl group having 1 to 4 carbon atoms; $Ar^{21}$ represents an aryl group having 6 to 25 carbon atoms; $R^{31}$ represents a hydrogen atom, an alkyl group having 1 to 4 carbon atoms, an aryl group having 6 to 25 carbon atoms, a halogen atom, or a haloalkyl group having 1 to 4 carbon atoms; $Ar^{31}$ represents an aryl group having 6 to 25 carbon atoms; and $R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

In addition, among anthracene derivatives represented by the general formula (1), an anthracene derivative represented by a general formula (4) is preferable.

(4)

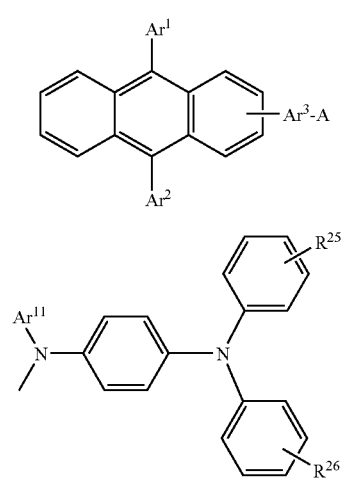

(4-1)

(4-2)

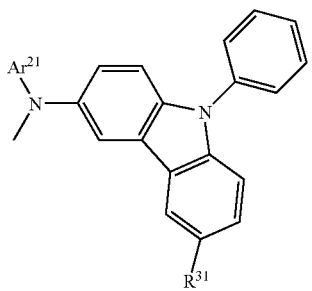

(4-3)

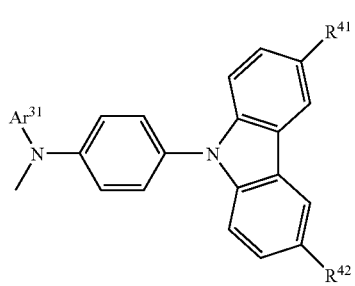

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (4-1) to (4-3). In the general formulae (4-1) to (4-3), $Ar^{11}$ represents a phenyl group, a 1-naphthyl group or a 2-naphthyl group; $R^{25}$ and $R^{26}$ each represent a hydrogen atom, an alkyl group having 1 to 4 carbon atoms, or an aryl group having 6 to 15 carbon atoms; $Ar^{21}$ represents a phenyl group, a 1-naphthyl group or a 2-naphthyl group; $R^{31}$ represents a hydrogen atom, an alkyl group having 1 to 4 carbon atoms, or an aryl group having 6 to 25 carbon atoms; $Ar^{31}$ represents a phenyl group, a 1-naphthyl group or a 2-naphthyl group; and $R^{41}$ and $R^{42}$ each represent a hydrogen atom, an alkyl group having 1 to 4 carbon atoms, or an aryl group having 6 to 25 carbon atoms.

In addition, among anthracene derivatives represented by, the general formula (1), an anthracene derivative represented by a general formula (5) is preferable.

(5)

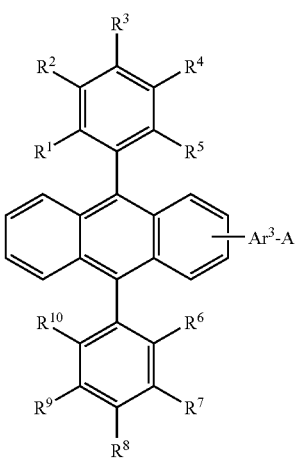

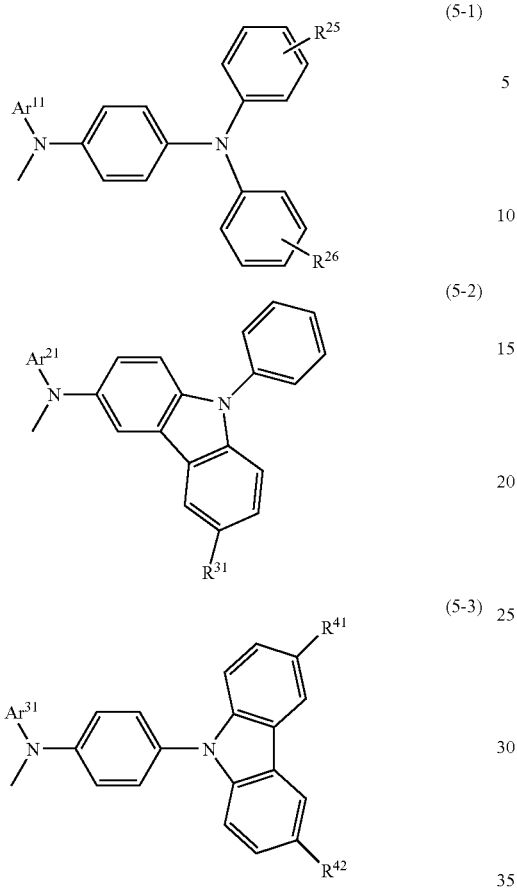

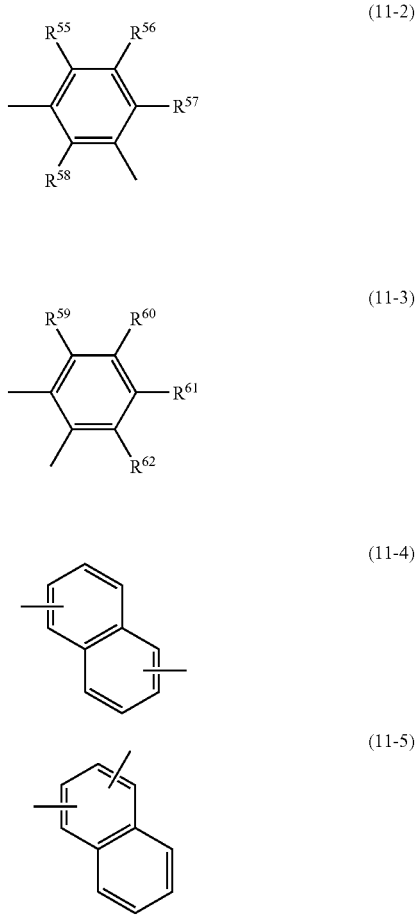

In the formula, $R^1$ to $R^{10}$ each represent a hydrogen atom, an alkyl group having 1 to 4 carbon atoms, an aryl group having 6 to 15 carbon atoms, a halogen atom, a haloalkyl group having 1 to 4 carbon atoms, $Ar^3$ represents an arylene group having 6 to 25 carbon atoms, and A represents any of substituents represented by general formulae (5-1) to (5-3). In the general formulae (5-1) to (5-3), $Ar^{11}$ represents a phenyl group, a 1-naphthyl group or a 2-naphthyl group; $R^{25}$ and $R^{26}$ each represent a hydrogen atom, an alkyl group having 1 to 4 carbon atoms, or an aryl group having 6 to 15 carbon atoms; $Ar^{21}$ represents a phenyl group, a 1-naphthyl group or a 2-naphthyl group; $R^{31}$ represents a hydrogen atom, an alkyl group having 1 to 4 carbon atoms, or an aryl group having 6 to 25 carbon atoms; $Ar^{31}$ represents a phenyl group, a 1-naphthyl group or a 2-naphthyl group; and $R^{41}$ and $R^{42}$ each represent a hydrogen atom, an alkyl group having 1 to 4 carbon atoms, or an aryl group having 6 to 25 carbon atoms.

In the general formulae (1) to (5), $Ar^3$ is preferably any of substituents represented by general formulae (11-1) to (11-5).

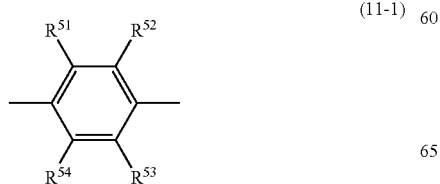

In the formula, R to $R^{62}$ each represent a hydrogen atom, an alkyl group having 1 to 4 carbon atoms, an aryl group having 6 to 15 carbon atoms, a halogen atom, or a haloalkyl group having 1 to 4 carbon atoms.

In addition, in the general formulae (1) to (5), $Ar^1$ and $Ar^2$ preferably have the same structure.

In the general formulae (1) to (5), A is preferably bound to the 2-position of the anthracene skeleton. By bonding at the 2-position, steric hindrance with each of $Ar^1$ and $Ar^2$ is reduced.

That is, a preferable anthracene derivative is represented by a general formula (6).

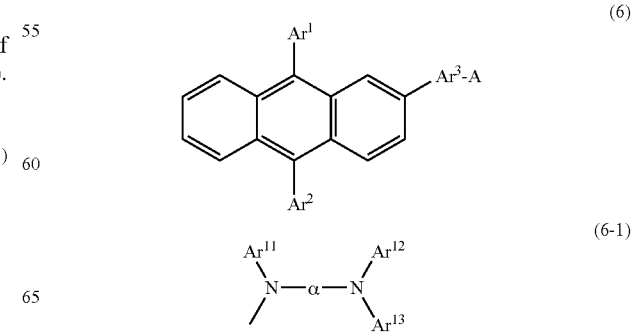

-continued (6-2)
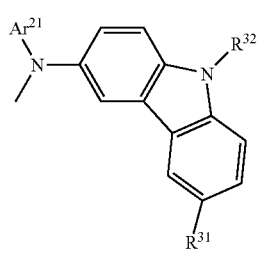

(6-3)
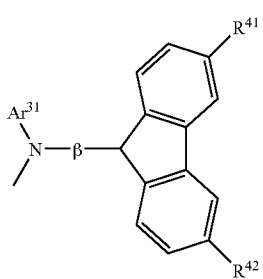

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (6-1) to (6-3). In the general formulae (6-1) to (6-3), $Ar^{11}$ to $Ar^{13}$ each represent an aryl group having 6 to 25 carbon atoms; a represents an arylene group having 6 to 25 carbon atoms; $Ar^1$ represents an aryl group having 6 to 25 carbon atoms; $R^{31}$ represents a hydrogen atom, an alkyl group having 1 to 4 carbon atoms, an aryl group having 6 to 25 carbon atoms, a halogen atom, or a haloalkyl group having 1 to 4 carbon atoms; $R^{32}$ represents an alkyl group having 1 to 4 carbon atoms, an aryl group having 6 to 25 carbon atoms, or a haloalkyl group having 1 to 4 carbon atoms; $Ar^{31}$ represents an aryl group having 6 to 25 carbon atoms; β represents an arylene group having 6 to 25 carbon atoms; and $R^{41}$ to $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

In addition, an anthracene derivative represented by a general formula (7) is preferable.

(7)
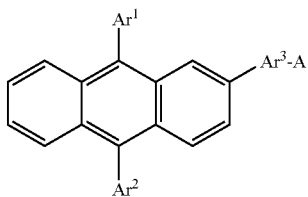

(7-1)
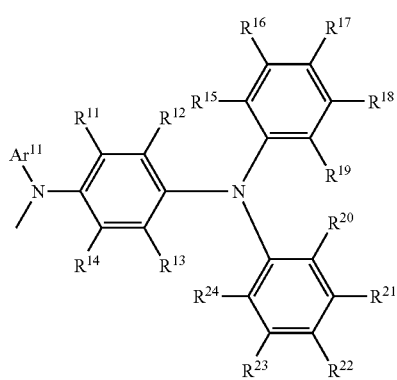

-continued (7-2)
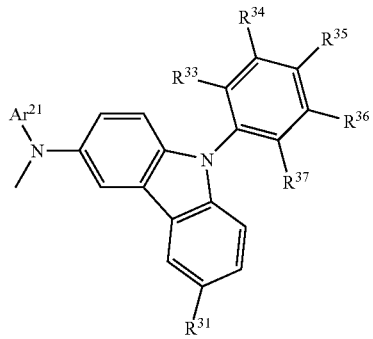

(7-3)
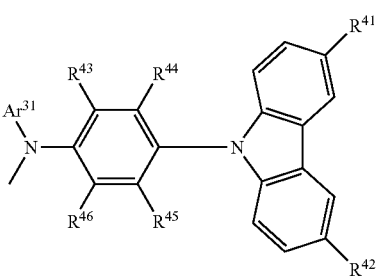

In the formula, $Ar^1$ and $Ar^2$ each represent an aryl group having 6 to 25 carbon atoms, $Ar^3$ represents an arylene group having 6 to 25 carbon atoms, and A represents any of substituents represented by general formulae (7-1) to (7-3). In the general formulae (7-1) to (7-3), $Ar^{11}$ represents an aryl group having 6 to 25 carbon atoms; $R^{11}$ to $R^{24}$ each represent a hydrogen atom, an alkyl group having 1 to 4 carbon atoms, an aryl group having 6 to 15 carbon atoms, a halogen atom, or a haloalkyl group having 1 to 4 carbon toms; $Ar^{21}$ represents an aryl group having 6 to 25 carbon atoms; $R^{31}$ represents a hydrogen atom, an alkyl group having 1 to 4 carbon atoms, an aryl group having 6 to 25 carbon atoms, a halogen atom, or a haloalkyl group having 1 to 4 carbon atoms; $R^{33}$ to $R^{37}$ each represent a hydrogen atom, an alkyl group having 1 to 4 carbon atoms, an aryl group having 6 to 15 carbon atoms, a halogen atom, or a haloalkyl group having 1 to 4 carbon toms; $Ar^{31}$ represents an aryl group having 6 to 25 carbon atoms; $R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms; and $R^{43}$ to $R^{46}$ each represent a hydrogen atom, an alkyl group having 1 to 4 carbon atoms, an aryl group having 6 to 15 carbon atoms, a halogen atom, or a haloalkyl group having 1 to 4 carbon atoms.

In addition, an anthracene derivative represented by a general formula (8) is preferable.

(8)
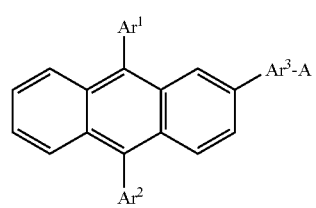

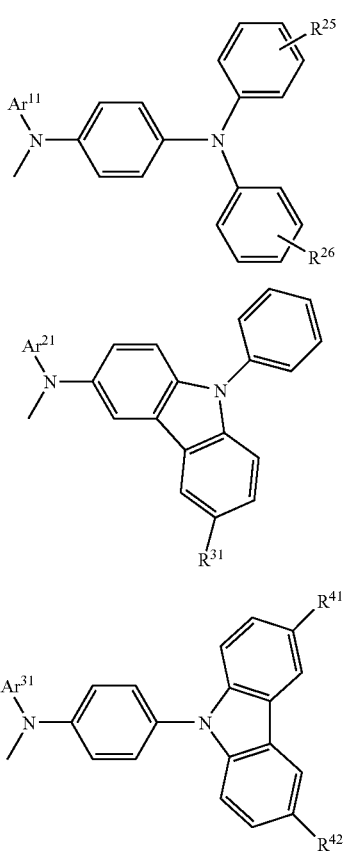

(8-1)

(8-2)

(8-3)

In the formula, Ar¹ and Ar² each represent an aryl group having 6 to 25 carbon atoms, $Ar^3$ represents an arylene group having 6 to 25 carbon atoms, and A represents any of substituents represented by general formulae (8-1) to (8-3). In the general formulae (8-1) to (8-3), $Ar^{11}$ represents an aryl group having 6 to 25 carbon atoms; $R^{25}$ and $R^{26}$ each represent a hydrogen atom, an alkyl group having 1 to 4 carbon atoms, an aryl group having 6 to 15 carbon atoms, a halogen atom, or a haloalkyl group having 1 to 4 carbon atoms; $Ar^{21}$ represents an aryl group having 6 to 25 carbon atoms; $R^{31}$ represents a hydrogen atom, an alkyl group having 1 to 4 carbon atoms, an aryl group having 6 to 15 carbon atoms, a halogen atom, or a haloalkyl group having 1 to 4 carbon atoms; $Ar^{31}$ represents an aryl group having 6 to 25 carbon atoms; and $R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

In addition, an anthracene derivative represented by a general formula (9) is preferable.

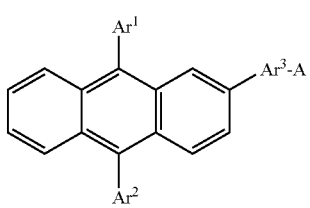

(9)

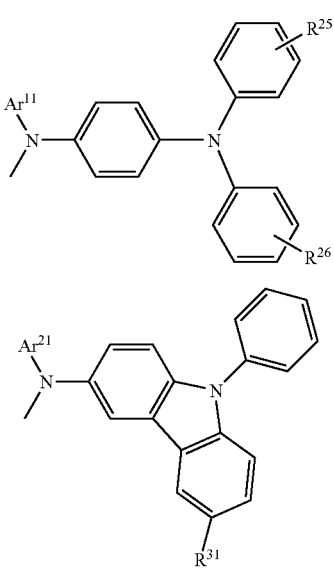

(9-1)

(9-2)

(9-3)

In the formula, Ar¹ to Ar² each represent an aryl group having 6 to 25 carbon atoms, $Ar^3$ represents an arylene group having 6 to 25 carbon atoms, and A represents any of substituents represented by general formulae (9-1) to (9-3). In the general formulae (9-1) to (9-3), $Ar^{11}$ represents a phenyl group, a 1-naphthyl group or a 2-naphthyl group; $R^{25}$ and $R^{26}$ each represent a hydrogen atom, an alkyl group having 1 to 4 carbon atoms, or an aryl group having 6 to 15 carbon atoms; $Ar^{21}$ represents a phenyl group, a 1-naphthyl group or a 2-naphthyl group; $R^{31}$ represents a hydrogen atom, an alkyl group having 1 to 4 carbon atoms, or an aryl group having 6 to 25 carbon atoms; $Ar^{31}$ represents a phenyl group, a 1-naphthyl group or a 2-naphthyl group; and $R^{41}$ and $R^{42}$ each represent a hydrogen atom, an alkyl group having 1 to 4 carbon atoms, or an aryl group having 6 to 25 carbon atoms.

In addition, an anthracene derivative represented by a general formula (10) is preferable.

(10)

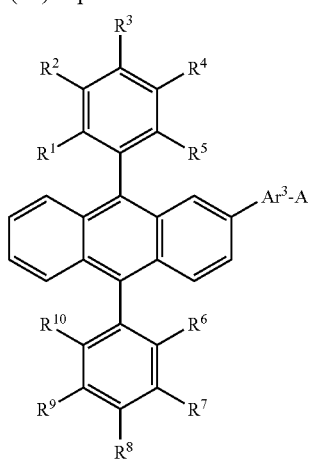

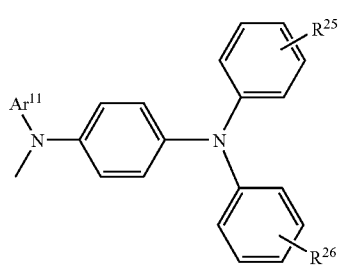
(10-1)

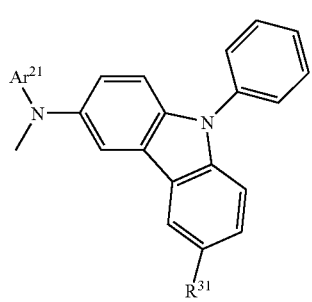
(10-2)

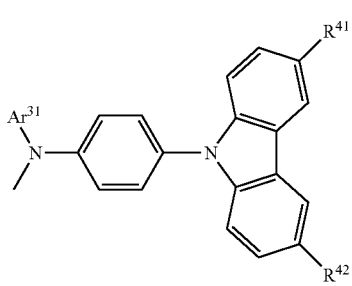
(10-3)

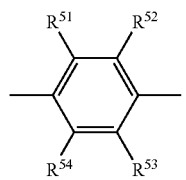
(11-1)

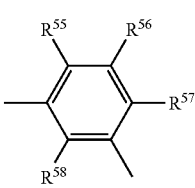
(11-2)

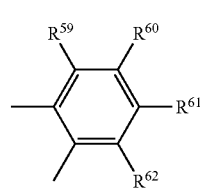
(11-3)

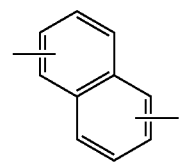
(11-4)

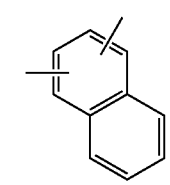
(11-5)

In the formula, $R^1$ to $R^{10}$ each represent a hydrogen atom, an alkyl group having 1 to 4 carbon atoms, an aryl group having 6 to 15 carbon atoms, a halogen atom, a haloalkyl group having 1 to 4 carbon atoms; $Ar^3$ represents an arylene group having 6 to 25 carbon atoms; and A represents any of substituents represented by general formulae (10-1) to (10-3). In the general formulae (10-1) to (10-3), $Ar^{11}$ represents a phenyl group, a 1-naphthyl group or a 2-naphthyl group; $R^{25}$ and $R^{26}$ each represent a hydrogen atom, an alkyl group having 1 to 4 carbon atoms, or an aryl group having 6 to 15 carbon atoms; $Ar^{21}$ represents a phenyl group, a 1-naphthyl group or a 2-naphthyl group; $R^{31}$ represents a hydrogen atom, an alkyl group having 1 to 4 carbon atoms, or an aryl group having 6 to 25 carbon atoms; $Ar^{31}$ represents a phenyl group, a 1-naphthyl group or a 2-naphthyl group; and $R^{41}$ and $R^{42}$ each represent a hydrogen atom, an alkyl group having 1 to 4 carbon atoms, or an aryl group having 6 to 25 carbon atoms.

In the general formulae (6) to (10), $Ar^3$ is preferably any of substituents represented by general formulae (11-1) to (11-5).

In the formulae, $R^{51}$ to $R^{62}$ each represent a hydrogen atom, an alkyl group having 1 to 4 carbon atoms, an aryl group having 6 to 15 carbon atoms, a halogen atom, or a haloalkyl group having 1 to 4 carbon atoms.

In the general formulae (6) to (10), $Ar^1$ and $Ar^2$ are preferably substituents having the same structure.

As a specific example of the anthracene derivative represented by the general formula (1), anthracene derivatives represented by structural formulae (101) to (223) can be given. However, the present invention is not limited to those examples.

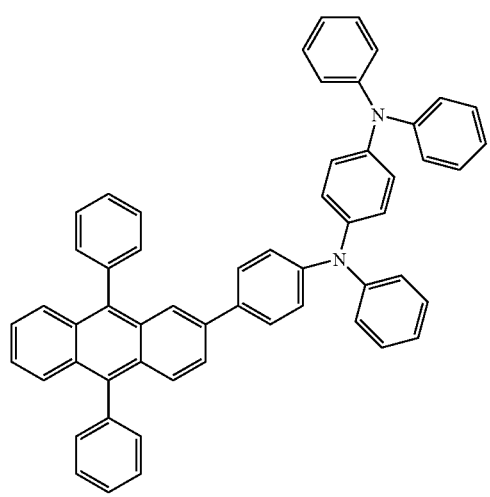
(101)
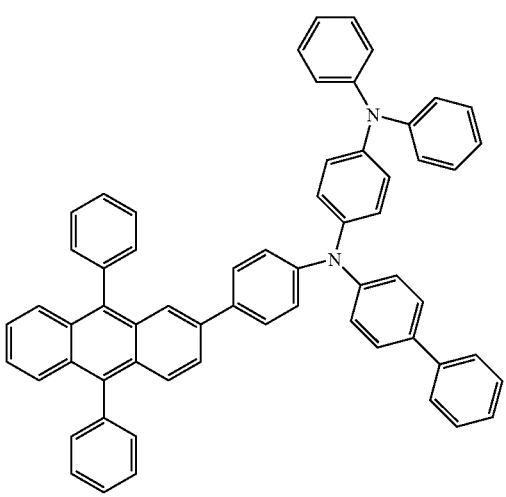
(102)
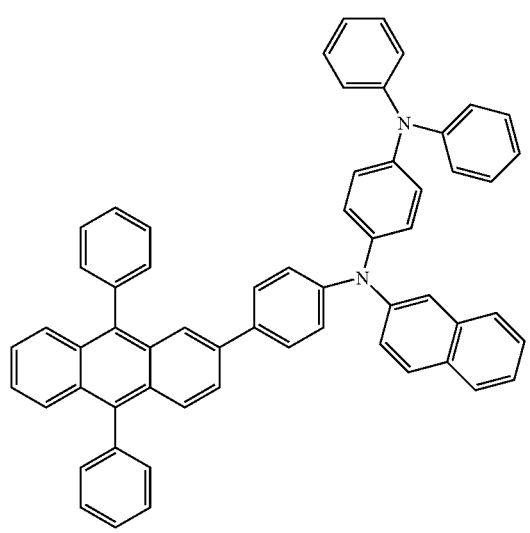
(103)
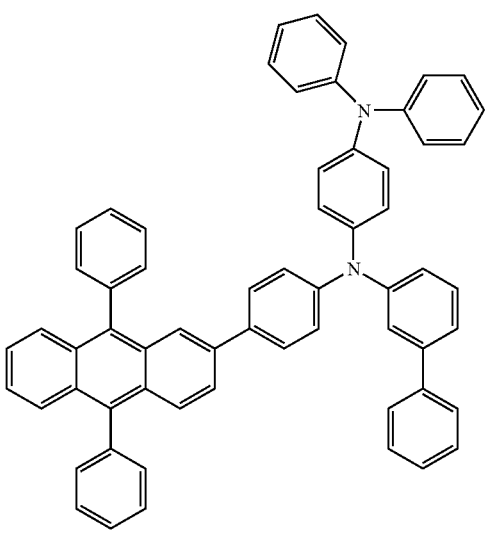
(104)
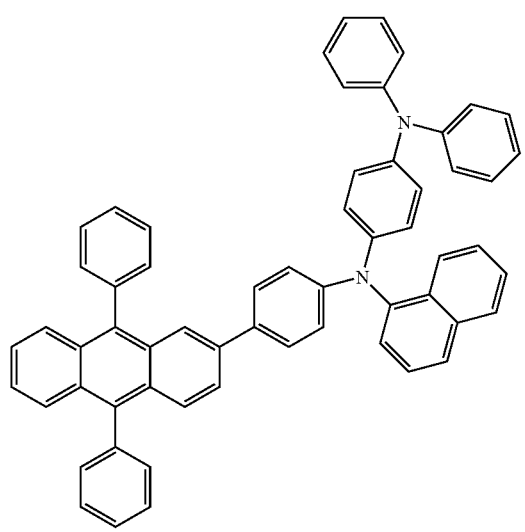
(105)
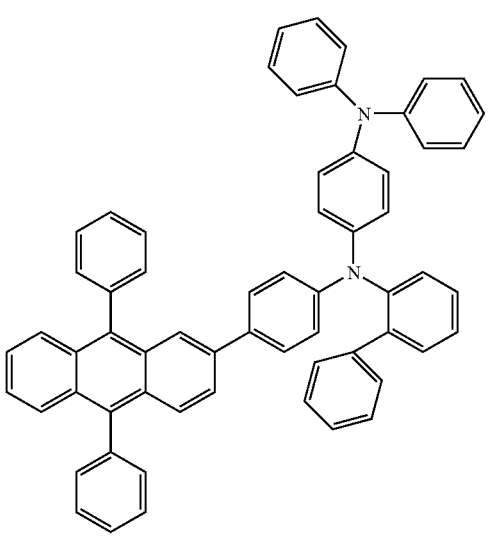
(106)

-continued
(107)
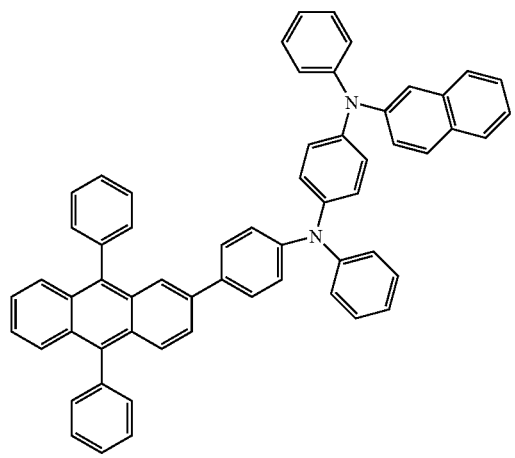
(108)
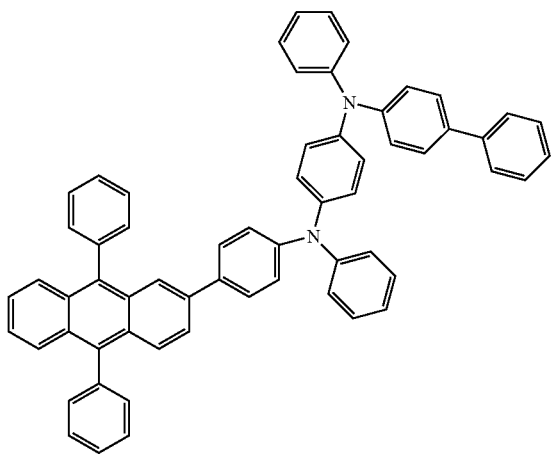
(109)
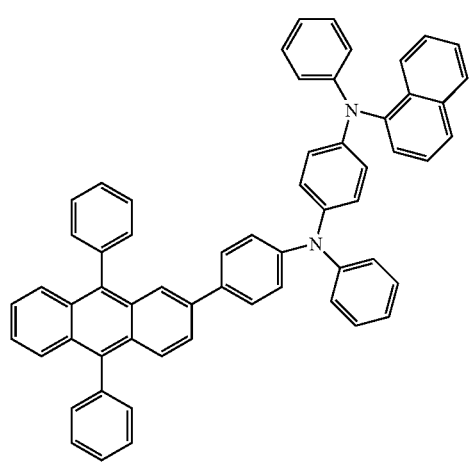
(110)
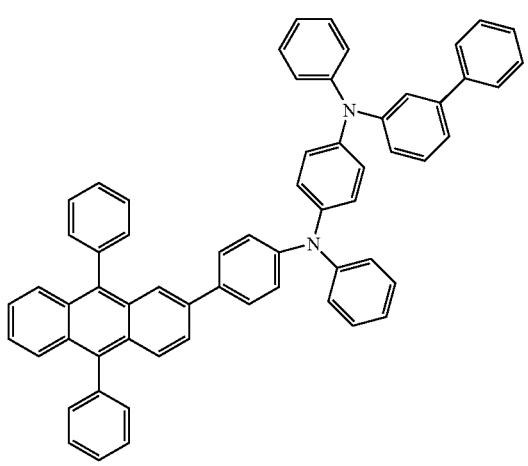
(111)
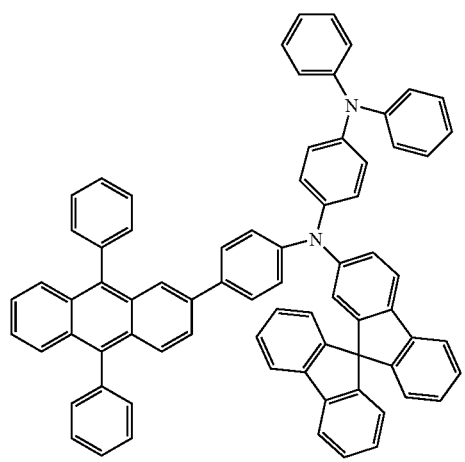
(112)
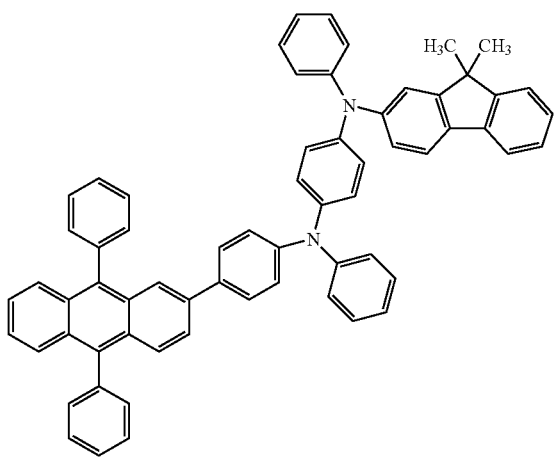

-continued
(113)
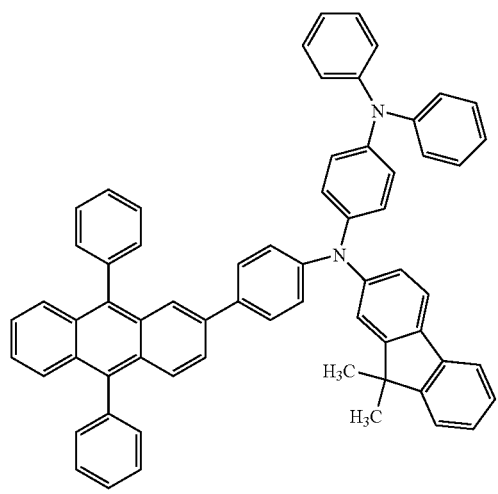
(114)
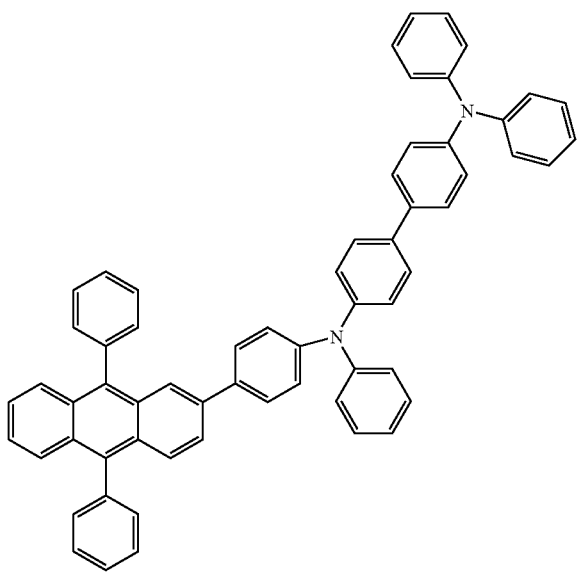
(115)
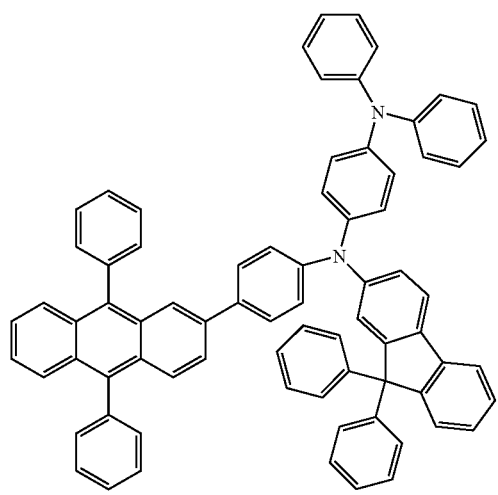
(116)
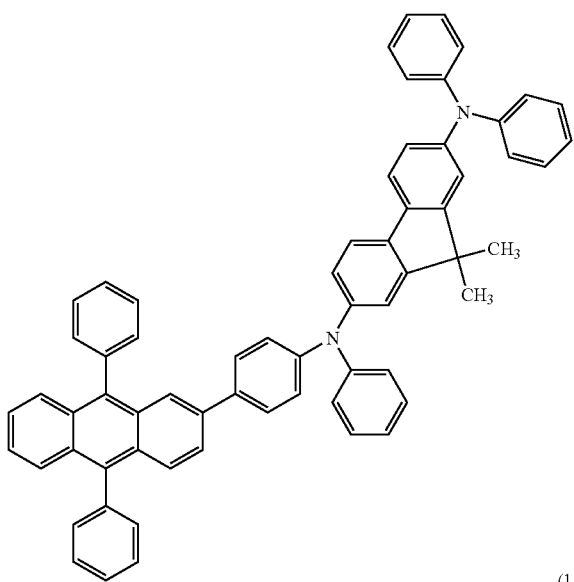
(117)
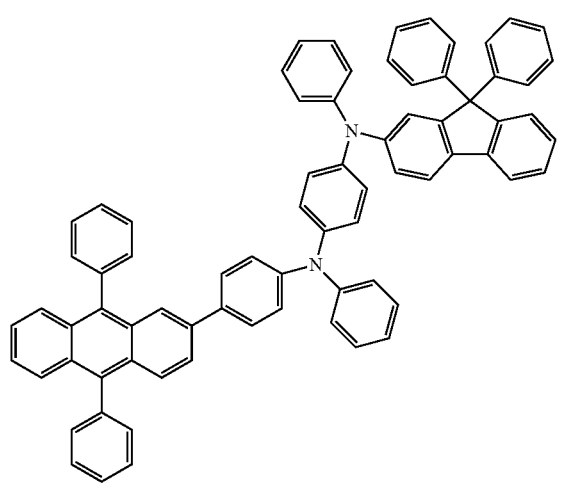
(118)
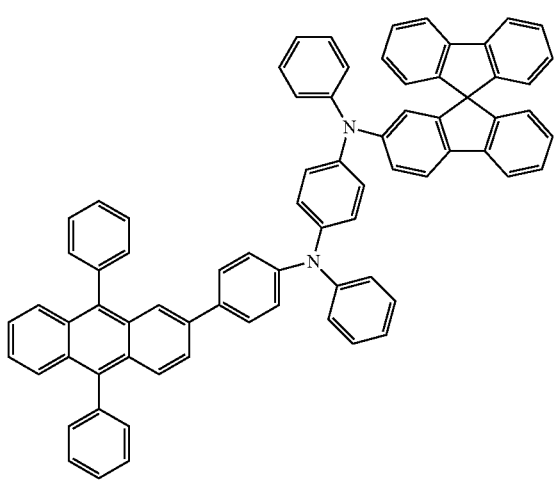

-continued
(119)
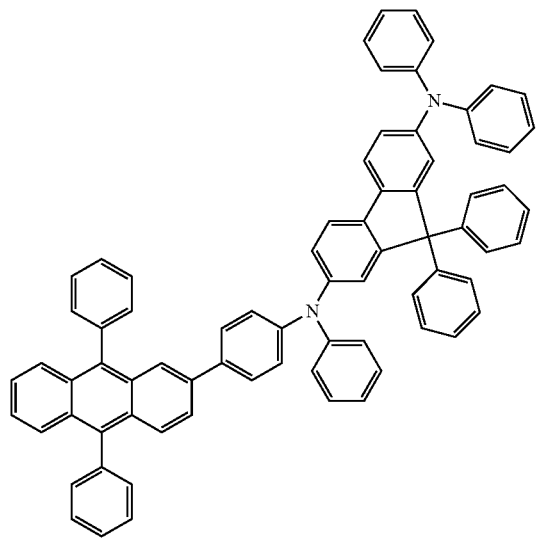
(120)
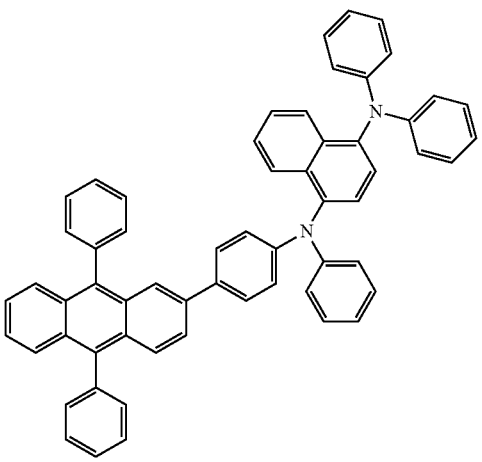
(121)
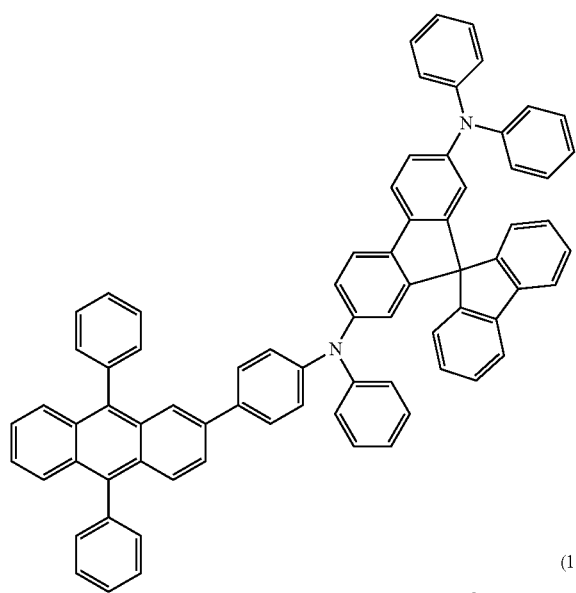
(122)
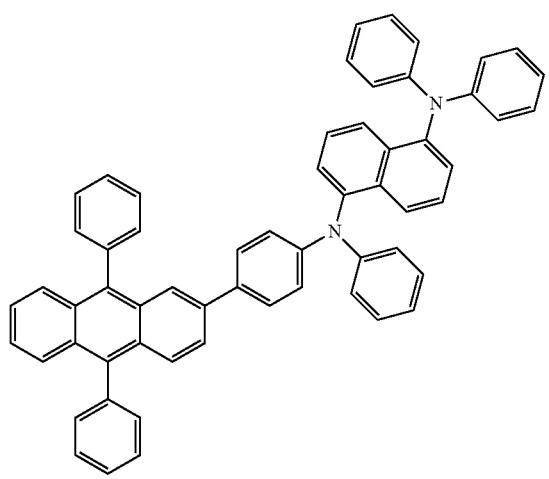
(123)
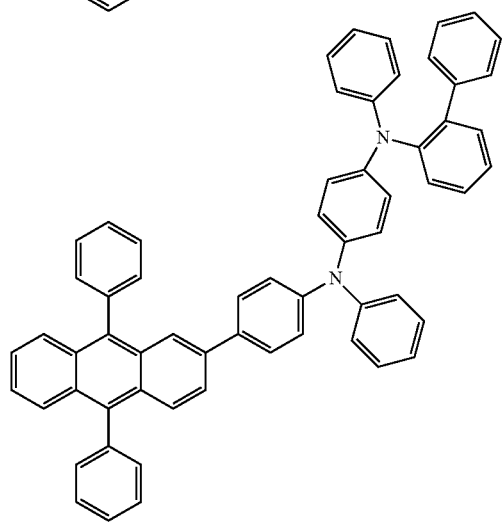
(124)
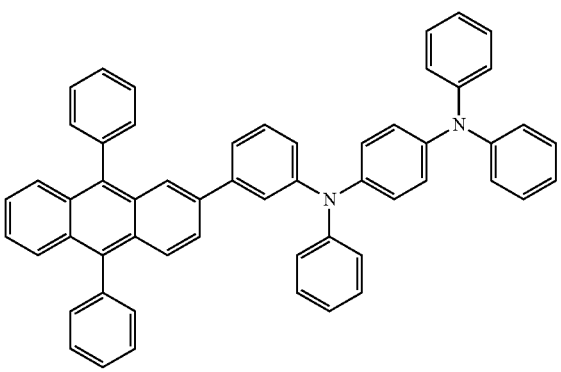

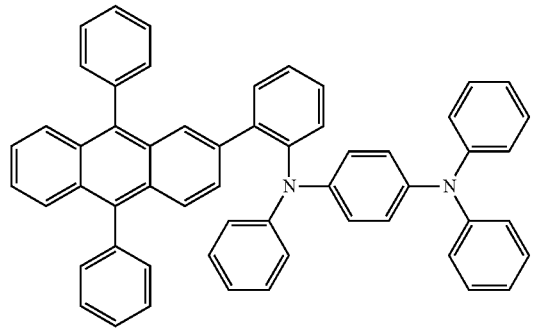
(126)
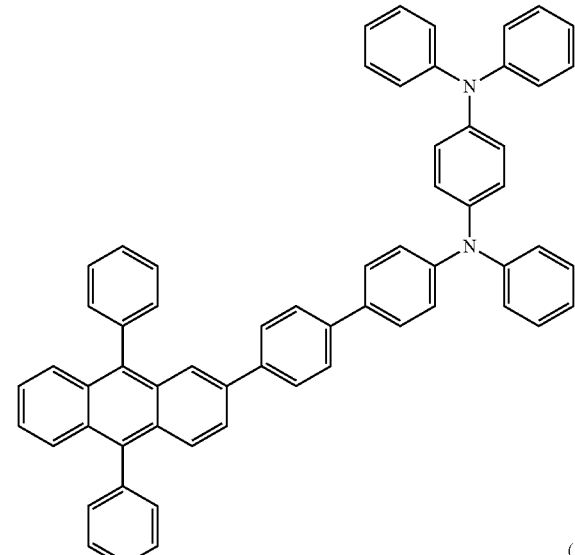
(127)
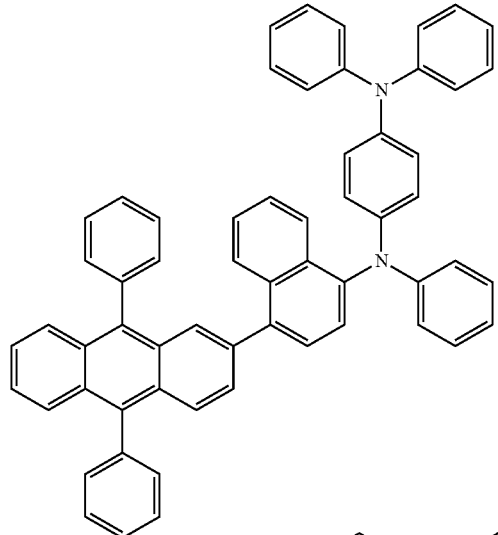
(128)
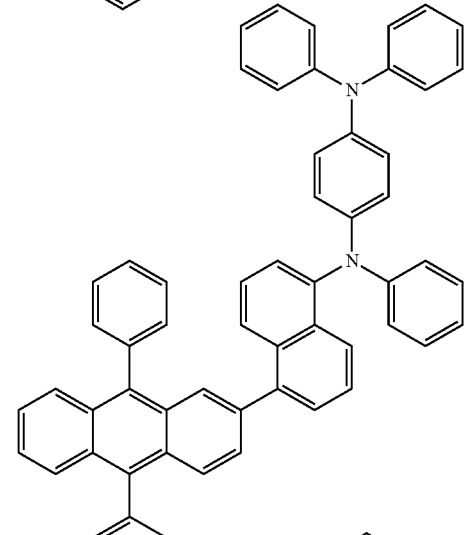
(129)
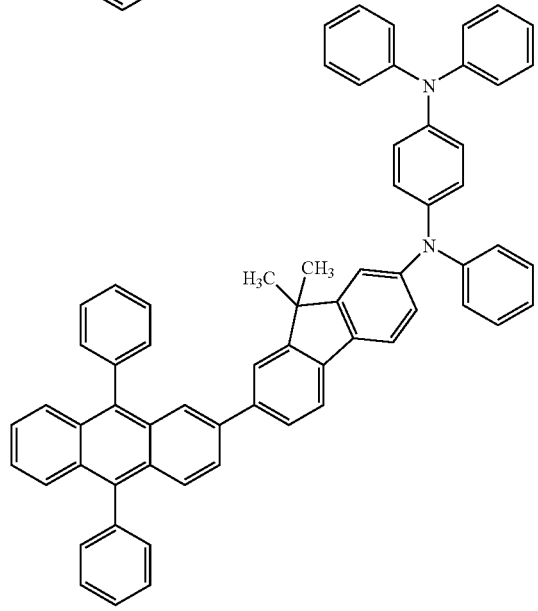
(130)
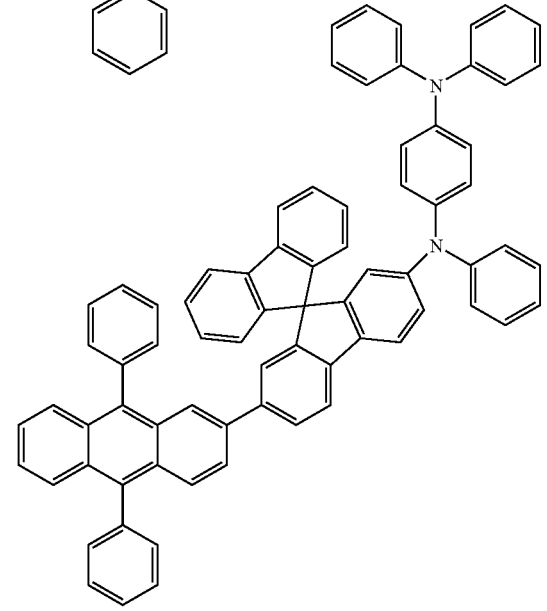

-continued
(131)
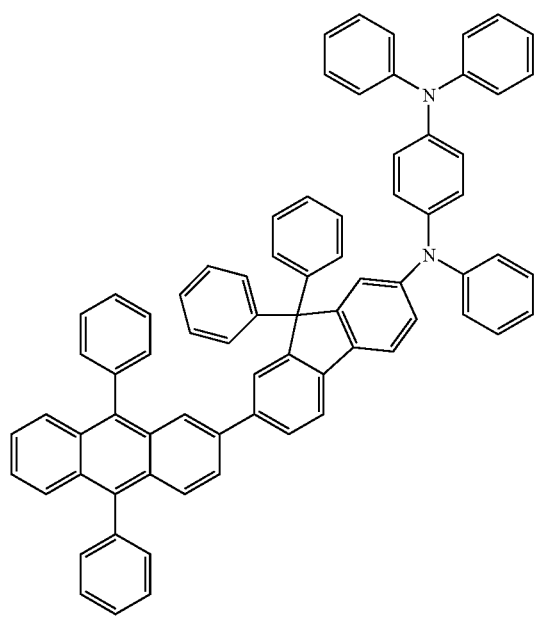
(132)
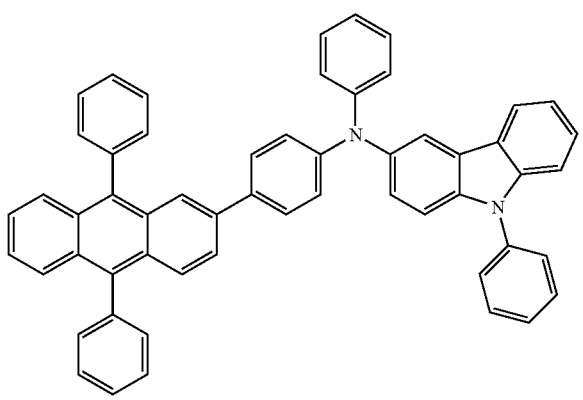
(133)
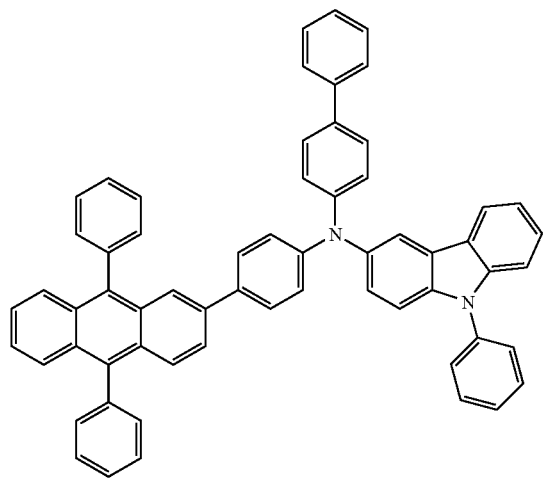
(134)
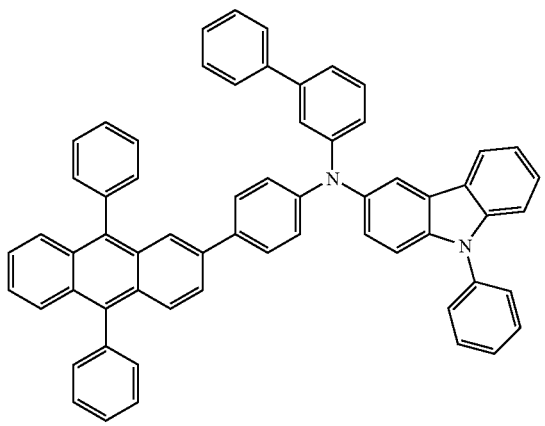
(135)
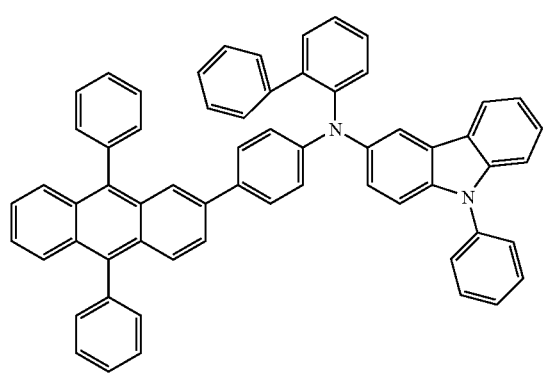
(136)
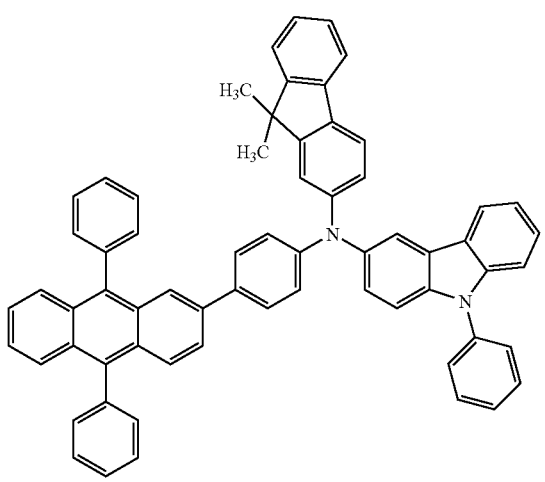

-continued
(137)
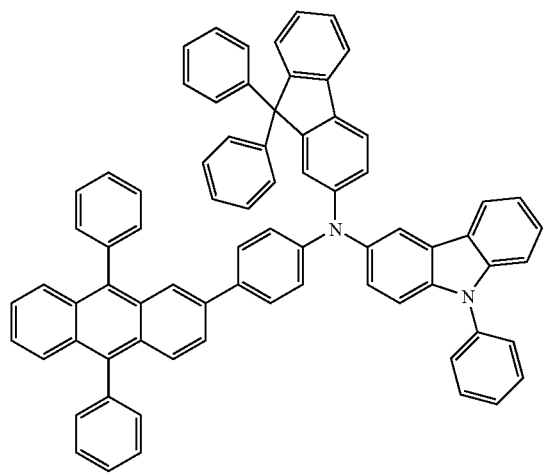
(138)
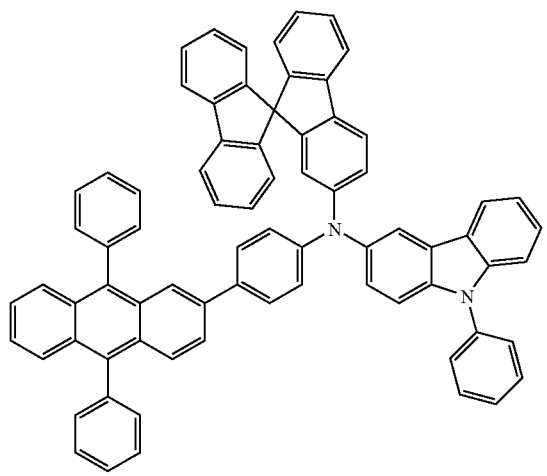
(139)
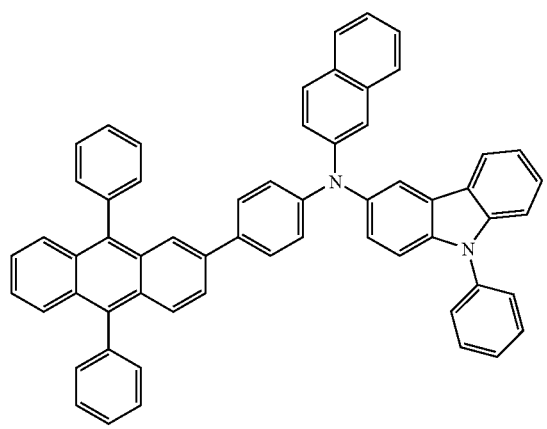
(140)
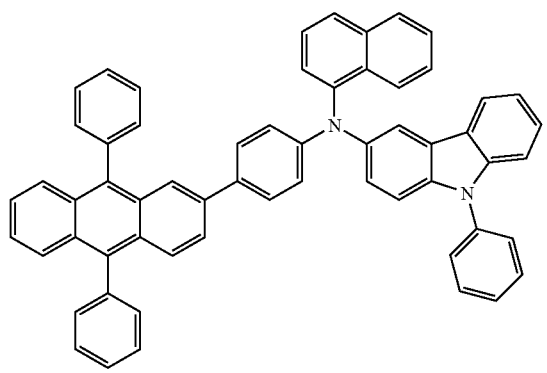
(141)
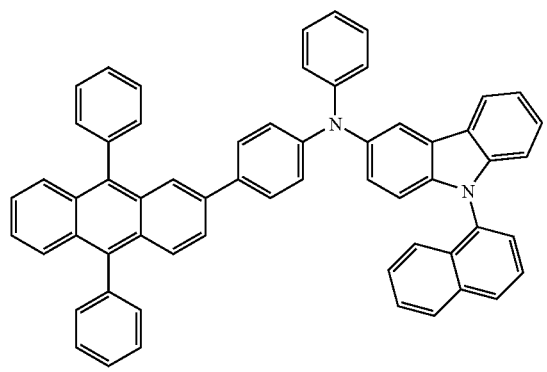
(142)
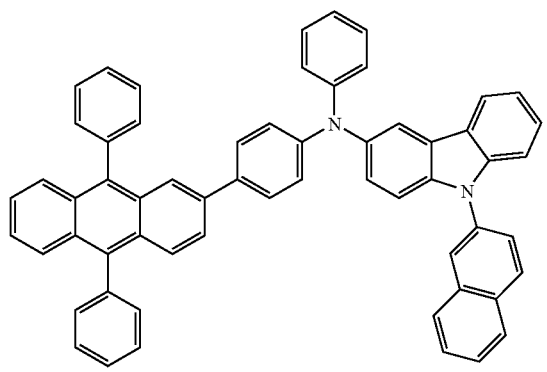

-continued
(143)
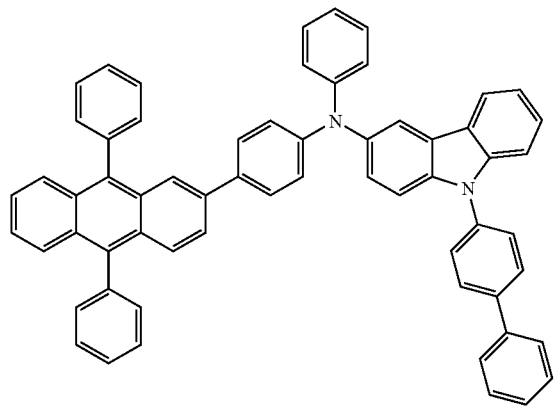
(144)
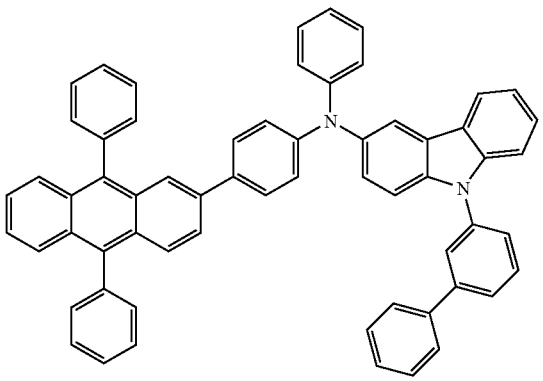
(145)
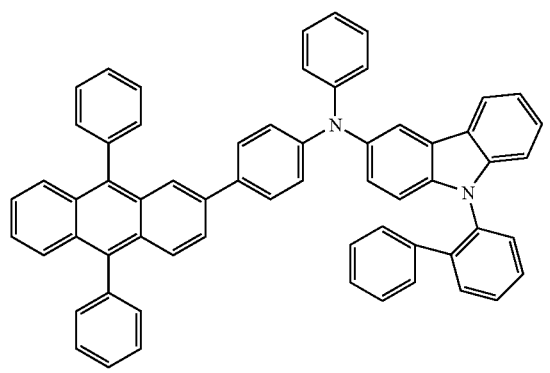
(146)
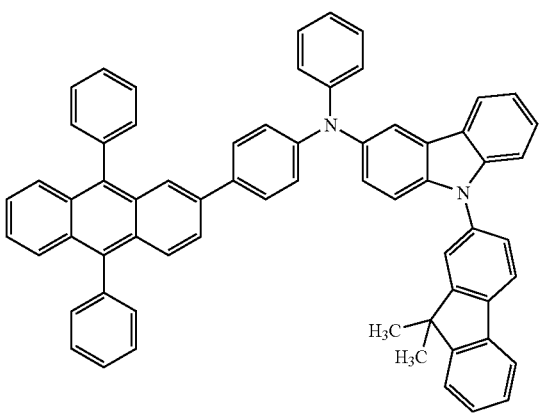
(147)
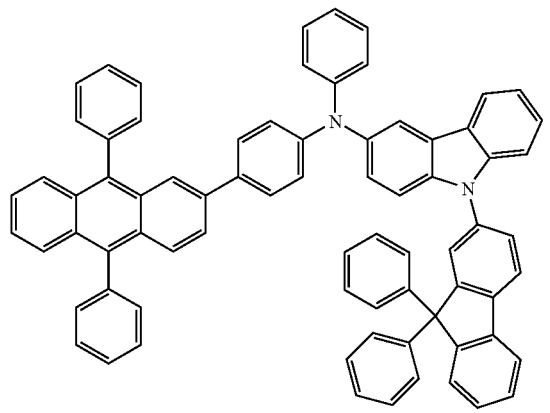
(148)
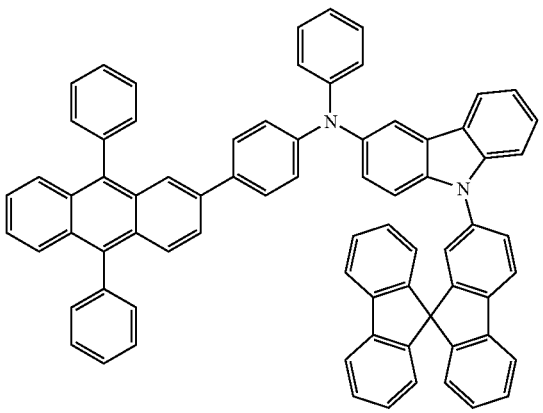
(149)
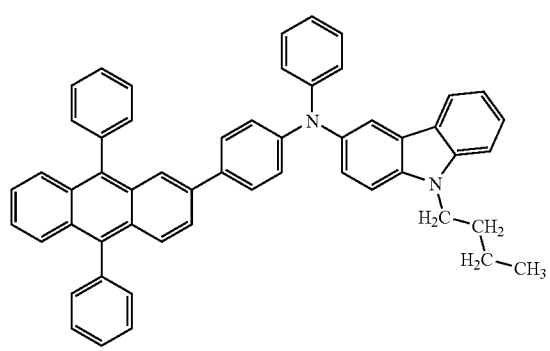
(150)
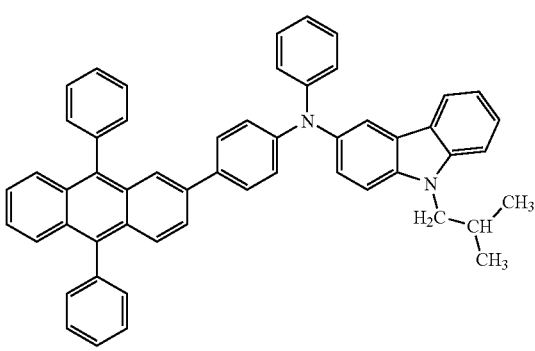

-continued
(151)
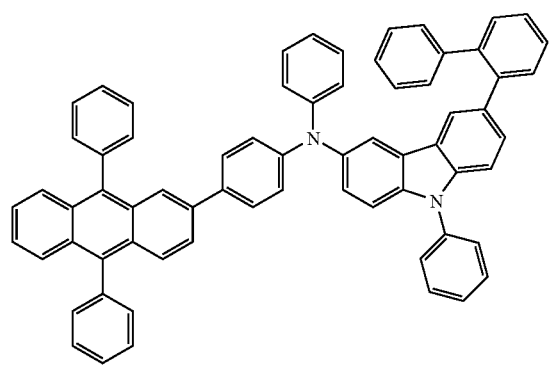
(152)
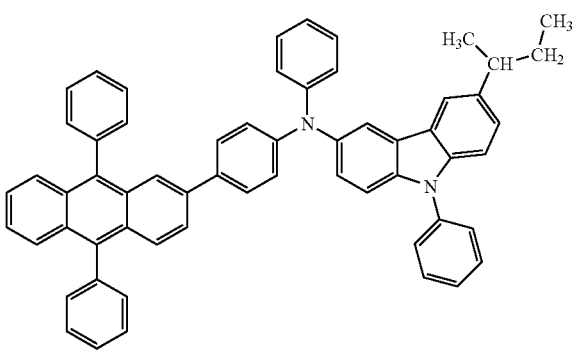
(153)
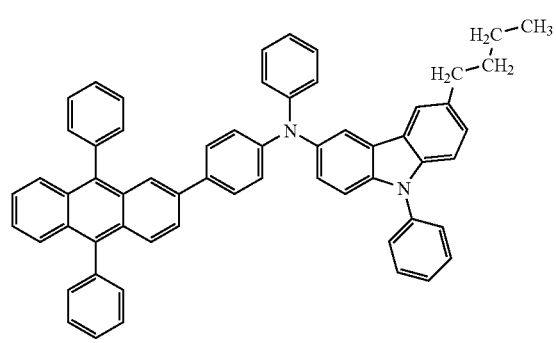
(154)
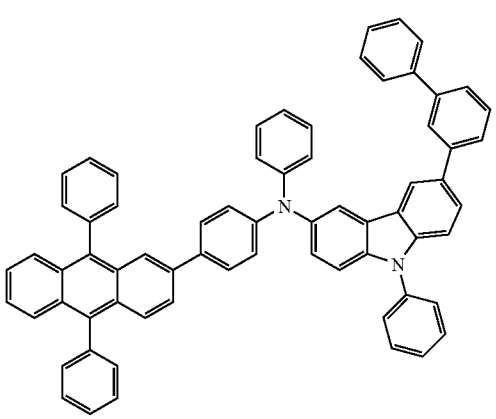
(155)
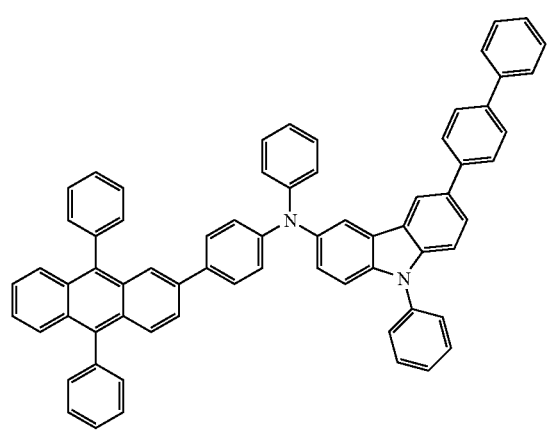
(156)
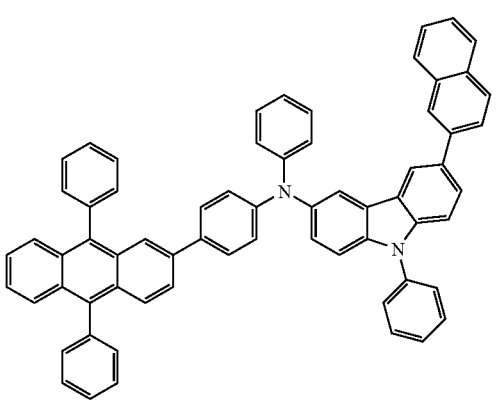

-continued
(157)
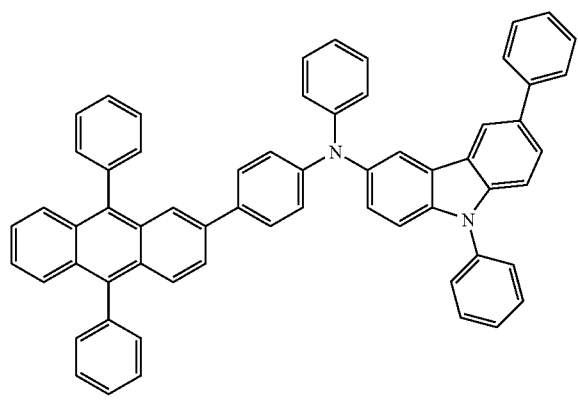
(158)
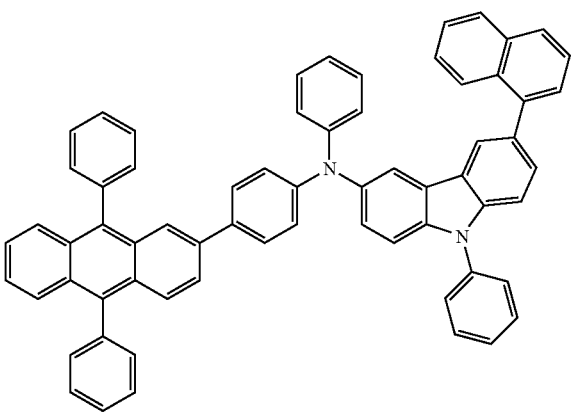
(159)
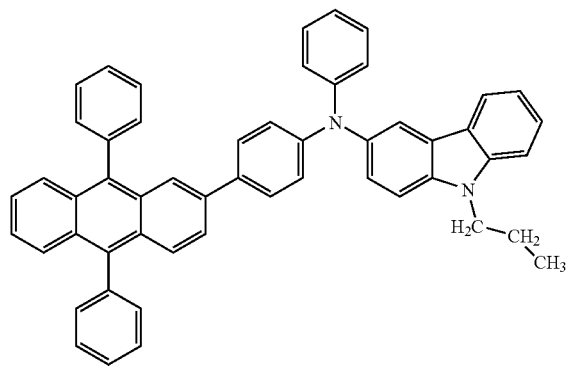
(160)
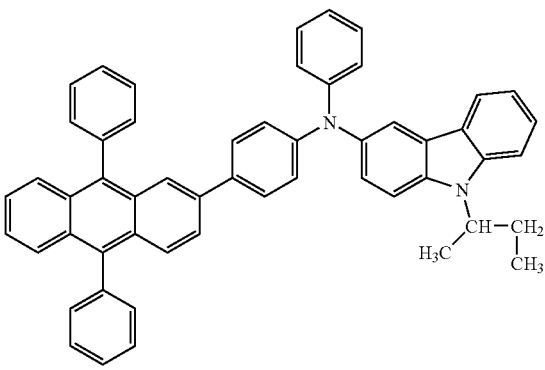
(161)
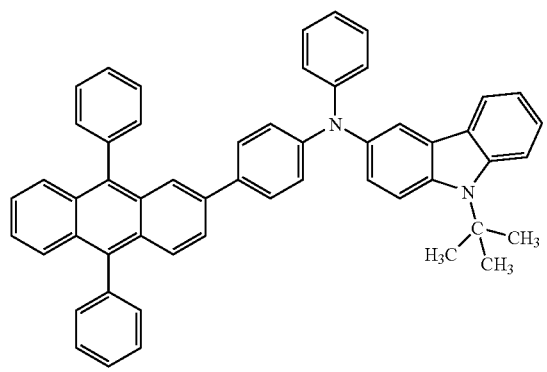
(162)
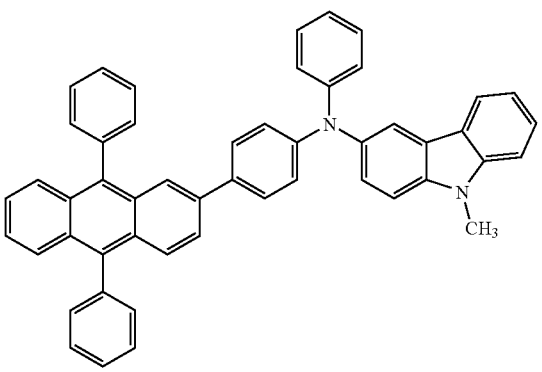
(163)
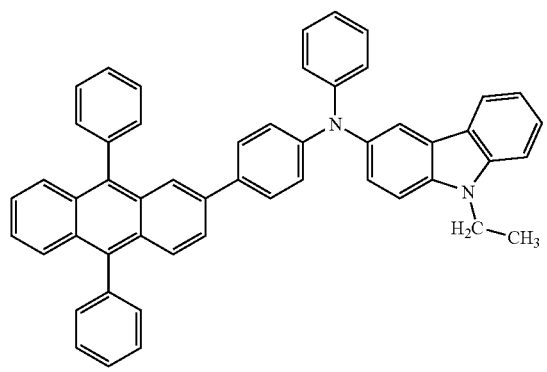
(164)
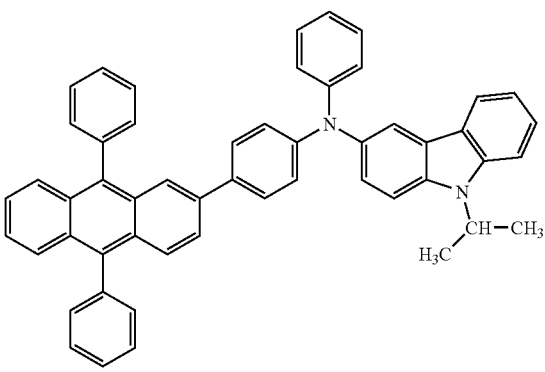

-continued
(165)
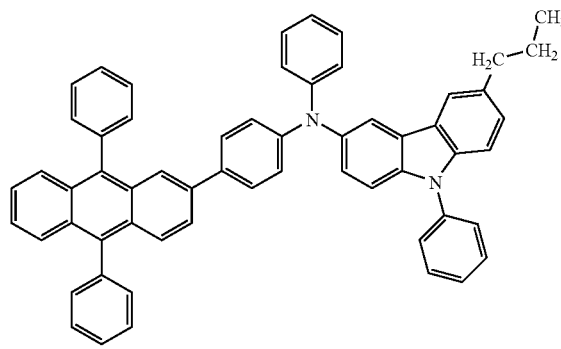
(166)
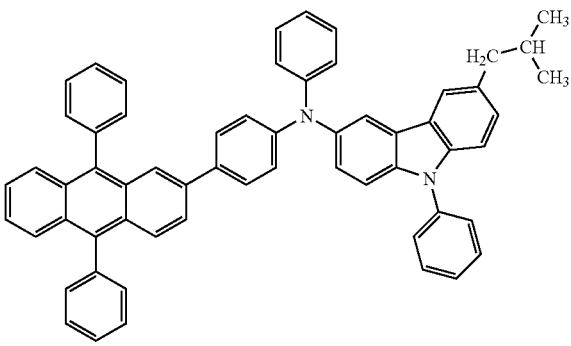
(167)
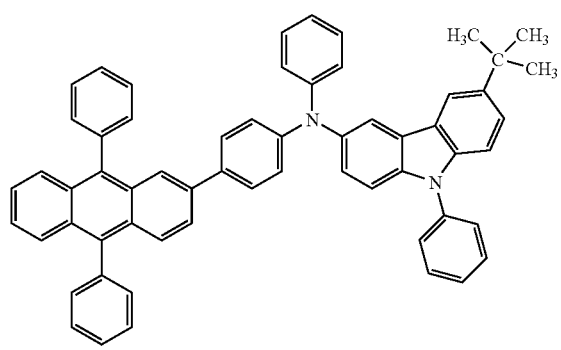
(168)
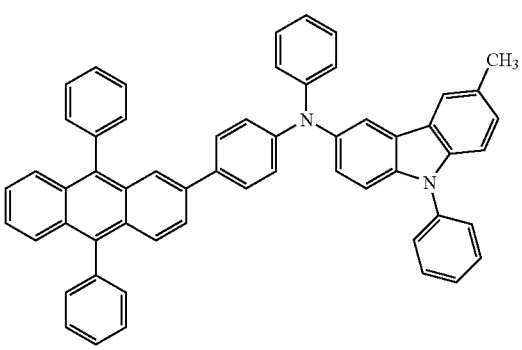
(169)
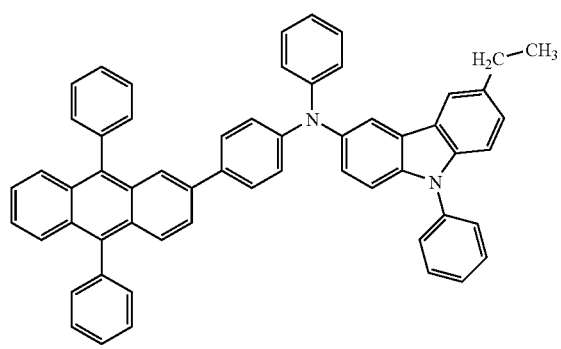
(170)
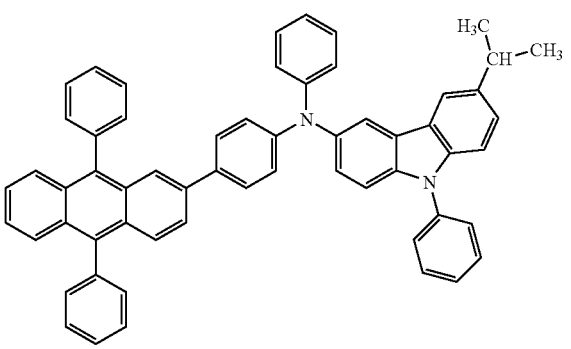
(171)
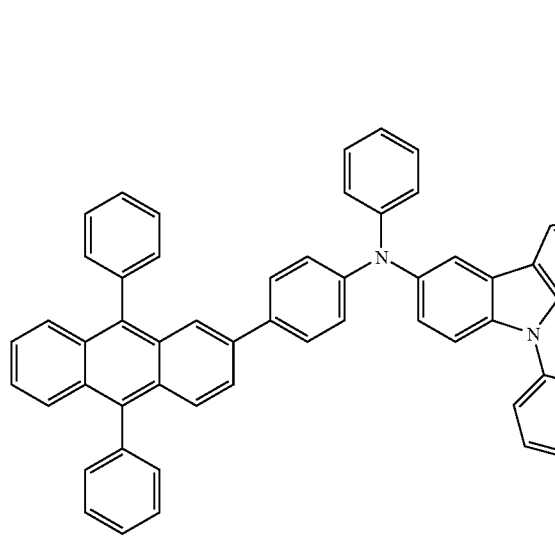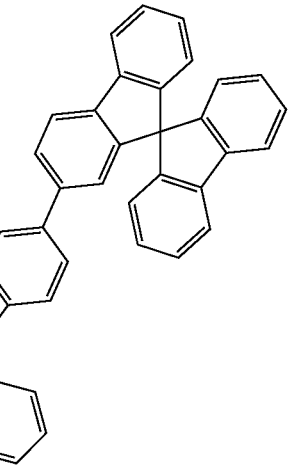

-continued
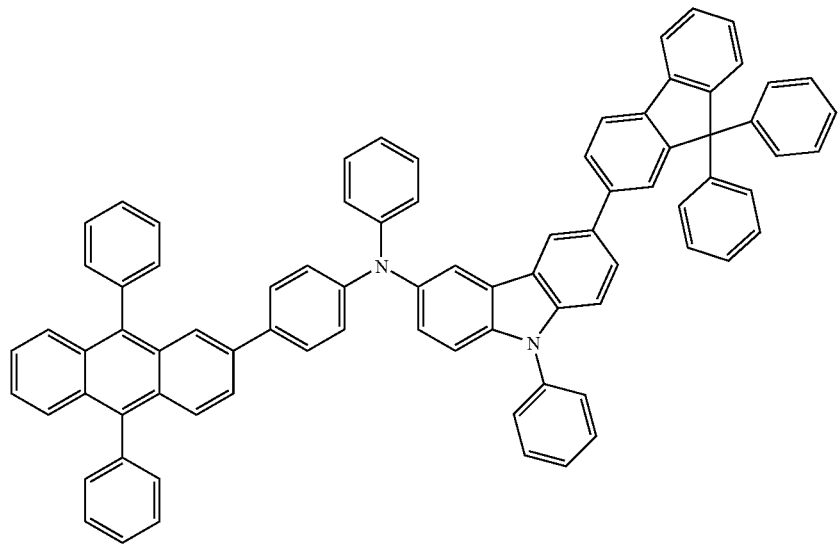
(172)
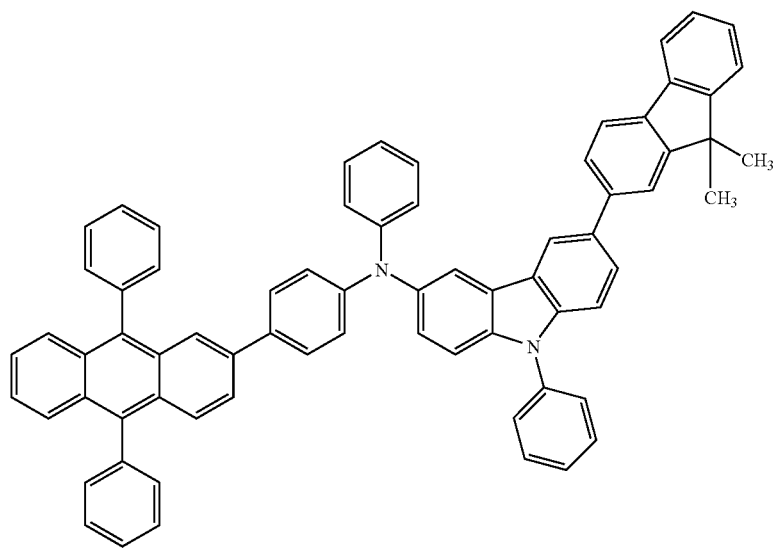
(173)
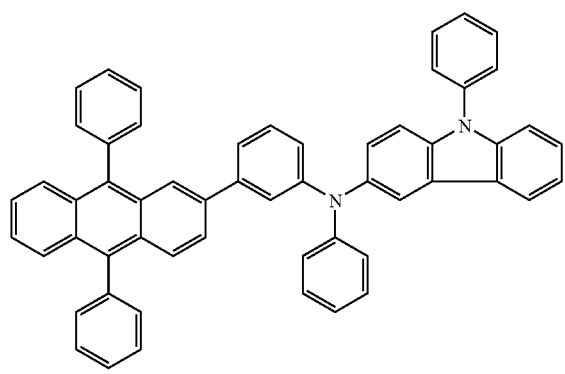
(174)
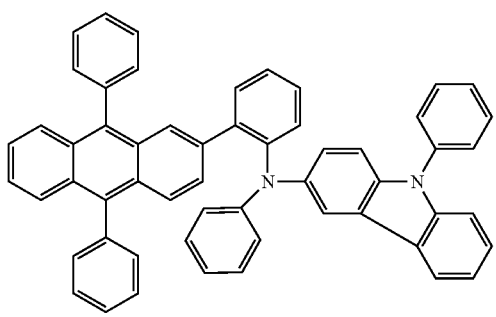
(175)

-continued
(176) 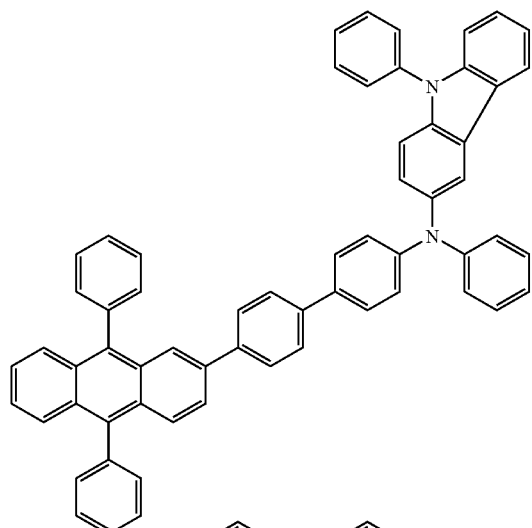
(177) 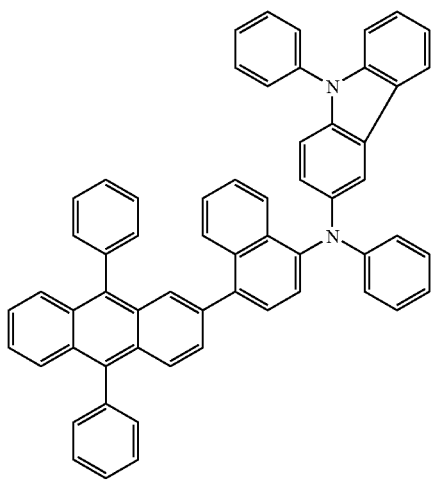
(178) 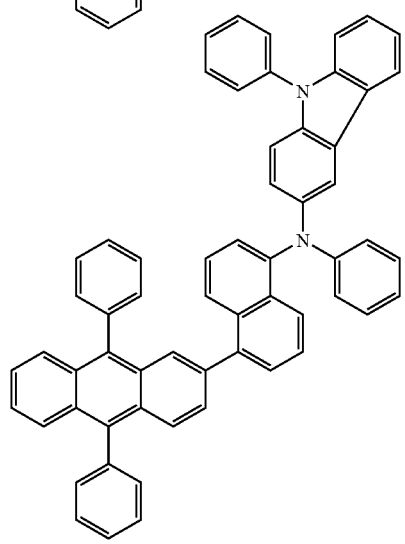
(179) 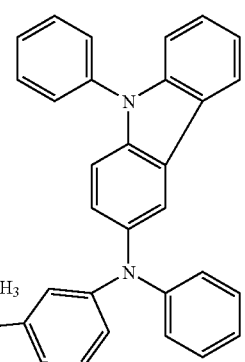
(180) 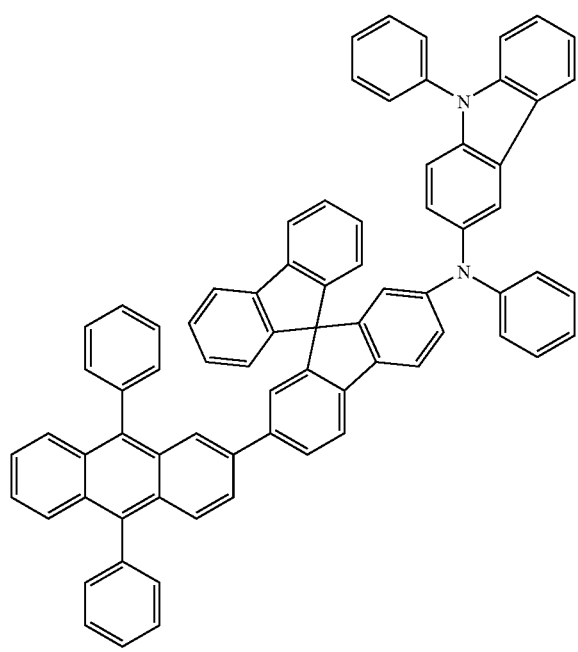
(181) 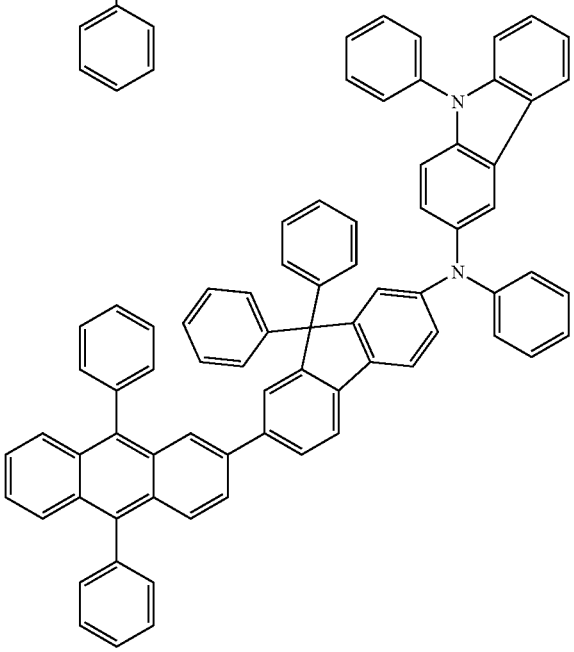

-continued
(182)
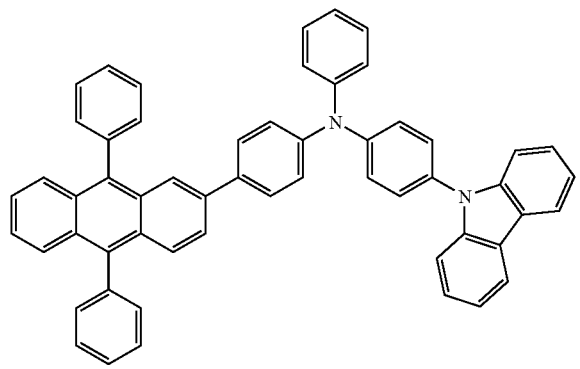
(183)
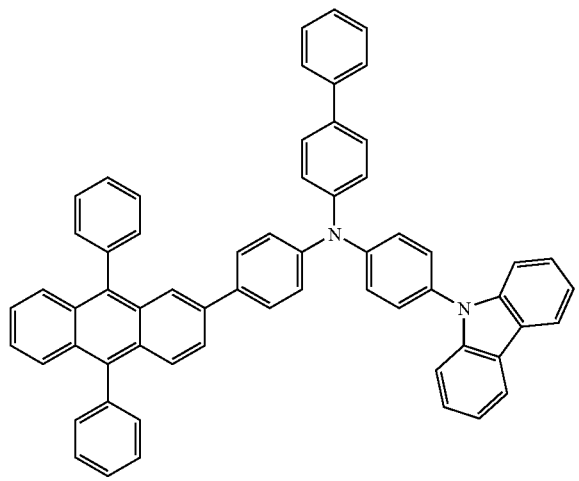
(184)
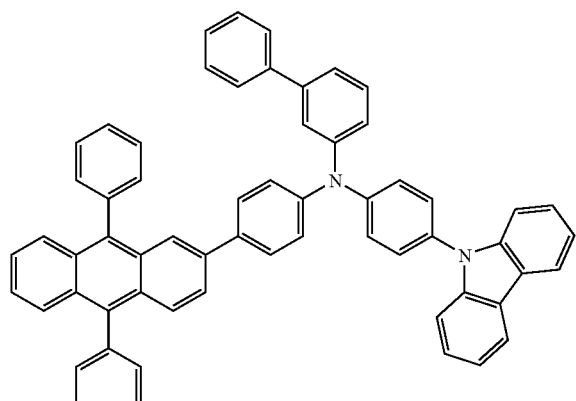
(185)
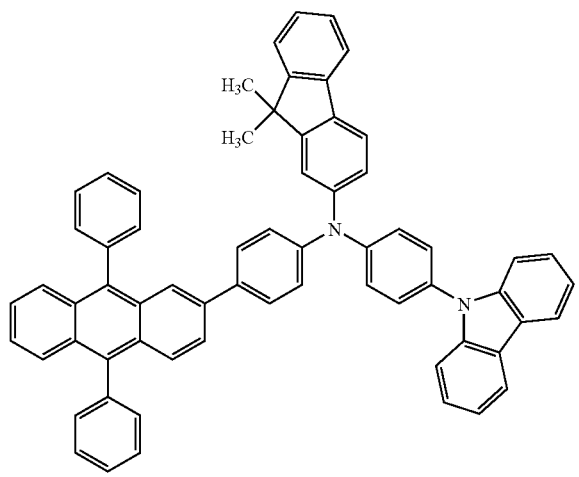
(186)
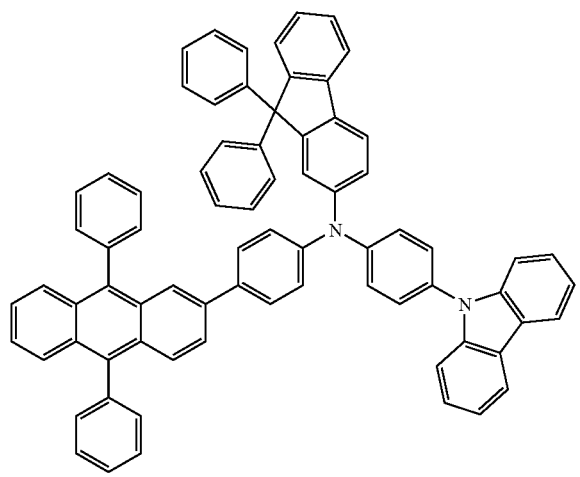
(187)
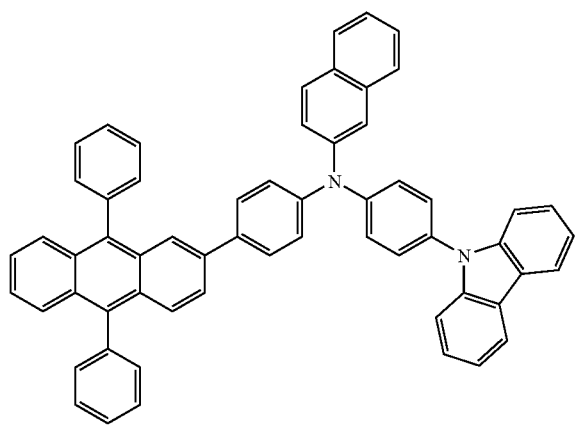

-continued (188)

(189)

(190)

(191)

-continued
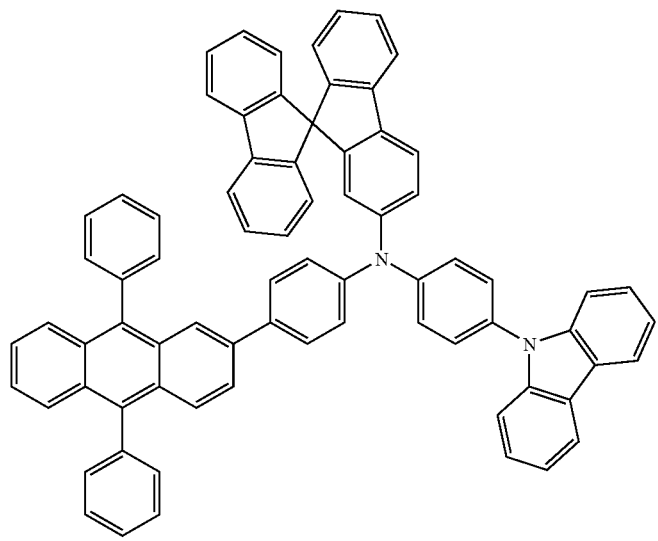
(192)
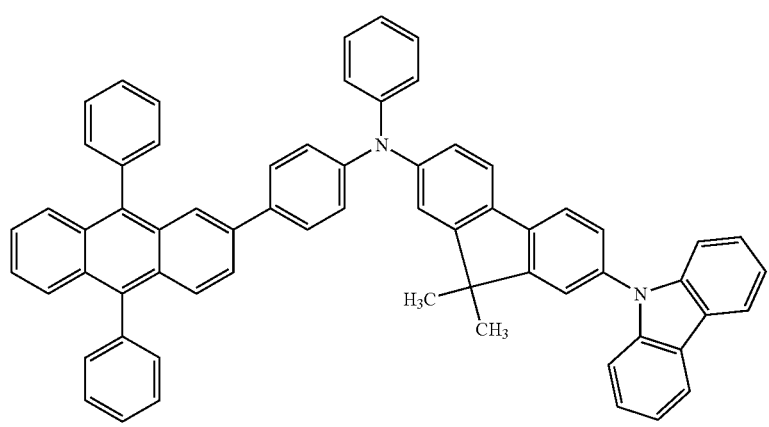
(193)
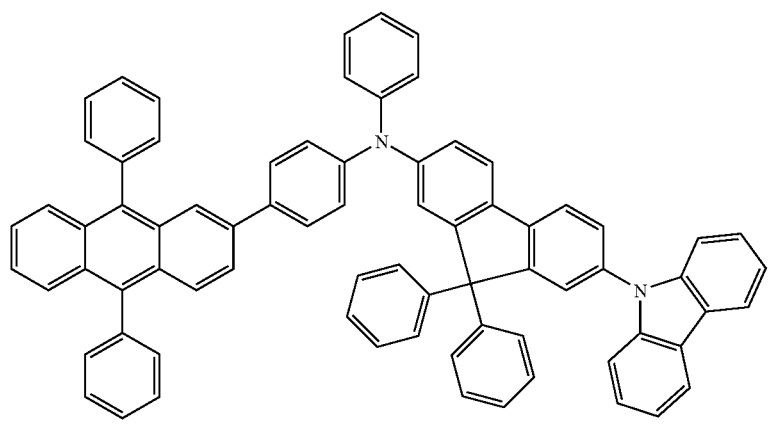
(194)

(195)
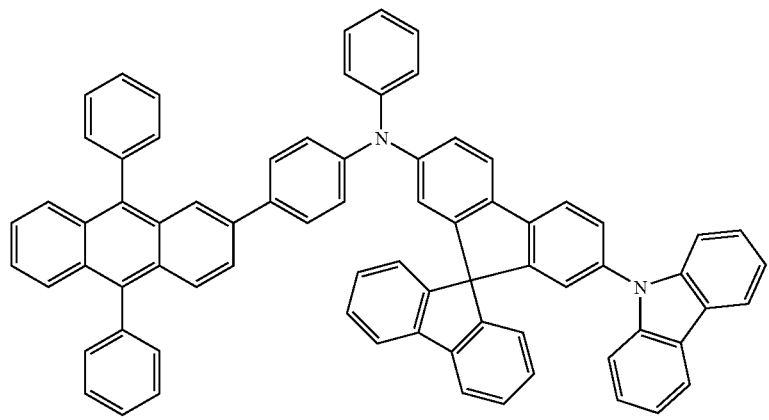
(196)
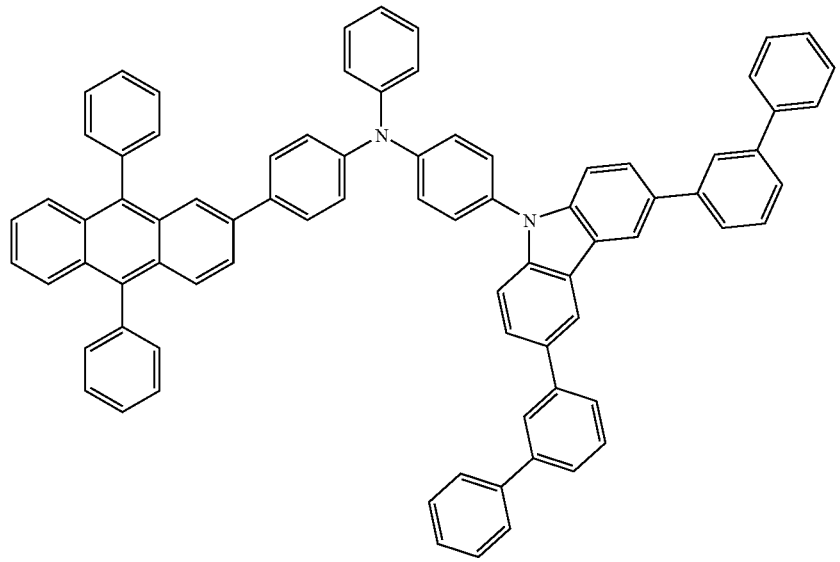
(197)
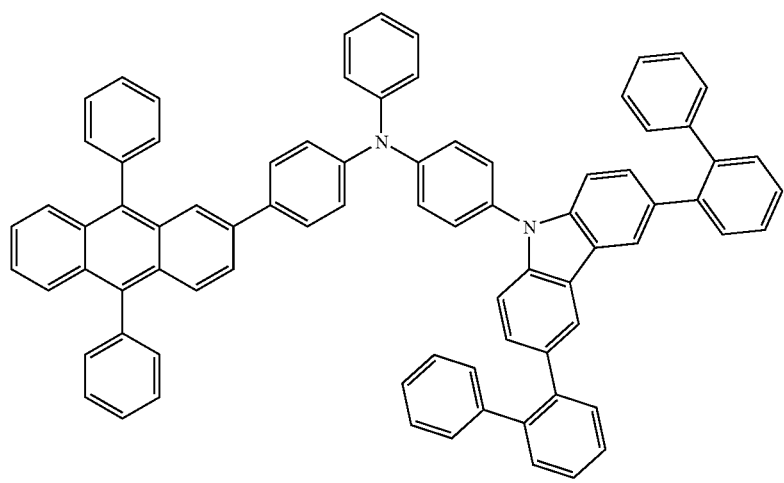

(198)
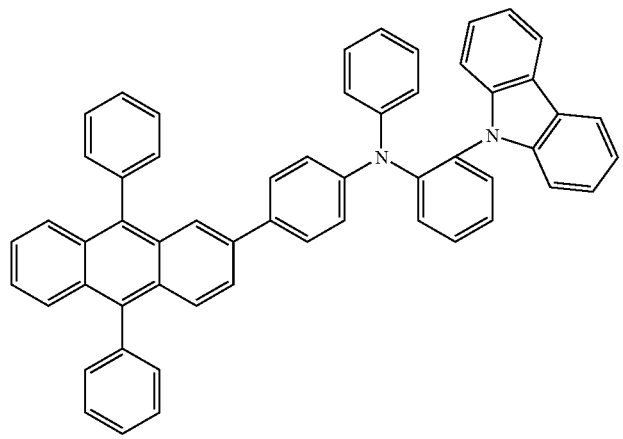
(199)
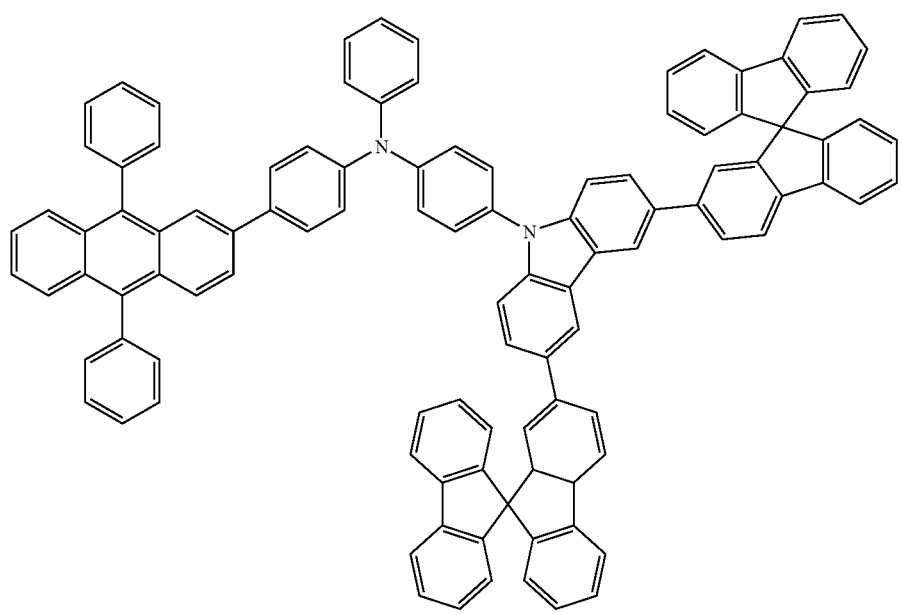
(200)
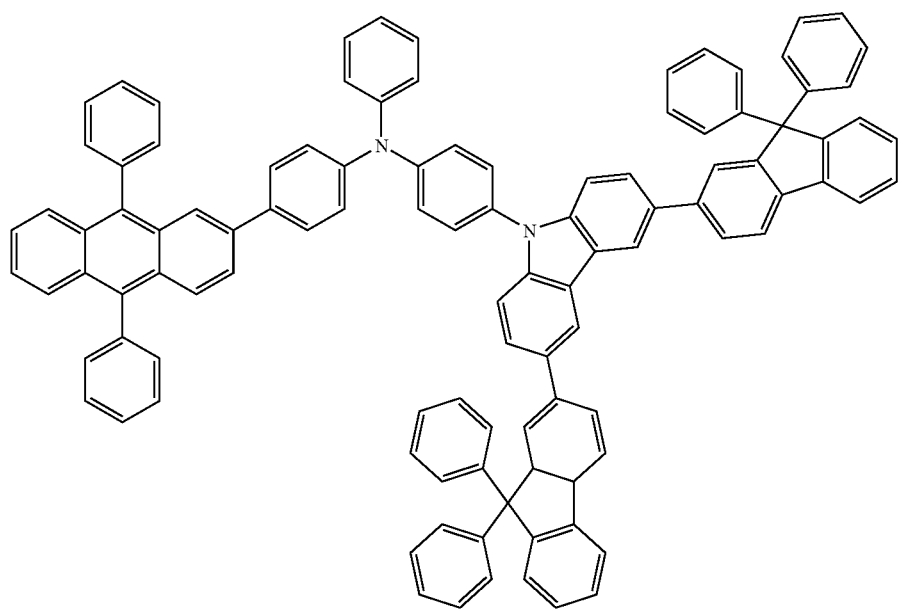

(201)
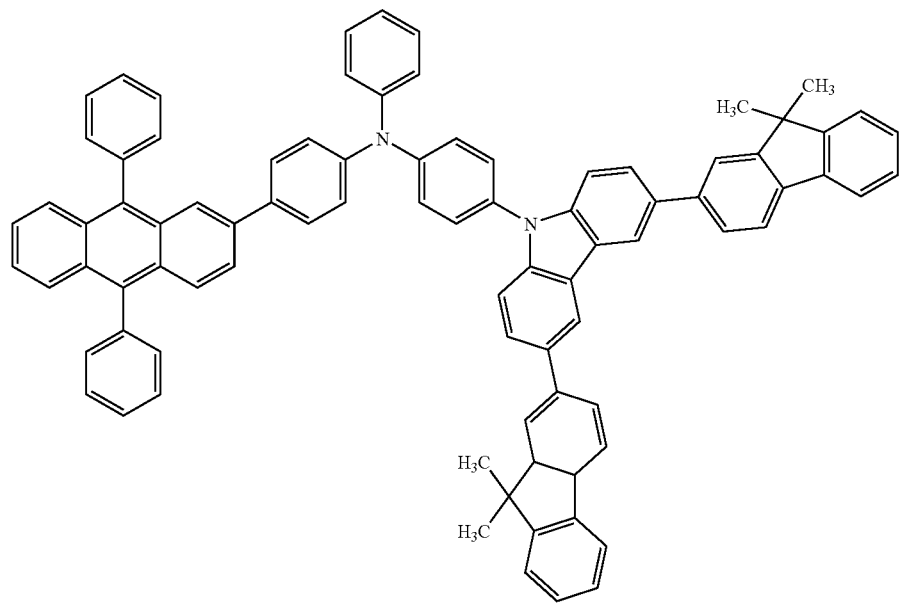
(202)
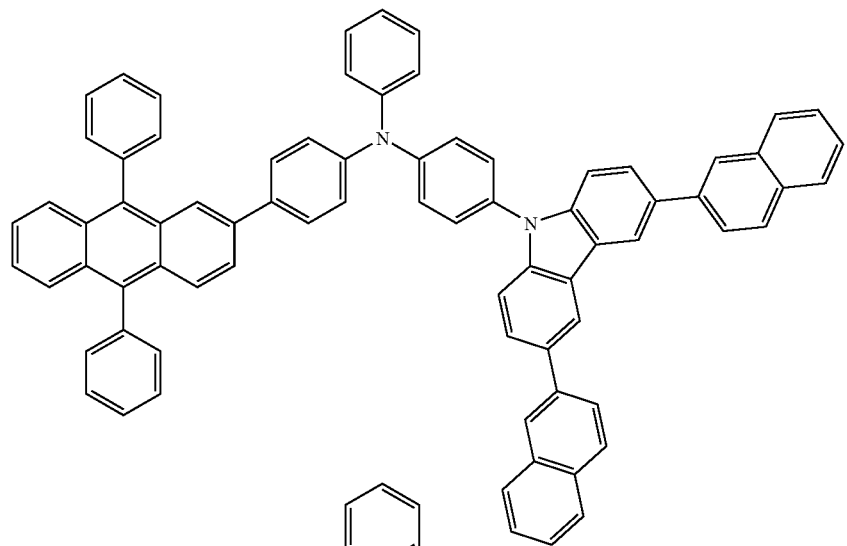
(203)
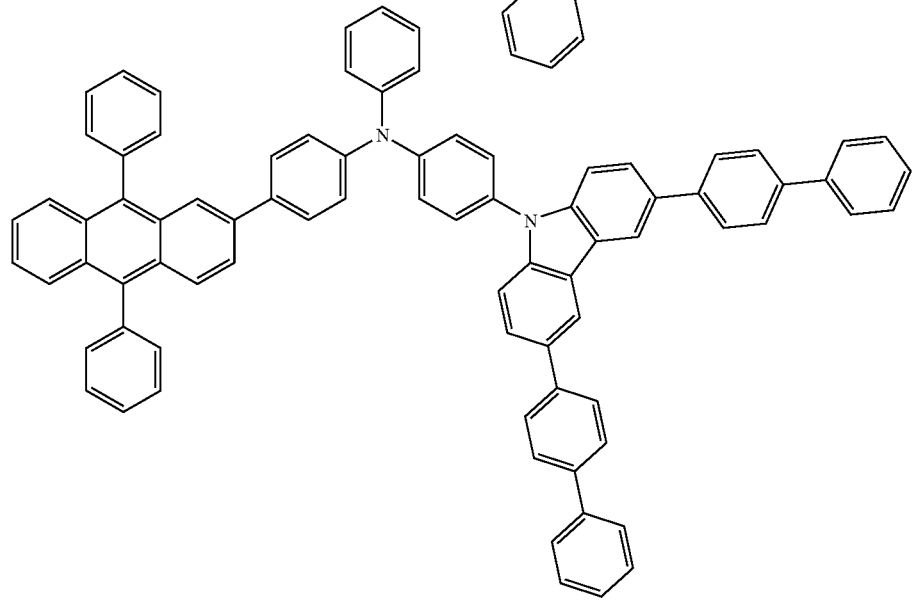

(204)
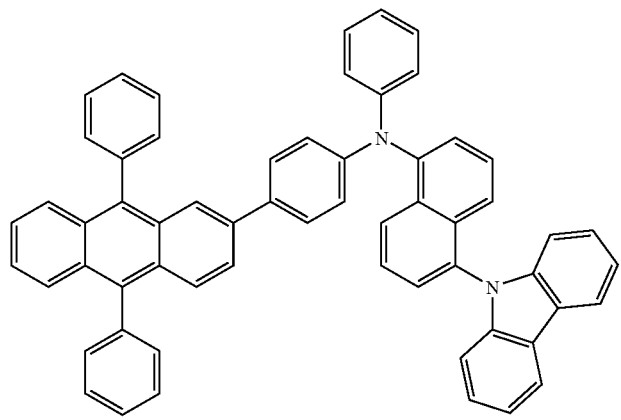
(205)
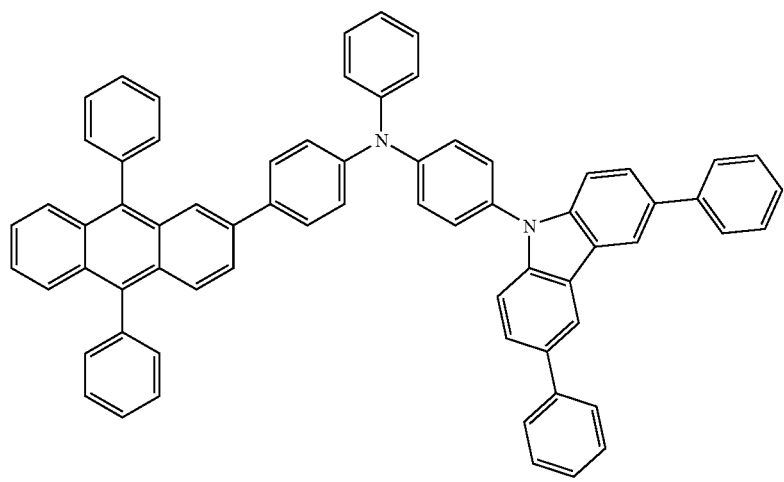
(206)
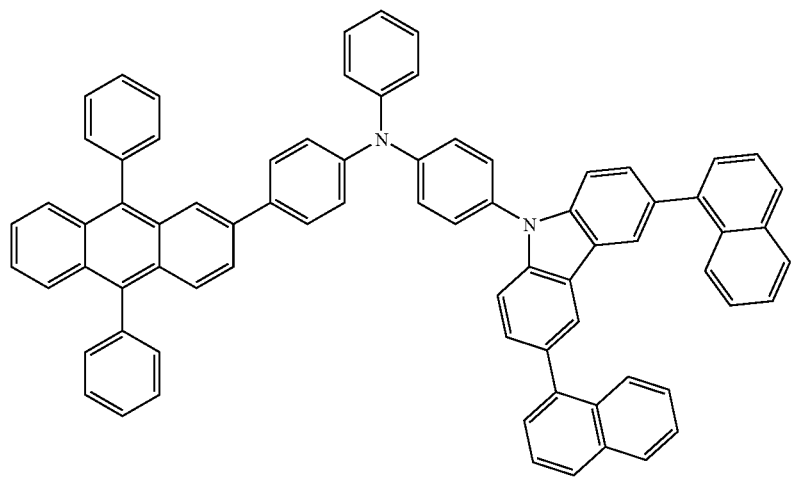

(207)
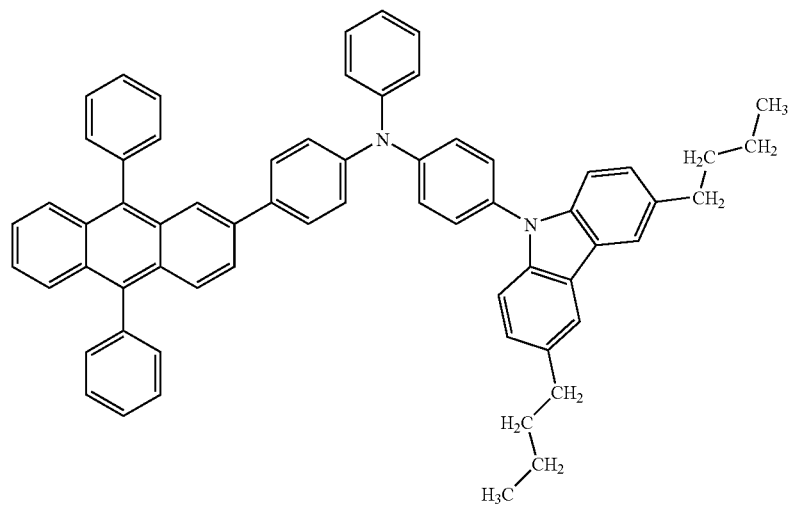
(208)
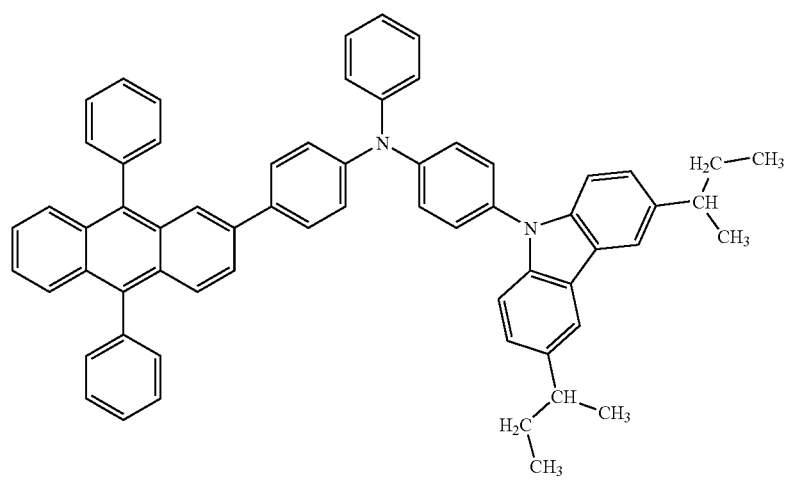
(209)
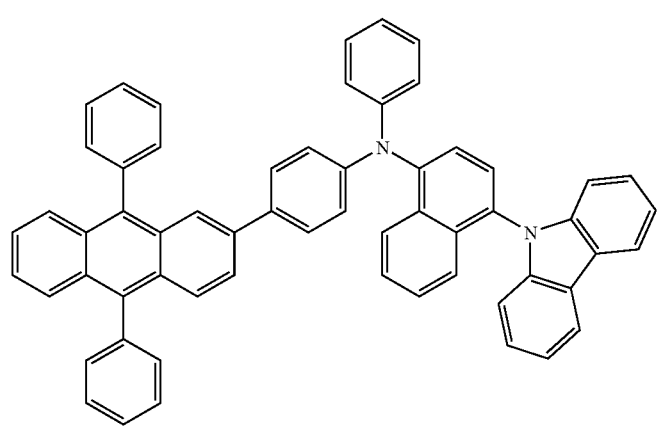

(210)
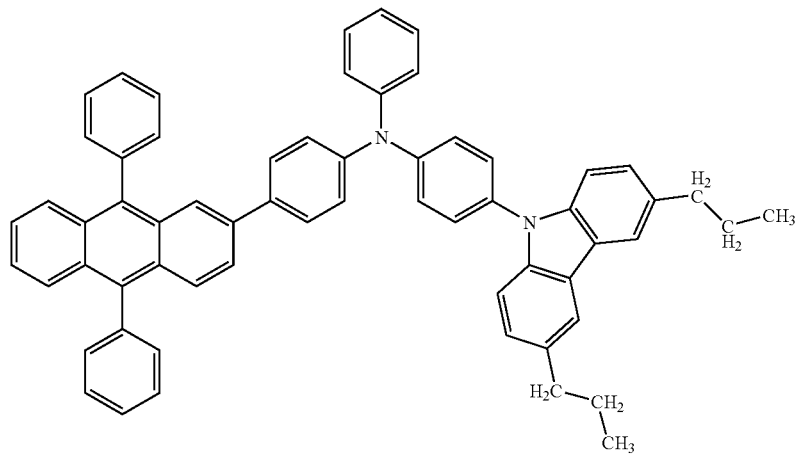
(211)
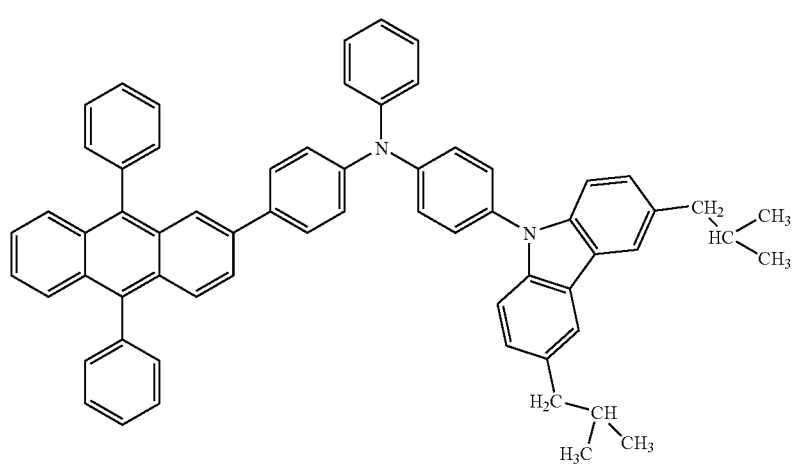
(212)
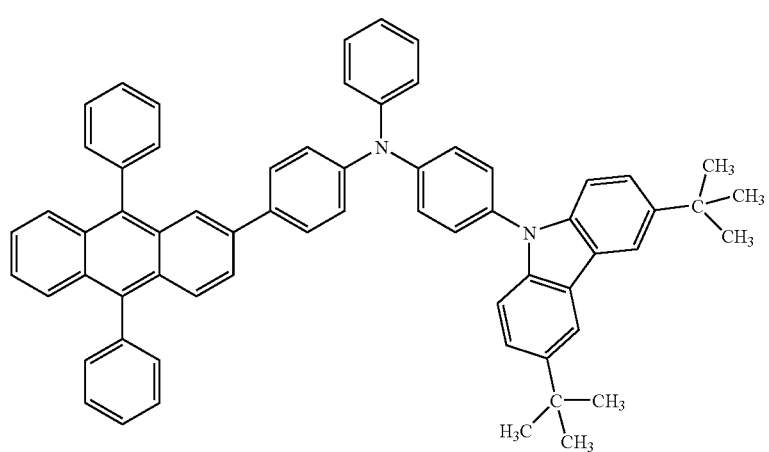

-continued
(213)
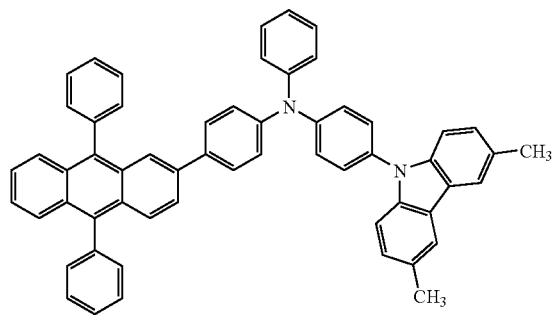
(214)
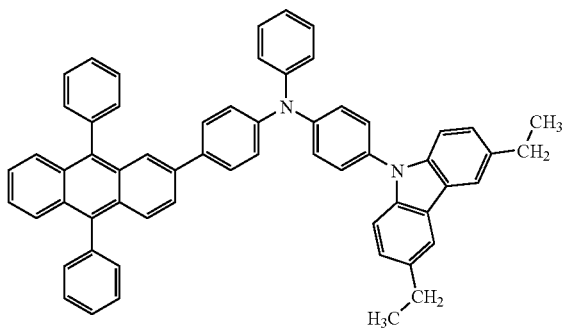
(215)
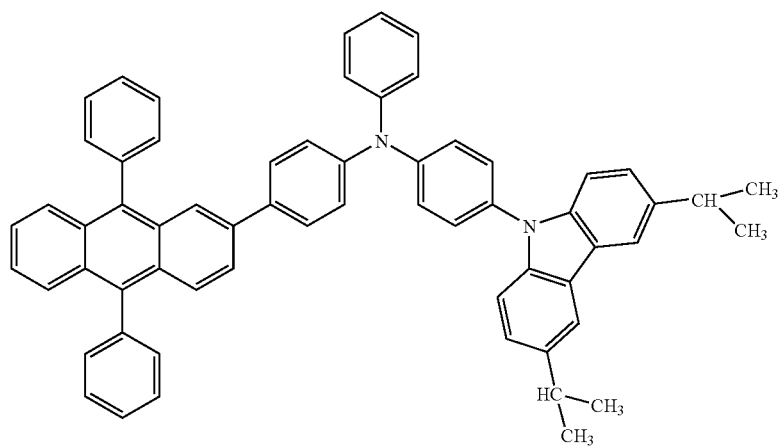
(216)
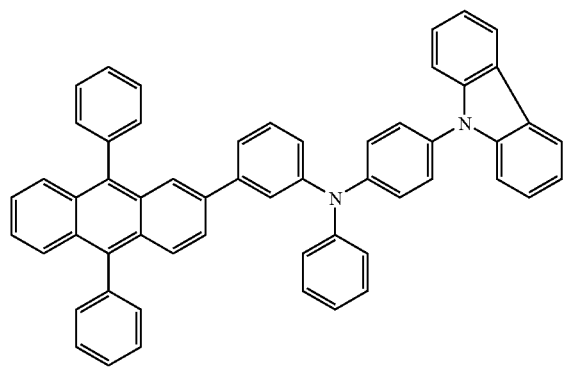
(217)
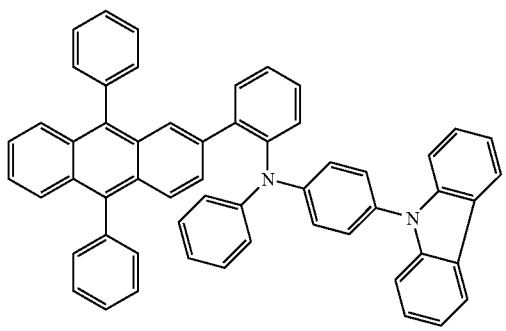

-continued
(218)
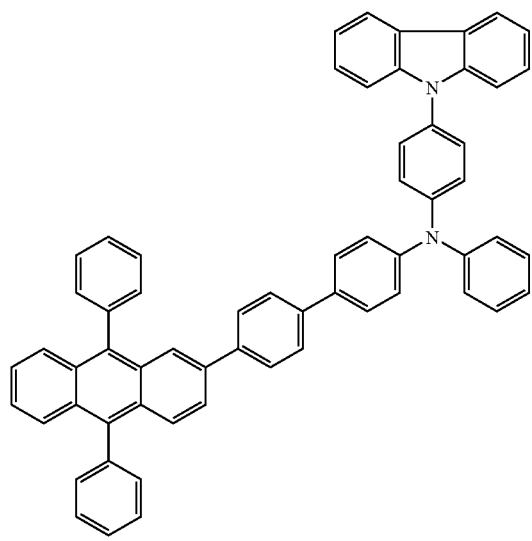
(219)
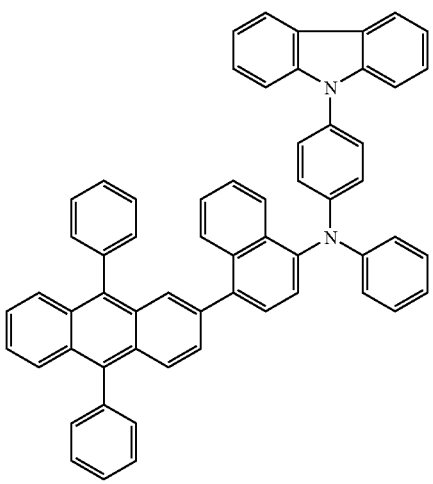
(220)
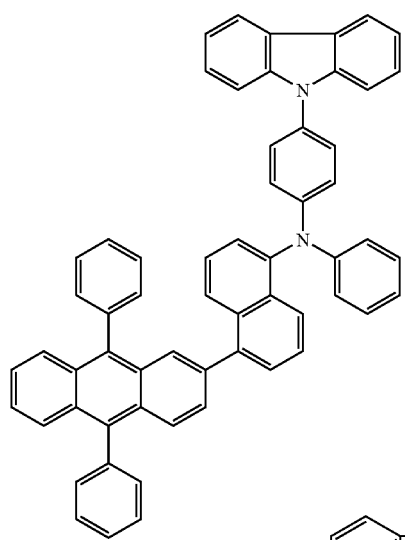
(221)
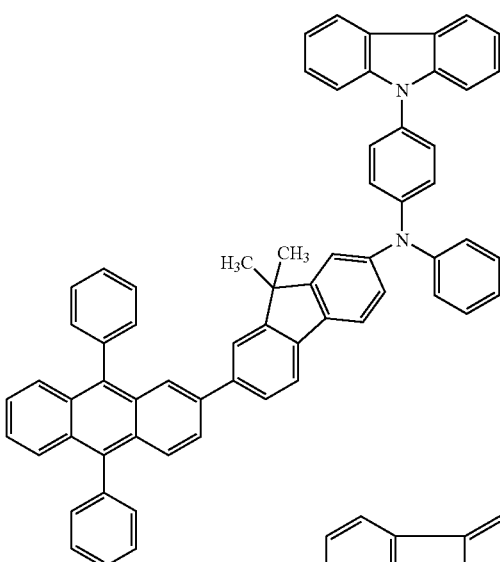
(222)
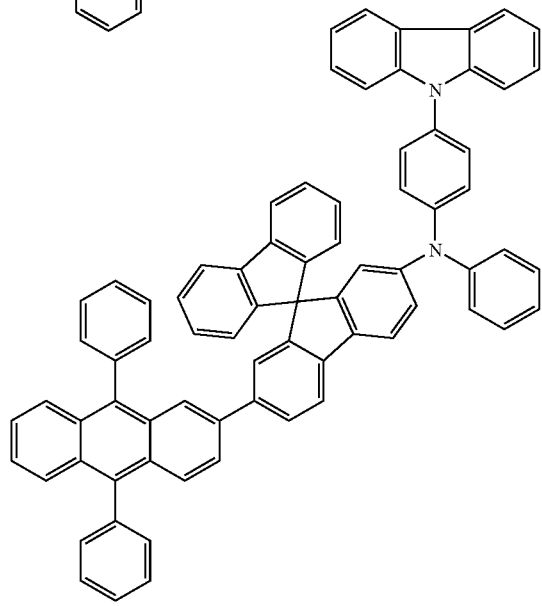
(223)
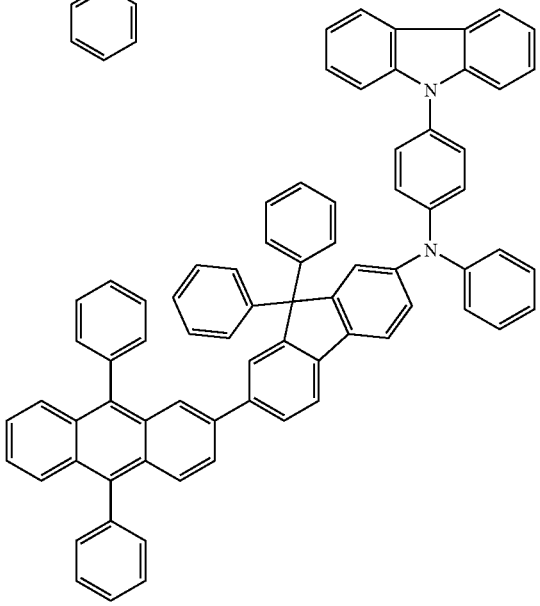

The anthracene derivatives represented by structural formulae (101) to (131) are specific examples of the general formula (1) in the case where A is the general formula (1-1), and the anthracene derivatives represented by structural formulae (132) to (181) are specific examples of the general formula (1) in the case where A is the general formula (1-2). Also, the anthracene derivatives represented by structural formulae (182) to (223) are specific examples of the general formula (1) in the case where A is the general formula (1-3).

A variety of reactions can be applied as a synthesis method of an anthracene derivative of the present invention. For example, the anthracene derivatives of the present invention can be synthesized by conducting the synthesis reactions shown in following reaction schemes (A-1) to (A-5) and (B-1) to (B-3).

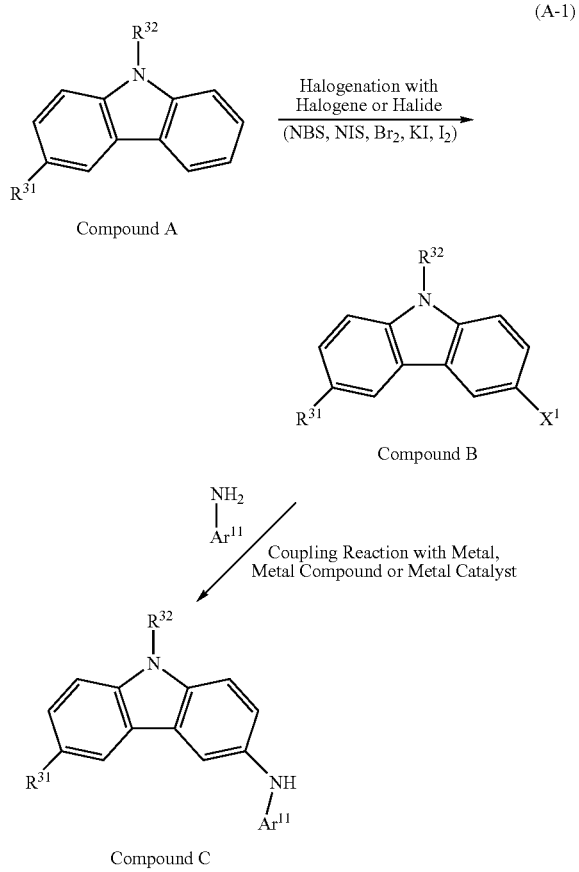

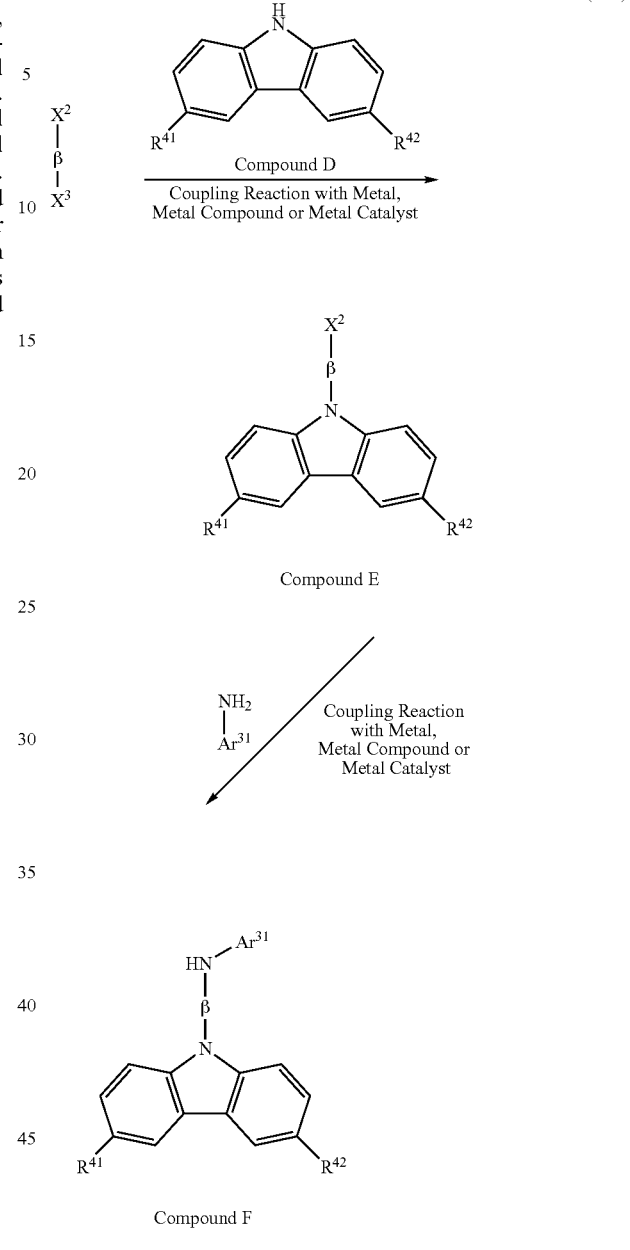

A compound including carbazole in a skeleton (Compound A) is reacted with a halogen or halide such as N-bromosuccinimide (NBS), N-iodosuccinimide (NIS), bromine ($Br_2$), potassium iodide (KI), or iodine ($I_2$) to synthesize a compound including 3-halogenated carbazole in a skeleton (Compound B), and then subjected to a coupling reaction with arylamine using a metal catalyst such as a palladium catalyst (Pd catalyst), a metal compound such as copper iodine, or a metal such as copper, thereby obtaining a compound C. In the synthesis scheme (A-1), a halogen element (X) is preferably iodine or bromine. $R^{31}$ represents any of a hydrogen atom, an alkyl group having 1 to 4 carbon atoms, and an aryl group having 6 to 25 carbon atoms. $R^{32}$ represents an alkyl group having 1 to 4 carbon atoms, or an aryl group having 6 to 25 carbon atoms. Further, $Ar^{11}$ represents an aryl group having 6 to 25 carbon atoms.

A compound including carbazole in a skeleton (Compound D) is reacted with a dihalide of an aromatic compound to synthesize a compound including N-(aryl halide)carbazole in a skeleton (Compound E), and Compound E is subjected to a coupling reaction with arylamine using a metal catalyst such as palladium, a metal compound such as copper iodine, or a metal such as copper, thereby obtaining Compound F. In the synthesis scheme (A-2), a halogen element ($X_1$ and $X_2$) of the dihalide of an aromatic compound is preferably iodine or bromine. $X_1$ and $X_2$ may be the same or different from each other. Each of $R^{41}$ and $R^{42}$ represents any of a hydrogen atom, an alkyl group having 1 to 4 carbon atoms, and an aryl group having 6 to 25 carbon atoms. β represents an arylene group having 6 to 25 carbon atoms. $Ar^{31}$ represents an aryl group having 6 to 25 carbon atoms.

(A-3)

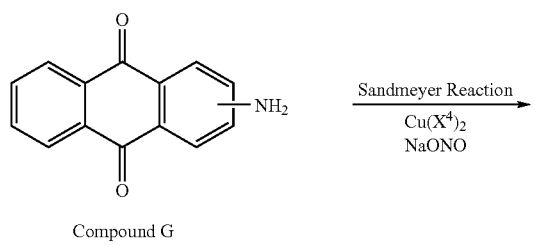

Compound G

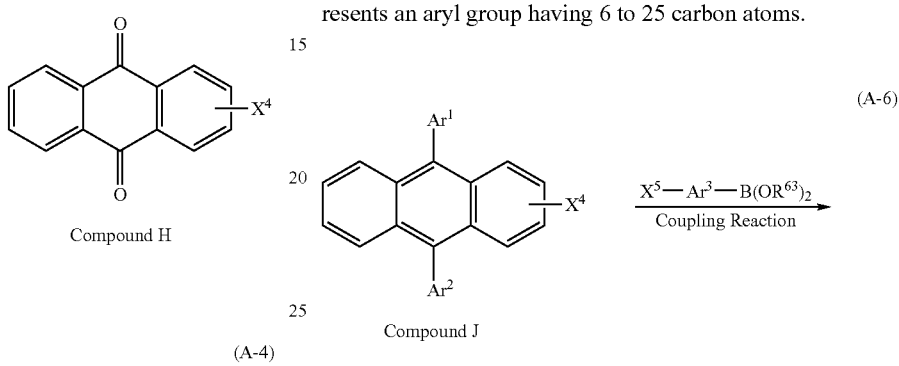

(A-4)

(A-5)

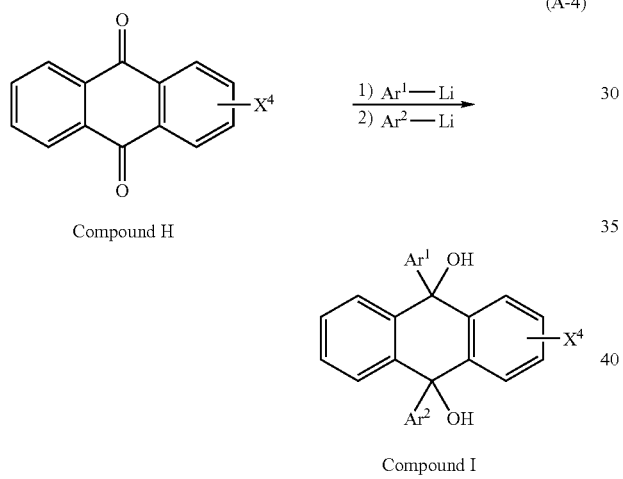

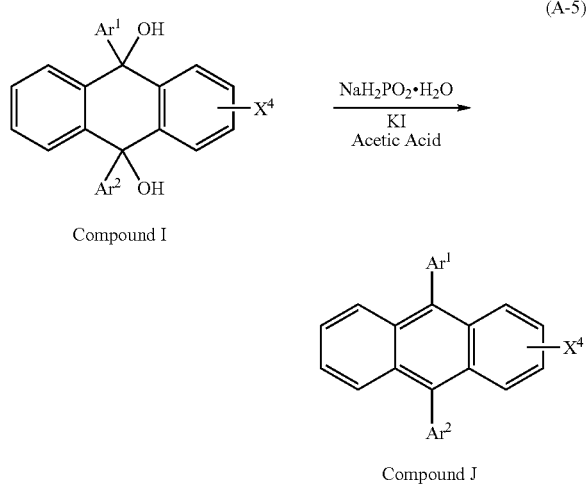

A halide of anthraquinone (Compound H) is synthesized by the Sandmyer reaction of 1-aminoanthraquinone or 2-aminoanthraquinone (Compound G). The halide of anthraquinone (Compound H) is reacted with aryllithium to synthesize a diol of a 9,10-dihydroanthracene derivative (Compound I). Then, the diol of the 9,10-dihydroanthracene derivative (Compound I) is subjected to dehydroxylation using sodium phosphinate monohydrate, potassium iodide and acetic acid, which allows the formation of 9,10-diarylanthracene halide (Compound J).

Note that in each of Synthesis schemes (A-3) to (A-5), $X^4$ represents a halogen element. Also, each of $Ar^1$ and $Ar^2$ represents an aryl group having 6 to 25 carbon atoms.

By the coupling reaction of 9,10-diarylanthracene halide (Compound J) with arylhalide with an organoboron compound or arylhalide with boronic acid, Compound K is synthesized. In the synthesis scheme (A-6), $R^{63}$ represents hydrogen or an alkyl group having 1 to 4 carbon atoms. $Ar^1$ and $Ar^2$ each represent an aryl group having 6 to 25 carbon atoms. In addition, $X^4$ and $X^5$ may be the same or different, and represent halogen elements. In particular, in consideration of yield, a combination in which $X^4$ is iodine and X5 is bromine is preferable.

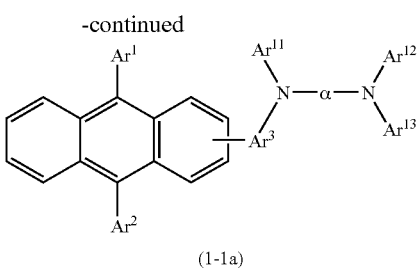

(1-1a)

An anthracene derivative of the present invention can be synthesized by the reaction shown in Synthesis scheme (B-1) using Compound K prepared in Synthesis scheme (A-6). By the coupling reaction of Compound K with an arylamine using a metal catalyst such as a palladium catalyst, a metal compound such as copper iodine, or a metal such as copper, the anthracene derivative of the present invention represented by the general formula (I-1a) can be synthesized. In Synthesis scheme (B-1), each of $Ar^1$ and $Ar^2$ represents an aryl group having 6 to 25 carbon atoms, $Ar^3$ represents an arylene group having 6 to 25 carbon atoms, each of $Ar^{11}$ to $Ar^{13}$ represents an aryl group having 6 to 25 carbon atoms, and a represents an arylene group having 6 to 25 carbon atoms. Note that the compound represented by the general formula (I-1a) corresponds to the case where A in the general formula (1) is the general formula (1-1).

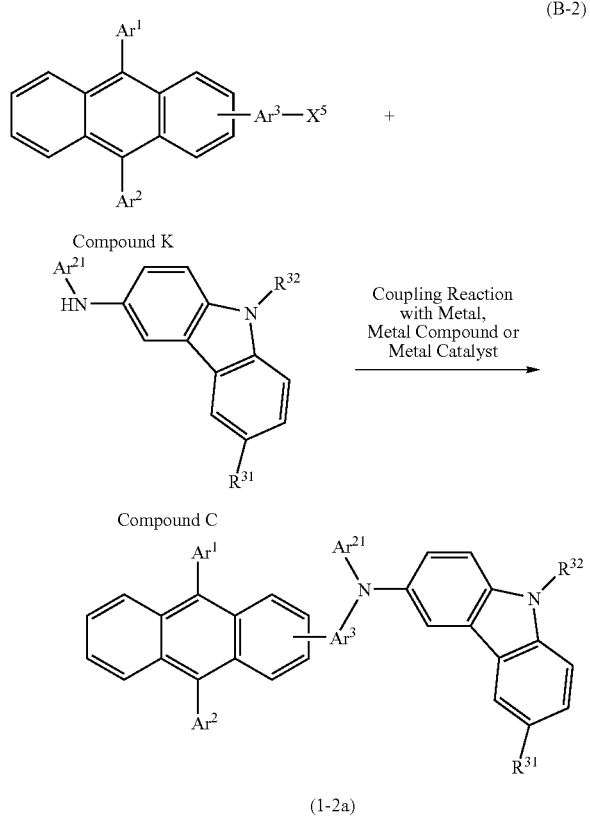

(1-2a)

An anthracene derivative of the present invention can be synthesized by a reaction shown in Synthesis scheme (B-2), using Compound C prepared according to Synthesis scheme (A-1) and Compound K provided by Synthesis scheme (A-6). The coupling reaction between Compound C and Compound K using a metal catalyst such as a palladium catalyst, a metal compound such as copper iodine, or a metal such as copper, can synthesize the anthracene derivative of the present invention represented by the general formula (I-2a). In Synthesis scheme (B-2), each of $Ar^1$ and $Ar^2$ represents an aryl group having 6 to 25 carbon atoms; $Ar^3$ represents an arylene group having 6 to 25 carbon atoms; $Ar^{21}$ represents an aryl group having 6 to 25 carbon atoms; $R^{31}$ represents any of a hydrogen atom, an alkyl group having 1 to 4 carbon atoms, and an aryl group having 6 to 25 carbon atoms; and $R^{32}$ represents any of an alkyl group having 1 to 4 carbon atoms, an aryl group having 6 to 25 carbon atoms, and a haloalkyl group having 1 to 4 carbon atoms. Note that the compound represented by the general formula (1-2a) corresponds to the case where A in foregoing the general formula (1) is the general formula (1-2).

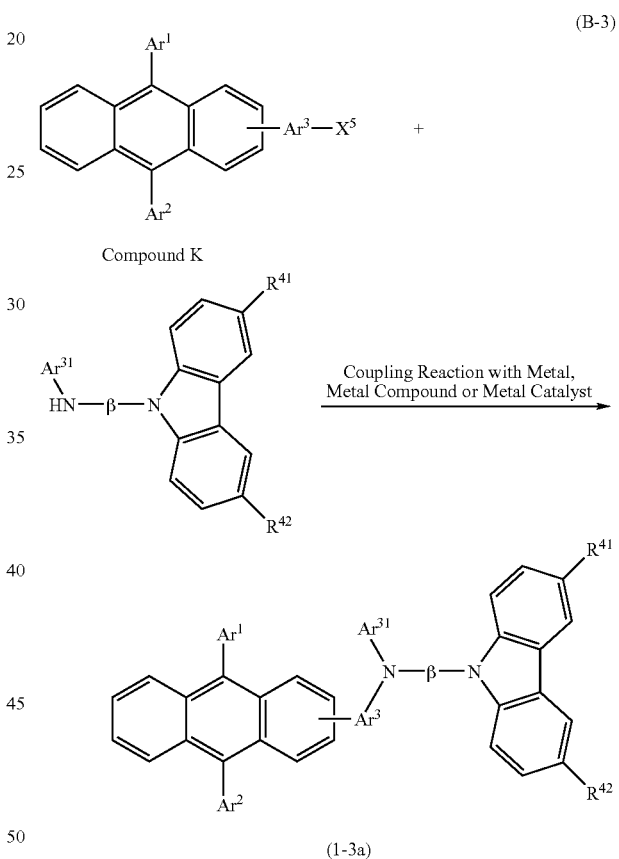

(1-3a)

An anthracene derivative of the present invention can be synthesized by a reaction shown in Synthesis scheme (B-3), using Compound F formed in Synthesis scheme (A-2) and Compound K prepared by Synthesis scheme (A-6). The coupling reaction between Compound F and Compound K using a metal catalyst such as a palladium catalyst, a metal compound such as copper iodine, or a metal such as copper, can synthesize the anthracene derivative of the present invention represented by the general formula (1-3a). In Synthesis scheme (B-3), each of $Ar^1$ and $Ar^2$ represents an aryl group having 6 to 25 carbon atoms; $Ar^{31}$ represents an aryl group having 6 to 25 carbon atoms; β represents an arylene group having 6 to 25 carbon atoms; and each of $R^{41}$ and $R^{42}$ represent any of a hydrogen atom, an alkyl group having 1 to 4 carbon atoms, an aryl group having 6 to 25 carbon atoms, a halogen atom and a haloalkyl group having 1 to 4 carbon atoms. Note that the compound represented by the general formula (1-3a) corresponds to the case where A in foregoing the general formula (1) is the general formula (1-3).

An anthracene derivative of the present invention has high luminous quantum yield, and emits blue green to yellow green light. Therefore, the anthracene derivative of the present invention can be favorably used for a light-emitting element. Also, since the anthracene derivatives of the present invention are stable against repeated redox reactions, light-emitting elements using such anthracene derivatives of the present invention can have a long lifetime. Also, since the anthracene derivatives of the present invention are capable of blue light emission or green light emission with high efficiency, they can be favorably used for a full-color display.

Note that in the anthracene derivative of the present invention, an amine unit A is bound to the anthracene skeleton via an arylene group $Ar^3$. The present inventors have found that by introducing the arylene group $Ar^3$ between the anthracene skeleton and the amine unit A, the interaction between the anthracene skeleton and the amine unit A is reduced and thus emission with a short wavelength is possible.

It is known that an anthracene derivative such as 9,10-diphenylanthracene can emit blue light, but it is difficult for holes to enter 9,10-diphenylanthracene and thus it is difficult for 9,10-diphenylanthracene to emit light efficiently in a light-emitting element. On the other hand, when an amine unit is introduced so that the anthracene derivative can easily accept holes, the emission wavelength is shifted to the long wavelength side and blue emission with excellent color purity cannot be obtained. However, the anthracene derivatives of the present invention can contribute to light-emission and can provide emission with a short wavelength, i.e., blue emission with excellent color purity, since the anthracene derivatives of the present invention each have a molecular structure in which an anthracene skeleton which contributes to light emission and has an electron-transporting property, and an amine unit A having a hole-transporting property are bound to each other via an arylene group $Ar^3$.

Further, in each of the anthracene derivatives of the present invention, as shown in the general formula (1), only one amine unit A is bound to the anthracene skeleton, and thus emission with short wavelength is possible. Since the anthracene derivatives of the present invention each have only one amine unit A, the anthracene derivatives of the present invention are hard to be decomposed at vacuum evaporation, and thus the anthracene derivatives of the present invention each can be easily formed as a film by an evaporation method. Since the anthracene derivatives of the present invention each have only one amine unit A, the anthracene derivatives of the present invention can be manufactured at low cost.

Embodiment Mode 2

One mode of a light-emitting element using an anthracene derivative of the present invention will be described below with reference to FIG. 1A.

The light-emitting element of the present invention includes a plurality of layers between a pair of electrodes. The plurality of layers are stacked by a combination of layers including a substance with a high carrier-injecting property and a substance with a high carrier-transporting property so that a light-emitting region is formed apart from the electrodes, in other words, recombination of carriers is performed in a portion apart from the electrodes.

In this embodiment mode, the light-emitting element includes a first electrode 102, a second electrode 104, and an EL layer 103 formed between the first electrode 102 and the second electrode 104. In addition, description in this embodiment mode is carried out on the assumption that the first electrode 102 serves as an anode and the second electrode 104 serves as a cathode. In other words, description is hereinafter carried out on the assumption that light emission can be obtained when a voltage is applied to the first electrode 102 and the second electrode 104 so that a potential of the first electrode 102 is higher than that of the second electrode 104.

The substrate 101 is used as a support of the light-emitting element. As the substrate 101, glass, plastic, or the like can be used, for example. Note that materials other than glass and plastic can be used as long as they can function as a support in a manufacturing process of a light-emitting element.

The first electrode 102 is preferably formed of a metal, an alloy, a conductive compound, a mixture of these, or the like each having a high work function (specifically, a work function of 4.0 eV or higher). Specifically, for example, indium oxide-tin oxide (ITO: indium tin oxide), indium oxide-tin oxide including silicon or silicon oxide, indium oxide-zinc oxide (IZO: indium zinc oxide), indium oxide including tungsten oxide and zinc oxide (IWZO), and the like are given. Films of these conductive metal oxides are usually formed by sputtering; however, a sol-gel method or the like may also be used. For example, a film of indium oxide-zinc oxide (IZO) can be formed by a sputtering method using a target in which 1 to 20 wt % of zinc oxide with respect to indium oxide is included. Moreover, a film of indium oxide (IWZO) including tungsten oxide and zinc oxide can be formed by a sputtering method using a target in which 0.5 to 5 wt % of tungsten oxide and 0.1 to 1 wt % of zinc oxide with respect to indium oxide are included. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal (such as titanium nitride), or the like can be used.

There is no particular limitation on the stacked structure of the EL layer 103, and layers formed of a substance with a high electron-transporting property, a substance with a high hole-transporting property, a substance with a high electron-injecting property, a substance with a high hole-injecting property, a bipolar substance (a substance with high electron-transporting and hole-transporting properties) and/or the like may be combined as appropriate with a light-emitting layer to be described in this embodiment mode. For example, a hole-injecting layer, a hole-transporting layer, a hole-blocking layer, a light-emitting layer, an electron-transporting layer, an electron-injecting layer, and/or the like can be combined as appropriate to constitute the EL layer 103. This embodiment mode describes a structure of the EL layer 103 in which a hole-injecting layer 111, a hole-transporting layer 112, a light-emitting layer 113 and an electron-transporting layer 114 are stacked sequentially over a first electrode 102. Specific materials to form each of the layers will be given below.

The hole-injecting layer 111 is a layer having a substance with a high hole-injecting property. As the substance with a high hole-injecting property, molybdenum oxide, vanadium oxide, ruthenium oxide, tungsten oxide, manganese oxide, or the like may be used. In addition, it is possible to use a phthalocyanine-based compound such as phthalocyanine ($H_2Pc$) or copper phthalocyanine (CuPc); an aromatic amine compound such as 4,4'-bis[N-(4-diphenylaminophenyl)-N-phenylamino]biphenyl (abbreviation: DPAB) or 4,4'-bis(N-{4-[N'-(3-methylphenyl)-N-phenylamino]phenyl}-N-phenylamino)biphenyl (abbreviation: DNTPD); a high molecule such as poly(3,4-ethylenedioxythiophene)/poly(styrenesulfonate) (abbreviation: PEDOT/PSS), or the like to form the hole-injecting layer 111.

Alternatively, as the hole-injecting layer 111, a composite material in which an acceptor substance is mixed into a substance with a high hole-transporting property can be used. It is to be noted that, by using such a composite material in which an acceptor substance is mixed into a substance with a high hole-transporting property, a material for forming an electrode can be selected regardless of the work function. In other words, besides a material with a high work function, a material with a low work function may also be used for the first electrode 102. As the acceptor substance, 7,7,8,8-tetracyano-2,3,5,6-tetrafluoroquinodimethane (abbreviation: $F_4$-TCNQ), chloranil, and the like can be given. In addition, a transition metal oxide can be given. In addition, oxides of metals that belong to Group 4 to Group 8 in the periodic table can be given. Specifically, vanadium oxide, niobium oxide, tantalum oxide, chromium oxide, molybdenum oxide, tungsten oxide, manganese oxide, and rhenium oxide are preferable since their electron-accepting properties are high. Among them, molybdenum oxide is especially preferable since it is stable in the air, has a low hygroscopic property, and is easily treated.

As an organic compound used for the composite material, various compounds such as an aromatic amine compound, carbazole derivatives, aromatic hydrocarbon, and a high molecular compound (such as oligomer, dendrimer, or polymer) can be used. The organic compound used for the composite material is preferably an organic compound having a high hole-transporting property. Specifically, a substance having a hole mobility of $10^{-6}$ cm$^2$/Vs or higher is preferably used. However, other substances than the above-described materials may also be used as long as the substances have higher hole-transporting properties than electron-transporting properties. The organic compounds which can be used for the composite material will be specifically shown below.

For example, the following can be given as the aromatic amine compound: N,N'-di(p-tolyl)-N,N'-diphenyl-p-phenylenediamine (abbreviation: DTDPPA); 4,4'-bis[N-(4-diphenylaminophenyl)-N-phenylamino]biphenyl (abbreviation: DPAB); 4,4'-bis(N-{4-[N'-(3-methylphenyl)-N-phenylamino]phenyl}-N-phenylamino)biphenyl (abbreviation: DNTPD); 1,3,5-tris[N-(4-diphenylaminophenyl)-N-phenylamino]benzene (abbreviation DPA3B); and the like.

As carbazole derivatives which can be used for the composite material, the following can be given specifically: 3-[N-(9-phenylcarbazol-3-yl)-N-phenylamino]-9-phenylcarbazole (abbreviation PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation PCzPCN1); and the like.

Moreover, 4,4'-di(N-carbazolyl)biphenyl (abbreviation: CBP); 1,3,5-tris[4-(N-carbazolyl)phenyl]benzene (abbreviation: TCPB); 9-[4-(N-carbazolyl)]phenyl-10-phenylanthracene (abbreviation: CzPA); 1,4-bis[4-(N-carbazolyl)phenyl]-2,3,5,6-tetraphenylbenzene; or the like can also be used.

As aromatic hydrocarbon which can be used for the composite material, the following can be given for example: 2-tert-butyl-9,10-di(2-naphthyl)anthracene (abbreviation: t-BuDNA); 2-tert-butyl-9,10-di(1-naphthyl)anthracene, 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]-2-tert-butylanthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; and the like. Besides those, pentacene, coronene, or the like can also be used. The aromatic hydrocarbon which has a hole mobility of $1 \times 10^{-6}$ cm$^2$/Vs or higher and which has 14 to 42 carbon atoms is particularly preferable.

The aromatic hydrocarbon which can be used for the composite material may have a vinyl skeleton. As the aromatic hydrocarbon having a vinyl group, the following are given for example: 4,4'-bis(2,2-diphenylvinyl)biphenyl (abbreviation: DPVBi); 9,10-bis[4-(2,2-diphenylvinyl)phenyl]anthracene (abbreviation: DPVPA); and the like.

Moreover, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: poly-TPD) can also be used.

The hole-transporting layer 112 is a layer that contains a substance with a high hole-transporting property. As the substance with a high hole-transporting property, for example, an aromatic amine compound such as 4,4'-bis[N-(1-naphthyl)-N-phenylamino]biphenyl (abbreviation: NPB), N,N'-bis(3-methylphenyl)-N,N-diphenyl-[1,1'-biphenyl]-4,4'-diamine (abbreviation TPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), or 4,4'-bis[N-(spiro-9,9'-bifluoren-2-yl)-N-phenylamino]biphenyl (abbreviation: BSPB) or the like can be used. These substances are mainly substances each having a hole mobility of $10^{-6}$ cm$^2$/Vs or higher. However, other substances than these substances may also be used as long as the substances have hole-transporting properties higher than electron-transporting properties. The layer containing a substance with a high hole-transporting property is not limited to a single layer, and two or more layers containing the aforementioned substances may be stacked.

Further, a high molecular compound such as poly(N-vinylcarbazole) (abbreviation: PVK) or poly(4-vinyltriphenylamine) (abbreviation: PVTPA) can also be used for the hole-transporting layer 112.

The light-emitting layer 113 is a layer including a substance having a high light-emitting property. In the light-emitting element of this embodiment mode, the light-emitting layer 113 includes the anthracene derivative of the present invention described in Embodiment Mode 1. The anthracene derivative of the present invention can favorably be applied to a light-emitting element as a highly light-emitting substance since the anthracene derivative of the present invention exhibits light emission of blue to yellow green.

The electron-transporting layer 114 is a layer that contains a substance with a high electron-transporting property. For example, a layer containing a metal complex having a quinoline skeleton or a benzoquinoline skeleton, such as tris(8-quinolinolato)aluminum (abbreviation: Alq); tris(4-methyl-8-quinolinolato)aluminum (abbreviation: Almq$_3$); bis(10-hydroxybenzo[h]-quinolinato)beryllium (abbreviation:

BeBq$_2$); or bis(2-methyl-8-quinolinolato)(4-phenylphenolato)aluminum (abbreviation: BAlq), or the like can be used. Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)benzothiazolato]zinc (abbreviation: Zn(BTZ)$_2$), or the like can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances mentioned here are mainly materials each having an electron mobility of $10^{-6}$ cm$^2$/Vs or higher. The electron-transporting layer may be formed of other materials than those described above as long as the materials have electron-transporting properties higher than hole-transporting properties. Furthermore, the electron-transporting layer is not limited to a single layer, and two or more layers made of the aforementioned substances may be stacked.

For the electron-transporting layer 114, a high molecular compound can be used. For example, poly[(9,9-dihexylfluorene-2,7-diyl)-co-(pyridin-3,5-diyl)] (abbreviation: PF-Py), poly[(9,9-dioctylfluorene-2,7-diyl)-co-(2,2'-bipyridin-6,6'-diyl)] (abbreviation PF-BPy), or the like can be used.

The second electrode 104 can be formed of a metal, an alloy, an electrically conductive compound, or a mixture of these, having a low work function (specifically, a work function of 3.8 eV or lower). As a specific example of such a cathode material, an element belonging to Group 1 or Group 2 in the periodic table, i.e., an alkali metal such as lithium (Li) or cesium (Cs), or an alkaline earth metal such as magnesium (Mg), calcium (Ca), or strontium (Sr); an alloy containing any of these (such as MgAg or AlLi); a rare earth metal such as europium (Er) or ytterbium (Yb); an alloy containing such a rare earth metal; or the like can be used. However, when an electron-injecting layer is provided between the second electrode 104 and the electron-transporting layer, the second electrode 104 can be formed of various conductive materials such as Al, Ag, ITO, and indium oxide-tin oxide including silicon or silicon oxide regardless of its work function. A film of these conductive materials can be formed by a sputtering method, an inkjet method, a spin coating method, or the like.

As the layer having a function of promoting electron injection, an alkali metal, an alkaline earth metal, or a compound thereof such as lithium fluoride (LiF), cesium fluoride (CsF), or calcium fluoride (CaF$_2$) can be used. Alternatively, a layer which contains a substance having an electron-transporting property and an alkali metal, an alkaline earth metal, or a compound thereof (Alq including magnesium (Mg) for example) can be used. The use of such a layer as electron-injecting layer is advantageous because electron injection from the second electrode 104 proceeds efficiently.

As a formation method of the EL layer 103, various methods can be employed regardless of a wet process or a dry process. For example, a vacuum evaporation method, an inkjet method, a spin coating method, or the like may be used. A different formation method may be employed for each electrode or each layer.

Further, the electrodes may be formed by a sol-gel method, which is a wet process, or may also be formed by a wet process using a paste of a metal material. Alternatively, a dry process such as a sputtering method or a vacuum evaporation method may also be employed.

Hereinafter, a specific formation method of a light-emitting element will be described. In the case where a light-emitting element of the present invention is applied to a display device and a light-emitting layer for each color is formed separately, it is preferable to form the light-emitting layers by a wet process. By forming the light-emitting layers by a wet process such as an inkjet method, the formation of the light-emitting layers for the respective colors becomes easy even when a large substrate is used.

For example, in the structure described in this embodiment mode, the first electrode may be formed by a sputtering method, which is a dry process; the hole-injecting layer may be formed by an inkjet method or a spin coating method, which are wet processes; the hole-transporting layer may be formed by a vacuum evaporation method, which is a dry process; the light-emitting layer may be formed by an inkjet method, which is a wet process; the electron-injecting layer may be formed by a co-evaporation method, which is a dry process; and the second electrode may be formed by an inkjet method or a spin coating method, which are wet processes. Alternatively, the first electrode may be formed by an inkjet method, which is a wet process; the hole-injecting layer may be formed by a vacuum evaporation method, which is a dry process; the hole-transporting layer may be formed by an inkjet method or a spin coating method, which are wet processes; the light-emitting layer may be formed by an inkjet method, which is a wet process; the electron-injecting layer may be formed by an inkjet method or a spin coating method, which are wet processes; and the second electrode may be formed by an inkjet method or a spin coating method, which are wet processes. Note that a wet process and a dry process can be combined as appropriate, without being limited to the above methods.

Further alternatively, for example, the first electrode can be formed by a sputtering method, which is a dry process; the hole-injecting layer and the hole-transporting layer can be formed by an inkjet method or a spin coating method, which are wet processes; the light-emitting layer can be formed by an inkjet method, which is a wet process; the electron-injecting layer can be formed by a vacuum evaporation method, which is a dry process; and the second electrode can be formed by a vacuum evaporation method, which is a dry process. In other words, over a substrate over which the first electrode is formed with a desired shape, from the hole-injecting layer to the light-emitting layer can be formed by a wet process, and from the electron-injecting layer to the second electrode can be formed by a dry process. In this method, the hole-injecting layer to the light-emitting layer can be formed at atmospheric pressure and the light-emitting layers for respective colors can be easily formed separately. In addition, from the electron-injecting layer to the second electrode can be formed in vacuum consistently. Therefore, the process can be simplified and productivity can be improved.

Figure 2:
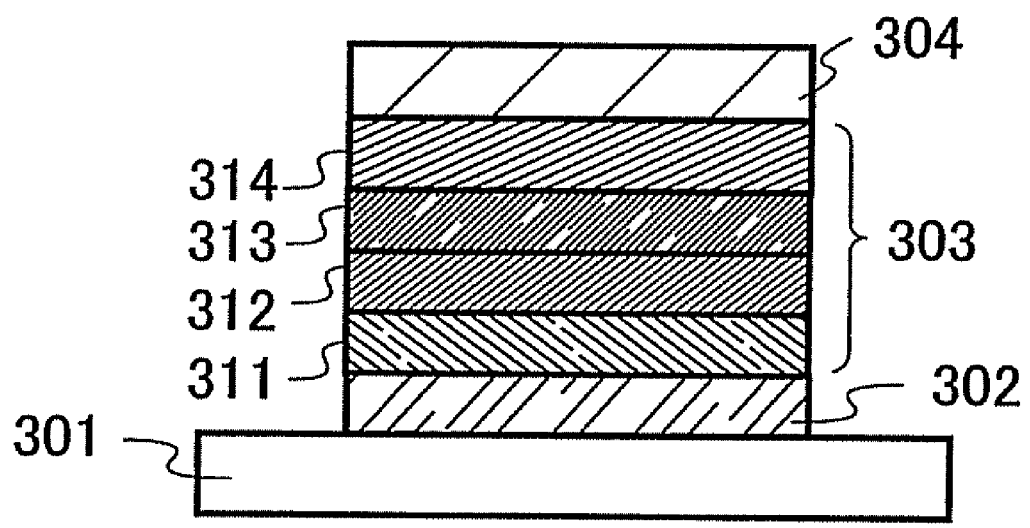
FIG. 2 illustrates a light-emitting element according to an aspect of the present invention.

In the case of the structure shown in FIG. 2, in the reverse order to the above-described method, the second electrode can be formed by a sputtering method or a vacuum evaporation method, which are dry processes; the electron-injecting layer can be formed by a vacuum evaporation method, which is a dry process; the light-emitting layer can be formed by an inkjet method, which is a wet process; the hole-transporting layer and the hole-injecting layer can be formed by an inkjet method or a spin coating method, which are wet processes; and the first electrode can be formed by an inkjet method or a spin coating method, which are wet processes. In this method, from the second electrode to the electron-injecting layer can be formed by a dry process in vacuum consistently, and from the light-emitting layer to the first electrode can be formed at atmospheric pressure. Therefore, the process can be simplified and productivity can be improved.

By applying voltage between the first electrode 102 and the second electrode 104, holes and electrons are recombined in the light-emitting layer 113 including a high light-emitting property, so that light is emitted from the light-emitting element of the present invention. In other words, a light-emitting region exists in the light-emitting layer 113.

Figure 1B:
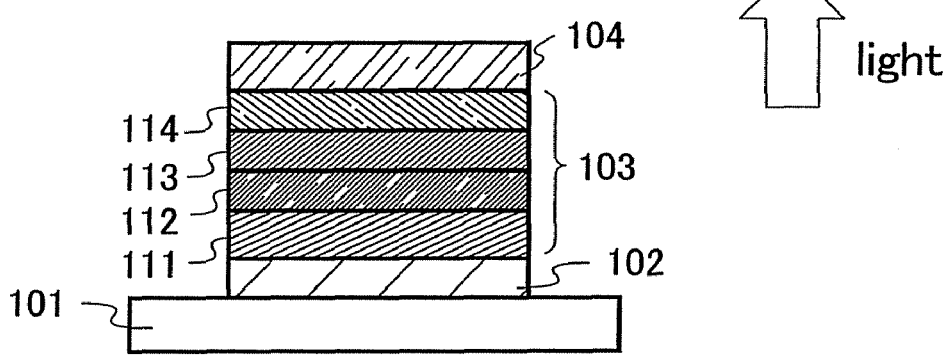
Figure 1C:
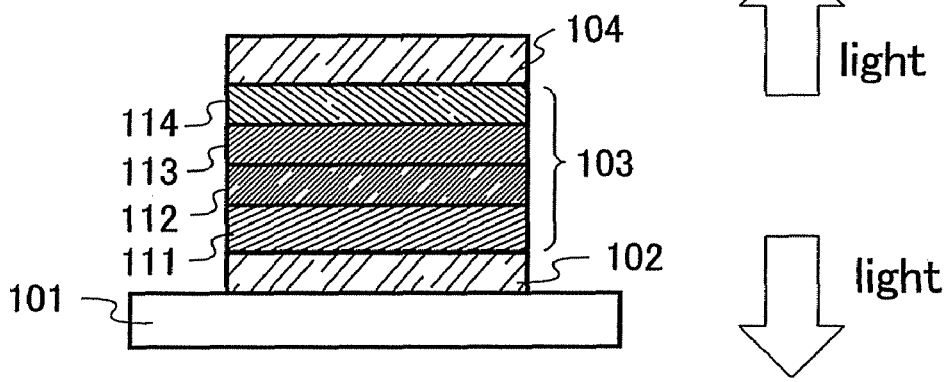

The emitted light is extracted out through one or both of the first electrode 102 and the second electrode 104. Accordingly, one or both of the first electrode 102 and the second electrode 104 is/are an electrode having a light-transmitting property. When only the first electrode 102 is an electrode having a light-transmitting property, light is extracted from the substrate side through the first electrode 102 as illustrated in FIG. 1A. In addition, when only the second electrode 104 is an electrode having a light-transmitting property, light is extracted from the opposite side to the substrate through the second electrode 104 as illustrated in FIG. 1B. Further, when the first electrode 102 and the second electrode 104 are both electrodes having light-transmitting properties, light is extracted to both sides, i.e., the substrate side and the opposite side, through the first electrode 102 and the second electrode 104 as illustrated in FIG. 1C.

The structure of layers provided between the first electrode 102 and the second electrode 104 is not limited to the above example. Besides the above-described structures, any structure can be employed as long as it has a light-emitting region for recombination of holes and electrons in a portion apart from the first electrode 102 and the second electrode 104 to prevent the quenching phenomenon caused by adjacency of the light-emitting region and a metal.

In other words, a stacked structure of the layer is not strictly limited to the abovementioned structure, and layers formed of a substance with a high electron-transporting property, a substance with a high hole-transporting property, a substance with a high electron-injecting property, a substance with a high hole-injecting property, a bipolar substance (a substance with high electron-transporting and hole-transporting properties), a hole-blocking material, and the like may be freely combined with an anthracene derivative of the present invention.

The light-emitting element illustrated in FIG. 2 has a structure in which a first electrode 302 serving as a cathode, an electron-transporting layer 311, a light-emitting layer 312, a hole-transporting layer 313, a hole-injecting layer 314, and a second electrode 304 serving as an anode are sequentially stacked over a substrate 301.

In this embodiment mode, the light-emitting element is formed over a substrate made of glass, plastic, or the like. A plurality of such light-emitting elements is formed over one substrate, thereby forming a passive matrix light-emitting device. In addition, for example, a thin film transistor (TFT) may be formed over a substrate of glass, plastic, or the like and a light-emitting element may be formed over an electrode that is electrically connected to the TFT. In this way, an active matrix light-emitting device in which the TFT controls the drive of the light-emitting element can be manufactured. It is to be noted that there is no particular limitation on the structure of the TFT. A staggered TFT or an inversely staggered TFT may be employed. Furthermore, there is no particular limitation on crystallinity of a semiconductor film used for the TFT. An amorphous semiconductor film may be used, or a crystalline semiconductor film may be used. In addition, a driver circuit formed over a TFT substrate may be formed using N-channel and P-channel TFTs, or using either N-channel or P-channel TFTs.

As shown in this embodiment mode, an anthracene derivative of the present invention can be used for a light-emitting layer without adding any other light-emitting substance, since the anthracene derivative exhibits light emission of blue to yellow green.

Since the anthracene derivative of the present invention has high quantum efficiency, a light-emitting element with high luminous efficiency can be obtained by using the anthracene derivative of the present invention for a light-emitting element. Also, since the anthracene derivative of the present invention is stable against repeated redox reactions, a light-emitting element using the anthracene derivative can have a long lifetime.

Because anthracene derivatives of the present invention are capable of blue light emission or green light emission with high efficiency, they can be favorably used for full-color displays. Further, the ability of the anthracene derivative of the present invention to achieve blue light emission with a long lifetime or green light emission with a long lifetime allows their application in a full-color display. In particular, blue light-emitting elements are less developed in terms of lifetime and efficiency than green light-emitting elements and red light-emitting elements; therefore, blue light-emitting elements having good characteristics are expected. A light-emitting element using an anthracene derivative of the present invention is capable of high efficiency, blue light emission with a long lifetime, and is suitable for full-color displays.

Furthermore, since the anthracene derivatives of the present invention is capable of blue light emission to yellow green light emission with high efficiency, white light emission can be obtained by combining with another light emission material. For example, in an attempt to realize white light emission using red (R), green (G), and blue (B) emissions which exhibit the corresponding NTSC chromaticity coordinates, white color cannot be obtained unless light emissions of these colors are mixed with a proportion of approximately red (R):green (G):blue (B)=1:6:3. That is, green light emission with high luminance is necessary; therefore, the anthracene derivatives of the present invention by which green light emission with high efficiency can be obtained are favorable for light-emitting elements.

Embodiment Mode 3

Embodiment Mode 3 will describe a light-emitting element having a different structure from that described in Embodiment Mode 2.

In this embodiment mode, the light-emitting layer 113 shown in Embodiment Mode 2 is formed by dispersing an anthracene derivative of the present invention into another substance, whereby light emission can be obtained from the anthracene derivative of the present invention. Since the anthracene derivative of the present invention exhibits light emission of blue to yellow green, a light-emitting element exhibiting light emission of blue to yellow green can be obtained.

Here, various materials can be used as a substance in which the anthracene derivative of the present invention is dispersed. In addition to the substance having a high hole-transporting property and the substance having a high electron-transporting property, which are described in Embodiment Mode 2, 4,4'-bis(N-carbazolyl)biphenyl (abbreviation: CBP), 2,2',2"-(1,3,5-benzenetriyl)tris[1-phenyl-1H-benzimidazole] (abbreviation: TPBI), 9,10-di(2-naphthyl)anthracene (abbreviation: DNA), 2-tert-butyl-9,10-di(2-naphthyl)anthracene (abbreviation: t-BuDNA), 9-[4-(N-carbazolyl)]phenyl-10-phenylanthracene (abbreviation:

CzPA), and the like are exemplified. Further, as a substance to disperse an anthracene derivative of the present invention, a high molecular material can be used. For example, poly(N-vinylcarbazole) (abbreviation: PVK); poly(4-vinyltriphenylamine) (abbreviation: PVTPA); poly[N-(4-{N [4-(4-diphenylamino)phenyl]phenyl-N'phenylamino}phenyl) methacrylamide] (abbreviation: PTPDMA); poly[N,N'-bis (4-butylphenyl)-N,N'-bis(phenyl)benzidine] (abbreviation: Poly-TPD), poly[(9,9-dihexylfluorene-2,7-diyl)-co-(pyridine-3,5-diyl)] (abbreviation: PF-Py); poly[(9,9-dioctylfluorene-2,7-diyl)-co-(2,2'-bipyridine-6,6'-diyl)] (abbreviation: PF-BPy), or the like can be used.

Since the anthracene derivative of the present invention has high luminous efficiency, a light-emitting element with high luminous efficiency can be obtained by using the anthracene derivative of the present invention in a light-emitting element. Also, by using the anthracene derivative of the present invention in a light-emitting element, a light-emitting element with a long lifetime can be obtained.

Further, since a light-emitting element using the anthracene derivative of the present invention is capable of blue light emission or green light emission with high efficiency, the light-emitting element can be favorably used for a full-color display. In addition, since the light-emitting element using the anthracene derivative of the present invention is capable of blue light emission or green light emission with a long lifetime, it can be favorably used for a full-color display.

Note that, regarding the layers other than the light-emitting layer 113, the structure shown in Embodiment Mode 2 can be as appropriate used.

Embodiment Mode 4

Embodiment Mode 4 will describe a light-emitting element with a structure different from the structures described in Embodiment Modes 2 and 3.

The light-emitting layer 113 shown in Embodiment Mode 2 is formed by dispersing a light-emitting substance in the anthracene derivative of the present invention, whereby light emission from the light-emitting substance can be obtained.

In a case where the anthracene derivative of the present invention is used as a material in which another light-emitting substance is dispersed, a light emission color derived from the light-emitting substance can be obtained. Further, emission of a mixed color resulted from the anthracene derivative of the present invention and the light-emitting substance dispersed in the anthracene derivative can also be obtained.

In this case, various materials can be used as a light-emitting substance dispersed in the anthracene derivative of the present invention. Specifically, a fluorescence emitting substance that emits fluorescence, such as 4-(dicyanomethylene)-2-methyl-6-(p-dimethylaminostyryl)-4H-pyran (abbreviation: DCM1), 4-(dicyanomethylene)-2-methyl-6-(julolidine-4-yl-vinyl)-4H-pyran (abbreviation: DCM2), N,N-dimethylquinacridone (abbreviation: DMQd), or rubrene can be used. Further, a phosphorescence emitting substance that emits phosphorescence such as (acetylacetonato)bis[2,3-bis(4-fluorophenyl)quinoxalinato]iridium(III) (abbreviation: Ir(Fdpq)$_2$(acac)), 2,3,7,8,12,13,17,18-octaethyl-21H,23H-porphyrinplatinum(II) (abbreviation: PtOEP), or the like can be used.

Note that, regarding the layers other than the light-emitting layer 113, the structure shown in Embodiment Mode 2 can be appropriately used.

Embodiment Mode 5

Embodiment Mode 5 will describe a light-emitting element with a structure different from those of Embodiment Modes 2 to 4.

An anthracene derivative of the present invention has a hole-transporting property. Therefore, a layer including the anthracene derivative of the present invention can be used between an anode and a light-emitting layer. Specifically, the anthracene derivative of the present invention can be used in the hole-injecting layer 111 and/or the hole-transporting layer 112 described in Embodiment Mode 2.

Also, in a case of applying the anthracene derivative of the present invention as the hole-injecting layer 111, it is preferable to compose the anthracene derivative of the present invention and an inorganic compound having an electron accepting property with respect to the anthracene derivative of the present invention. By using such a composite material, the carrier density increases, which contributes to improvement of the hole-injecting property and hole-transporting property. Also, in a case of using the composite material in the hole-injecting layer 111, the hole-injecting layer 111 can achieve an ohmic contact with the first electrode 102; therefore, a material of the first electrode can be selected regardless of work function.

As the inorganic compound used for the composite material, an oxide of a transition metal is preferably used. Moreover, oxides of metals belonging to Groups 4 to 8 in the periodic table can be represented. Specifically, it is preferable to use vanadium oxide, niobium oxide, tantalum oxide, chromium oxide, molybdenum oxide, tungsten oxide, manganese oxide, and rhenium oxide, because of their high electron accepting properties. Among them, molybdenum oxide is especially preferable since it is stable in the air, has a low hygroscopic property, and is easily treated.

Note that this embodiment mode can be combined with another embodiment mode as appropriate.

Embodiment Mode 6

Figure 39:
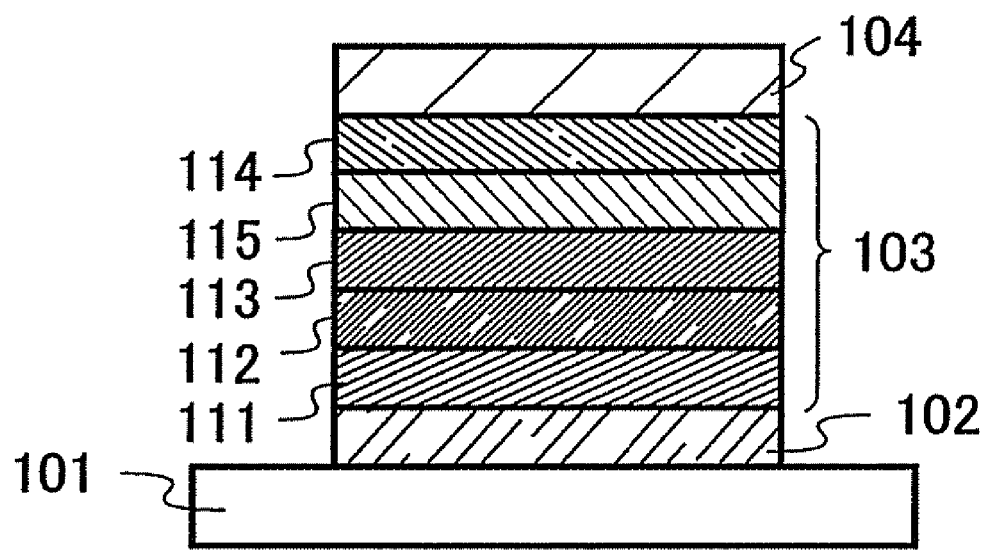
FIG. 39 illustrates a light-emitting element according to an aspect of the present invention.

Embodiment Mode 6 will describe a light-emitting element with a structure different from the structures described in Embodiment Modes 2 to 5 with reference to FIG. 39.

A light-emitting element shown in this embodiment mode is provided with a functional layer 115 between the light-emitting layer 113 and the electron-transporting layer 114 of the light-emitting element shown in Embodiment Mode 2.

In this embodiment mode, the light-emitting layer 113 preferably includes a first organic compound and a second organic compound. That is, the light-emitting layer 113 preferably has a structure in which the first organic compound with a light-emitting property is dispersed in the second organic compound. Since the anthracene derivative of the present invention has high luminous efficiency, it can be favorably used as the first organic compound with a light-emitting property.

As the second organic compound in which the anthracene derivative of the present invention is dispersed, various materials can be used as shown in Embodiment Mode 3. In this embodiment mode, a functional layer which controls the rate of carrier transport is provided between the light-emitting layer and the second electrode serving as the cathode. Therefore, the light-emitting layer 113 preferably has an electron-transporting property. That is, the light-emitting layer 113 preferably has a higher electron-transporting property than a hole-transporting property. Therefore, the second organic compound included in the light-emitting layer 113 is preferably an organic compound with an electron-transporting property. Specifically, the following materials can be used: metal complexes such as tris(8-quinolinolato)aluminum(III) (abbreviation: Alq), tris(4-methyl-8-quinolinolato)aluminum(III) (abbreviation: Almq$_3$), bis(10-hydroxybenzo[h]-quinolinato)beryllium(II) (abbreviation: BeBq$_2$), bis(2-methyl-8-quinolinolato)(4-phenylphenolato)aluminum(III) (BAlq), bis(8-quinolinolato)zinc(II) (abbreviation: Znq), bis[2-(2-benzoxazolyl)phenolato]zinc(II) (Abbreviation: ZnPBO), and bis[2-(2-benzothiazolyl)phenolato]zinc(II) (abbreviation: Zn(BTZ)$_2$); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), and bathocuproine (abbreviation: BCP); and condensed aromatic compounds such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilben-3,3'-diyl)diphenanthrene (abbreviation: DPNS), 9,9'-(stilben-4,4'-diyl)diphenanthrene (abbreviation: DPNS2), and 3,3',3''-(benzene-1,3,5-triyl)tripyrene (abbreviation: TPB3). Alternatively, the following materials can also be used: 4,4'-(quinoxaline-2,3-diyl)bis(N,N-diphenylaniline) (abbreviation: TPAQn), 9,10-diphenylanthracene (abbreviation: DPAnth), 2,3-bis{4-[N-(4-biphenylyl)-N-phenylamino]phenyl}quinoxaline (abbreviation: BPAPQ), and 4,4'-(quinoxaline-2,3-diyl)bis{N-[4-(9H-carbazol-9-yl)phenyl]-N-phenylaniline}(abbreviation: YGAPQ).

The functional layer 115 includes a third organic compound and a fourth organic compound. The functional layer 115 functions to control the rate of transport of electrons injected from the second electrode 104.

Generally, when a light-emitting layer has an electron-transporting property, an electron-blocking layer is often provided between the light-emitting layer and an anode and closer to the light-emitting layer, in order to prevent electrons from passing through the light-emitting layer. However, when the electron-blocking layer is deteriorated over time, a recombination region expands to the inside of the electron blocking layer (or inside of the hole-transporting layer), which results in a significant decrease in current efficiency (i.e., luminance decay). On the other hand, in the light-emitting element shown in this embodiment mode, the rate of transport of electrons is controlled before electrons reach the light-emitting layer (on the cathode side), and thus the recombination region is kept in the light-emitting layer, which is hard to cause luminance decay, even if electrons are somewhat unbalanced.

The functional layer 115 can have various structures. The first structure is a structure in which a third organic compound having a function of trapping electrons is added into a fourth organic compound having an electron-transporting property. In this structure, electrons injected from the second electrode 104 serving as the cathode are injected into the functional layer 115 through the electron-transporting layer and/or the like. The electrons injected into the functional layer 115 are temporarily trapped by the third organic compound, whereby the transport of the electrons becomes slow so that electron injection to the light-emitting layer is controlled.

In this structure, the third organic compound included in the functional layer 115 is an organic compound having a function of trapping electrons. Therefore, the lowest unoccupied molecular orbital (LUMO) level of the third organic compound is preferably lower than the lowest unoccupied molecular orbital (LUMO) level of the fourth organic compound included in the functional layer 115 by 0.3 eV or more. When the functional layer 115 includes the third organic compound, the electron-transporting rate of this layer is lower as compared with the case where this layer is made of only the fourth organic compound. That is, the transporting rate of carriers can be decreased by adding the third organic compound. Furthermore, the transporting rate of electrons can be controlled by adjusting the concentration of the third organic compound. The third organic compound may emit light. In that case, the light-emission colors of the first organic compound and the third organic compound are preferably similar in order to keep the color purity of the light-emitting element.

As the third organic compound included in the functional layer 115, for example, the following substances exhibiting light emission of blue green to yellow green can be used: N,N'-dimethylquinacridone (abbreviation: DMQd), N,N'-diphenylquinacridone (abbreviation: DPQd), 9,18-dihydrobenzo[h]benzo[7,8]quino[2,3-b]acridine-7,16-dione (abbreviation: DMNQd-1), 9,18-dihydro-9,18-dimethylbenzo[h]benzo[7,8]quino[2,3-b]acridine-7,16-dione (abbreviation: DMNQd-2), Coumarin 30, Coumarin 6, Coumarin 545T, and Coumarin 153.

The fourth organic compound included in the functional layer 115 is an organic compound having an electron-transporting property. That is, the fourth organic compound is a substance having a higher electron-transporting property than a hole-transporting property. Specifically, the following materials can be used: metal complexes such as tris(8-quinolinolato)aluminum(III) (abbreviation: Alq), Almq$_3$, BeBq$_2$, BAlq, Znq, BAlq, ZnPBO, and ZnBTz; heterocyclic compounds such as PBD, OXD-7, TAZ, TPBI, BPhen, and BCP; and condensed aromatic compounds such as CzPA, DPCzPA, DPPA, DNA, t-BuDNA, BANT, DPNS, DPNS2, and TPB3. Among them, metal complexes that are stable against electrons are preferably used. In addition, as has been mentioned earlier, the LUMO level of the third organic compound is preferably lower than that of the fourth organic compound by 0.3 eV or more. Therefore, a material of the fourth organic compound may be selected as appropriate so as to satisfy the condition, according to the kind of a material used for the third organic compound.

In the light-emitting element of the present invention having the above structure, a current flows by a potential difference applied between the first electrode 102 and the second electrode 104, whereby holes and electrons are recombined in the EL layer 103 to produce light emission. Specifically, a light-emitting region is formed in a region from the light-emitting layer 113 to the interface between the light-emitting layer 113 and the functional layer 115. The mechanism for this phenomenon is explained below.

Holes injected from the first electrode 102 are injected into the light-emitting layer 113 through the hole-injecting layer 111 and the hole-transporting layer 112. Meanwhile, electrons injected from the second electrode 104 are injected into the functional layer 115 which is the layer for controlling the transporting rate of carriers, through the electron-transporting layer 114. The transport of the electrons injected into the functional layer 115 becomes slow by the third organic compound having an electron trapping property. The electrons whose transporting rate is slow are injected into the light-emitting layer 113 and recombined with holes, thereby providing light emission.

When the light-emitting layer 113 has an electron-transporting property, the transport of holes injected from the hole-transporting layer 112 to the light-emitting layer 113 becomes slow. In addition, electrons, injected into the light-emitting layer 113 from the functional layer 115, moves slowly also in the light-emitting layer 113, due to the control by the functional layer 115. Therefore, the recombination probability is increased and luminous efficiency is improved, since slow holes and slow electrons are recombined in the light-emitting layer 113.

The second structure of the functional layer 115 is a structure including the third organic compound and the fourth organic compound. The weight percent of the fourth organic compound is higher than the weight percent of the third organic compound. In addition, the fourth organic compound and the third organic compound transport different carriers. This embodiment mode will describe a case where the functional layer for controlling the transporting rate of carriers is provided closer to the side of the second electrode serving as the cathode than the light-emitting layer. That is, the functional layer is provided between the light-emitting layer 113 and the second electrode 104.

When the functional layer is provided on the side of the second electrode serving as the cathode than the light-emitting layer, the fourth organic compound is preferably an organic compound with an electron-transporting property, while the third organic compound is preferably an organic compound with a hole-transporting property. That is, the fourth organic compound is preferably a substance having a higher electron-transporting property than a hole-transporting property, while the third organic compound is preferably a substance having a higher hole-transporting property than an electron-transporting property. In addition, the difference between the lowest unoccupied molecular orbital (LUMO) levels of the fourth organic compound and the third organic compound is preferably less than 0.3 eV, or more preferably less than 0.2 eV. That is, it is preferable that, in thermodynamic terms, electron can be easily transported between the fourth organic compound and the third organic compound.

In this structure, as described above, the fourth organic compound is preferably an organic compound with an electron-transporting property. Specifically, metal complexes such as Alq, Almq$_3$, BeBq$_2$, BAlq, Znq, ZnPBO, and ZnBTz; heterocyclic compounds such as PBD, OXD-7, TAZ, TPBI, BPhen, and BCP; and condensed aromatic compounds such as CzPA, DPCzPA, DPPA, DNA, t-BuDNA, BANT, DPNS, DPNS2, and TPB3 can be used.

In addition, the third organic compound is preferably an organic compound with a hole-transporting property. Specifically, the following materials can be used: condensed aromatic hydrocarbons such as 9,10-diphenylanthracene (abbreviation: DPAnth) and 6,12-dimethoxy-5,11-diphenylchrysene; aromatic amine compounds such as N,N-dipheyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}9H-carbazol-3-amine (abbreviation: PCAPBA), N-(9,10-diphenyl-2-anthryl)-N,9-diphenyl-9H-carbazol-3-amine (abbreviation: 2PCAPA), NPB (or α-NPD), TPD, DFLDPBi, and BSPB; and compounds having an amino group such as Coumarin 7 and Coumarin 30.

With the abovementioned combinations, the transport of electrons from the fourth organic compound to the third organic compound or from the third organic compound to the fourth organic compound can be controlled, whereby the transport rate of electrons through the functional layer 115 can be decreased. Further, since the functional layer 115 has a structure in which the third organic compound is dispersed in the fourth organic compound, crystallization or agglutination over time does not readily occur. Therefore, the abovementioned effect of controlling the electron transport rate does not easily change over time. As a result, carrier balance can be maintained over time. This leads to improvement of the lifetime of the light-emitting element, that is, improvement of reliability.

It is to be noted that among the abovementioned combinations, it is preferable to combine a metal complex and an aromatic amine compound as the fourth organic compound and the third organic compound, respectively. A metal complex has a high electron-transporting property and has large dipole moment, whereas an aromatic amine compound has a high hole-transporting property and has comparatively small dipole moment. Thus, by combination of substances whose dipole moments differ greatly from each other, the abovementioned effect of electron transport can be further increased. Specifically, it is preferable to combine substances which satisfy $P_1/P_2 \geqq 3$ or $P_1/P_2 \leqq 0.33$, where the dipole moment of the fourth organic compound is $P_1$ and the dipole moment of the third organic compound is $P_2$.

In the light-emitting element of the present invention having the above structure, a current flows by a potential difference applied between the first electrode 102 and the second electrode 104, whereby holes and electrons are recombined in the EL layer 103 to produce light emission. Specifically, a light-emitting region is formed in a region from the light-emitting layer 113 of the EL layer 103 to the interface between the light-emitting layer 113 and the functional layer 115. The mechanism for this phenomenon is explained below.

Since the fourth organic compound has an electron-transporting property, electrons are easily injected to the functional layer 115 and easily transported toward the neighboring fourth organic compound. That is, the rate at which electrons are injected into the fourth organic compound and the rate (v) at which electrons are released from the fourth organic compound are high.

Meanwhile, in thermodynamic terms, there is a possibility that electrons are injected into the third organic compound which is the organic compound having a hole-transporting property because the third organic compound has a close LUMO level to that of the fourth organic compound. However, the rate ($v_1$) at which electrons are injected from the fourth organic compound which is the organic compound having an electron-transporting property into the third organic compound which is the organic compound having a hole-transporting property, or the rate ($v_2$) at which electrons are injected from the third organic compound into the fourth organic compound is lower than the rate (v) at which electrons are transported between the fourth organic compounds.

Therefore, when the functional layer 115 includes the third organic compound, the electron-transporting rate of this layer is lower as compared with the case where the layer is made of only the fourth organic compound. That is, the transport of carriers can be controlled by adding the third organic compound. Also, the transport rate of carriers can be controlled by adjusting the concentration of the third organic compound.

In the case of a conventional light-emitting element without the functional layer 115 having the abovementioned structures, the transport of electrons does not slow down and the electrons are injected to the light-emitting layer 113, reaching the vicinity of the interface between the light-emitting layer 113 and the hole-transporting layer 112. Therefore, a light-emitting region is formed around the interface between the hole-transporting layer 112 and the light-emitting layer 113. In that case, there is a possibility that the electrons may reach and deteriorate the hole-transporting layer 112. Further, as the amount of electrons that is transported into the hole-transporting layer 112 is increased over time, the recombination probability in the light-emitting layer decreases over time, which leads to a shorter lifetime of the light-emitting element (luminance decay over time).

The light-emitting element shown in this embodiment mode is characterized by having the functional layer 115. Electrons injected from the second electrode 104 are injected into the functional layer 115 through the electron-transporting layer 114. The transport of the electrons injected into the functional layer 115 is slow and, thus, the quantity of carriers in the light-emitting layer 113 is well-balanced. As a result, a light-emitting region, which has conventionally been localized in the vicinity of the interface between the hole-transporting layer 112 and the light-emitting layer 113, is formed in a region from the light-emitting layer 113 to the vicinity of the interface between the light-emitting layer 113 and the functional layer 115. Therefore, there is a low possibility that electrons may reach and deteriorate the hole-transporting layer 112. Similarly, as for holes, there is also a low possibility that holes may reach and deteriorate the electron-transporting layer 114 because the second organic compound included in the light-emitting layer 113 has an electron-transporting property.

Further, it is an important point of this embodiment mode that not merely a substance with low electron mobility is applied to the functional layer 115, but an organic compound having an electron-trapping function or an organic compound having a hole-transporting property is added to an organic compound having an electron-transporting property. With such a structure, it becomes possible not only to control the electron injection to the light-emitting layer 113 but also to suppress changes in the controlled amount of injected electron over time. Further, since the second organic compound included in the light-emitting layer 113 has an electron-transporting property and the first organic compound which is the light-emissive substance is added into the light-emitting layer 113, the amount of holes in the light-emitting layer 113 also does not readily change over time. Therefore, the light-emitting element of the present invention can prevent a phenomenon that carrier balance is lost over time, which could otherwise lower the recombination probability in the light-emitting element. Thus, the lifetime of the element can be improved (luminance decay over time can be suppressed).

In the light-emitting element shown in this embodiment mode, the light-emitting region is not localized at the interface between the light-emitting layer and the hole-transporting layer or the interface between the light-emitting layer and the electron-transporting layer, but formed around the center of the light-emitting layer. Therefore, there is no adverse effect of deterioration which would otherwise be caused if the light-emitting region is positioned close to the hole-transporting layer or the electron-transporting layer. Further, changes in carrier balance over time (in particular, changes in amount of injected electron over time) can be suppressed. Therefore, a long-lifetime light-emitting element which does not easily deteriorate and has a long lifetime can be obtained.

It is preferable that the light-emission colors of the third organic compound included in the functional layer 115 and the first organic compound included in the light-emitting layer 113 be similar colors. Specifically, it is preferable that the difference between a peak value of the emission spectrum of the first organic compound and a peak value of the emission spectrum of the third organic compound be within the range of 30 nm. When the difference in peak values is within 30 nm, the light-emission colors of the third organic compound and the first organic compound can be similar colors. Therefore, even when the third organic compound emits light due to changes in driving voltage or the like, changes in light-emission color can be suppressed. It is to be noted that the third organic compound does not necessarily emit light.

The thickness of the functional layer 115 is preferably in the range of 5 to 20 nm. When the functional layer 115 is too thick, the transport of carriers becomes too slow, which could result in high driving voltage. When the functional layer 115 is too thin, on the other hand, it is impossible to implement the function of controlling the transporting rate of carriers. Therefore, the thickness of the functional layer 115 is preferably in the range of 5 to 20 nm.

In the light-emitting element shown in this embodiment mode, the first organic compound and the third organic compound have similar light-emission colors. Therefore, light emission with good color purity can be obtained even if not only the first organic compound but also the third organic compound emits light. Further, since the anthracene derivative of the present invention exhibits light emission of blue green to yellow green, the element structure shown in this embodiment mode is particularly effective for a light-emitting element for a green color and a light-emitting element for a green color. Blue and green colors are needed for fabrication of full-color displays; therefore, a problem of the deterioration of can be solved by applying the present invention.

Embodiment Mode 7

Embodiment Mode 7 will describe a light-emitting element in which a plurality of light-emitting units according to the present invention is stacked (hereinafter, referred to as a stacked type element) with reference to FIG. 3. This light-emitting element is a light-emitting element that has a plurality of light-emitting units between a first electrode and a second electrode. A structure similar to that described in Embodiment Modes 2 to 6 can be used for each light-emitting unit. In other words, the light-emitting elements described in Embodiment Modes 2 to 6 are each a light-emitting element having one light-emitting unit. In this embodiment mode, a light-emitting element having a plurality of light-emitting units will be explained.

Figure 3:
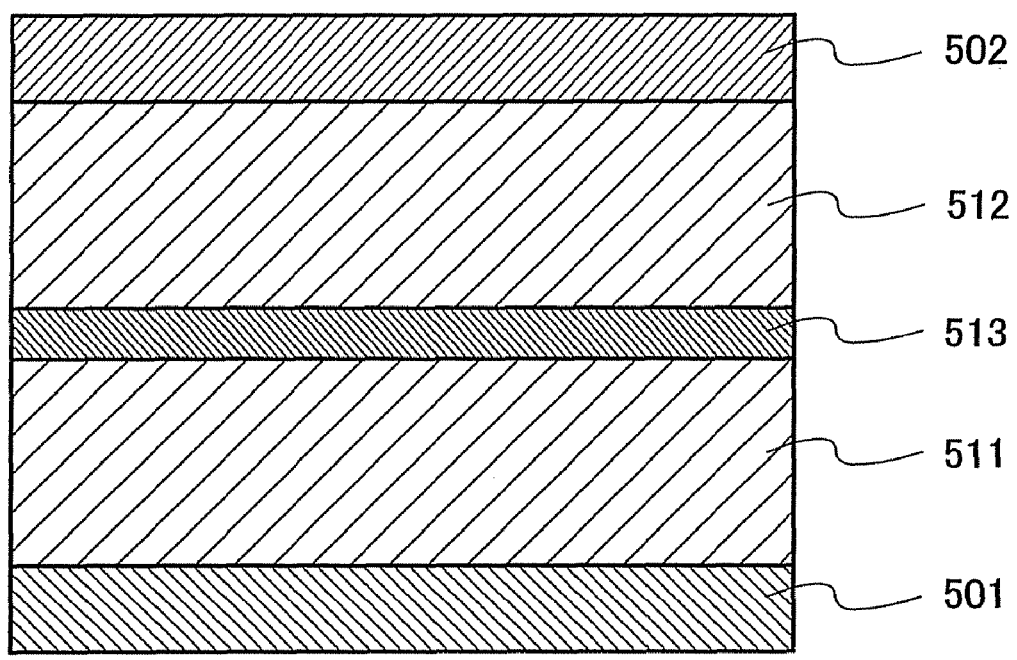
FIG. 3 illustrates a light-emitting element according to an aspect of the present invention.

In FIG. 3, a first light-emitting unit 511 and a second light-emitting unit 512 are stacked between a first electrode 501 and a second electrode 502, a charge generation layer 513 is provided between the first light-emitting unit 511 and the second light-emitting unit 512. Electrodes similar to that described in Embodiment Mode 2 can be applied to the first electrode 501 and the second electrode 502. The first light-emitting unit 511 and the second light-emitting unit 512 may have the same structure or different structures, and a structure similar to those described in Embodiment Modes 2 to 6 can be applied.

The charge generation layer 513 includes a composite material of an organic compound and metal oxide. The composite material of an organic compound and metal oxide is described in Embodiment Mode 2 or 5, and includes an organic compound and metal oxide such as vanadium oxide, molybdenum oxide, or tungsten oxide. As the organic compound, various compounds such as an aromatic amine compound, a carbazole derivative, aromatic hydrocarbon, and a high molecular compound (oligomer, dendrimer, polymer, or the like) can be used. An organic compound having a hole mobility of greater than or equal to $1\times10^{-6}$ cm$^2$/Vs is preferably applied as the organic compound. However, other substances than these compounds may also be used as long as the hole-transporting properties thereof are higher than the electron-transporting properties thereof. The composite material of an organic compound and metal oxide is superior in carrier-injecting property and carrier-transporting property; accordingly, low-voltage driving and low-current driving can be realized.

It is to be noted that the charge generation layer 513 may be formed with a combination of a layer including a composite material of an organic compound and metal oxide with a layer including another material. For example, the charge generation layer 513 may be formed with a combination of a layer including the composite material of an organic compound and metal oxide with a layer including one compound selected among electron donating substances and a compound having a high electron-transporting property. Further, the charge generation layer 513 may be formed with a combination of a layer including the composite material of an organic compound and metal oxide with a transparent conductive film.

In any case, the charge generation layer 513 interposed between the first light-emitting unit 511 and the second light-emitting unit 512 is acceptable, as long as electrons are injected to one light-emitting unit and holes are injected to the other light-emitting unit when a voltage is applied between the first electrode 501 and the second electrode 502.

In this embodiment mode, the light-emitting element having two light-emitting units is explained; however, the present invention can be applied to a light-emitting element in which three or more light-emitting units are stacked, similarly. By arranging a plurality of light-emitting units between a pair of electrodes in such a manner that the plurality of light-emitting units is partitioned with a charge generation layer, high luminance emission can be realized at a low current density, which contributes to enhancement of the lifetime of the light-emitting element. For example, when the light-emitting element is applied to a lighting device, voltage drop due to resistance of an electrode material can be suppressed, which leads to uniform emission in a large area. In other words, a light-emitting device capable of low-voltage driving and low-power consuming can be realized.

This embodiment mode can be combined with another embodiment mode as appropriate.

Embodiment Mode 8

Embodiment Mode 8 will describe a light-emitting device manufactured using an anthracene derivative of the present invention.

Figure 4A:
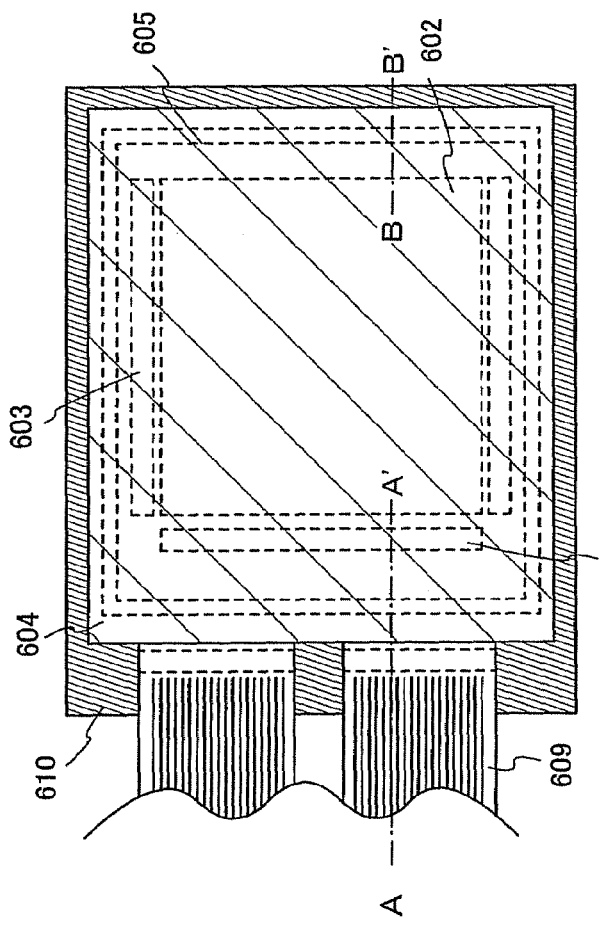
FIGS. 4A and 4B illustrate a light-emitting device according to an aspect of the present invention.
Figure 4B:
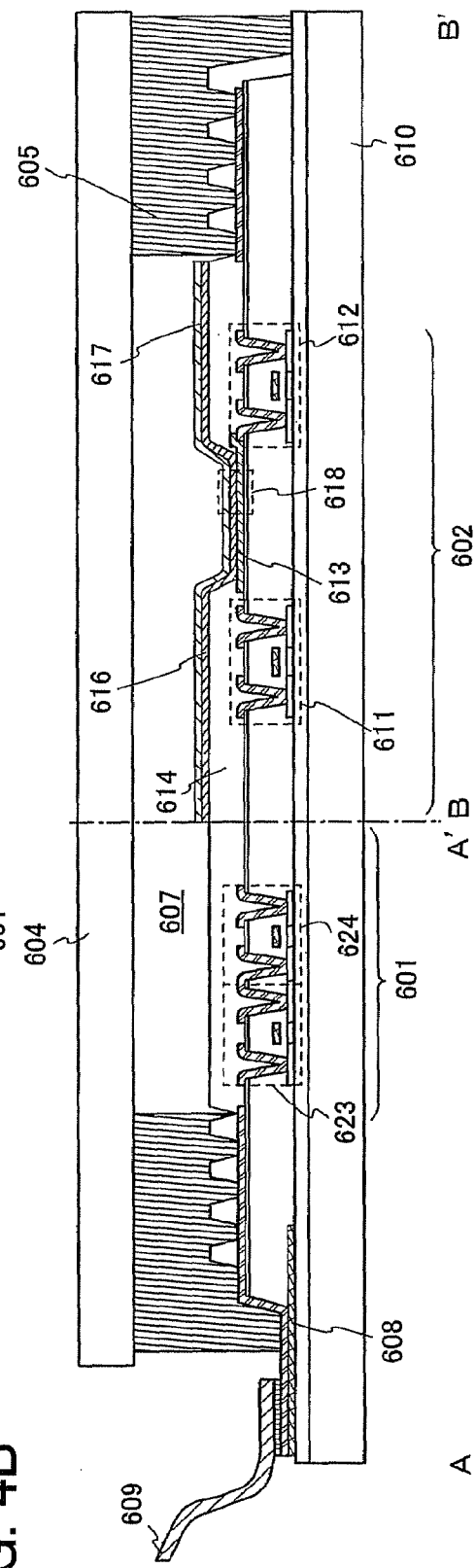

In this embodiment mode, a light-emitting device manufactured using the anthracene derivative of the present invention will be explained with reference to FIGS. 4A and 4B. FIG. 4A is a top view showing a light-emitting device, and FIG. 4B is a cross-sectional view of FIG. 4A taken along lines A-A' and B-B'. A driver circuit portion (source side driver circuit), a pixel portion, and a driver circuit portion (gate side driver circuit) are denoted by reference numerals 601, 602, and 603, respectively, and are indicated by dotted lines. Also, a sealing substrate and a sealing material are denoted by reference numerals 604 and 605, respectively, and a portion surrounded by the sealing material 605 corresponds to a space 607.

A leading wiring 608 is a wiring for transmitting a signal to be inputted to the source side driver circuit 601 and the gate side driver circuit 603, and this wiring 608 receives a video signal, a clock signal, a start signal, a reset signal, and the like from an FPC (flexible printed circuit) 609 that is an external input terminal. It is to be noted that only the FPC is shown here; however, the FPC may be provided with a printed wiring board (PWB). The light-emitting device in this specification includes not only a light-emitting device itself but also a light-emitting device attached with an FPC or a PWB.

Subsequently, a cross-sectional structure will be explained with reference to FIG. 4B. The driver circuit portion and the pixel portion are formed over an element substrate 610. Here, the source side driver circuit 601, which is the driver circuit portion, and one pixel in the pixel portion 602 are shown.

A CMOS circuit, which is a combination of an N-channel TFT 623 and a P-channel TFT 624, is formed as the source side driver circuit 601. The driver circuit may be formed with various types of circuits such as CMOS circuits, PMOS circuits, or NMOS circuits. Although a driver-integration type device, in which a driver circuit is formed over the substrate provided with the pixel portion, is described in this embodiment mode, a driver circuit is not necessarily formed over the substrate provided with the pixel portion, but can be formed outside a substrate.

The pixel portion 602 has a plurality of pixels, each of which includes a switching TFT 611, a current control TFT 612, and a first electrode 613 which is electrically connected to a drain of the current control TFT 612. It is to be noted that an insulator 614 is formed so as to cover an edge portion of the first electrode 613. Here, a positive photosensitive acrylic resin film is used for the insulator 614.

The insulator 614 is formed so as to have a curved surface having curvature at an upper end portion or a lower end portion thereof in order to obtain favorable coverage. For example, in a case of using positive photosensitive acrylic resin as a material for the insulator 614, the insulator 614 is preferably formed so as to have a curved surface with a curvature radius (0.2 μm to 3 μm) only at the upper end portion thereof. Either a negative type resin which becomes insoluble in an etchant by photo-irradiation or a positive type resin which becomes soluble in an etchant by photo-irradiation can be used for the insulator 614.

An EL layer 616 and a second electrode 617 are formed over the first electrode 613. Here, a material having a high work function is preferably used as a material for the first electrode 613 serving as an anode. For example, the first electrode 613 can be formed by using stacked layers of a titanium nitride film and a film including aluminum as its main component; a three-layer structure of a titanium nitride film, a film including aluminum as its main component, and a titanium nitride film; or the like, as well as a single-layer film such as an ITO film, an indium tin oxide film including silicon, an indium oxide film including 2 to 20 wt % of zinc oxide, a titanium nitride film, a chromium film, a tungsten film, a Zn film, or a Pt film. When the first electrode 613 has a stacked structure, the first electrode 613 shows resistance low enough to serve as a wiring, giving an good ohmic contact, so that the first electrode 613 can function as an anode.

In addition, the EL layer 616 is formed by various methods such as an evaporation method using an evaporation mask, an inkjet method, and a spin coating method. The EL layer 616 has an anthracene derivative of the present invention described in Embodiment Mode 1. Further, the EL layer 616 may be formed using another material such as a low molecular compound, oligomer and dendrimer or a high molecular compound.

As a material used for the second electrode 617, which is formed over the EL layer 616 and serves as a cathode, a material having a low work function (Al, Mg, Li, Ca, or an alloy or a compound thereof such as MgAg, MgIn, AlLi, LiF, or $CaF_2$) is preferably used. In a case where light generated in the EL layer 616 is transmitted through the second electrode 617, stacked layers of a metal thin film with reduced thickness and a transparent conductive film (ITO, indium oxide including 2 to 20 wt % of zinc oxide, indium oxide-tin oxide including silicon or silicon oxide, zinc oxide (ZnO), or the like) are preferably used as the second electrode 617.

By attachment of the sealing substrate 604 to the element substrate 610 with the sealing material 605, a light-emitting element 618 is provided in the space 607 surrounded by the element substrate 610, the sealing substrate 604, and the sealing material 605. It is to be noted that the space 607 is filled with filler. There are cases where the space 607 is filled with an inert gas (nitrogen, argon, or the like, or the space 607 is filled with the sealing material 605.

It is to be noted that an epoxy-based resin is preferably used as the sealing material 605. It is desired that the material allows as little moisture and oxygen as possible to penetrate. As the sealing substrate 604, a plastic substrate formed using FRP (Fiberglass-Reinforced Plastics), PVF (polyvinyl fluoride), polyester, acrylic resin, or the like can be used as well as a glass substrate or a quartz substrate.

By the abovementioned process, a light-emitting device having the anthracene derivative of the present invention can be obtained.

Since the anthracene derivative described in Embodiment Mode 1 is used for the light-emitting device of the present invention, a light-emitting device having high performance can be obtained. Specifically, a light-emitting device having a long lifetime can be obtained.

Also, since the anthracene derivative of the present invention has high luminous efficiency, a light-emitting device with low power consumption can be provided.

Further, since anthracene derivatives of the present invention are capable of blue light emission or green light emission with high efficiency, the anthracene derivatives can be favorably used for a full-color display. Further, since the anthracene derivatives of the present invention are capable of blue light emission or green light emission with a long lifetime, it can be favorably used for full-color displays.

As described above, in this embodiment mode, an active matrix light-emitting device in which driving of a light-emitting element is controlled by a transistor is explained. Alternatively, a passive matrix light-emitting device may also be used.

Figure 5A:
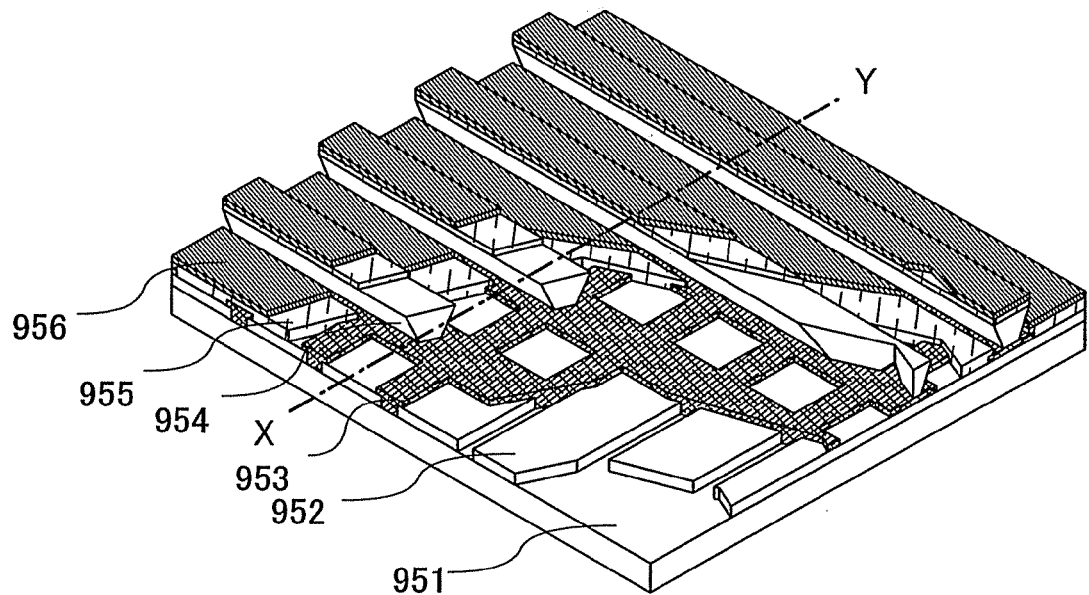
FIGS. 5A and 5B illustrate a light-emitting device according to an aspect of the present invention.
Figure 5B:
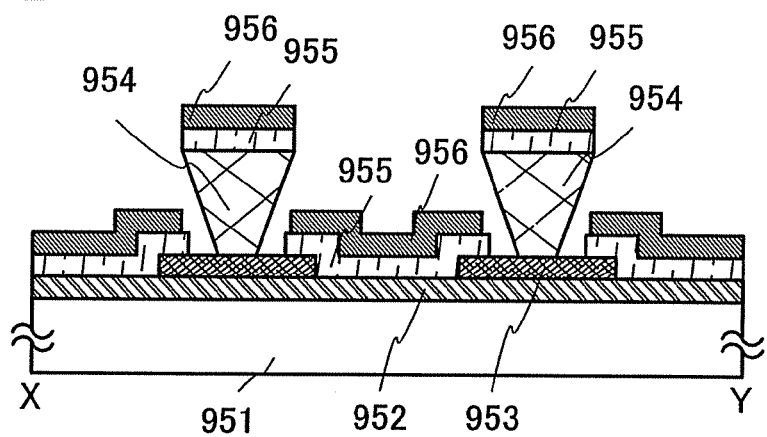

FIGS. 5A and 5B show a passive matrix light-emitting device which is manufactured by applying the present invention. FIG. 5A is a perspective view showing the passive matrix light-emitting device, and FIG. 5B is a sectional view taken along the section X-Y of FIG. 5A. In FIG. 5A, an EL layer 955 is provided between an electrode 952 and an electrode 956 over a substrate 951. An end portion of the electrode 952 is covered with an insulating layer 953. Then, a partition layer 954 is provided over the insulating layer 953. A side wall of the partition layer 954 slopes so that a distance between one side wall and the other side wall becomes narrow toward a substrate surface. In other words, a cross section of the partition layer 954 in the direction of a short side is trapezoidal, and a base (a side expanding in a similar direction as a plane direction of the insulating layer 953 and in contact with the insulating layer 953) is shorter than an upper side (a side expanding in a similar direction as the plane direction of the insulating layer 953 and not in contact with the insulating layer 953). The partition layer 954 provided in this manner allows patterning the electrode 956. By using the light-emitting element of the present invention to a passive matrix light-emitting device, the passive matrix light-emitting device can have a long lifetime. Further, a light-emitting device with low power consumption can be provided.

Embodiment Mode 9

Embodiment Mode 9 will describe electronic devices of the present invention including the light-emitting device described in Embodiment Mode 8. The electronic devices of the present invention include the anthracene derivatives described in Embodiment Mode 1, and has display portions with long lifetime. Also, the electronic devices of the present invention possess a display portion with reduced power consumption.

As electronic devices including light-emitting elements fabricated using the anthracene derivative of the present invention, cameras such as video cameras or digital cameras, goggle type displays, navigation systems, audio reproducing devices (car audio component stereo, audio component stereo, or the like), computers, game machines, portable information terminals (mobile computers, mobile phones, portable game machines, electronic books, or the like), and image reproducing devices provided with a recording medium (specifically, a device capable of reproducing content of a recording medium such as a Digital Versatile Disc (DVD) and provided with a display device that can display the image), and the like are given. Specific examples of these electronic devices are shown in FIGS. 6A to 6D.

Figure 6A:
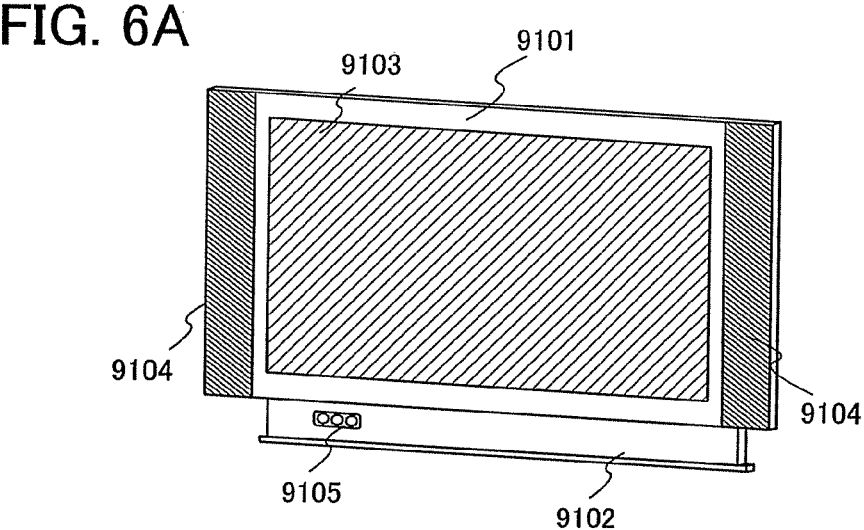
FIGS. 6A to 6D illustrate electronic devices according to an aspect of the present invention.

FIG. 6A shows a television device according to the present invention, which includes a housing 9101, a supporting base 9102, a display portion 9103, a speaker portion 9104, a video input terminal 9105, and the like. In the television device, the display portion 9103 has light-emitting elements similar to those described in Embodiment Modes 2 to 7, and the light-emitting elements are arranged in matrix. The features of the light-emitting element are exemplified by the luminous efficiency and long lifetime. The display portion 9103 which includes the light-emitting elements has similar features. Therefore, in the television device, image quality is scarcely deteriorated and low power consumption is achieved. Therefore, deterioration compensation function circuits and power supply circuits can be significantly reduced or downsized in the television device, which enables reduction of the size and weight of the housing 9101 and supporting base 9102. In the television device according to the present invention, low power consumption, high image quality, and small size and lightweight are achieved; therefore, products suitable for living environment can be provided. Also, since the anthracene derivatives described in Embodiment Mode 1 are capable of blue light emission or green light emission, full-color display is possible, and television devices having a display portion with long life can be provided.

Figure 6B:
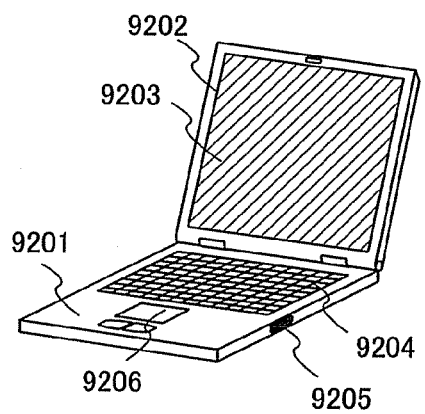

FIG. 6B shows a computer according to the present invention, which includes a main body 9201, a housing 9202, a display portion 9203, a keyboard 9204, an external connection port 9205, a pointing device 9206, and the like. In the computer, the display portion 9203 has light-emitting elements similar to those described in Embodiment Modes 2 to 7, and the light-emitting elements are arranged in matrix. The features of the light-emitting element are given by high luminous efficiency and long lifetime. The display portion 9203 which includes the light-emitting elements has similar features. Therefore, in the computer, image quality is scarcely deteriorated and lower power consumption is achieved. Due to these features, deterioration compensation function circuits and power supply circuits can be significantly reduced or downsized in the computer; therefore, small sized and lightweight main body 9201 and housing 9202 can be achieved. In the computer according to the present invention, low power consumption, high image quality, and small size and lightweight are achieved; therefore, products suitable for an environment can be supplied. Further, since the anthracene derivative described in Embodiment Mode 1 is capable of blue light-emission or green light emission, full-color display is possible, and computers having a display portion with a long lifetime can be provided.

Figure 6C:
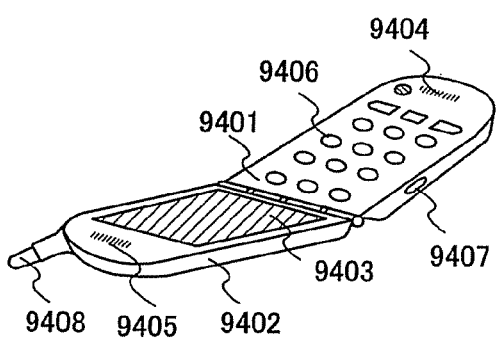

FIG. 6C shows a mobile phone according to the present invention, which includes a main body 9401, a housing 9402, a display portion 9403, an audio input portion 9404, an audio output portion 9405, an operation key 9406, an external connection port 9407, an antenna 9408, and the like. In the mobile phone, the display portion 9403 has light-emitting elements similar to those described in Embodiment Modes 2 to 7, and the light-emitting elements are arranged in matrix. The features of the light-emitting element are exemplified by high luminous efficiency and long lifetime. The display portion 9403 which includes the light-emitting elements has similar features. Therefore, in the mobile phone, image quality is scarcely deteriorated and lower power consumption is achieved. Owing to these features, deterioration compensation function circuits and power supply circuits can be significantly reduced or downsized in the mobile phone; therefore, small sized and lightweight main body 9401 and housing 9402 can be supplied. In the mobile phone according to the present invention, low power consumption, high image quality, and a small size and lightweight are achieved; therefore, products suitable for carrying can be provided. Further, since the anthracene derivative described in Embodiment Mode 1 is capable of blue light emission or green light emission, full-color display is possible, and mobile phones having a display portion with a long lifetime can be provided.

Figure 6D:
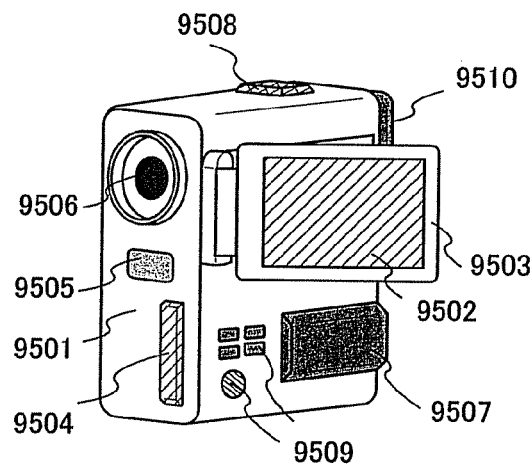

FIG. 6D shows a camera according to the present invention, which includes a main body 9501, a display portion 9502, a housing 9503, an external connection port 9504, a remote control receiving portion 9505, an image receiving portion 9506, a battery 9507, an audio input portion 9508, operation keys 9509, an eye piece portion 9510, and the like. In the camera, the display portion 9502 has light-emitting elements similar to those described in Embodiment Modes 2 to 7, and the light-emitting elements are arranged in matrix. Some features of the light-emitting element are its high luminous efficiency and long lifetime. The display portion 9502 which includes the light-emitting elements has similar features. Therefore, in the camera, image quality is hardly deteriorated and lower power consumption can be achieved. Such features contribute to significant reduction and downsizing of the deterioration compensation function circuits and power supply circuits in the camera; therefore, a small sized and lightweight main body 9501 can be supplied. In the camera according to the present invention, low power consumption, high image quality, and small size and lightweight are achieved; therefore, products suitable for carrying can be provided. Further, the anthracene derivative described in Embodiment Mode 1 is capable of blue light emission or green light emission, full-color display is possible, and cameras having a display portion with a long lifetime can be provided.

As described above, the applicable range of the light-emitting devices of the present invention is so wide that the light-emitting devices can be applied to electronic devices in various fields. By using the anthracene derivatives of the present invention, electronic devices which have display portions with a long lifetime can be provided.

Such light-emitting devices of the present invention can also be used for a lighting device. One mode using the light-emitting device of the present invention as the lighting device will be explained with reference to FIG. 7.

Figure 7:
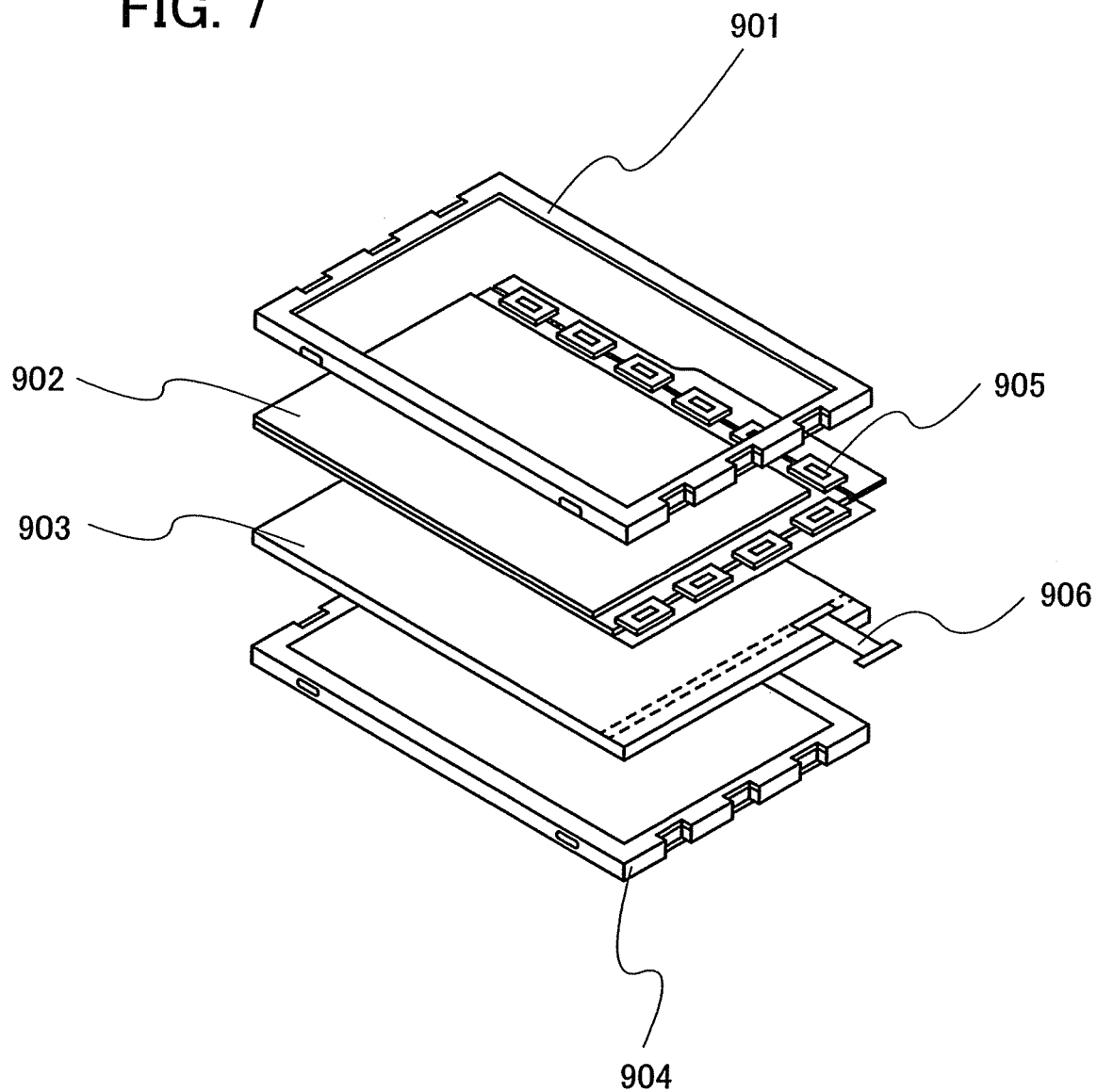
FIG. 7 illustrates an electronic device according to an aspect of the present invention.

FIG. 7 shows an example of a liquid crystal display device using the light-emitting device of the present invention as a backlight. The liquid crystal display device shown in FIG. 7 includes a housing 901, a liquid crystal layer 902, a backlight 903, and a housing 904, and the liquid crystal layer 902 is connected to a driver IC 905. The light-emitting device of the present invention is used for the backlight 903, and current is supplied through a terminal 906.

By using the light-emitting device of the present invention as the backlight of the liquid crystal display device, a backlight with reduced power consumption and high luminous efficiency can be provided. The light-emitting device of the present invention is a lighting device with plane light emission, and can have a large area. Therefore, the backlight can have a large area, and a liquid crystal display device having a large area can be provided. Furthermore, the light-emitting device of the present invention has a thin shape and has low power consumption; therefore, a thin shape and low power consumption of a display device can also be achieved. Since the light-emitting device of the present invention has a long lifetime, a liquid crystal display device using the light-emitting device of the present invention also has a long lifetime.

Figure 8:
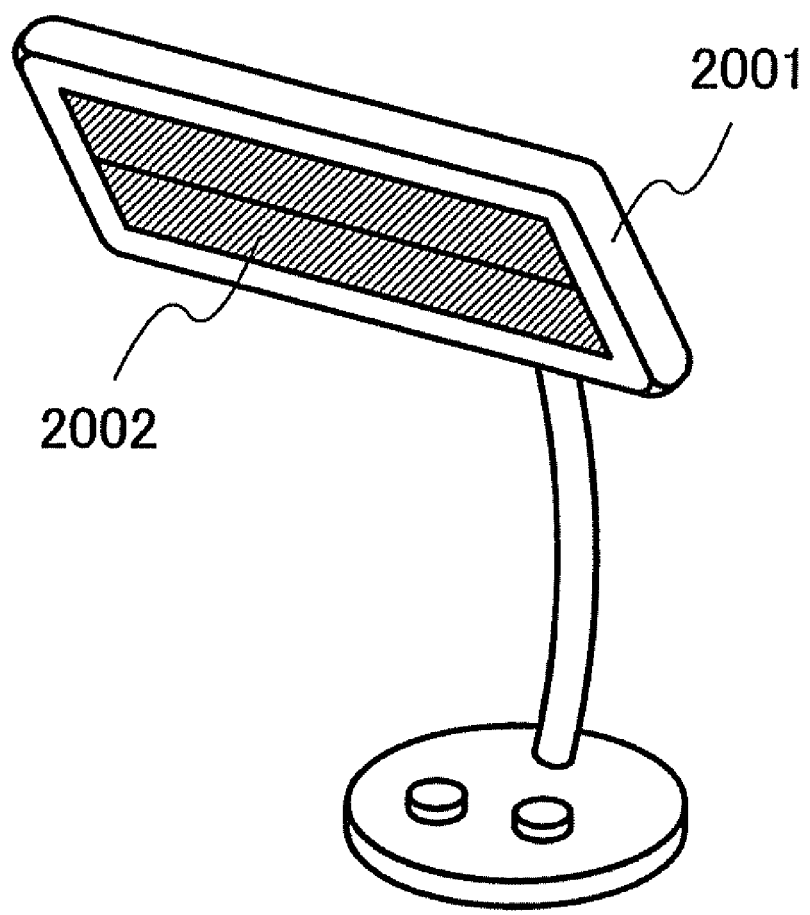
FIG. 8 illustrates a lighting device according to an aspect of the present invention.

FIG. 8 shows an example of using the light-emitting device to which the present invention is applied, as a table lamp which is an example of a lighting device. The table lamp shown in FIG. 8 has a housing 2001 and a light source 2002, and the light-emitting device of the present invention is used as the light source 2002. The light-emitting device of the present invention has high luminous efficiency and has a long lifetime; therefore, the table lamp also has high luminous efficiency and a long lifetime.

Figure 9:
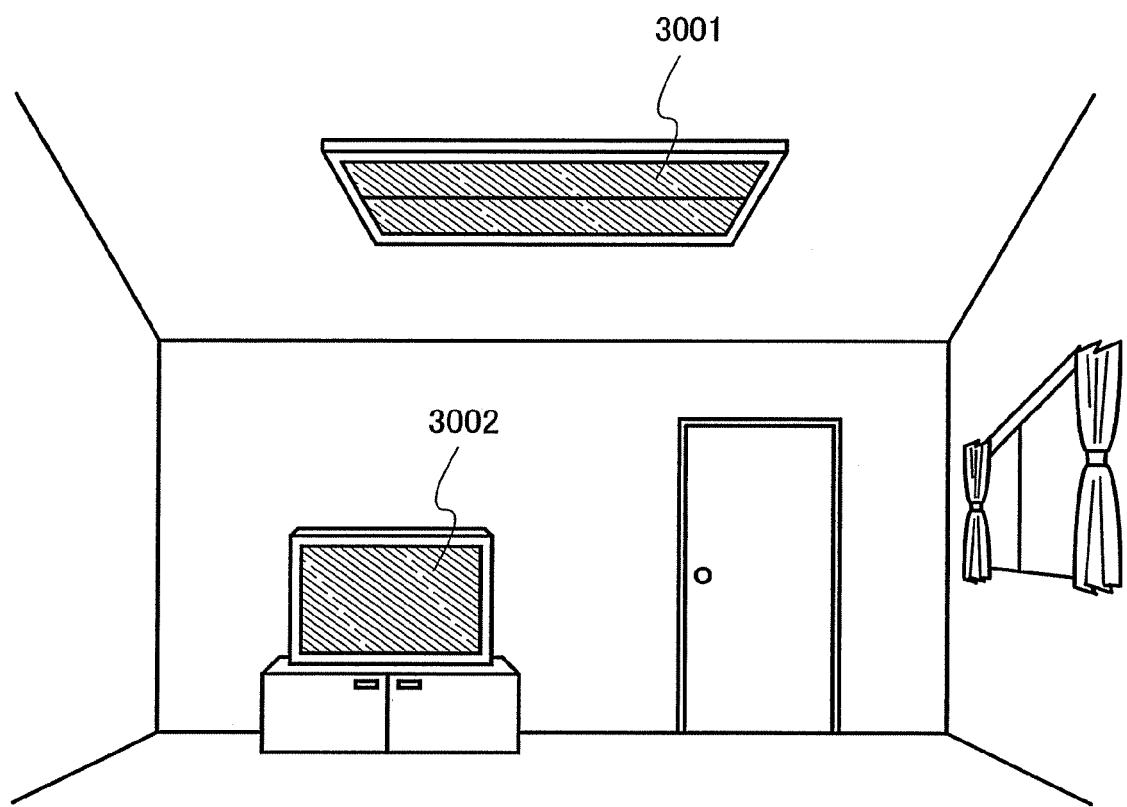
FIG. 9 illustrates a lighting device according to an aspect of the present invention.

FIG. 9 shows an example of using a light-emitting device to which the present invention is applied, as an indoor lighting device 3001. Since the light-emitting device of the present invention can also have a large area, the light-emitting device of the present invention can be used as a lighting device having a large emission area. Further, the light-emitting device of the present invention has a thin shape and consumes low power; therefore, the light-emitting device of the present invention can be used as a lighting device having a thin shape and low-power consumption. A television device 3002 according to the present invention as shown in FIG. 6A is placed in a room in which the light-emitting device fabricated by the present invention is used as the indoor lighting device 3001, and public broadcasting and movies can be watched. In such a case, since both of the devices consume low power, a powerful image can be watched in a bright room without concern about electricity charges.

EXAMPLE 1

Example 1 will specifically describe a synthesis method of an anthracene derivative of the present invention represented by a structural formula (101), 2-{4-[N-(4-diphenylaminophenyl)-N-phenylamino]phenyl}-9,10-diphenylanthracene (abbreviation: 2DPAPPA).

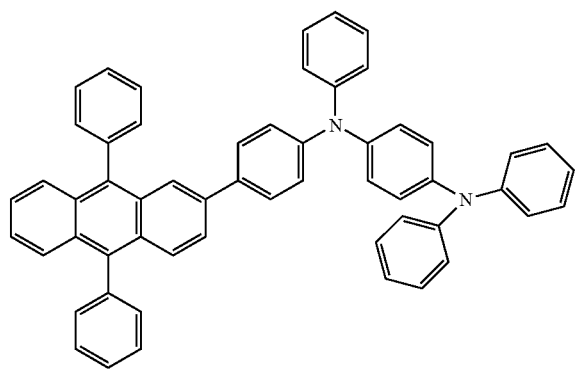

(101)

[Step 1] Synthesis of 2-bromo-9,10-diphenylanthracene (i) Synthesis of 2-bromo-9,10-anthraquinone A synthesis scheme of 2-bromo-9,10-anthraquinone is represented by (C-1).

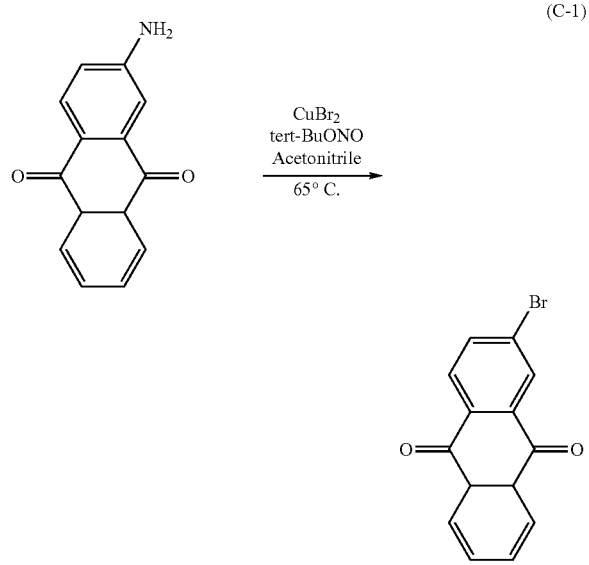

(C-1)

46 g (0.20 mol) of copper(II) bromide and 500 mL of acetonitrile were put in a 1 L three-neck flask. Further, 17 g (0.17 mol) of tert-butyl nitrite was added thereto, and the mixture was heated to 65° C. 25 g (0.11 mol) of 2-amino-9,10-anthraquinone was added to the mixture and stirred for six hours at the same temperature. After reaction, the reaction solution was poured into 500 mL of hydrochloric acid (3 mol/L) and this suspension was stirred for three hours, so that a solid substance was precipitated. The precipitation was collected by suction filtration and washed with water and ethanol while being subjected to suction filtration. The residue was dissolved in toluene and was subjected to suction filtration through Florisil (manufactured by Floridin Company), Celite (manufactured by Celite Co., Ltd.), and alumina, and the filtrate was obtained. The obtained filtrate was concentrated, so that a solid substance was obtained. The obtained solid substance was recrystallized with a mixed solvent of chloroform and hexane, so that 18.6 g of a milky white powdered solid substance, 2-bromo-9,10-anthraquinone was obtained in 58% yield.

(ii) Synthesis of 2-bromo-9,10-diphenyl-9,10-dihydroanthracene-9,10-diol

A synthesis scheme of 2-bromo-9,10-diphenyl-9,10-dihydroanthracene-9,10-diol is shown in (C-2).

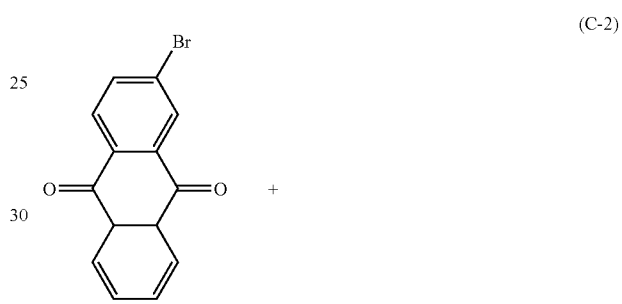

(C-2)

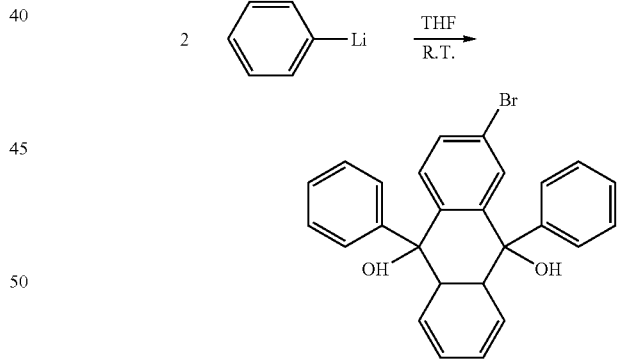

4.9 g (17 mmol) of 2-bromo-9,10-anthraquinone was put in a 300 mL three-neck flask, the atmosphere in the flask was substituted by nitrogen, and 100 mL of tetrahydrofuran (THF) was added thereto and dissolved well. Then, 18 mL (37 mmol) of phenyllithium was dropped into this solution and stirred at room temperature for about 12 hours. After reaction, the solution was washed with water, and an aqueous layer was extracted with ethyl acetate. The extracted solution and an organic layer were dried with magnesium sulfate. After drying, the mixture was subjected to suction filtration, and the filtrate was concentrated, so that 2-bromo-9,10-diphenyl-9,10-dihydroanthracene-9,10-diol (about 7.6 g) was obtained.

(iii) Synthesis of 2-bromo-9,10-diphenylanthracene

A synthesis scheme (C-3) of 2-bromo-9,10-diphenylanthracene is shown in (C-3).

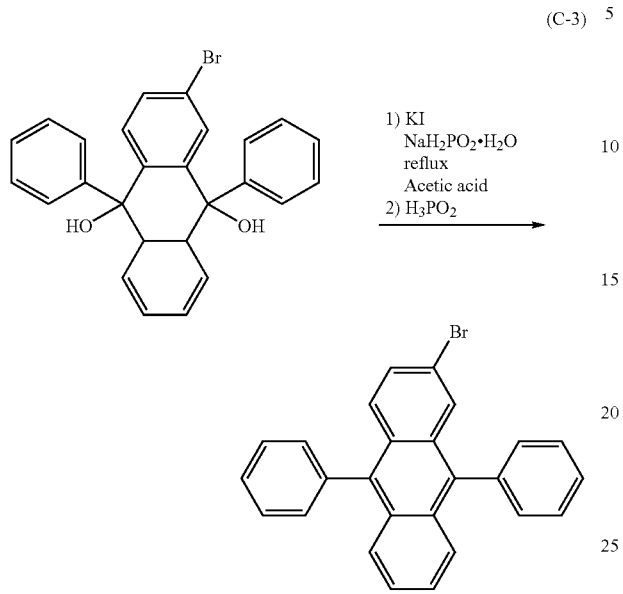

(C-3)

About 7.6 g (17 mmol) of the obtained 2-bromo-9,10-diphenyl-9,10-dihydroanthracene-9,10-diol, 5.1 g (31 mmol) of potassium iodide, 9.7 g (92 mmol) of sodium phosphinate monohydrate, and 50 mL of glacial acetic acid were put into a 500 mL three-neck flask, and the mixture was refluxed at 120° C. for two hours. Thereafter, 30 mL of 50% phosphinic acid was added to the reactive mixture, and the mixture was stirred for one hour at 120° C. After the reaction, the solution was washed with water, and the aqueous layer was extracted with ethyl acetate. The extracted solution and an organic layer were dried with magnesium sulfate, filtered by suction filtration and the obtained filtrate was concentrated to obtain a solid substance. The solid substance was dissolved in toluene, and the solution was filtered through Celite (manufactured by Celite Co., Ltd.), Florisil (manufactured by Floridin Company), and alumina. The obtained filtrate was concentrated to obtain a solid substance, and the solid substance was recrystallized with a mixed solvent of chloroform and hexane, giving 5.1 g of 2-bromo-9,10-diphenylanthracene as a light yellow powdered solid substance. The yield of the two stages (ii) and (iii) was 74%.

[Step 2] Synthesis of 2-(4-bromophenyl)-9,10-diphenylantracene

(i) Synthesis of 2-iodo-9,10-diphenylanthracene

Synthesis scheme of 2-iodo-9,10-diphenylanthracene is shown in (C-4)

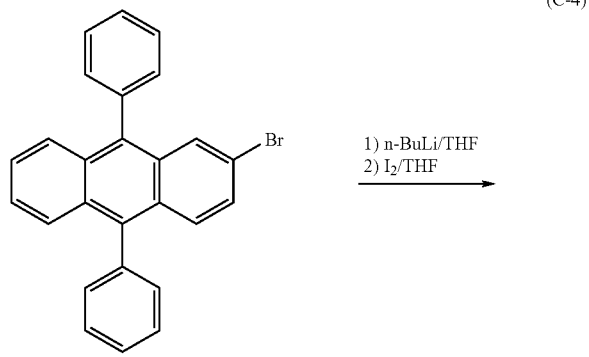

(C-4)

-continued

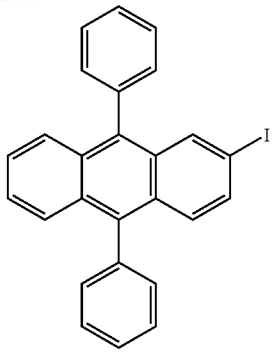

10 g (24 mmol) of 2-bromo-9,10-diphenylanthracene was put in a 500 mL three neck flask, the atmosphere in the flask was substituted by nitrogen, and then 150 mL of tetrahydrofuran (THF) was added thereto and dissolved well. This solution was stirred at −78° C. Then, 19 mL of n-butyllithium solution (1.6 mmol/L) was dropped into this solution, with a syringe and stirred for one hour at −78° C., so that a white solid substance was precipitated. After reaction, a solution in which 12 g (49 mmol) of iodine was dissolved into 80 mL of tetrahydrofuran was dropped into this reacted mixture using a funnel for dropping. After dropping, the mixture was stirred for one hour at −78° C. and for 12 hours at room temperature. After reaction, a sodium thiosulfate solution was added into the reaction solution, and was stirred for one hour at room temperature. Ethyl acetate was added into this mixture for extraction. An aqueous layer and an organic layer were separated, and the organic layer was washed with sodium thiosulfate and saturated brine in this order. The aqueous layer and the organic layer were separated and the organic layer was dried with magnesium sulfate. This mixture was subjected to suction filtration so that the magnesium sulfate was removed. The obtained filtrate was concentrated, so that a solid substance was obtained. Methanol was added into this solid substance and washed by ultrasonic wave irradiation, so that a solid substance was precipitated. This solid substance was collected by suction filtration, so that 9.9 g of a light yellow powdered solid substance was obtained in a yield of 90%.

(ii) Synthesis of 2-(4-bromophenyl)-9,10-diphenylanthracene

Synthesis scheme of 2-(4-bromophenyl)-9,10-diphenylanthracene is shown in (C-5)

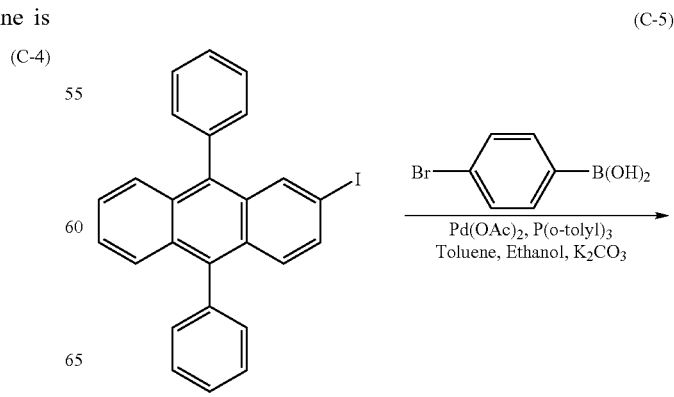

(C-5)

-continued

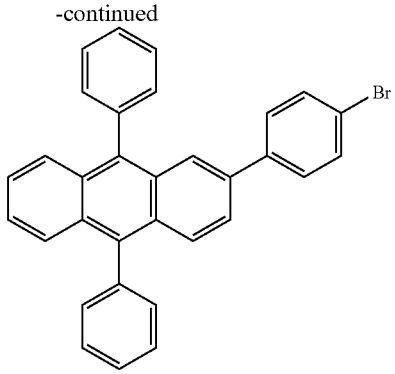

2.0 g (9.9 mmol) of 4-bromophenyl boronic acid, 0.02 g (0.089 mmol) of palladium(0) acetate, 5.0 g (11 mmol) of 2-iodo-9,10-diphenylanthracene, 0.30 g (0.99 mmol) of tris (o-tolyl)phosphine were put into a 200 mL three neck flask, and the atmosphere in the flask was substituted by nitrogen. 50 mL of toluene, 20 mL (2 mol/L) of a potassium carbonate aqueous solution, and 10 mL of ethanol were put into this mixture. This mixture was stirred at 100° C. for eight hours to be reacted. After reaction, toluene was added into the reacted mixture, and this suspension was washed saturated sodium hydrogen carbonate water and a saturated brine in this order. An organic layer and an aqueous layer were separated, and the organic layer was filtrated through Celite (manufactured by Celite Co., Ltd.), alumina, and Florisil (manufactured by Floridin Company), by suction filtration and a filtrate was obtained. The obtained filtrate was concentrated to obtain a solid substance. Methanol was added into this solid substance and washed with ultrasonic wave irradiation, so that a solid substance was precipitated. This solid substance was collected by suction filtration, so that 4.6 g of a light yellow powdered solid substance was obtained in 87% yield. By a nuclear magnetic resonance measurement (NMR), this compound was proved to be 2-(4-bromophenyl)-9,10-diphenylanthracene.

Figure 40A:
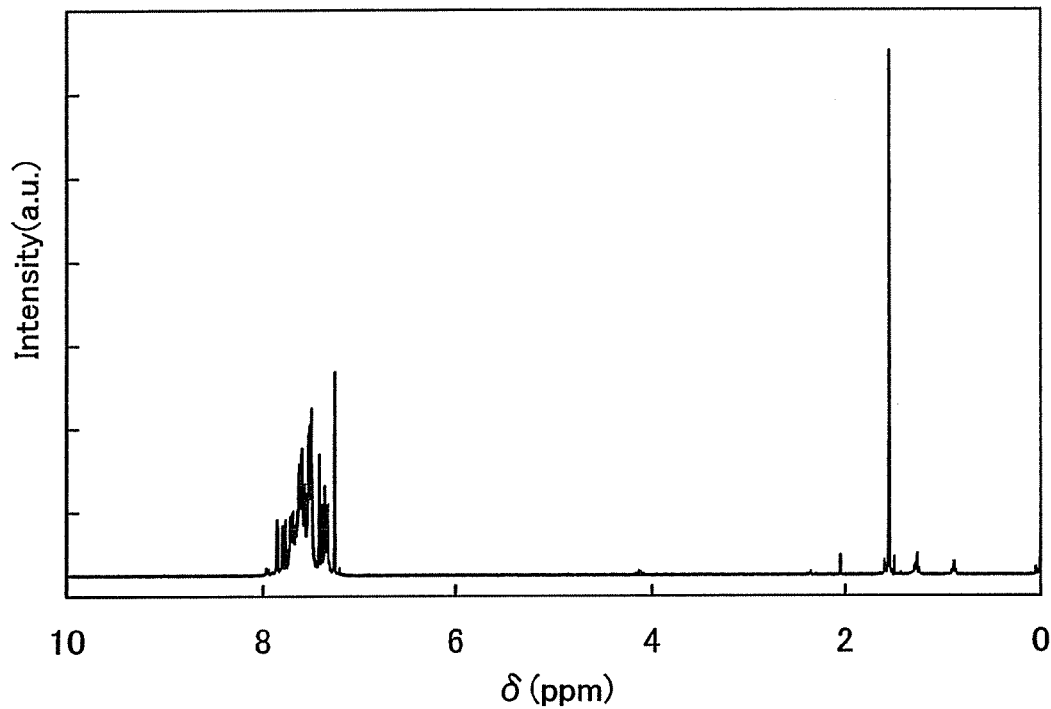
FIGS. 40A and 40B are each a $^1$H NMR chart of 2-(4-bromophenyl)-9,10-diphenylanthracene.
Figure 40B:
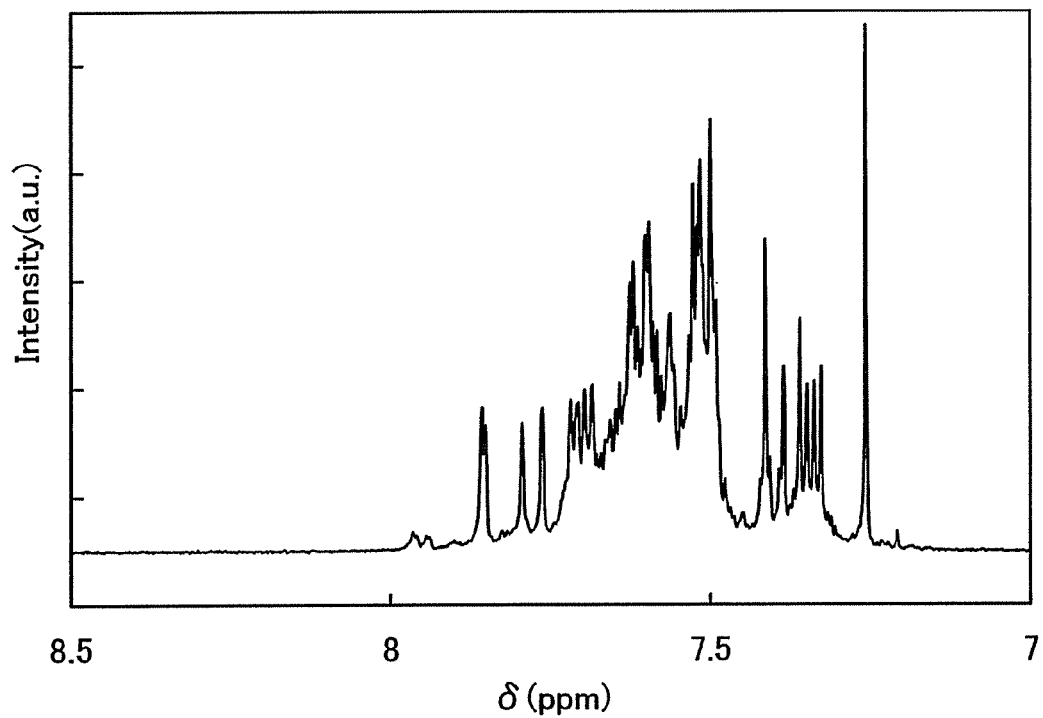

$^1$H NMR data of 2-(4-bromophenyl)-9,10-diphenylanthracene is shown below. $^1$H NMR (CDCl$_3$, 300 MHz): δ=7.33-7.36 (m, 2H), 7.40 (d, J=8.4 Hz, 2H), 7.49-7.72 (m, 15H), 7.78 (d, J=9.3 Hz, 1H), 7.85 (d, J=1.5 Hz, 1H). FIGS. 40A and 40B show $^1$H NMR charts. Note that FIG. 40B is a chart in which the range of 7.0 ppm to 8.5 ppm in FIG. 40A is enlarged.

[Step 3] Synthesis Method of 2DPAPPA

A synthesis scheme of 2DPAPPA is shown in (C-6).

(C-6)

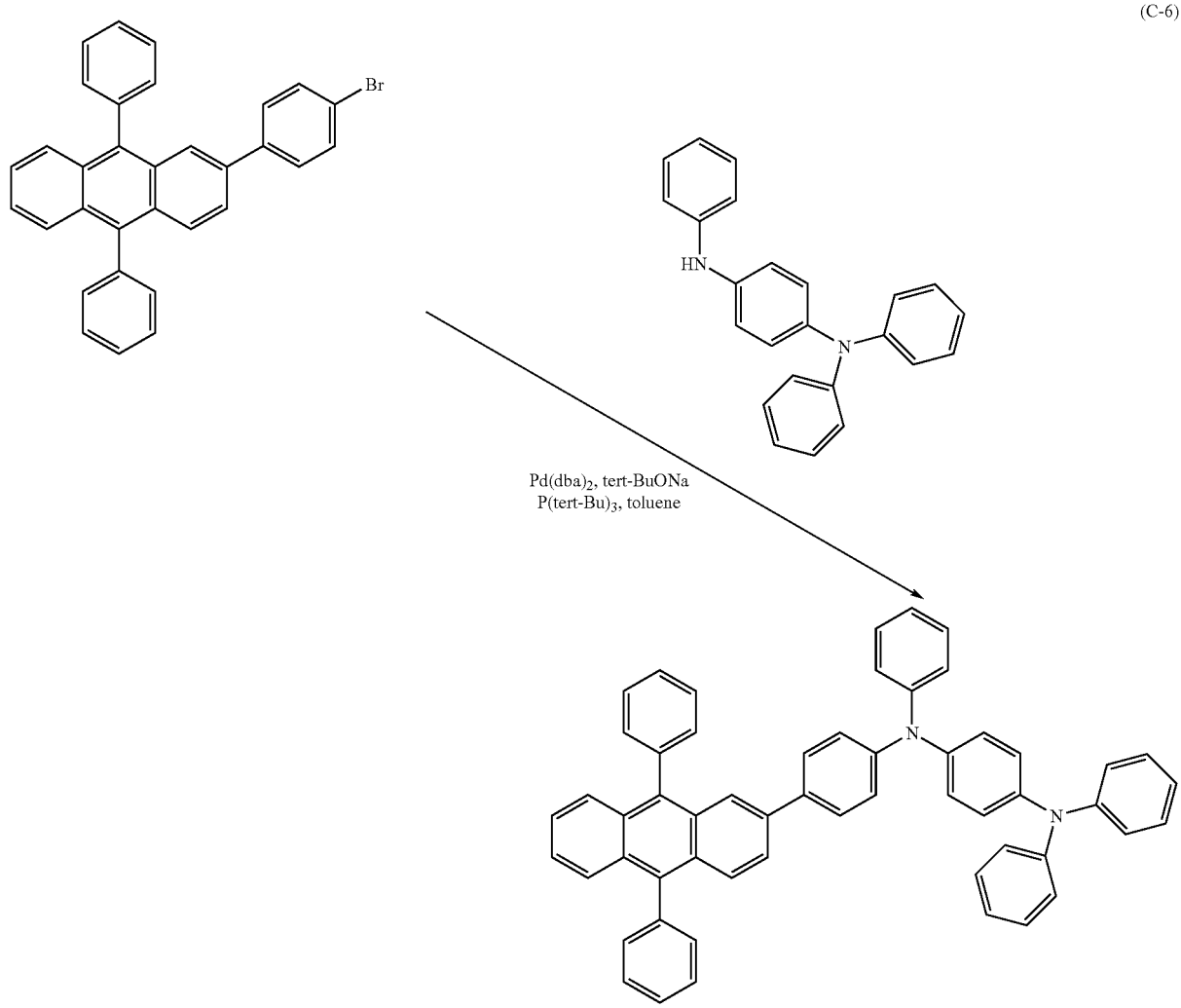

0.84 g (1.7 mmol) of 2-(4-bromophenyl)-9,10-diphenylanthracene synthesized in Step 2 of Example 1, 0.30 g (3.1 mmol) of sodium tert-butoxide, 0.53 g (1.60 mmol) of N,N′,N′-triphenyl-1,4-phenylenediamine, and 0.03 g (0.06 mmol) of bis(dibenzylideneacetone)palladium(0) were put into a 50 mL three-neck flask and the atmosphere in the flask was substituted by nitrogen. 10 mL of toluene and 0.02 mL of tri(tert-butyl)phosphine 10 wt % hexane solution were added to this mixture. This mixture was stirred while being heated at 80° C. for five hours to be reacted. After reaction, toluene was added into the reacted mixture, and this suspension was subjected to suction filtration through Celite (manufactured by Celite Co., Ltd.), Florisil (manufactured by Floridin Company), and alumina so that a filtrate was obtained. The obtained filtrate was washed with water and saturated brine, and magnesium sulfate was added to an organic layer to be dried. This mixture was subjected to suction filtration to remove magnesium sulfate, so that a filtrate was obtained. A solid substance obtained by concentrating the obtained filtrate was purified by silica gel column chromatography (a developing solvent was a mixed solvent of toluene:hexane=1:10 and then a developing solvent was a mixed solvent of toluene: hexane=1:3). The obtained fraction was concentrated to obtain a solid substance. The solid substance was recrystallized with a mixture solvent of dichloromethane and methanol, so that 0.84 g of a light yellow powdered solid substance was obtained in 66% yield. By a nuclear magnetic resonance measurement (NMR), this compound was proved to be 2-{4-[N-(4-diphenylaminophenyl)-N-phenylamino]phenyl}-9,10-diphenylanthracene (abbreviation: 2DPAPPA).

Figure 11A:
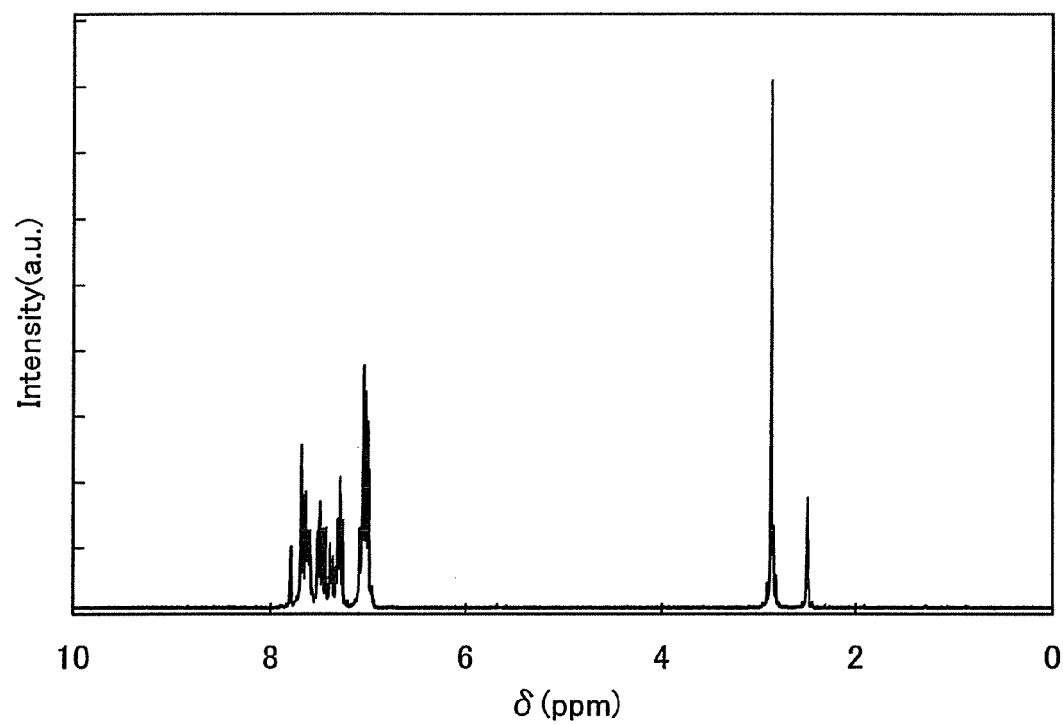
FIGS. 11A and 11B are each a $^1$H NMR chart of 2-{4-[N-(4-diphenylaminophenyl)-N-phenylamino]phenyl}-9,10-diphenylanthracene (abbreviation: 2DPAPPA)
Figure 11B:
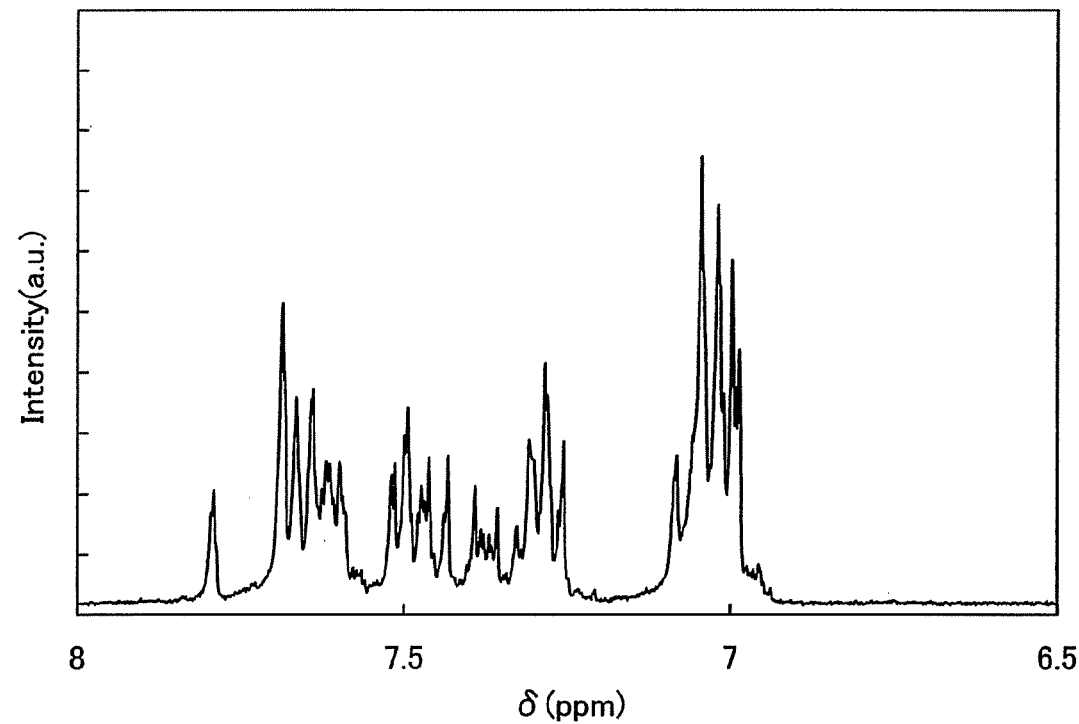

$^1$H NMR data of 2DPAPPA is shown below. $^1$H NMR (DMSO-d$_6$, 300 MHz, 120° C.): δ=6.93-7.12 (m, 15H), 7.24-7.54 (m, 14H), 7.72-7.56 (m, 10H), 7.79 (s, 1H). FIGS. 11A and 11B show $^1$H NMR charts. Note that FIG. 11B is a chart in which the range of 6.5 ppm to 8.0 ppm in FIG. 11A is enlarged.

Figure 12:
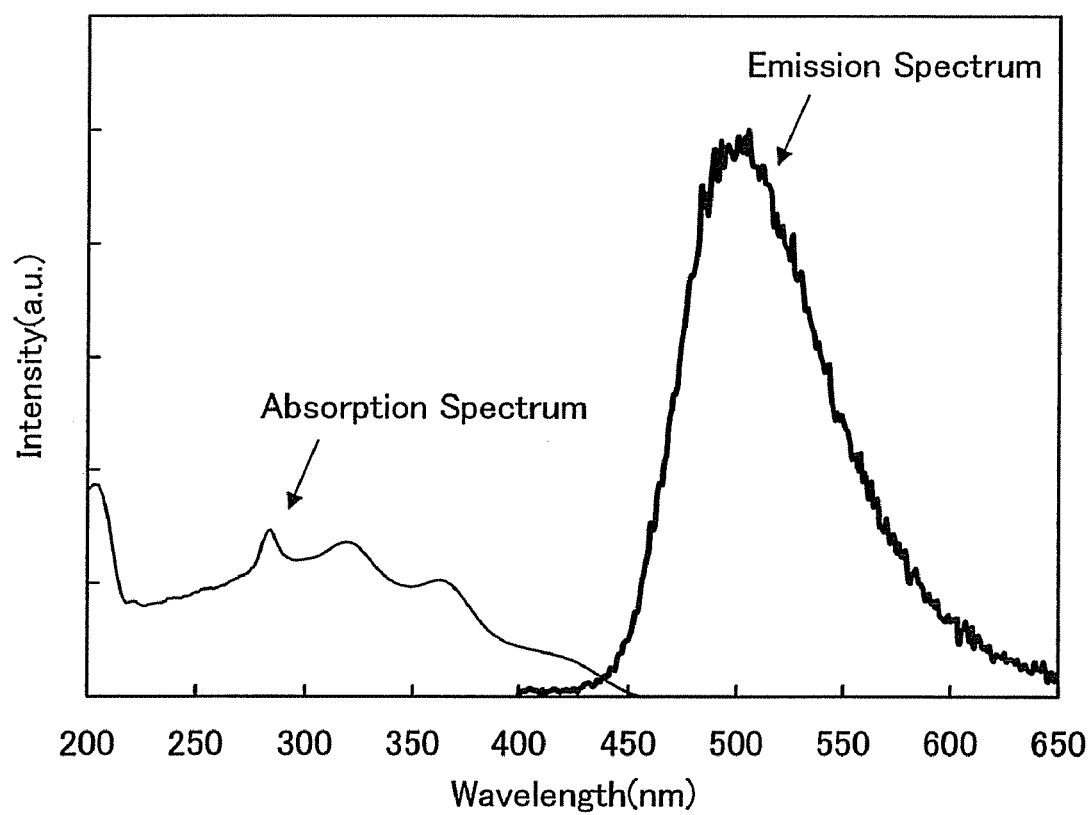
FIG. 12 is a graph showing an absorption spectrum and an emission spectrum of 2-{4-[N-(4-diphenylaminophenyl)-N-phenylamino]phenyl}-9,10-diphenylanthracene (abbreviation: 2DPAPPA)

FIG. 12 shows absorption spectrum and emission spectrum in a toluene solution of 2DPAPPA. An ultraviolet-visible spectrophotometer (V550, manufactured by Japan Spectroscopy Corporation) was used for measurement. The solution was put in a quartz cell and the absorption spectrum of the solution and the quartz cell was measured. The absorption spectrum of the solution which was obtained by subtracting the absorption spectrum of the quartz cell from the absorption spectrum of the solution and the quartz cell is shown in FIG. 12. In FIG. 12, the horizontal axis shows wavelength (nm) and the vertical axis shows intensity (an arbitrary unit). In the case of the toluene solution, absorptions were observed at around 284 nm, 319 nm and 362 nm. In the case of the toluene solution, the maximum emission wavelength was 505 nm (excitation wavelength of 361 nm).

In addition, when the ionizing potential of 2DPAPPA in a thin film state was measured with a photoelectron spectrometer (AC-2, manufactured by RIKEN KEIKI CO., LTD) in the air, the ionizing potential was 5.26 eV. As a result, the HOMO level was proved to be −5.26 eV. Further, an absorption edge was obtained from a Tauc plot assuming direct transition by using the data of the absorption spectrum of 2DPAPPA in the thin film state, and the absorption edge was regarded as an optical energy gap. The energy gap was 2.65 eV. Therefore, a LUMO level of −2.61 eV was obtained from the obtained values of the energy gap value and HOMO level.

EXAMPLE 2

Example 2 will specifically describe a synthesis method of 2-{4-[N-phenyl-N-(9-phenylcarbazol-3-yl)amino]phenyl}-9,10-diphenylanthracene (abbreviation: 2PCAPPA), represented by a structural formula (132).

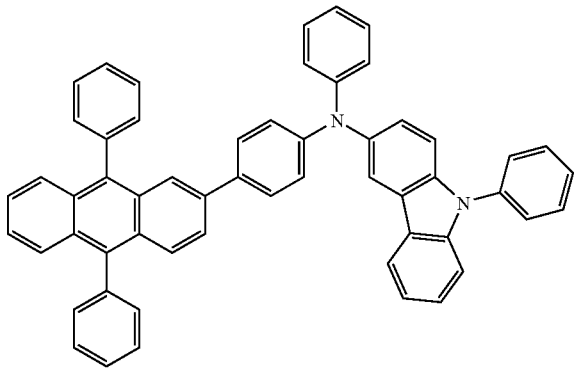

(132)

[Step 1] Synthesis of N-phenyl-(9-phenyl-9H-carbazol-3-yl)amine (abbreviation PCA)

(i) Synthesis of 3-bromo-9-phenylcarbazole

A synthesis scheme of 3-bromo-9-phenylcarbazole is shown in (D-1).

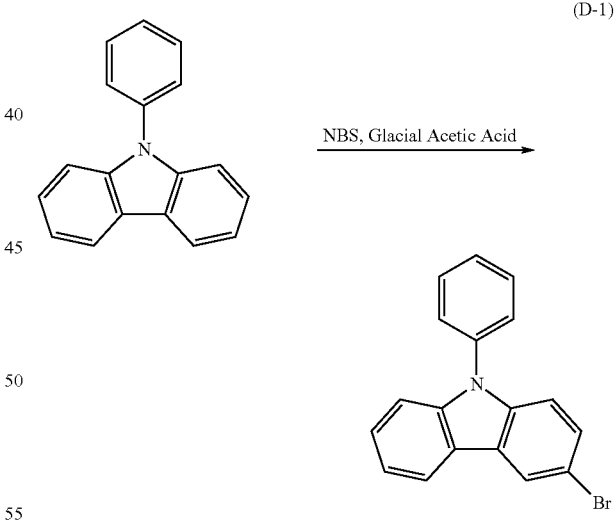

(D-1)

24.3 g (100 mmol) of 9-phenylcarbazole was put into a 2 L Meyer flask, and dissolved in 600 mL of glacial acetic acid. Then, 17.8 g (100 mmol) of N-bromosuccinimide was slowly added thereto, and the solution was stirred at room temperature for about 12 hours. This glacial acetic acid solution was dropped into 1 L of ice water while being stirred. A white solid substance precipitated was collected by suction filtration, and then washed with water three times. This solid substance was dissolved in 150 mL of diethyl ether, and the solution was washed with a saturated sodium hydrogen carbonate aqueous solution and then with water. The organic layer was dried with magnesium sulfate, the mixture was filtered by suction filtration, and the filtrate was concentrated. Thus, an oily substance was obtained. The oily substance was dissolved in about 50 mL of methanol. A precipitate of a white solid substance was produced by keeping this solution still. This solid substance was collected by suction filtration and dried. Then, 28.4 g (88% yield) of 3-bromo-9-phenylcarbazole was obtained as white powder.

(ii) Synthesis of N-phenyl-(9-phenyl-9H-carbazol-3-yl)amine (abbreviation: PCA)

A synthesis scheme of N-phenyl-(9-phenyl-9H-carbazol-3-yl)amine (abbreviation: PCA) is shown in (D-2).

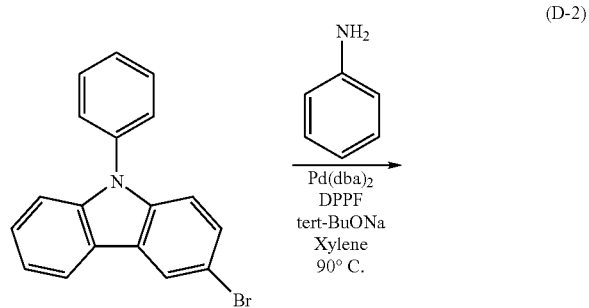

Into a 500 mL three-neck flask were added 19 g (60 mmol) of 3-bromo-9-phenylcarbazole, 0.34 g (0.60 mmol) of bis(dibenzylideneacetone)palladium(0), 1.6 g (3.0 mmol) of 1,1-bis(diphenylphosphino)ferrocene, and 13 g (0.18 mol) of sodium tert-butoxide, and the atmosphere in the flask was substituted by nitrogen. Then, 110 mL of dehydrated xylene and 7.0 g (75 mmol) of aniline were added to the mixture. This mixture was heated and stirred at 90° C. for 7.5 hours-under nitrogen gas flow. After the reaction was completed, about 500 mL of hot toluene was added to the reacted mixture, and this mixture was filtered through Florisil (manufactured by Floridin Company), alumina, and Celite (manufactured by Celite Co., Ltd.). A solid substance was obtained by concentration of the filtrate, and hexane and ethyl acetate were added to the substance, which was followed by irradiation with ultrasonic waves, so that a solid substance was precipitated. The solid substance was collected by suction filtration and dried to produce 15 g (75% yield) of N-phenyl-(9-phenyl-9H-carbazol-3-yl)amine (abbreviation: PCA) as milky-white powder. By a nuclear magnetic resonance measurement (NMR), this compound was proved to be N-phenyl-(9-phenyl-9H-carbazol-3-yl)amine (abbreviation: PCA).

Figure 13A:
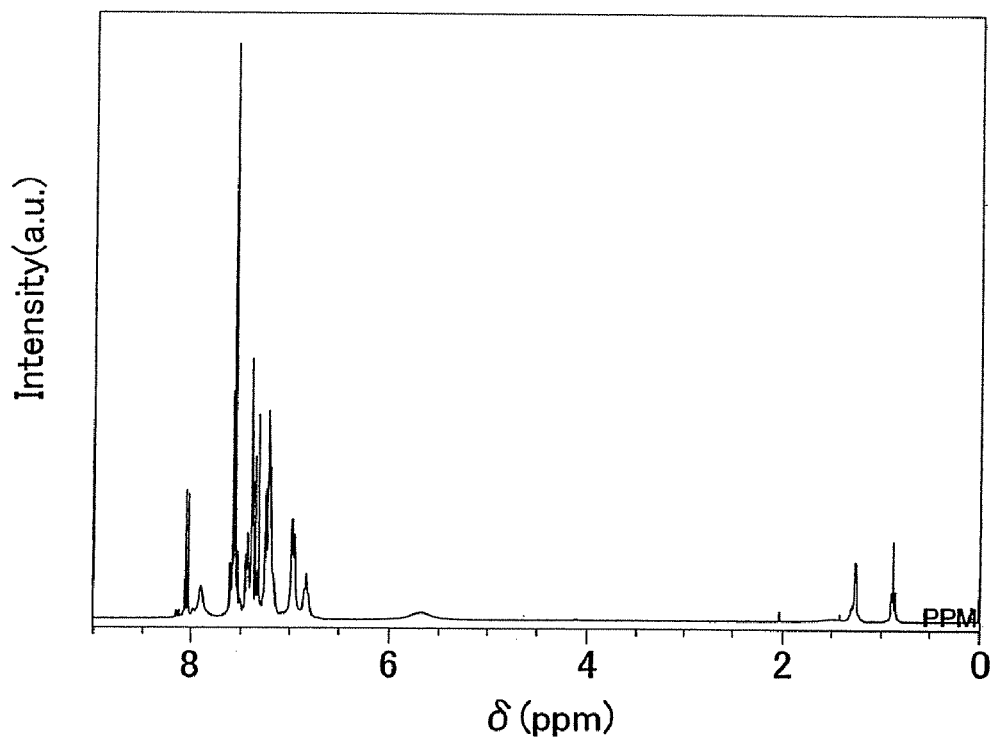
FIGS. 13A and 13B are each a $^1$H NMR chart of N-phenyl-(9-phenyl-9H-carbazol-3-yl)amine (abbreviation: PCA)
Figure 13B:
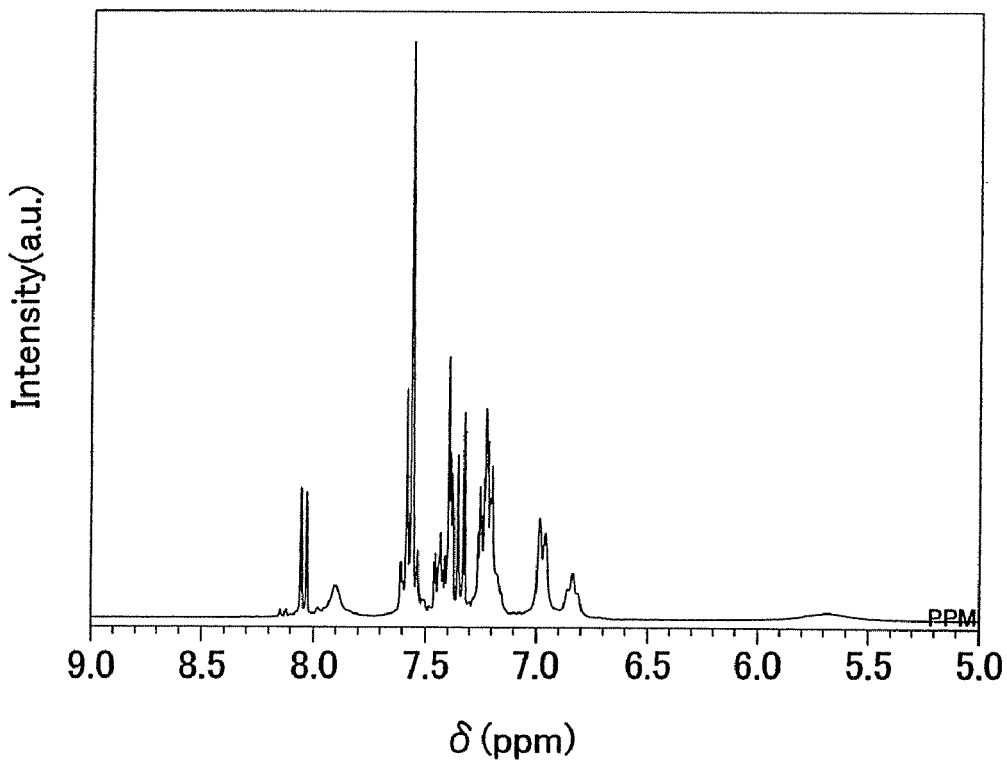

$^1$H NMR data of this compound is shown below. $^1$H NMR (300 MHz, CDCl$_3$); 6.84 (t, J=6.9 Hz, 1H), 6.97 (d, J=7.8 Hz, 2H), 7.20-7.61 (m, 13H), 7.90 (s, 1H), 8.04 (d, J=7.8 Hz, 1H). $^1$H NMR charts are shown in FIGS. 13A and 13B. Note that the range of 5.0 ppm to 9.0 ppm in FIG. 13A is expanded and shown in FIG. 13B. Data obtained when a DMSO-d$_6$ solvent was used is shown. $^1$H NMR (300 MHz, DMSO-d$_6$): δ=6.73 (t, j=7.5, 1H), 7.02 (d, j=8.1, 2H), 7.16-7.70 (m, 12H), 7.95 (s, 1H), 8.06 (s, 1H), 8.17 (d, j=7.8, 1H). $^{13}$C NMR (75.5 MHz, DMSO-d$_6$): δ=109.55, 110.30, 110.49, 114.71, 118.22, 119.70, 120.14, 120.61, 122.58, 123.35, 126.18, 126.48, 127.37, 129.15, 130.14, 135.71, 136.27, 137.11, 140.41, 145.61.

[Step 2] Synthesis Method of 2PCAPPA

A synthesis scheme of 2PCAPPA is shown in (D-3).

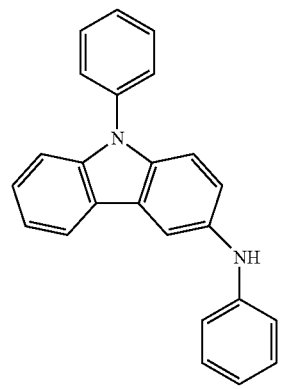

PCA

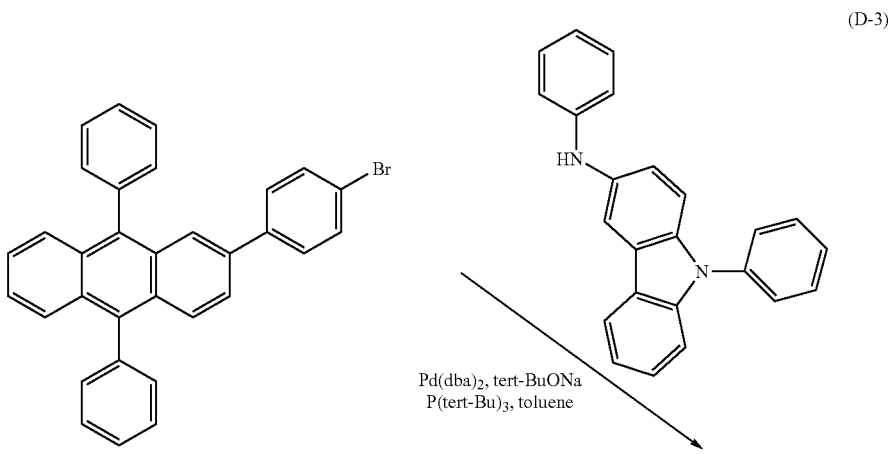

-continued

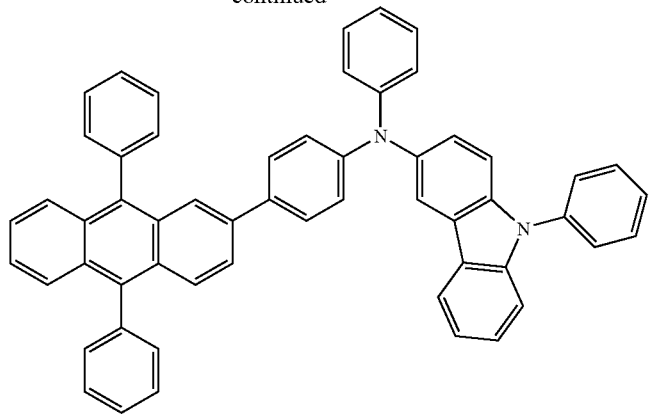

0.52 g of (1.1 mmol) of 2-(4-bromophenyl)-9,10-diphenylanthracene synthesized in Step 2 of Example 1, 0.30 g (3.1 mmol) of sodium tert-butoxide, 0.32 g (0.96 mmol) of N-phenyl-9-phenylacarbazol-3-amine, 0.030 g (0.060 mmol) of bis(dibenzylideneacetone)palladium(0) were put into a 50 mL three-neck flask, and the atmosphere in the flask was substituted by nitrogen. 10 mL of toluene and 0.02 mL of tri(tert-butyl)phosphine 10 wt % hexane solution were added into the mixture. This mixture was heated at 80° C. for five hours while being stirred, so that the mixture was reacted. After the reaction, toluene was added to the reacted mixture, and this suspension was subjected to suction filtration through Florisil (manufactured by Floridin Company), Celite (manufactured by Celite Co., Ltd.), and alumina. The obtained filtrate was washed with water and saturated brine, and magnesium sulfate was added into an organic layer for drying. The mixture was subjected to suction filtration to remove magnesium sulfate, and the obtained filtrate was concentrated to obtain a solid substance. The obtained solid substance was purified with a silica gel column chromatography (developing solvent was a mixed solvent of toluene:hexane=1:10 and then developing solvent was a mixed solvent of toluene:hexane=1:3). The obtained fraction was concentrated to obtain a solid substance. The solid substance was recrystallized with a mixture solution of dichloromethane and methanol, so that 0.50 g of a light yellow powdered solid substance was obtained in yield of 61%. By a nuclear magnetic resonance measurement (NMR), this compound was found to be 2-[4-[N-phenyl-N-(9-phenylcarbazol-3-yl)amino]phenyl]-9,10-diphenylanthracene (abbreviation: 2PCAPPA).

1.4 g of the obtained yellow solid substance was purified by train sublimation. The sublimation was conducted under a low pressure of 7.0 Pa, the argon flow rate of 3 mL/min, at 335° C. and for 15 hours. 1.1 g of 2PCAPPA was obtained in yield 79%.

Figure 14A:
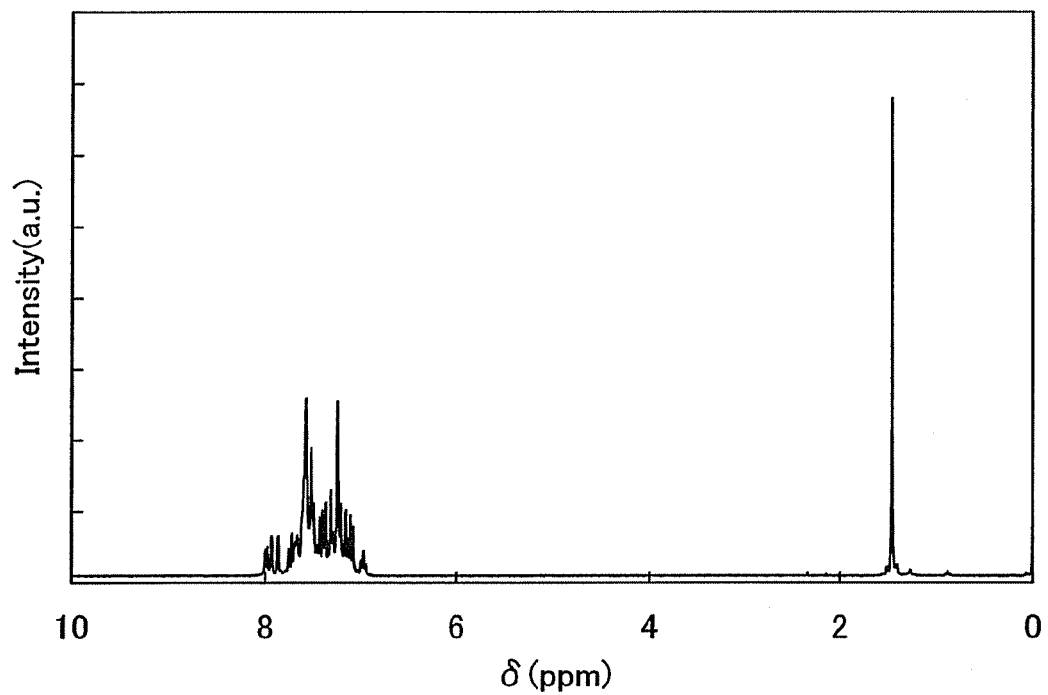
FIGS. 14A and 14B are each a $^1$H NMR chart of 2-{4-[N-phenyl-N-(9-phenylcarbazol-3-yl)amino]phenyl}-9,10-diphenylanthracene (abbreviation: 2PCAPPA)
Figure 14B:
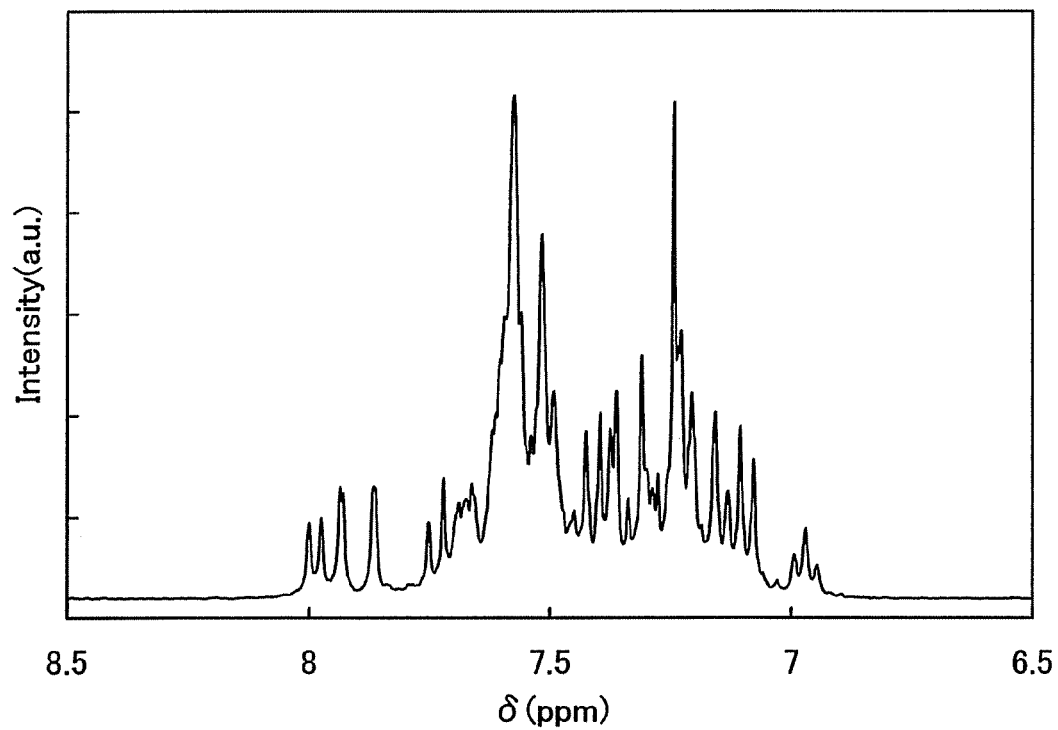

$^1$H NMR data of the obtained compound is shown below. $^1$H NMR (CDCl$_3$, 300 MHz, 50° C.): δ=6.03-7.02 (m, 1H), 7.04-7.78 (m, 34H), 7.86 (s, 1H), 7.93 (s, 1H), 7.99 (d, J=7.8 Hz, 1H). FIGS. 14A and 14B show $^1$H NMR charts. Note that FIG. 14B is a chart in which the range of 6.5 ppm to 8.5 ppm is enlarged in FIG. 14A.

Figure 15:
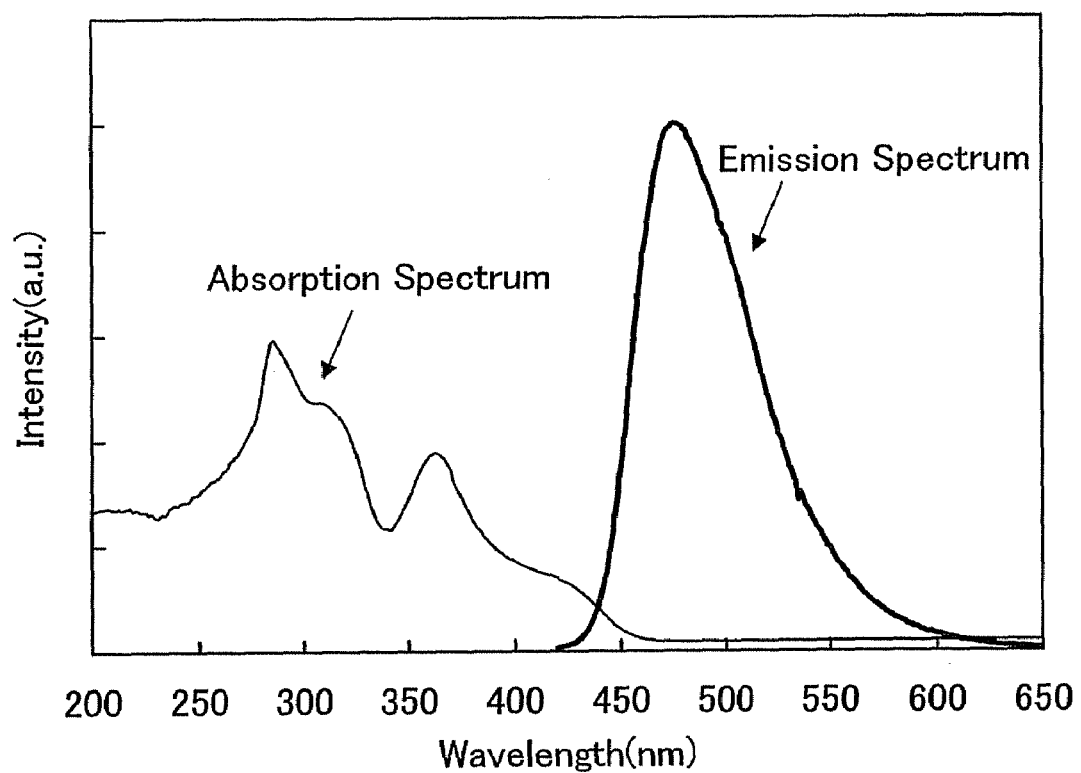
FIG. 15 is a graph showing an absorption spectrum and an emission spectrum of 2-{4-[N-phenyl-N-(9-phenylcarbazol-3-yl)amino]phenyl}-9,10-diphenylanthracene (abbreviation: 2PCAPPA)

FIG. 15 shows absorption spectrum and emission spectrum in a toluene solution of 2PCAPPA. An ultraviolet-visible spectrophotometer (V550, manufactured by Japan Spectroscopy Corporation) was used for measurement. The solution was put in a quartz cell and the absorption spectrum of the solution and the quartz cell was measured. The absorption spectrum of the solution which was obtained by subtracting the absorption spectrum of the quartz cell from the absorption spectrum of the solution and the quartz cell is shown in FIG. 15. In FIG. 15, the horizontal axis shows wavelength (nm) and the vertical axis shows absorption intensity (an arbitrary unit). In the case of the toluene solution, absorptions were observed at around 285 nm and 362 nm. In the case of the toluene solution, the maximum emission wavelength was 477 nm (excitation wavelength of 363 nm).

In addition, when the ionizing potential of 2PCAPPA in a thin film state was measured with a photoelectron spectrometer (AC-2, by RIKEN KEIKI CO., LTD.) in the air, the ionizing potential was 5.32 eV. As a result, the HOMO level was proved to be −5.32 eV. Further, an absorption edge was obtained from a Tauc plot assuming direct transition by using the data of the absorption spectrum of 2PCAPPA in the thin film state, and the absorption edge was regarded as an optical energy gap. The energy gap was 2.63 eV. Therefore, a LUMO level of −2.69 eV was obtained from the obtained values of the energy gap value and HOMO level.

EXAMPLE 3

Example 3 will specifically describe a synthesis method of 2-(4-{N-[4-carbazol-9-yl]phenyl]-N-phenylamino}phenyl)-9,10-diphenzylanthracene (abbreviation: 2YGAPPA), which is an anthracene of the present invention represented by a structural formula (182).

(182)

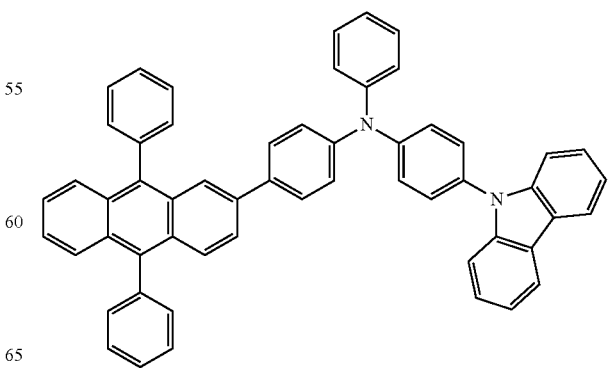

[Step 1] Synthesis of 4-(carbazol-9-yl)diphenylamine (abbreviation: YGA)

(i) Synthesis of N-(4-bromophenyl)carbazole

A synthesis scheme of N-(4-bromophenyl)carbazole is shown in (E-1).

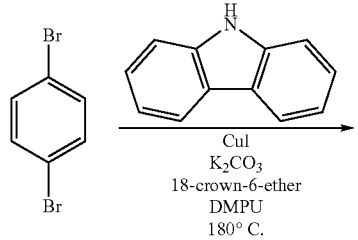

(E-1)

(ii) Synthesis of 4-(carbazol-9-yl)diphenylamine (abbreviation: YGA)

A synthesis scheme of 4-(carbazol-9-yl)diphenylamine (abbreviation: YGA) is shown in (E-2).

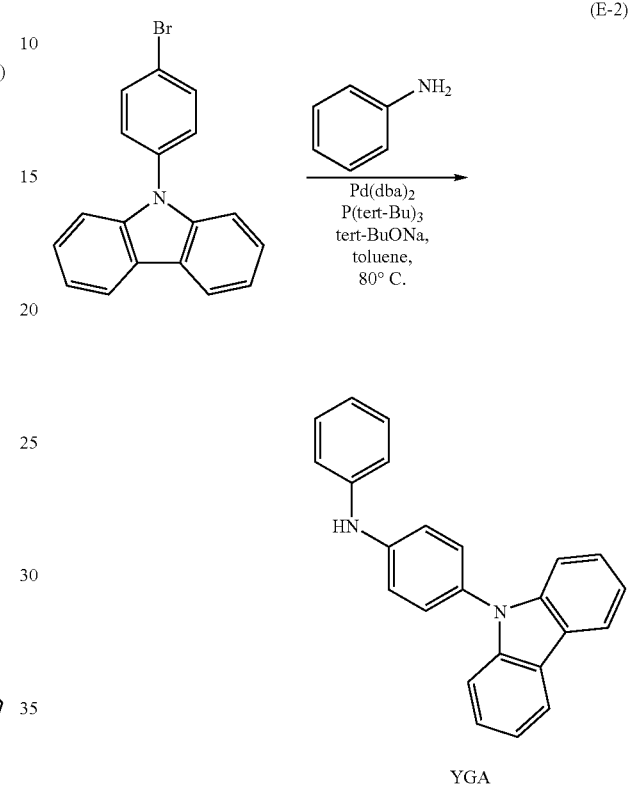

(E-2)

First, a synthesis method of N-(4-bromophenyl)carbazole is described. 56 g (0.24 mol) of 1,4-dibromobenzene, 31 g (0.18 mol) of carbazole, 4.6 g (0.024 mol) of copper(I) iodide, 66 g (0.48 mol) of potassium carbonate, and 2.1 g (0.008 mol) of 18-crown-6-ether were put into a 300 mL three-neck flask, and the atmosphere in the flask was substituted with nitrogen. Then, 8 mL of 1,3-dimethyl-3,4,5,6-tetrahydro-2(1H)-pyrimidinone (abbreviation: DMPU) was added, and the mixture was stirred at 180° C. for six hours. After the reacted mixture was cooled to room temperature, the precipitation was removed by suction filtration. The filtrate was washed with a diluted hydrochloric acid, a saturated sodium hydrogen carbonate aqueous solution, and saturated brine in this order, and an organic layer was dried with magnesium sulfate. After drying, the mixture was filtered, and the obtained filtrate was concentrated to produce an oily substance. The oily substance was purified by silica gel column chromatography (hexane:ethyl acetate=9:1). The resulting solid substance was recrystallized with a mixed solvent of chloroform and hexane, so that 21 g of N-(4-bromophenyl)carbazole as a light brown plate-like crystal in 35% yield. By the nuclear magnetic resonance measurement (NMR), this compound was proved to be N-(4-bromophenyl)carbazole.

$^1$H NMR data of this compound is shown below. $^1$H NMR (300 MHz, CDCl$_3$): δ=8.14 (d, J=7.8 Hz, 2H), 7.73 (d, J=8.7 Hz, 2H), 7.46 (d, J=8.4 Hz, 2H), 7.42-7.26 (m, 6H).

5.4 g (17.0 mmol) of N-(4-bromophenyl)carbazole obtained in the abovementioned step (i), 1.8 mL (20.0 mmol) of aniline, 100 mg (0.17 mmol) of bis(dibenzylideneacetone)palladium(0), and 3.9 g (40 mmol) of sodium tert-butoxide were put into a 200 mL three-neck flask, and the atmosphere in the flask was substituted with nitrogen. Then, 0.1 mL of tri(tert-butyl)phosphine (10 wt % hexane solution) and 50 mL of toluene were added to the mixture, and the solution was stirred at 80° C. for six hours. After reaction, the reacted mixture was filtered through Florisil (manufactured by Floridin Company), Celite (manufactured by Celite Co., Ltd.), and alumina. The filtrate was washed with water, and then saturated brine, and dried with magnesium sulfate. The mixture was filtered, and the filtrate was concentrated to give an oily substance. The oily substance was purified by silica gel column chromatography (hexane:ethyl acetate=9:1), thereby providing 4.1 g of 4-(carbazol-9-yl)diphenylamine (abbreviation: YGA) in 73% yield. By a nuclear magnetic resonance measurement (NMR), this compound was proved to be 4-(carbazol-9-yl)diphenylamine (abbreviation: YGA).

Figure 16A:
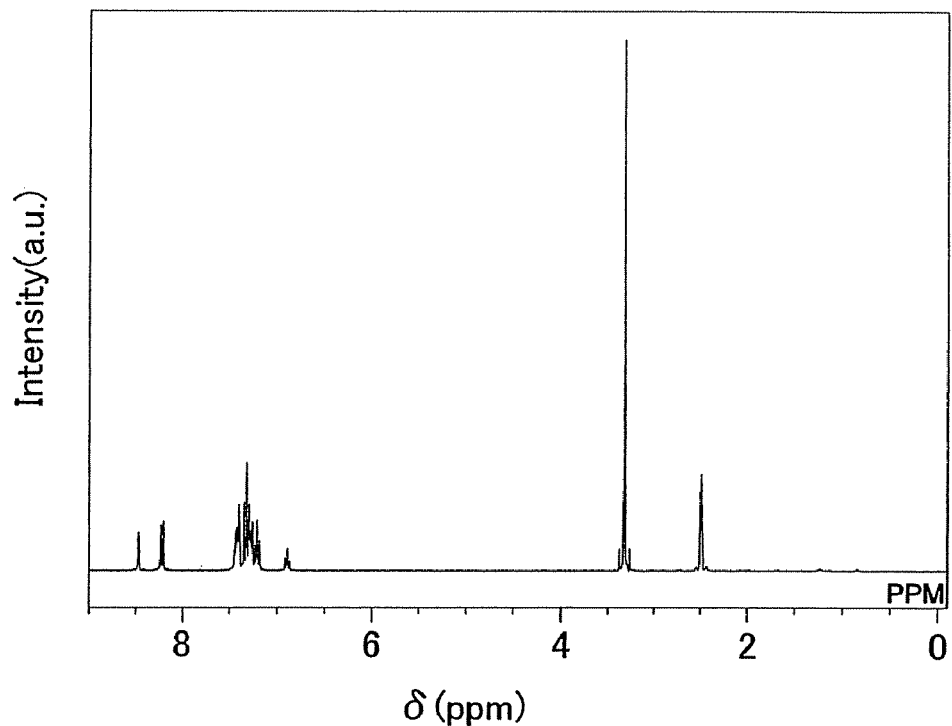
FIGS. 16A and 16B are each a $^1$H NMR chart of 4-(carbazol-9-yl)diphenylamine (abbreviation: YGA)
Figure 16B:
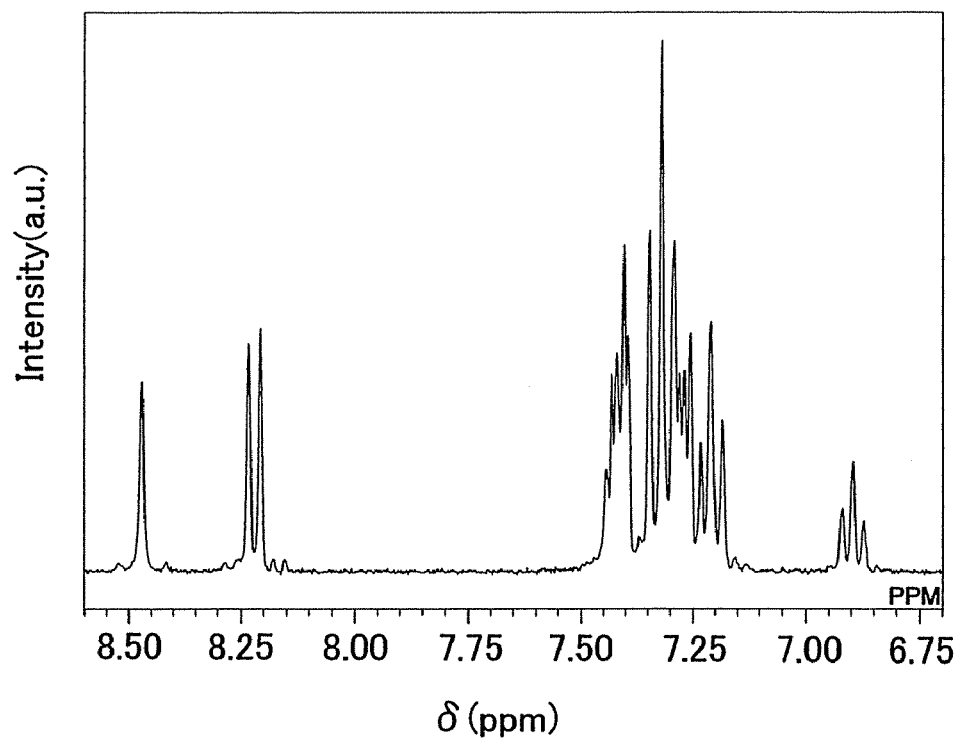

$^1$H NMR data of this compound is shown below. $^1$H NMR (300 MHz, DMSO-d$_6$): δ=8.47 (s, 1H), 8.22 (d, J=7.8 Hz, 2H), 7.44-7.16 (m, 14H), 6.92-6.87 (m, 1H). $^1$H NMR charts are shown in FIGS. 16A and 16B. Note that the range of 6.5 ppm to 8.5 ppm in FIG. 16A is expanded and shown in FIG. 16B.

[Step 2] Synthesis Method of 2YGAPPA

A synthesis scheme of 2YGAPPA is shown in (E-3).

(NMR), this compound was proved to be 2-(4-{N-[4-(carbazol-9-yl)phenyl]-N-phenylamino}phenyl)-9,10-diphenylanthracene (abbreviation: 2YGAPPA).

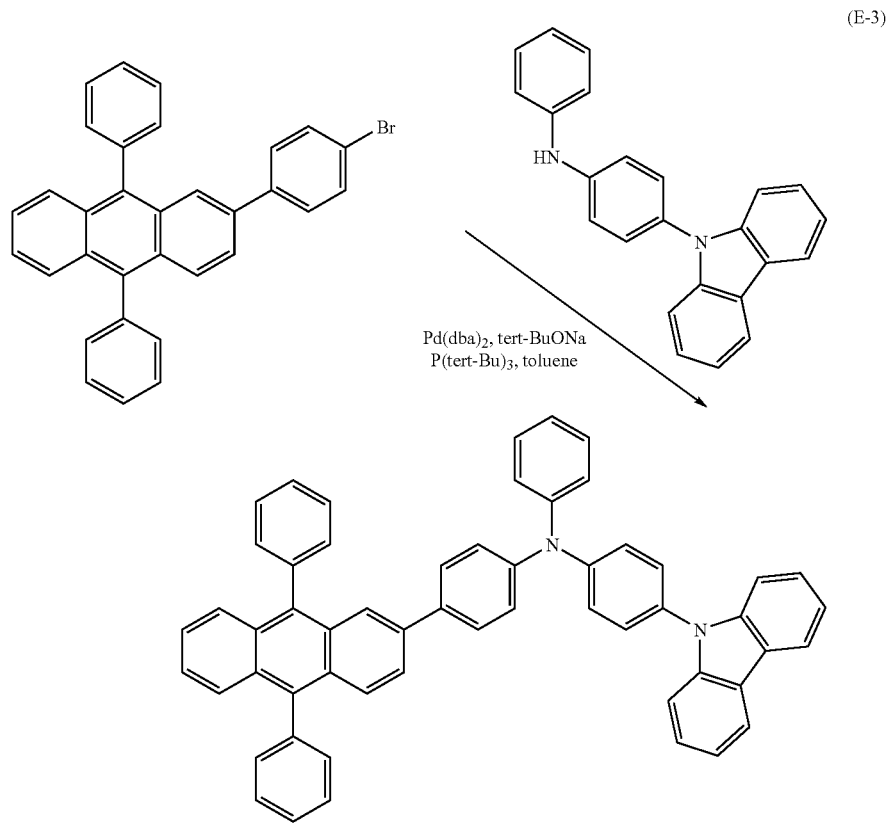

(E-3)

0.51 g of (1.1 mmol) of 2-(4-bromophenyl)-9,10-diphenylanthracene synthesized in Step 2 of Example 1, 0.20 g (2.1 mmol) of sodium tert-butoxide, 0.35 g (1.1 mmol) of 4-(carbazol-9-yl)diphenylamine, 0.02 g (0.04 mmol) of bis(dibenzylideneacetone)palladium(0) were put into a 50 mL three-neck flask, and the atmosphere in the flask was substituted by nitrogen. 10 mL of toluene and 0.02 mL of tri(tert-butyl) phosphine 10 wt % hexane solution were added into the mixture. This mixture was heated at 80° C. for three hours while being stirred, so that the mixture was reacted. After the reaction, toluene was added to the reacted mixture, and this suspension was subjected to suction filtration through Florisil (manufactured by Floridin Company), Celite (manufactured by Celite Co., Ltd.), and alumina. The obtained filtrate was washed with water and saturated brine and magnesium sulfate was added into an organic layer for drying. The mixture was subjected to suction filtration to remove magnesium sulfate, and the obtained filtrate was concentrated to obtain a solid substance. The obtained solid substance was purified using a silica gel column chromatography (developing solvent was a mixed solvent of toluene:hexane=1:10 and developing solvent was a mixed solvent of toluene:hexane=1:5). The obtained fraction was concentrated to obtain a solid substance. The solid substance was recrystallized with a mixture solvent of dichloromethane and methanol, so that 0.51 g of a light yellow powdered solid substance was obtained in yield of 65%. By a nuclear magnetic resonance measurement 1.4 g of the obtained yellow solid substance was purified by train sublimation. The sublimation was conducted under a low pressure of 7.0 Pa, the argon flow rate of 3 mL/min, at 333° C. and for nine hours. 1.2 g of the solid substance was obtained in 86% yield.

Figure 17A:
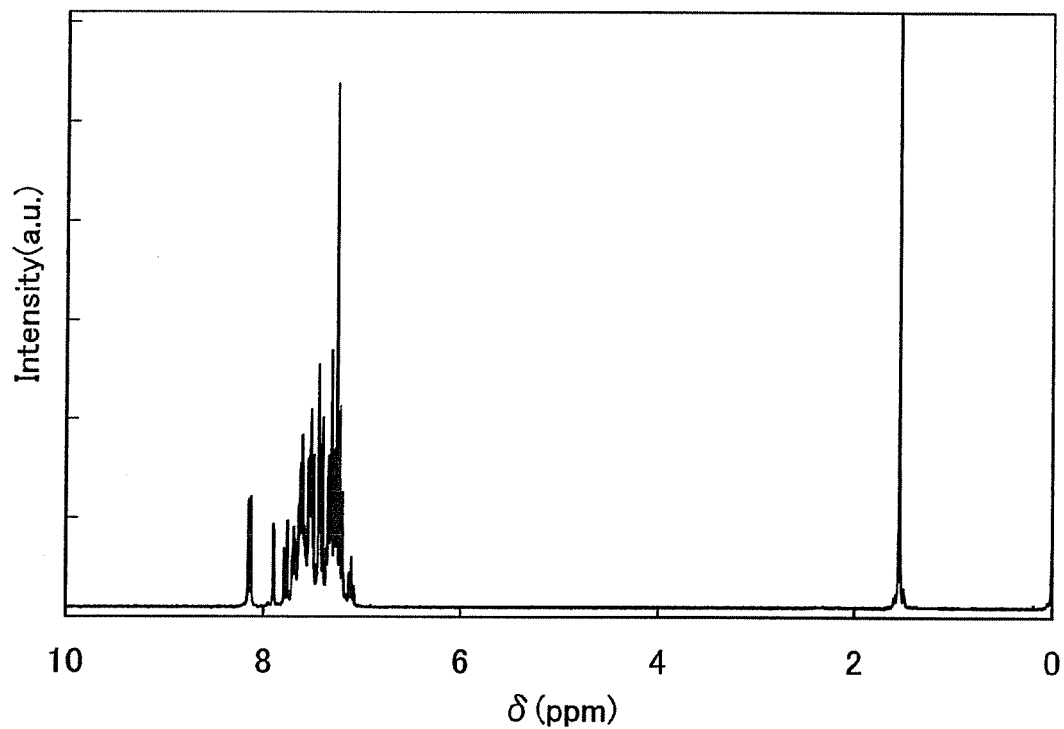
FIGS. 17A and 17B are each a $^1$H NMR chart of 2-(4-{N-[4-carbazol-9-yl]phenyl]-N-phenylamino}phenyl)-9,10-diphenylanthracene (abbreviation: 2YGAPPA)
Figure 17B:
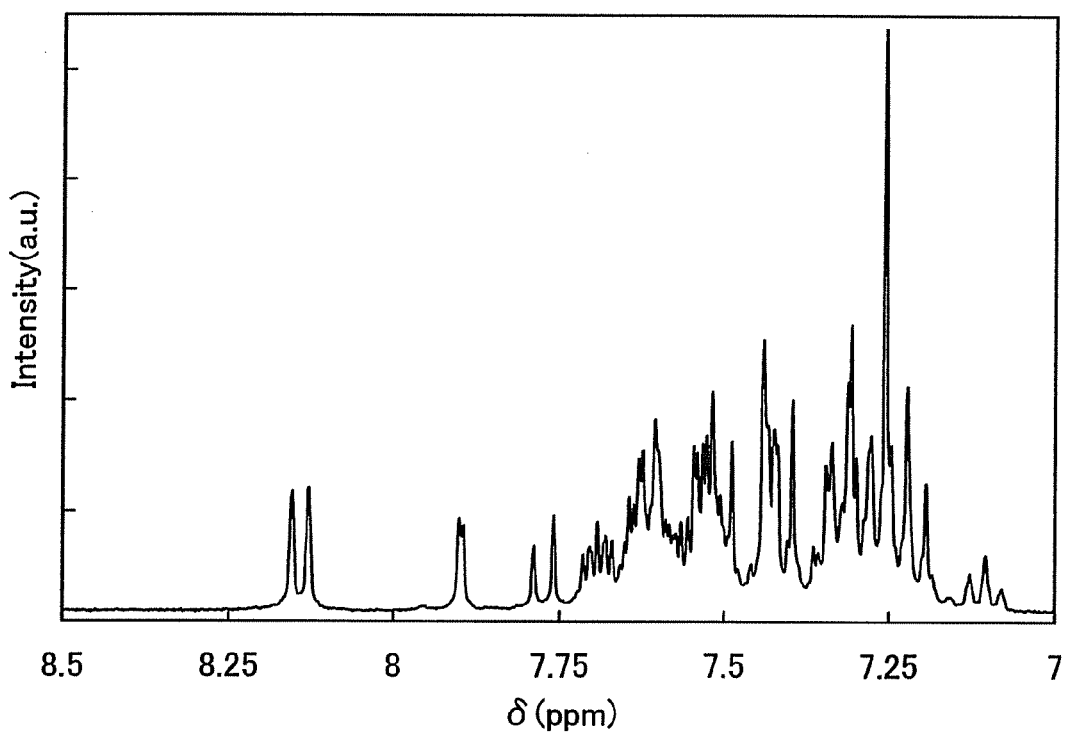

$^1$H NMR data of the obtained compound is shown below.
$^1$H NMR (CDCl$_3$, 300 MHz): δ=7.06-7.15 (m, 1H), 7.17-7.74 (m, 33H), 7.78 (d, J=9.8 Hz, 1H), 7.90 (s, 1H), 8.14 (d, J=7.8 Hz, 2H). $^1$H NMR charts are shown in FIGS. 17A and 17B. Note that FIG. 11B is a chart in which the range of 7.0 ppm to 8.5 ppm in FIG. 17A is enlarged.

Figure 18:
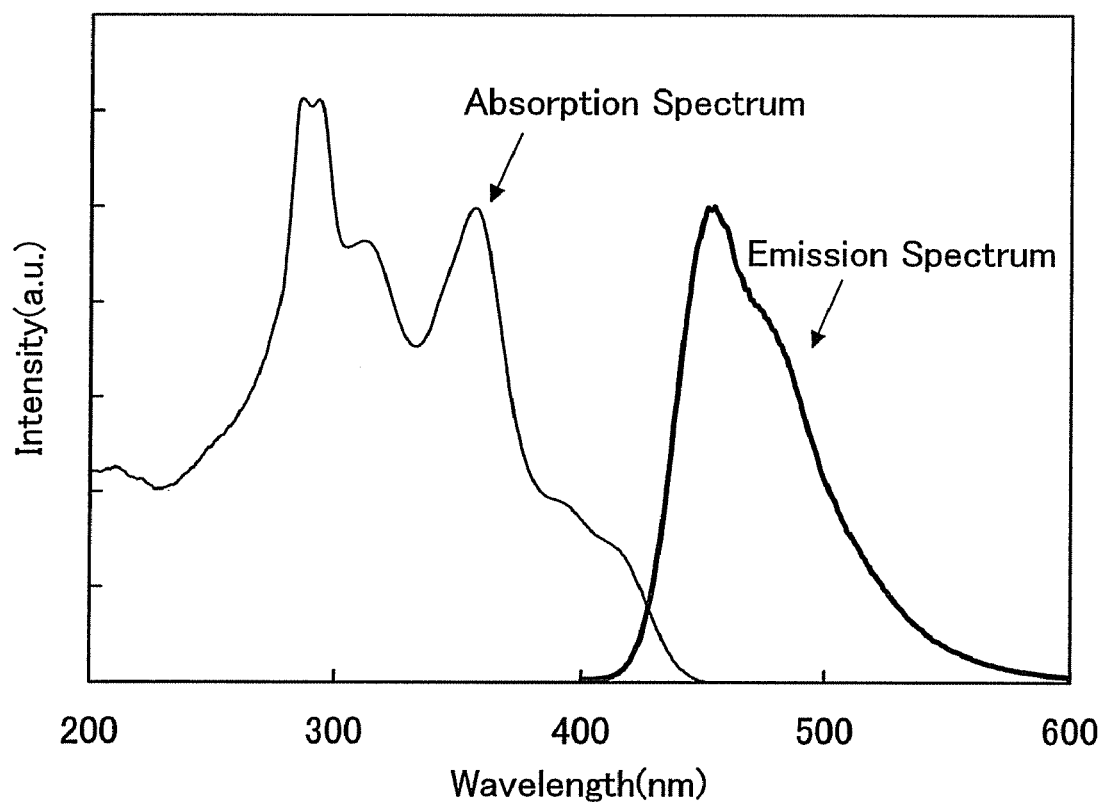
FIG. 18 is a graph showing an absorption spectrum and an emission spectrum of 2-(4-{N-[4-carbazol-9-yl]phenyl]-N-phenylamino}phenyl)-9,10-diphenylanthracence (abbreviation: 2YGAPPA)

FIG. 18 shows absorption spectrum and emission spectrum in a toluene solution of 2YGAPPA. An ultraviolet-visible spectrophotometer (V550, manufactured by Japan Spectroscopy Corporation) was used for measurement. The solution was put in a quartz cell and the absorption spectrum of the solution and the quartz cell was measured. The absorption spectrum of the solution which was obtained by subtracting the absorption spectrum of the quartz cell from the absorption spectrum of the solution and the quartz cell is shown in FIG. 18. In FIG. 18, the horizontal axis shows wavelength (nm) and the vertical axis shows absorption intensity (an arbitrary unit). In the case of the toluene solution, absorptions were observed at around 286 nm, 293 nm, 312 nm and 357 nm. In the case of the toluene solution, the maximum emission wavelength was 454 nm (excitation wavelength of 356 nm).

In addition, when the ionizing potential of 2YGAPPA in a thin film state was measured with a photoelectron spectrometer (AC-2, by RIKEN KEIKI CO., LTD) in the air, the

165 ionizing potential was 5.48 eV. As a result, the HOMO level was proved to be −5.48 eV. Further, an absorption edge was obtained from a Tauc plot assuming direct transition by using the data of the absorption spectrum of 2YGAPPA in the thin film state, and the absorption edge was regarded as an optical energy gap. The energy gap was 2.75 eV. Therefore, a LUMO level of −2.73 eV was obtained from the obtained values of the energy gap value and HOMO level.

Redox reaction characteristics of 2YGAPPA were measured by a cyclic voltammetry (CV) measurement. For the measurement, an electrochemical analyzer (ALS model 600A, manufactured by BAS Inc.) was used.

As for a solution used in the CV measurement, dehydrated N,N-dimethylformamide (DMF) (manufactured by Aldrich, 99.8%, catalog number: 22705-6) was used as a solvent. Tetra-n-butylammonium perchlorate (n-Bu$_4$NClO$_4$) (manufactured by Tokyo Chemical Industry Co., Ltd., catalog number: T0836), a supporting electrolyte, was dissolved in DMF at the concentration of 100 mmol/L to prepare the electrolysis solution. The measurement object, 2YGAPPA was tried to be dissolved in the electrolysis solution at a concentration of 10 mmol/L; however, 2YGAPPA was difficult to be dissolved and an undissolved portion thereof is left. At this time, supernatant fluid was skimmed with the undissolved portion deposited, and was used in the measurement. A platinum electrode (a PTE platinum electrode, manufactured by BAS Inc.) was used as a working electrode. A platinum electrode (a VC-3 Pt counter electrode (5 cm), manufactured by BAS Inc.) was used as a counter electrode. An Ag/Ag$^+$ electrode (an RE5 non-aqueous solvent type reference electrode, manufactured by BAS Inc.) was used as a reference electrode. The measurement was conducted at room temperature.

An oxidation characteristic of 2YGAPPA was evaluated in the following manner. The potential of the working electrode with respect to the reference electrode was shifted from −0.27 V to 0.70 V, which was followed by shifting the potential from 0.70 V to −0.27 V. This cycle was set as one cycle, and 100 cycles were performed. Also, reduction characteristics of 2YGAPPA were evaluated in the following manner. The potential of the working electrode with respect to the reference electrode was shifted from −0.35 V to −2.60 V, which was followed by shifting the potential from −2.60 V to −0.35 V. This cycle was set as one cycle, and 100 cycles were performed. Scan speed of the CV measurement was set to be 0.1 V/s.

Figure 22:
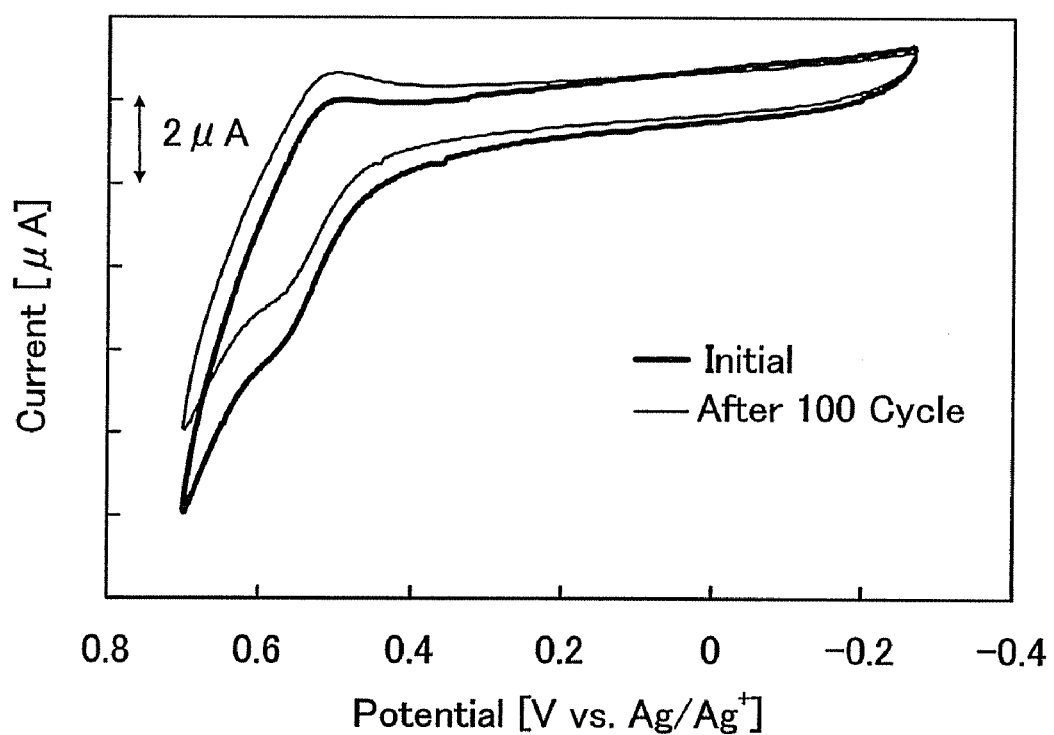
FIG. 22 is a graph showing an oxidation reaction of 2-(4-{N-[4-carbazol-9-yl]phenyl]-N-phenylamino}phenyl)-9,10-diphenylanthracene (abbreviation: 2YGAPPA)
Figure 23:
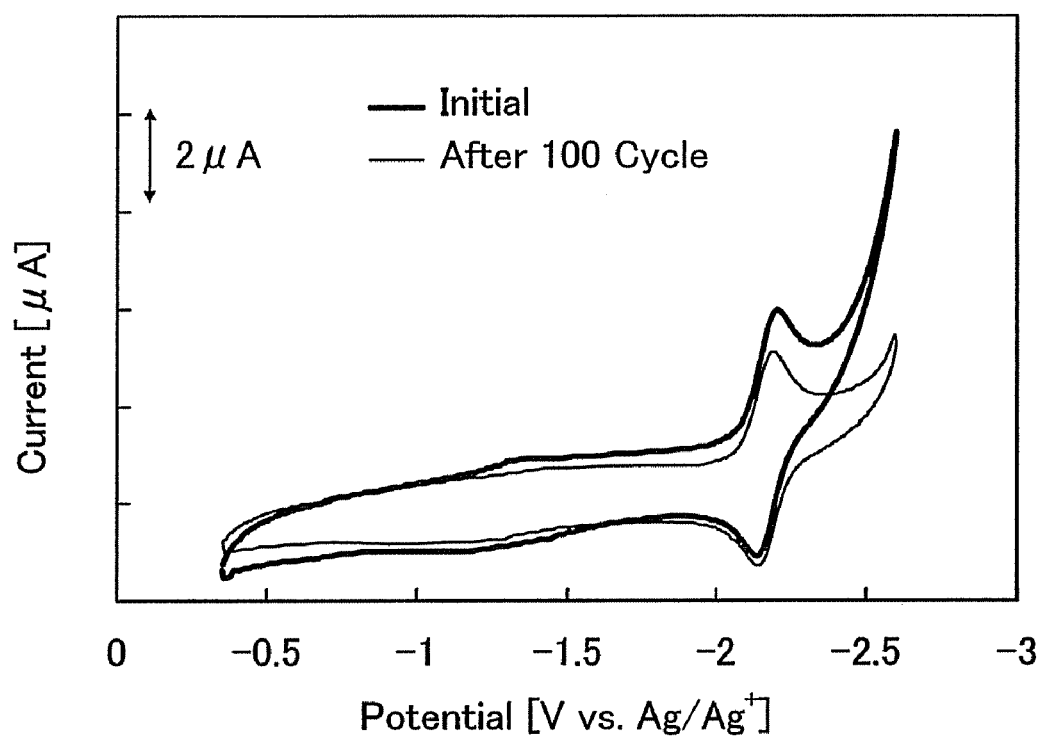
FIG. 23 is a graph showing a reduction reaction of 2-(4-{N-[4-carbazol-9-yl]phenyl]-N-phenylamino}phenyl)-9,10-diphenylanthracene (abbreviation: 2YGAPPA)
Figure 24:
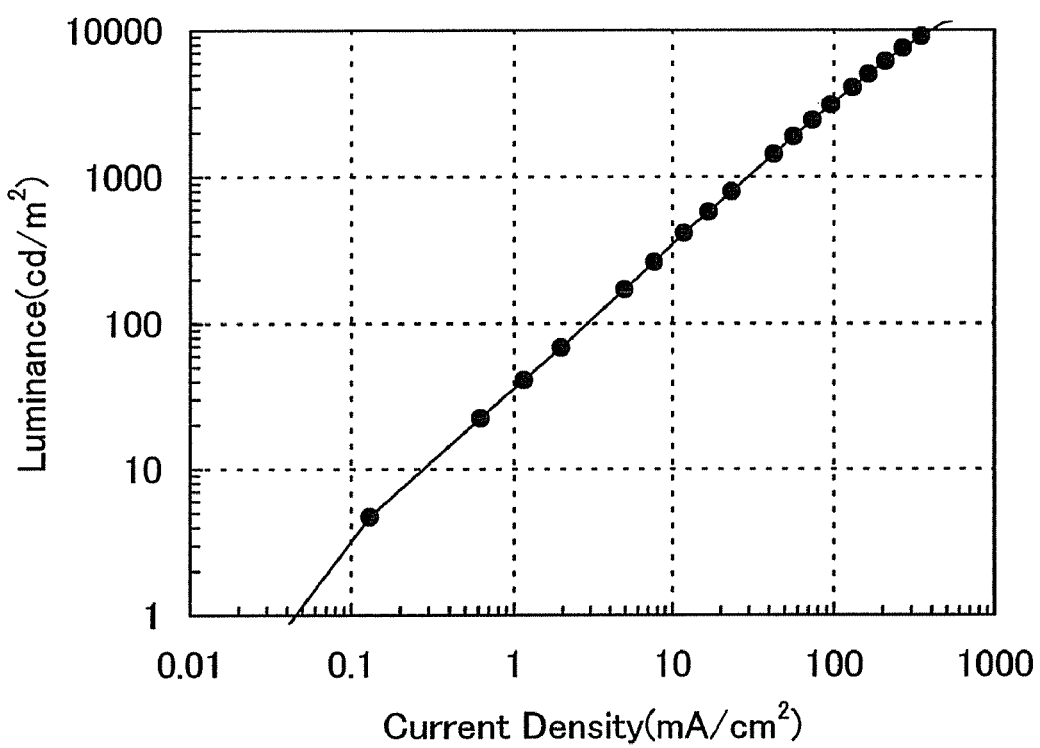
FIG. 24 is a graph showing current density-luminance characteristics of a light-emitting element 1.
Figure 25:
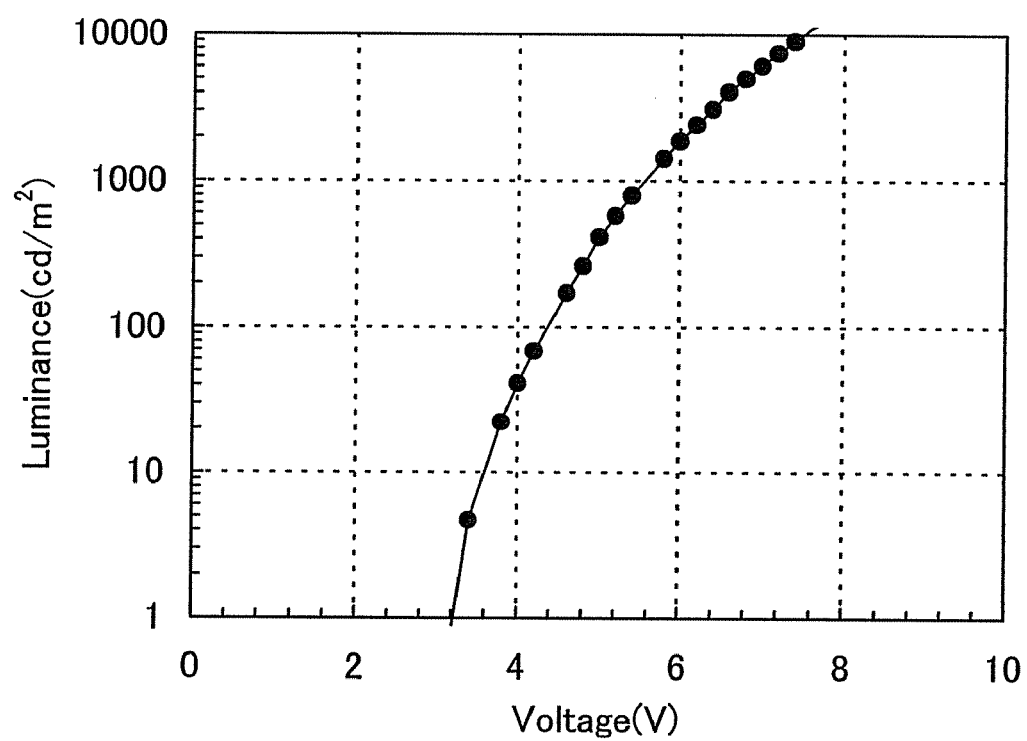
FIG. 25 is a graph showing voltage-luminance characteristics of the light-emitting element 1.
Figure 26:
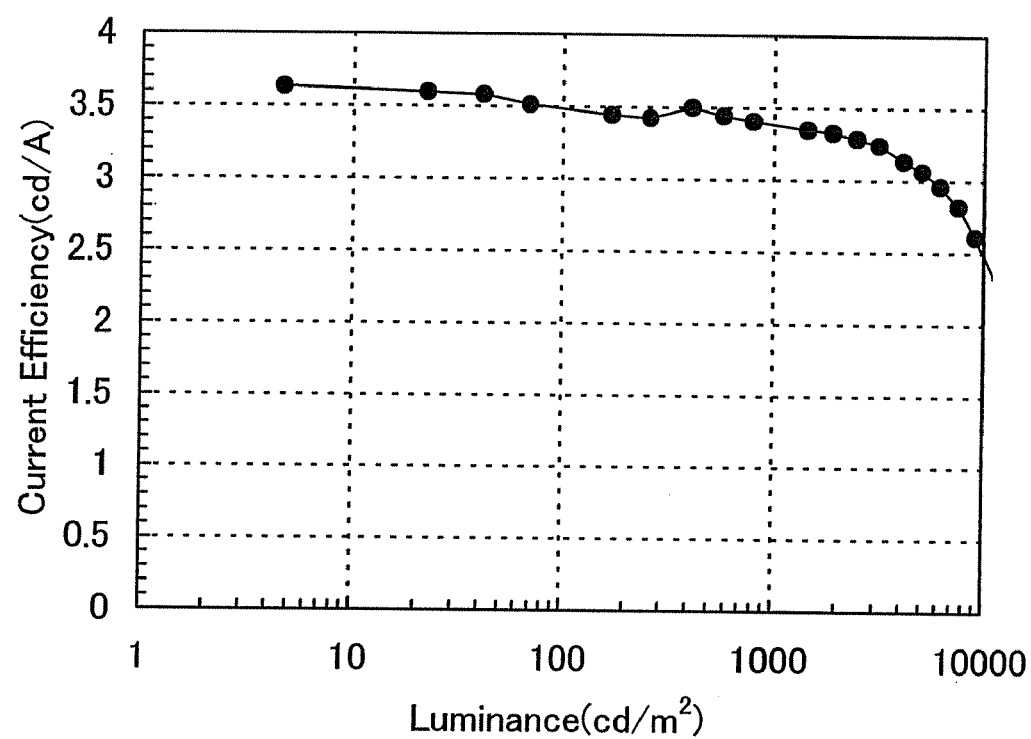
FIG. 26 is a graph showing luminance-current efficiency characteristics of the light-emitting element 1.
Figure 27:
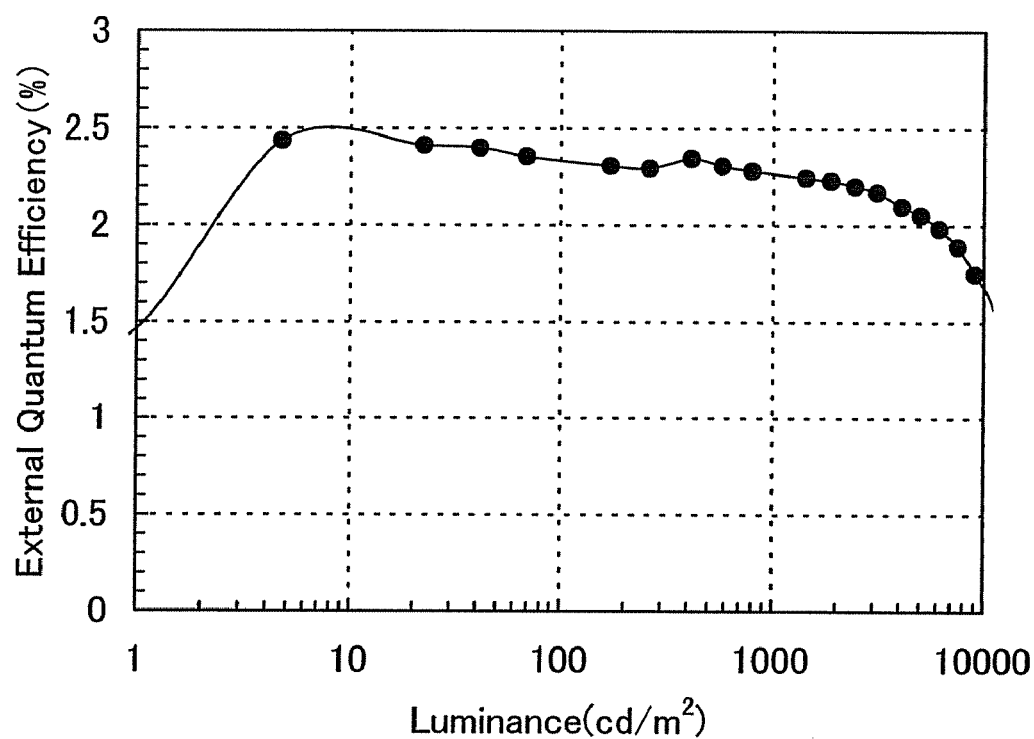
FIG. 27 is a graph showing luminance-external quantum efficiency characteristics of the light-emitting element 1.

The CV measurement result on an oxidation side of 2YGAPPA and the CV measurement result on a reduction side of 2YGAPPA are shown in FIGS. 22 and 23, respectively. In each of FIGS. 22 and 23, the horizontal axis shows a potential (V) of the working electrode with respect to the reference electrode, and the vertical axis shows a current value (μA) that flowed between the working electrode and the counter electrode. From FIG. 22, a current exhibiting oxidation was observed around 0.57 to 0.59 V (vs. Ag/Ag$^+$). From FIG. 23, a current exhibiting reduction was observed around −2.21 V (vs. Ag/Ag$^+$).

In spite of the fact that 100 cycles of scanning were conducted repeatedly, a peak position and a peak intensity at the CV curve scarcely changed in the oxidation and reduction, which reveals that the anthracene derivative of the present invention is extremely stable against repetition of the oxidation and reduction.

166

EXAMPLE 4

Example 4 will specifically describe a synthesis method of 2-{3-[N-phenyl-N-(9-phenylcarbazol-3-yl)amino]phenyl}-9,10-diphenylanthracene (abbreviation: 2 mPCAPPA), which is an anthracene derivative of the present invention represented by a structural formula (174).

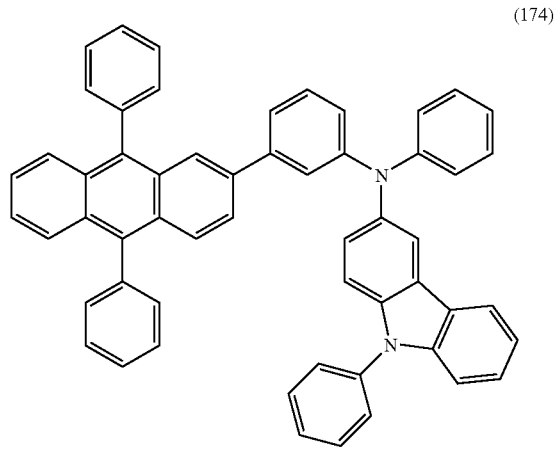

(174)

[Step 1] Synthesis of 2-(3-bromophenyl)-9,10-diphenylanthracene

A synthesis scheme of 2-(3-bromophenyl)-9,10-diphenylanthracene is shown in (F-1).

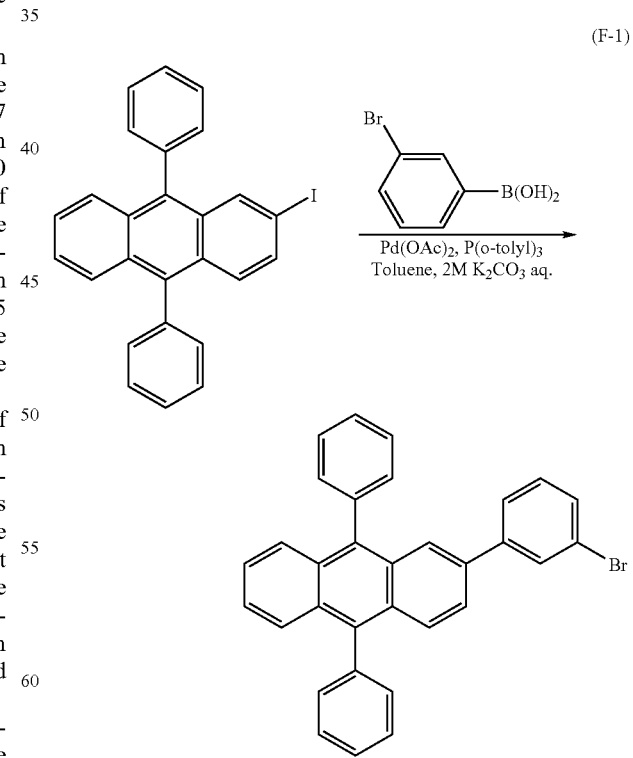

(F-1)

2.0 g (10 mmol) of 3-bromophenylboronic acid, 4.6 g (10 mmol) of 9,10-diphenyl-2-iodoanthracene, and 0.15 mg (0.50 mmol) of tris(o-tolyl)phosphine were put in a 200 mL three-neck flask, and the atmosphere in the flask was substituted by nitrogen. 50 mL of toluene and 14 mL of potassium carbonate aqueous solution (2 mol/L) were added. The mixture was stirred to be deaerated while reducing the pressure of the flask, and then 23 mg (0.10 mmol) of palladium(II) acetate was added into the mixture. The mixture was refluxed at 110° C. for eight hours. After the reaction, toluene was added to the reacted mixture, and this suspension was washed with water. An organic layer and an aqueous layer were separated, the aqueous layer was extracted with toluene, and the extracted solution and the organic layer were dried together with magnesium sulfate. The mixture was filtrated to remove magnesium sulfate, and the filtrate was concentrated to obtain an oily substance. The oily substance was purified by silica gel column chromatography (developing solvent was hexane) so that 0.4 g of a milky-white solid substance was obtained in 18% yield. By a nuclear magnetic resonance measurement (NMR), this compound was found to be 2-(3-bromophenyl)-9,10-diphenylanthracene.

Figure 41A:
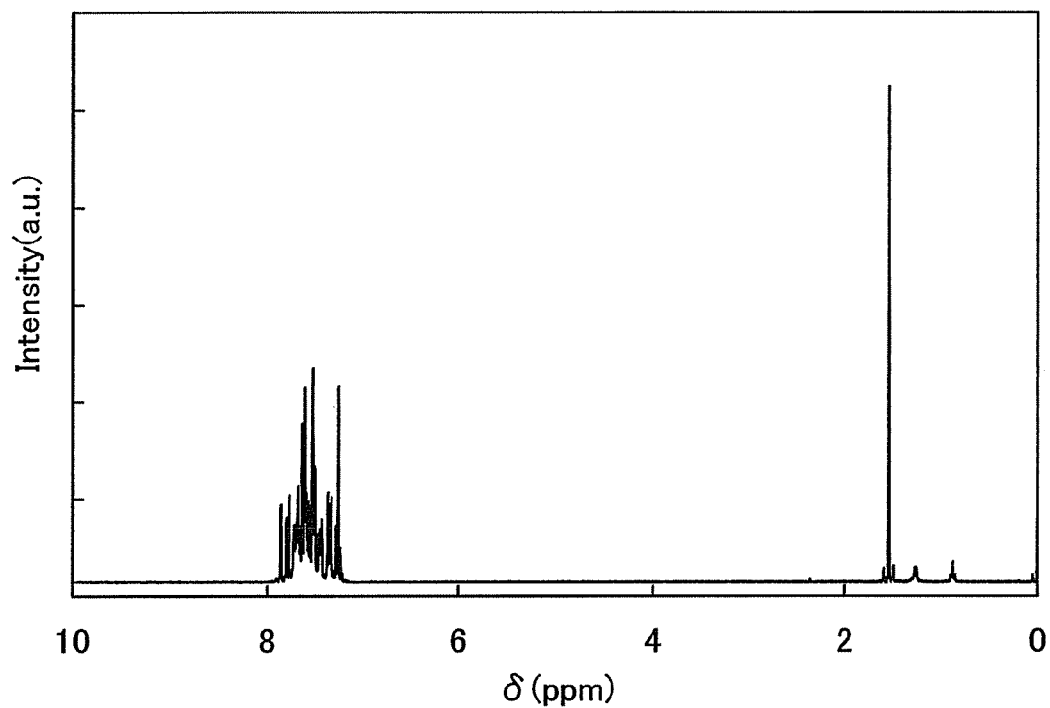
FIGS. 41A and 41B are each a $^1$H NMR chart of 2-(3-bromophenyl)-9,10-diphenylanthracene.
Figure 41B:
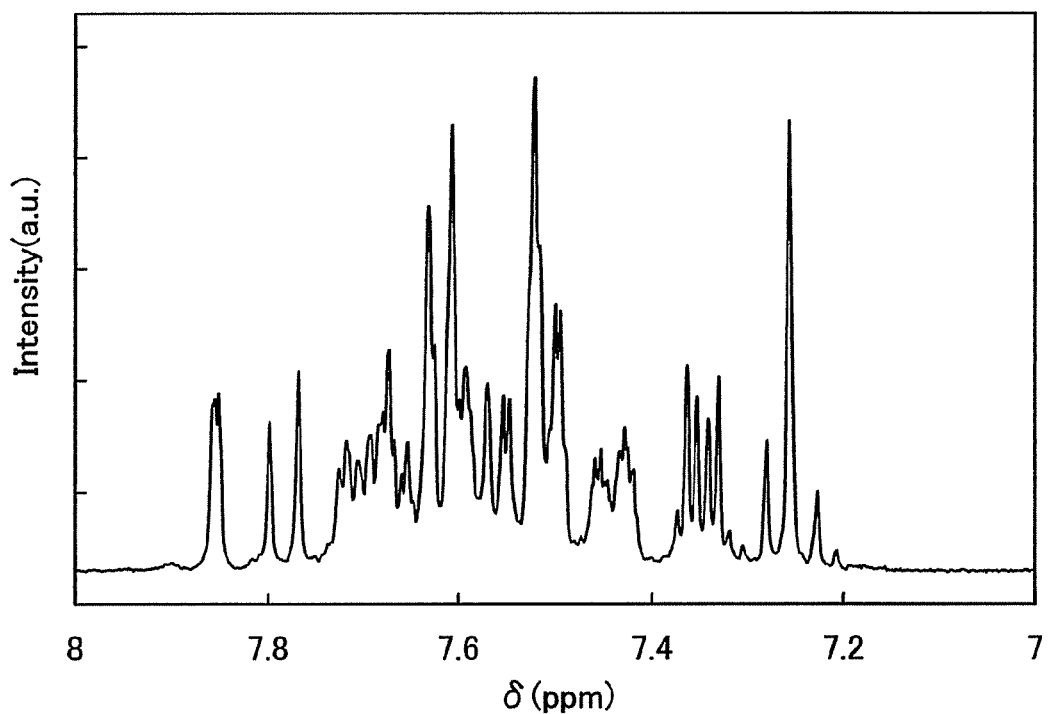

$^1$H NMR data of 2-(3-bromophenyl)-9,10-diphenylanthracene is shown below. $^1$H NMR (CDCl$_3$, 300 MHz): δ=7.33-7.36 (m, 2H), 7.43-7.46 (m, 2H), 7.50-7.73 (m, 15H), 7.78 (d, J=9.3 Hz, 1H), 7.85 (d, J=1.2 Hz, 1H). $^1$H NMR charts are shown in FIGS. 41A and 41B. Note that FIG. 41B is a chart in which the range of 7.0 ppm to 8.0 ppm in FIG. 41A is enlarged.

[Step 2] A Synthesis Method of 2 mPCAPPA

A synthesis scheme of 2 mPCAPPA is shown in (F-2).

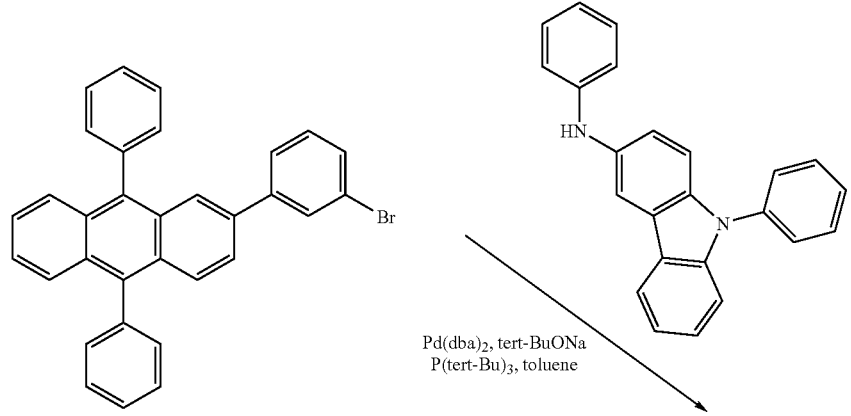

(F-2)

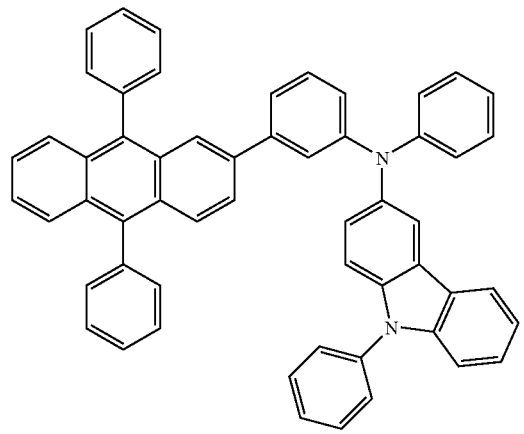

0.45 g of (0.93 mmol) of 2-(3-bromophenyl)-9,10-diphenylanthracene, 0.2 g (2.1 mmol) of sodium tert-butoxide, 0.31 g (0.93 mmol) of N-phenyl-9-phenylcarbazol-3-amine, 0.02 g (0.04 mmol) of bis(dibenzylideneacetone)palladium(0) were put into a 50 mL three-neck flask, and the atmosphere in the flask was substituted by nitrogen. 10 mL of toluene and 0.02 mL of tri(tert-butyl)phosphine 10 wt % hexane solution were added into the mixture. This mixture was heated at 80° C. for five hours while being stirred, so that the mixture was reacted. After the reaction, toluene was added to the reacted mixture, and this suspension was subjected to suction filtration through Florisil (manufactured by Floridin Company), Celite (manufactured by Celite Co., Ltd.), and alumina. The obtained filtrate was washed with water and saturated brine, and the organic layer and an aqueous layer were separated. Then, magnesium sulfate was added into an organic layer for drying. The mixture was subjected to suction filtration to remove magnesium sulfate, and the obtained filtrate was concentrated to obtain a solid substance. The obtained solid substance was dissolved in toluene and a slight amount of hexane, and purified using a silica gel column chromatography (developing solvent was a mixed solvent of toluene: hexane=1:9 and then developing solvent was a mixed solvent of toluene:hexane=1:3). The obtained fraction was concentrated to obtain a solid substance. The solid substance was recrystallized with a mixture solvent of chloroform and methanol, so that 0.46 g of a yellow powdered solid substance was obtained in 67% yield. By a nuclear magnetic resonance measurement (NMR), this compound was found to be 2-{3-[N-phenyl-N-(9-phenylcarbazol-3-yl)amino]phenyl}-9,10-diphenylanthracene (abbreviation: 2 mPCAPPA).

Figure 19A:
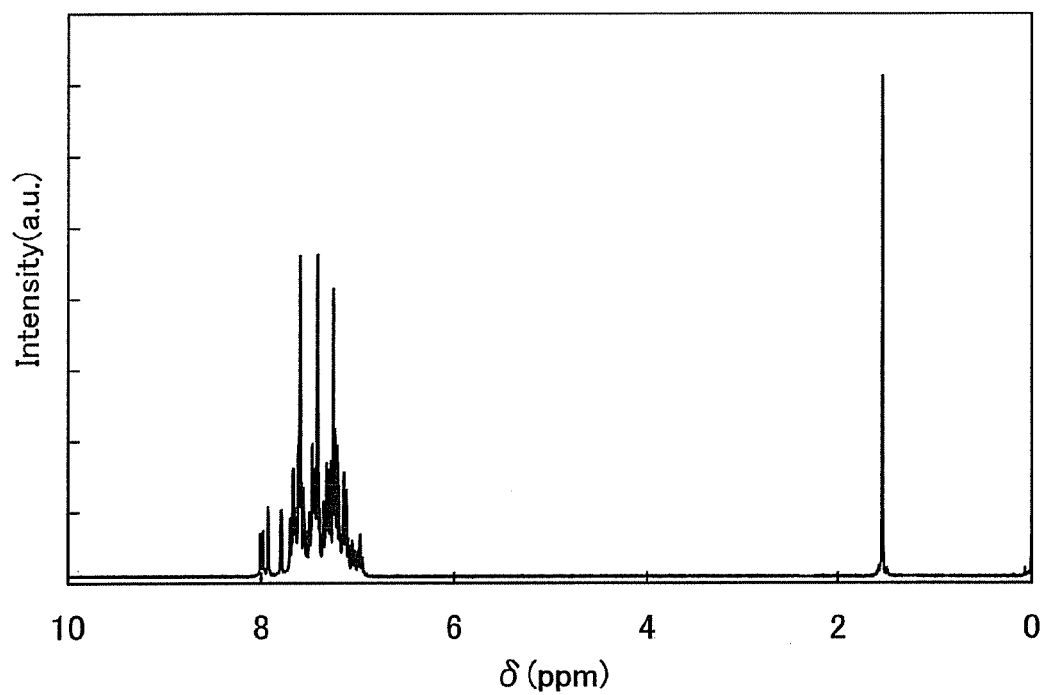
FIGS. 19A and 19B are each a $^1$H NMR chart of 2-{3-[N-phenyl-N-(9-phenylcarbazol-3-yl)amino]phenyl}-9,10-diphenylanthracene (abbreviation: 2mPCAPPA)
Figure 19B:
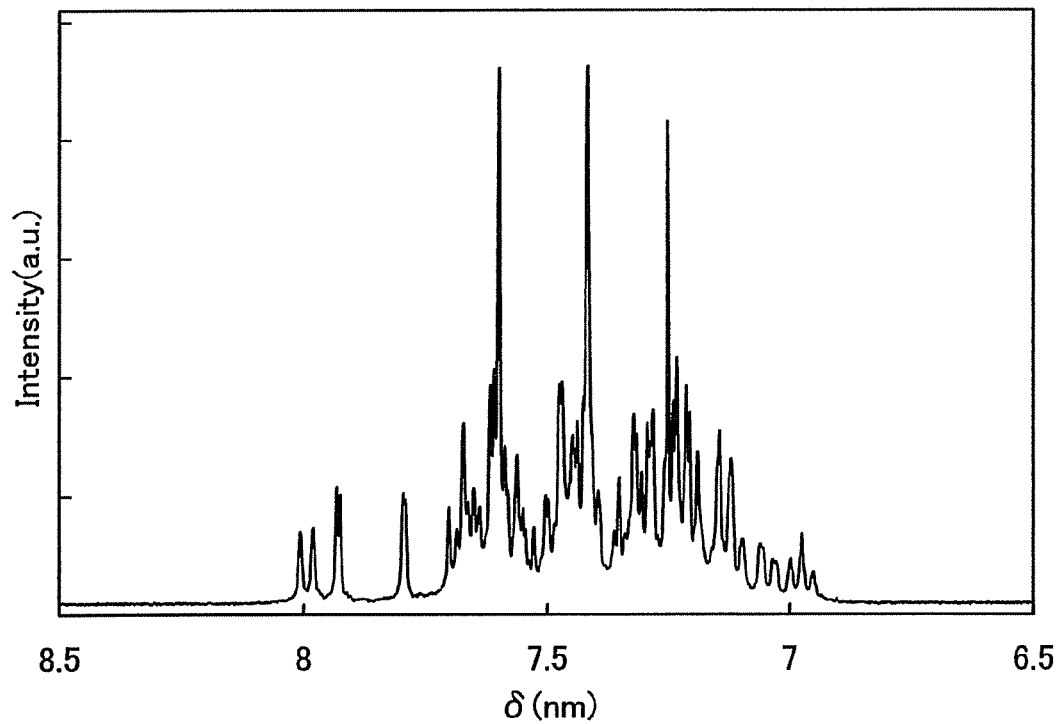

$^1$H NMR data of the obtained compound is shown below.
$^1$H NMR (CDCl$_3$, 300 MHz): δ=6.91-7.75 (m, 35H), 7.79 (s, 1H), 7.93 (s, 1H), 7.99 (d, J=7.8 Hz, 1H). $^1$H NMR charts are shown in FIGS. 19A and 19B. Note that FIG. 19B is a chart in which the range of 6.5 ppm to 8.5 ppm in FIG. 19A is enlarged.

Figure 20:
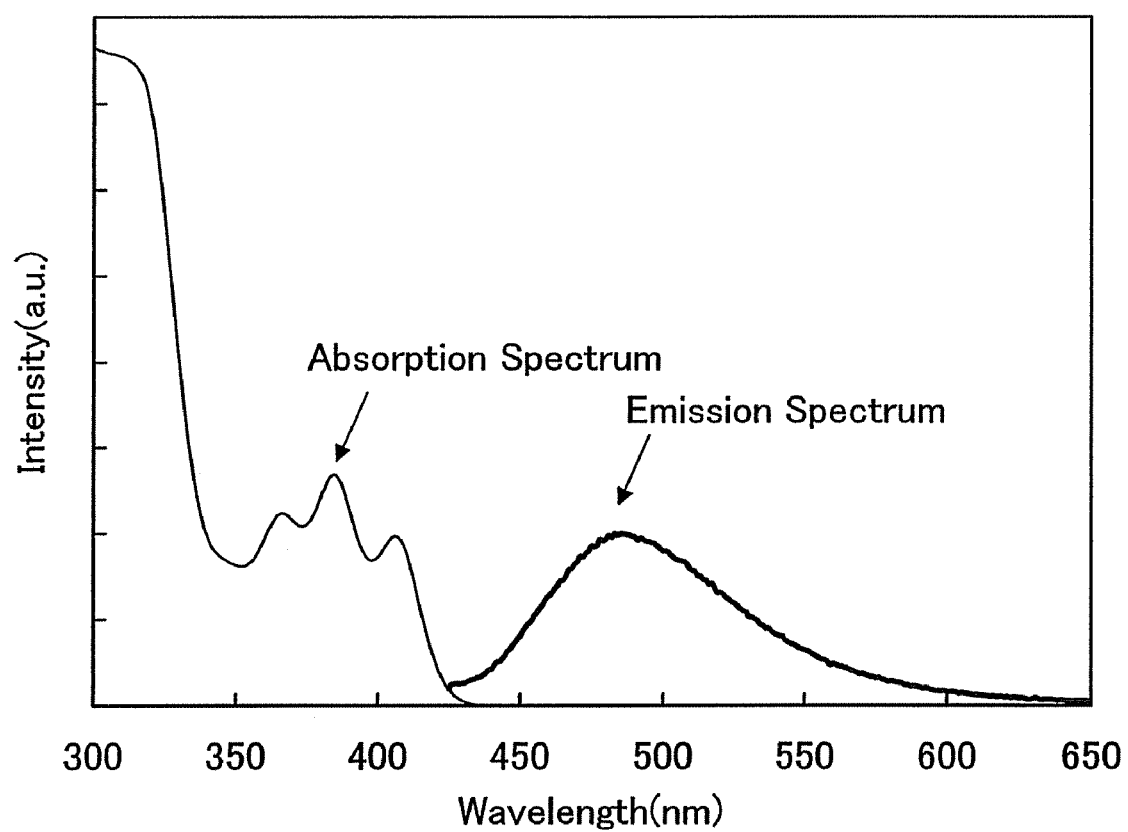
FIG. 20 is a graph showing an absorption spectrum and an emission spectrum of 2-{3-[N-phenyl-N-(9-phenylcarbazol-3-yl)amino]phenyl}-9,10-diphenylanthracene (abbreviation: 2 mPCAPPA)

FIG. 20 shows absorption spectrum and emission spectrum in a toluene solution of 2 mPCAPPA. An ultraviolet-visible spectrophotometer (V550, manufactured by Japan Spectroscopy Corporation) was used for measurement. The solution was put in a quartz cell and the absorption spectrum of the solution and the quartz cell was measured. The absorption spectrum of the solution which was obtained by subtracting the absorption spectrum of the quartz cell from the absorption spectrum of the solution and the quartz cell is shown in FIG. 20. In FIG. 20, the horizontal axis shows wavelength (nm) and the vertical axis shows absorption intensity (an arbitrary unit). In the case of the toluene solution, absorptions were observed at around 366 nM, 384 nm, and 406 nm. In the case of the toluene solution, the maximum emission wavelength was 485 nm (excitation wavelength of 369 nm).

In addition, when the ionizing potential of 2 mPCAPPA in a thin film state was measured with a photoelectron spectrometer (AC-2, manufactured by RIKEN KEIKI CO., LTD.) in the air, the ionizing potential was 5.34 eV. As a result, the HOMO level was proved to be −5.34 eV. Further, an absorption edge was obtained from a Tauc plot assuming direct transition by using the data of the absorption spectrum of 2 mPCAPPA in the thin film state, and the absorption edge was regarded as an optical energy gap. The energy gap was 2.83 eV. Therefore, a LUMO level of −2.51 eV was obtained from the obtained values of the energy gap value and HOMO level.

EXAMPLE 5

Example 5 will specifically describe a synthesis method of 2-(3-{N-[4-(carbazol-9-yl)phenyl]-N-phenylamino}phenyl)-9,10-diphenylanthracene (abbreviation: 2mYGAPPA), which is an anthracene derivative of the present invention represented by a structural formula (216).

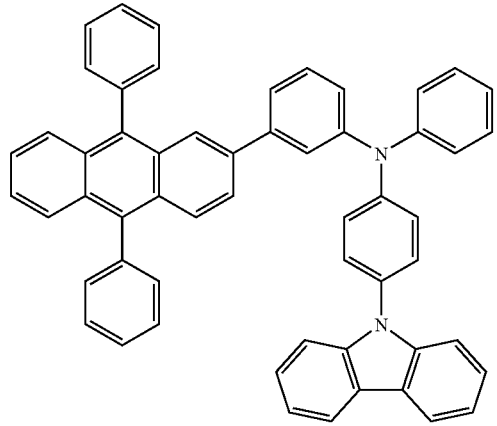

(216)

[Step 1] Synthesis Method of 2mYGAPPA

A synthesis scheme of 2mYGAPPA is shown in (G-1).

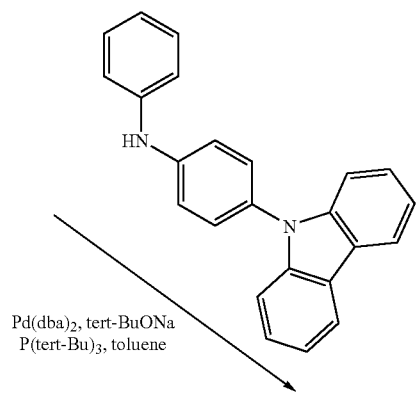

(G-1)

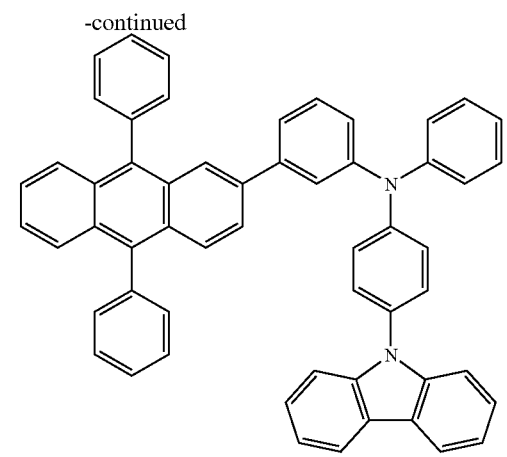

0.45 g of (0.93 mmol) of 2-(3-bromophenyl)-9,10-diphenylanthracene, 0.2 g (2.1 mmol) of sodium tert-butoxide, 0.31 g (0.93 mmol) of 4-(9-carbazolyl)diphenylamine, 0.010 g (0.02 mmol) of bis(dibenzylideneacetone)palladium(0) were put into a 50 mL three-neck flask, and the atmosphere in the flask was substituted by nitrogen. 10 mL of toluene and 0.01 mL of tri(tert-butyl)phosphine 10 wt % hexane solution were added into the mixture. This mixture was heated at 80° C. for five hours while being stirred, so that the mixture was reacted. After the reaction, toluene was added to the reacted mixture, and this suspension was subjected to suction filtration through Florisil (manufactured by Floridin Company), Celite (manufactured by Celite Co., Ltd.), and alumina. The obtained filtrate was washed with water and saturated brine, and an aqueous layer and an organic layer were separated. Then, magnesium sulfate was added into the organic layer for drying. The mixture was subjected to suction filtration to remove magnesium sulfate, and the obtained filtrate was concentrated to obtain a solid substance. The obtained solid substance was dissolved in toluene and a slight amount of hexane, and purified using a silica gel column chromatography (developing solvent was a mixed solvent of toluene: hexane=1:9 and then developing solvent was a mixed solvent of toluene:hexane=1:2). The obtained fraction was concentrated to obtain a solid substance. The solid substance was recrystallized with a mixture solvent of chloroform and methanol, so that 0.45 g of a yellow powdered solid substance was obtained in 65% yield. By a nuclear magnetic resonance measurement (NMR), this compound was found to be 2-(3-{N-[4-(carbazol-9-yl)phenyl]-N-phenylamino}phenyl)-9,10-diphenylanthracene (abbreviation: 2mYGAPPA).

Figure 21A:
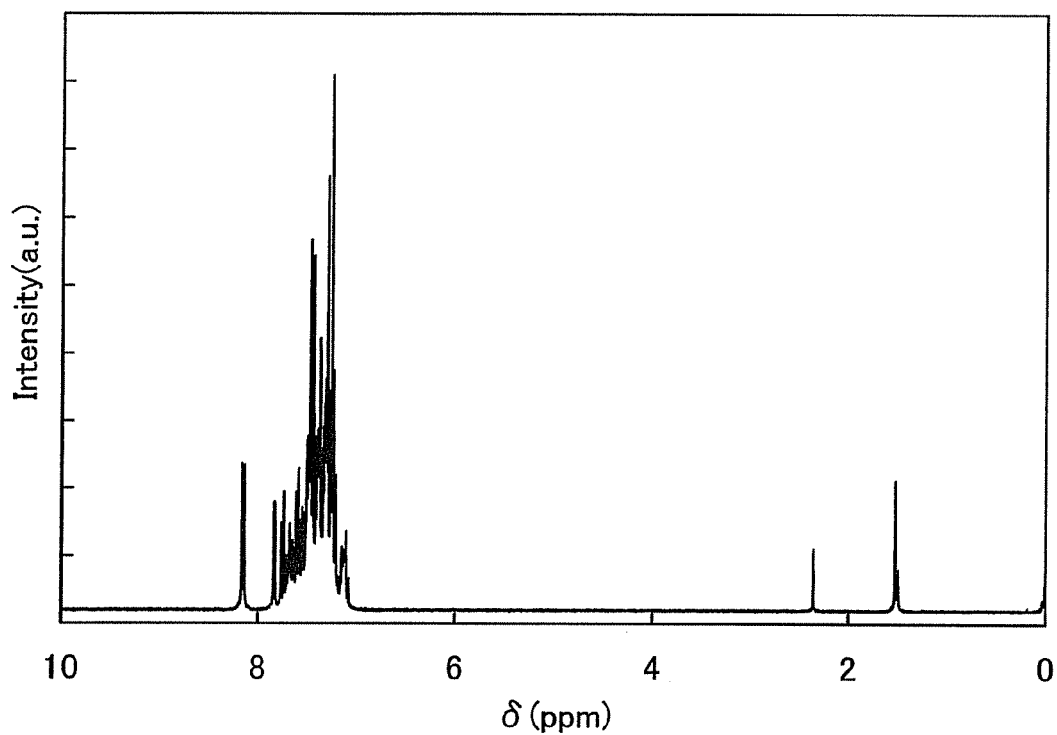
FIGS. 21A and 21B are each a $^1$H NMR chart of 2-(3-{N-[4-(carbazol-9-yl)phenyl]-N-phenylamino}phenyl)-9,10-diphenylanthracene (abbreviation: 2mYGAPPA)
Figure 21B:
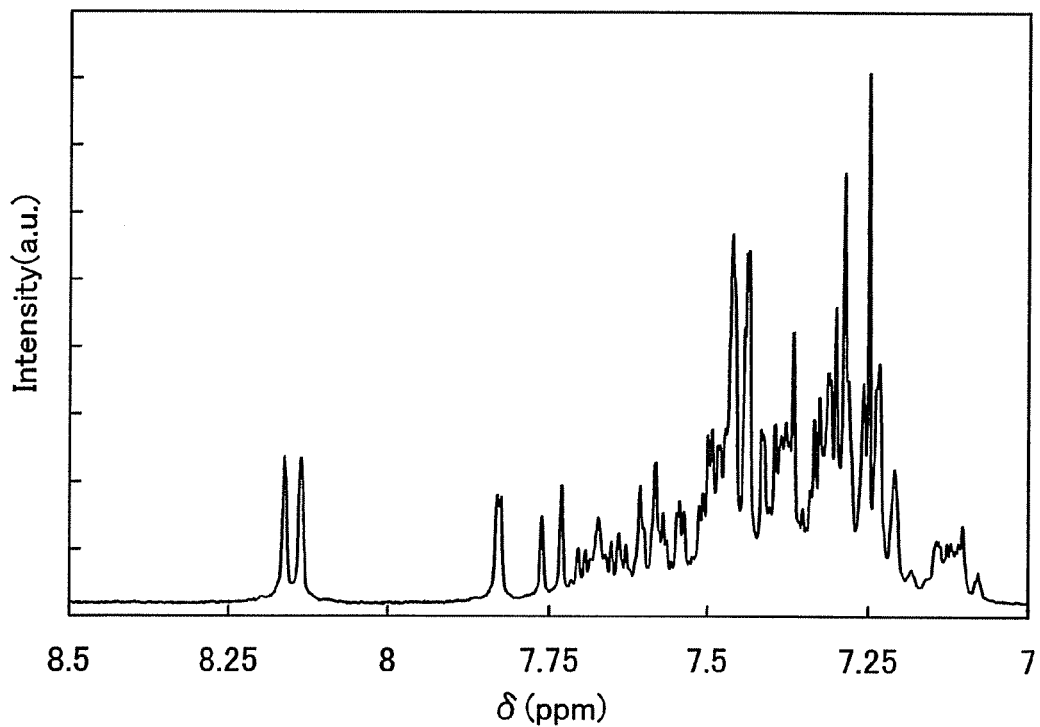

$^1$H NMR data of the obtained compound is shown below. $^1$H NMR (CDCl$_3$, 300 MHz): δ=7.06-7.72 (m, 34H), 7.75 (d, J=9.3 Hz, 1H), 7.83 (s, 1H), 8.15 (d, J=7.8 Hz, 2H). $^1$H NMR charts are shown in FIGS. 21A and 21B. Note that FIG. 21B is a chart in which the range of 7.0 ppm to 8.5 ppm in FIG. 21A is enlarged.

EXAMPLE 6

Figure 10:
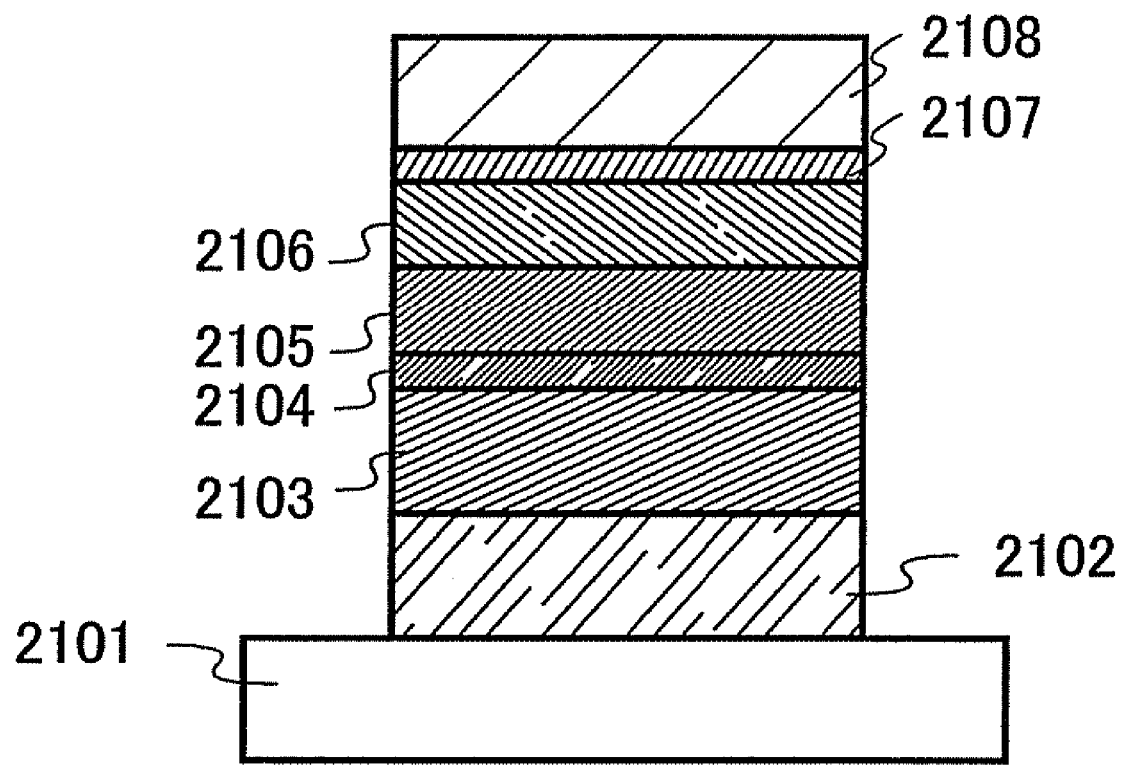
FIG. 10 illustrates a light-emitting element in Examples.

Example 6 will describe a light-emitting element of the present invention with reference to FIG. 10. Chemical formulae of materials used in this example are shown below.

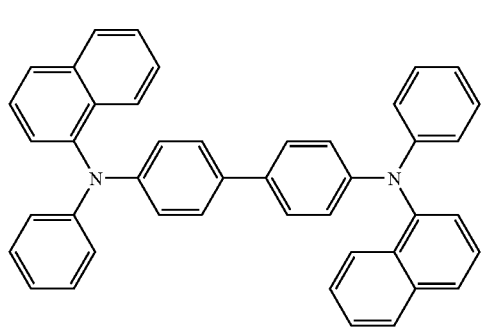

NPB

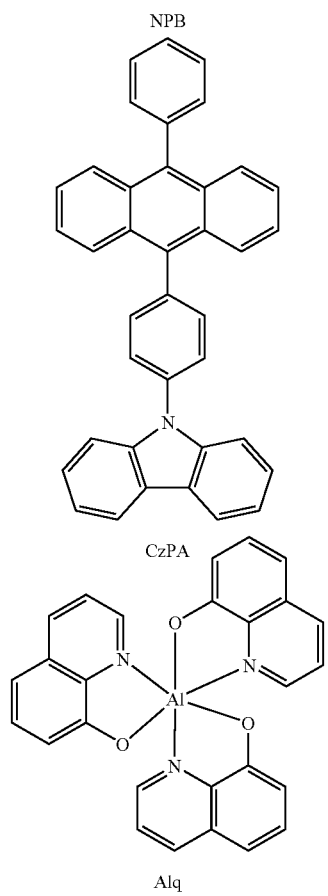

CzPA

Alq (Light-Emitting Element 1)

First, a film of indium tin oxide containing silicon oxide (ITSO) was formed by sputtering over a glass substrate 2101 to form a first electrode 2102. Note that the film thickness of the first electrode was 110 nm, and the area of the electrode was 2 mm×2 mm.

Next, the substrate over which the first electrode was formed was fixed to a substrate holder provided in a vacuum evaporation apparatus, so that a surface over which the first electrode was formed faced down. Then, after reducing the pressure of the vacuum evaporation apparatus to about $10^{-4}$ Pa, a layer 2103 containing a composite material, which was formed of an organic compound and an inorganic compound, was formed over the first electrode 2102 by co-evaporating NPB and molybdenum(VI) oxide. The film thickness of the layer 2103 was to be 50 nm, and the ratio of NPB and molybdenum(VI) oxide was adjusted to be 4:1 (=NPB:molybdenum oxide) in weight ratio. Note that the co-evaporation method is an evaporation method in which evaporation is carried out from a plurality of evaporation sources at the same time in one treatment chamber.

Subsequently, a film of 4,4'-bis[N-(1-napthyl)-N-phenylamino]biphenyl (abbreviation: NPB) was formed at a thickness of 10 nm over the layer 2103 containing the composite material by an evaporation method using the resistance heating system, thereby forming a hole transporting layer 2104.

Further, by co-evaporating 9-[4-(N-carbazolyl)]phenyl-10-phenylanthracene (abbreviation: CzPA) and 2-(4-{N-[4-carbazol-9-yl]phenyl]-N-phenylamino}phenyl)-9,10-diphenylanthracene (abbreviation: 2YGAPPA), represented by a structural formula (182), a light-emitting layer 2105 with a thickness of 30 nm was formed over the hole-transporting layer 2104. The weight ratio of CzPA and 2YGAPPA was adjusted to 1:0.05 (=CzPA: 2YGAPPA).

Thereafter, tris(8-quinolinolato)aluminum (abbreviation: Alq) having a film thickness of 30 nm was formed over the light-emitting layer 2105 by an evaporation method using the resistance heating system, thereby an electron-transporting layer 2106 is formed.

Furthermore, a film of lithium fluoride having a thickness of 1 nm was formed over the electron-transporting layer 2106 to form an electron-injecting layer 2107.

Finally, by forming a film of aluminum with a film thickness of 200 nm over the electron-injecting layer 2107 by the evaporation method using the resistance heating system, a second electrode 2108 was formed. Accordingly, a light-emitting element 1 was fabricated.

Figure 28:
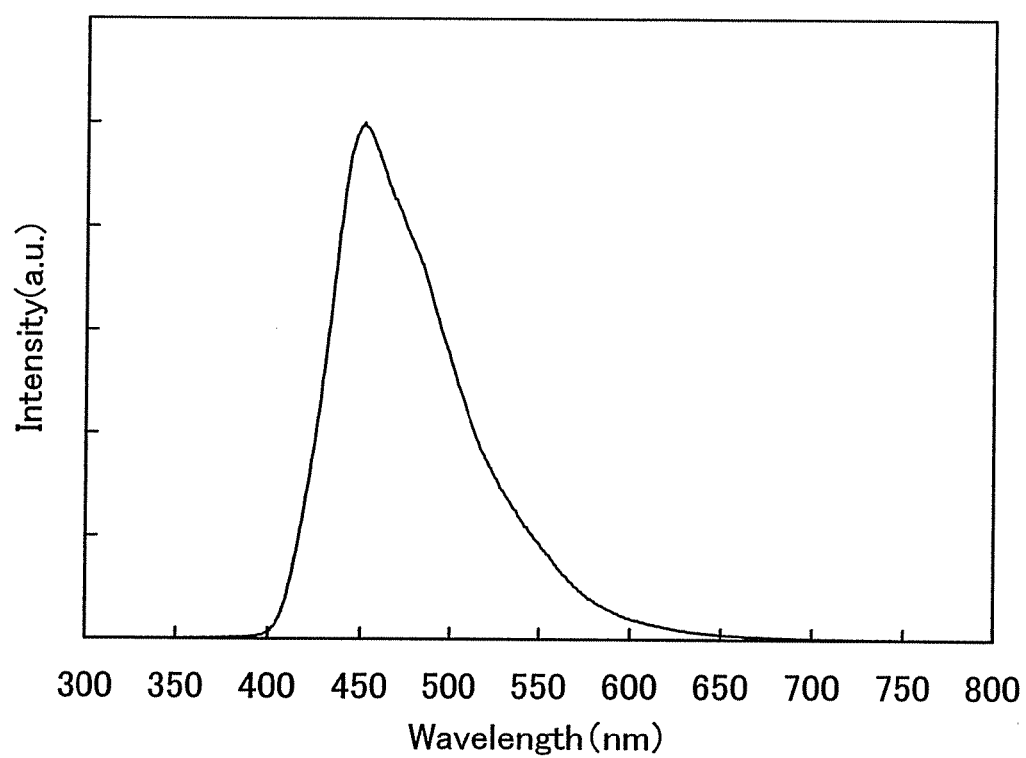
FIG. 28 is a graph showing an emission spectrum of the light-emitting element 1.
Figure 29:
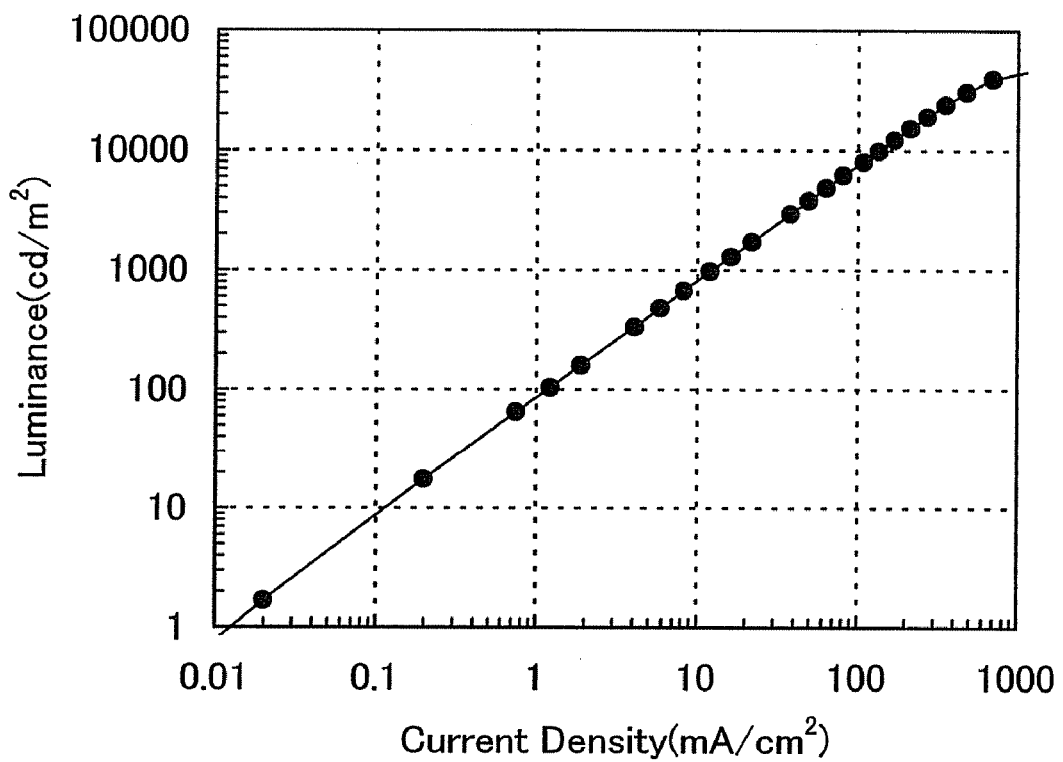
FIG. 29 is a graph showing current density-luminance characteristics of a light-emitting element 2.
Figure 30:
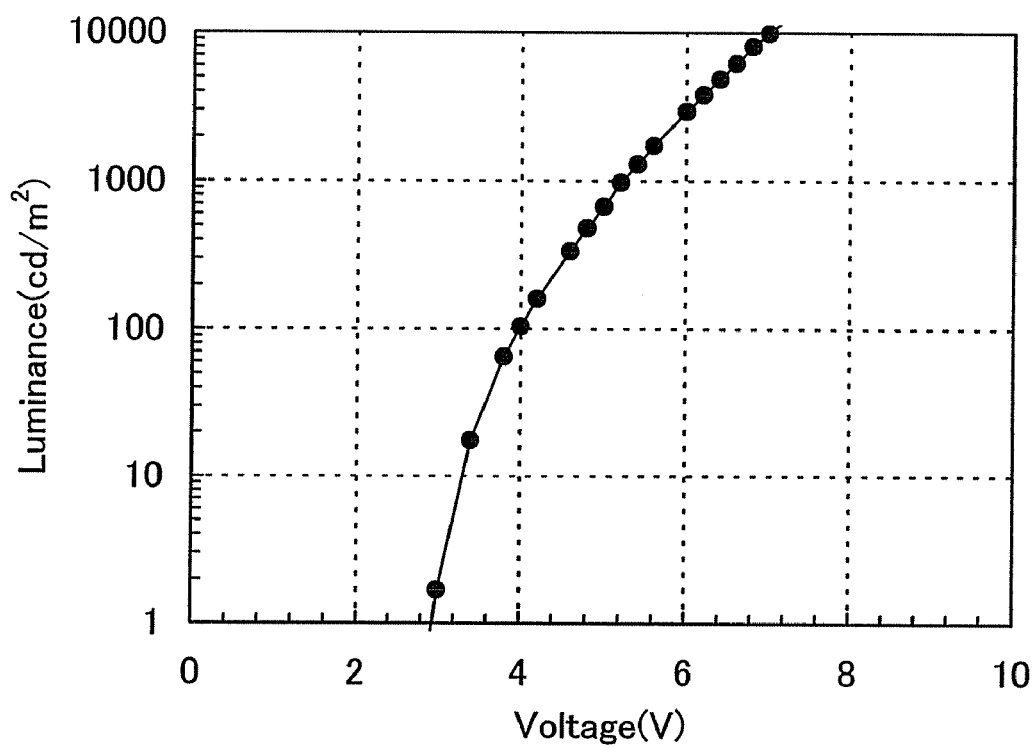
FIG. 30 is a graph showing voltage-luminance characteristics of the light-emitting element 2.
Figure 31:
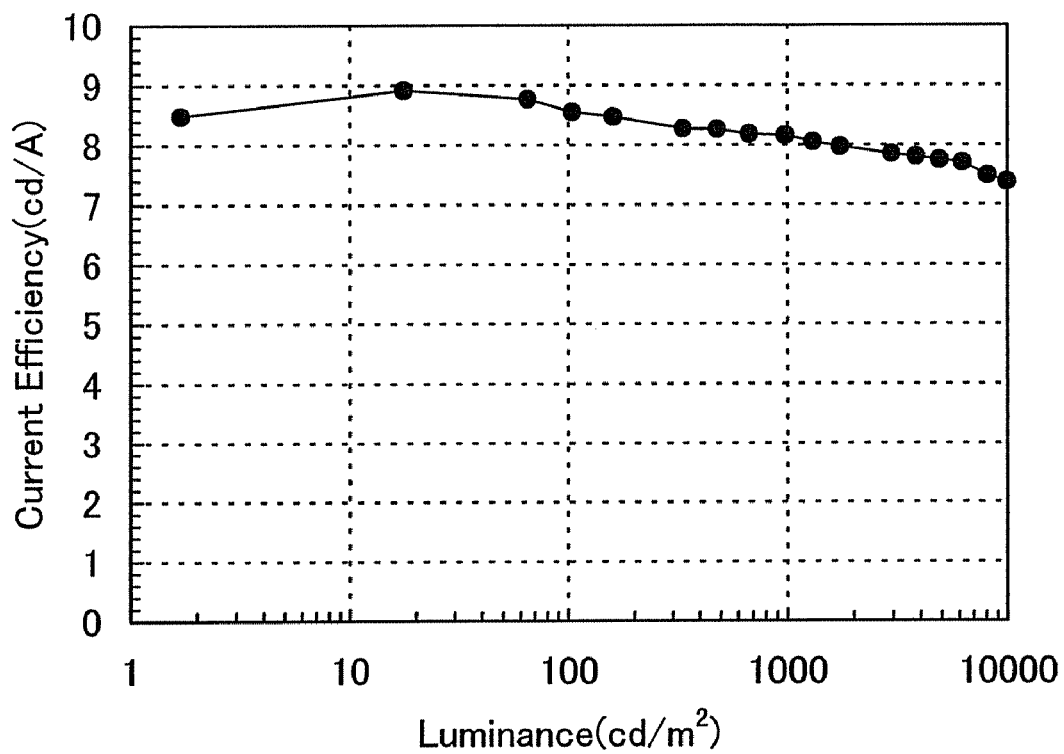
FIG. 31 is a graph showing luminance-current efficiency characteristics of the light-emitting element 2.
Figure 32:
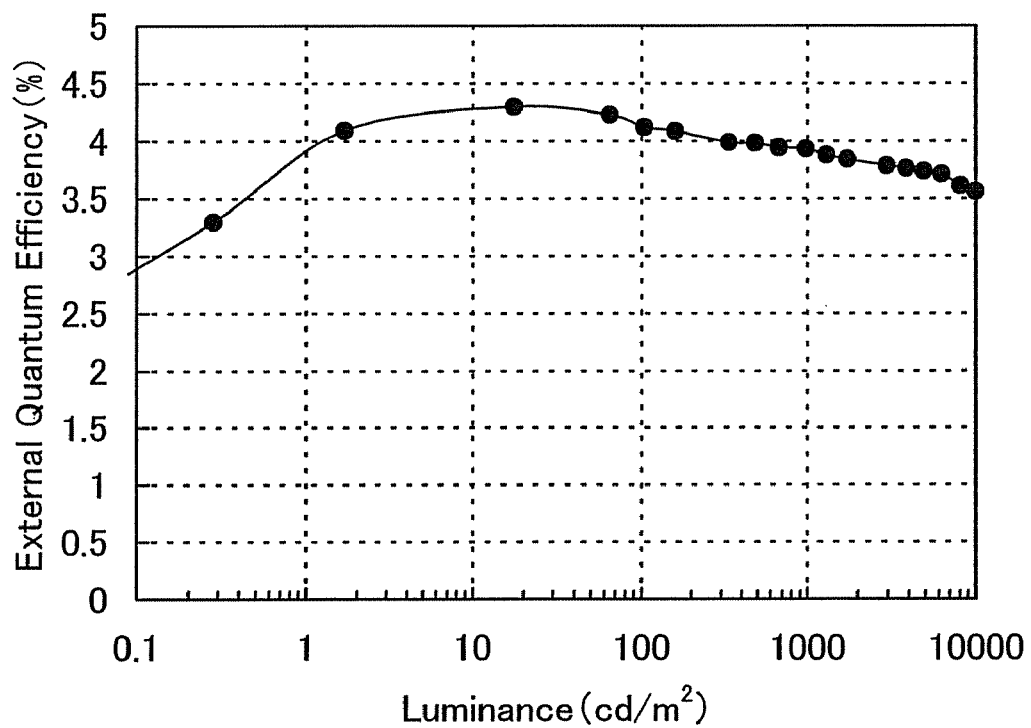
FIG. 32 is a graph showing luminance-external quantum efficiency characteristics of the light-emitting element 2.

Current density-luminance characteristics, voltage-luminance characteristics, luminance-current efficiency characteristics, and luminance-external quantum efficiency characteristics of the light-emitting element 1 are shown in FIGS. 24, 25, 26, and 27, respectively. Also, the emission spectrum which was obtained at a current of 1 mA is shown in FIG. 28. As shown in FIG. 28, the emission of the light-emitting element 1 found to be emission from 2YGAPPA. A CIE chromaticity coordinate of the light-emitting element 1 at luminance of about 800 cd/m$^2$ was (x=0.16, y=0.22), and light emission from the light-emitting element 1 was blue. It can be concluded from FIG. 27 that the light-emitting element 1 exhibits relatively excellent luminance-external quantum efficiency characteristics. Thus, the light-emitting element 1 has good luminous efficiency.

EXAMPLE 7

Example 7 will specifically describe an example of a light-emitting element using 2-{4-[N-phenyl-N-(9-phenylcarbazol-3-yl)amino]phenyl}-9,10-diphenylanthracene (abbreviation: 2PCAPPA), which is an anthracene derivative of the present invention represented by a structural formula (132).

(Light-Emitting Element 2)

The light-emitting element 2 fabricated in Example 7 was formed in the same way as the light-emitting element 1 of Example 6, except that 2PCAPPA was used instead of 2YGAPPA. In other words, as illustrated in FIG. 10, CzPA and 2PCAPPA represented by the structural formula (132) were co-evaporated to form a light-emitting layer 2105 having a thickness of 30 nm over the hole-transporting layer 2104, and the other layers of the light-emitting element 2 are formed in the same way as the light-emitting element 1. The weight ratio of CzPA and 2PCAPPA was adjusted to 1:0.05 (=CzPA: 2PCAPPA).

Figure 33:
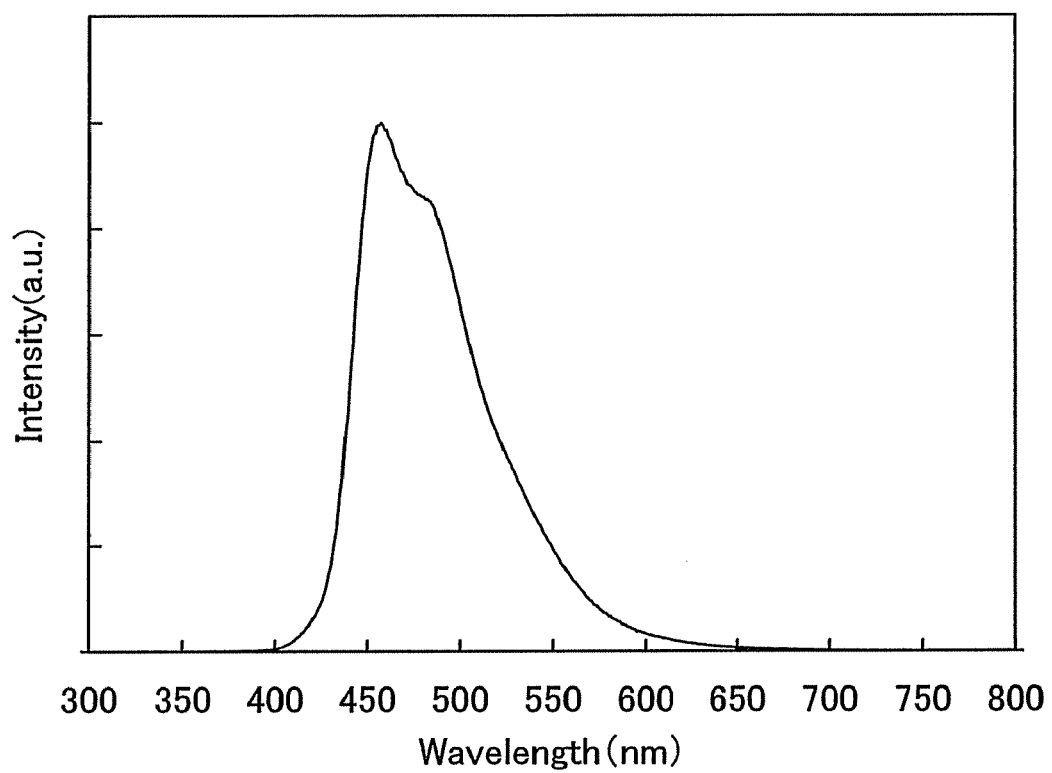
FIG. 33 is a graph showing an emission spectrum of the light-emitting element 2.
Figure 34:
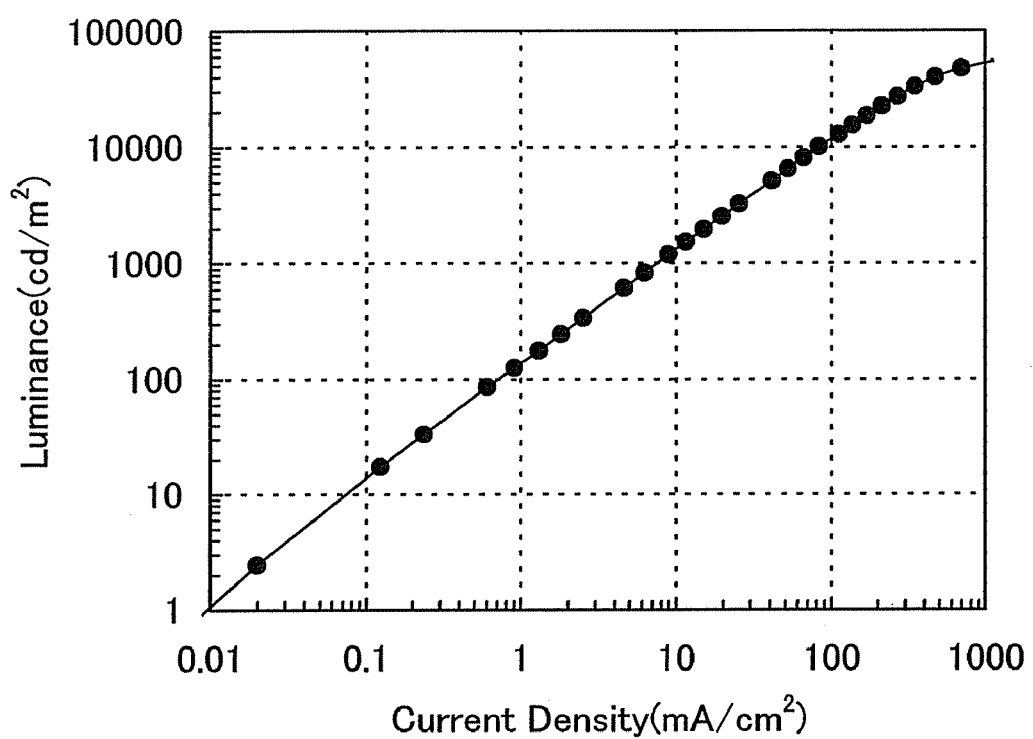
FIG. 34 is a graph showing current density-luminance characteristics of a light-emitting element 3.
Figure 35:
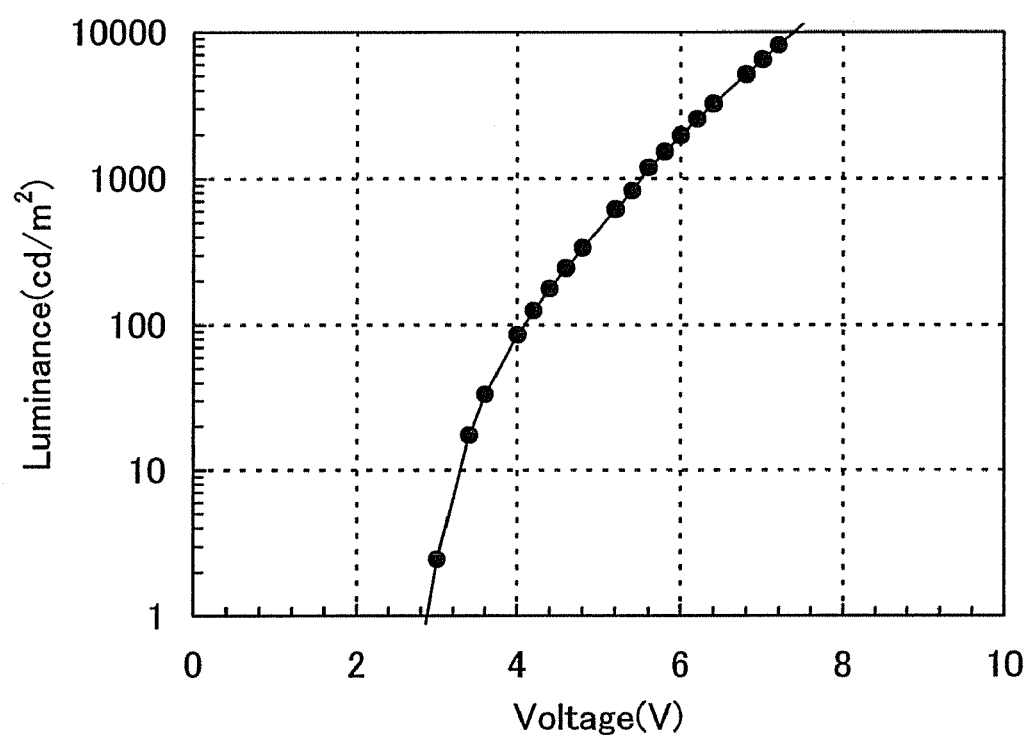
FIG. 35 is a graph showing voltage-luminance characteristics of the light-emitting element 3.
Figure 36:
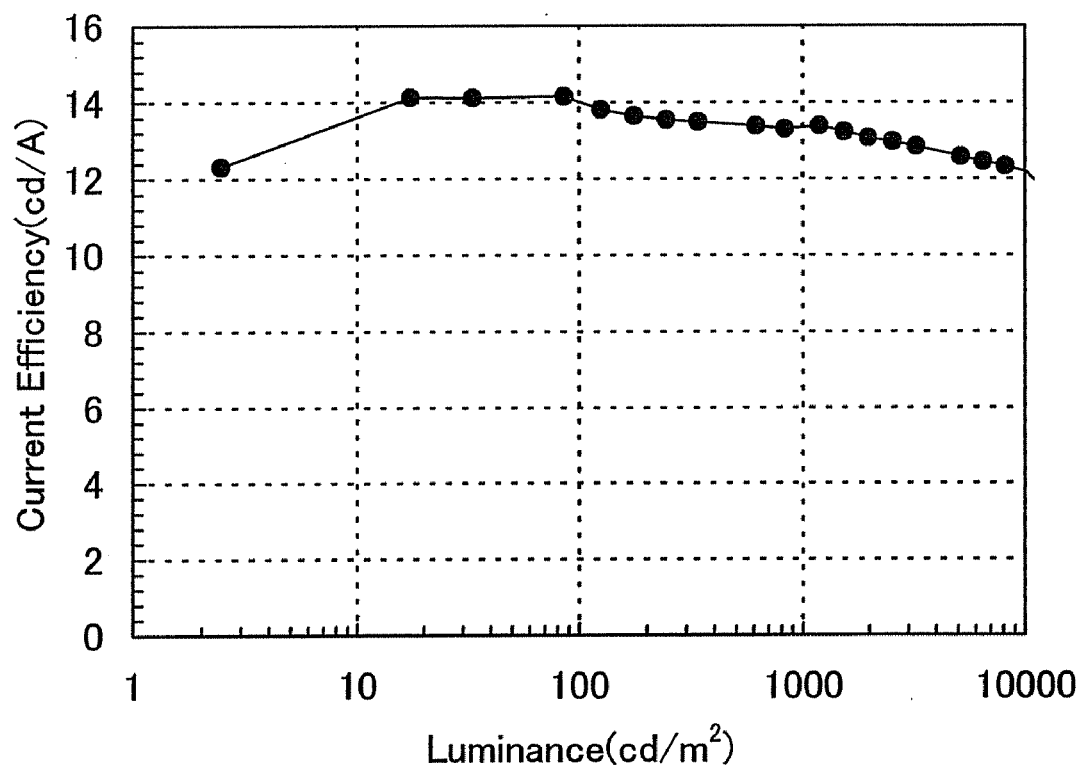
FIG. 36 is a graph showing luminance-current efficiency characteristics of the light-emitting element 3.
Figure 37:
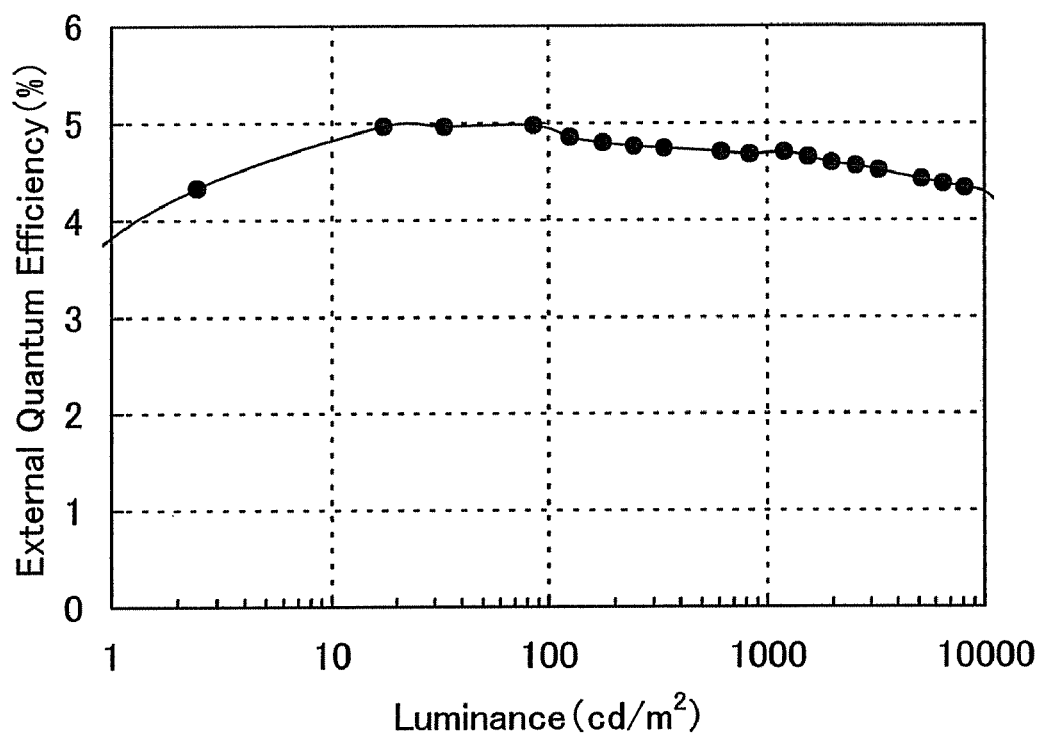
FIG. 37 is a graph showing luminance-external quantum efficiency characteristics of the light-emitting element 3.

Current density-luminance characteristics, voltage-luminance characteristics, luminance-current efficiency characteristics, and luminance-external quantum efficiency characteristics of the light-emitting element 2 are shown in FIGS. 29, 30, 31, and 32, respectively. Also, the emission spectrum which was obtained at a current of 1 mA is shown in FIG. 33. As shown in FIG. 33, the emission of the light-emitting element 2 found to be emission from 2PCAPPA. A CIE chromaticity coordinate of the light-emitting element 2 at luminance of 1000 cd/m) was (x=0.17, y=0.36), and light emission from the light-emitting element 2 was light blue. It can be concluded from FIG. 32 that the light-emitting element 2 exhibits high external quantum efficiency. Thus, the light-emitting element 2 has high luminous efficiency.

EXAMPLE 8

Example 8 will specifically describe an example of a light-emitting element using 2-{4-[N-(4-diphenylaminophenyl)-N-phenylamini]phenyl}-9,10-diphenylanthracene (abbreviation: 2DPAPPA), which is an anthracene derivative of the present invention represented by the structural formula (101).

(Light-Emitting Element 3)

The light-emitting element 3 fabricated in Example 8 was formed in the same way as the light-emitting element 1 of Example 6, except that 2DPAPPA is used instead of 2YGAPPA. In other words, as illustrated in FIG. 10, CzPA and 2DPAPPA represented by the structural formula (101) were co-evaporated to form a light-emitting layer 2105 having a thickness of 30 nm over the hole-transporting layer 2104, and the other layers of the light-emitting element 3 are formed in the same way as the light-emitting element 1. The weight ratio of CzPA and 2DPAPPA was adjusted to 1:0.1 (=CzPA: 2DPAPPA).

Figure 38:
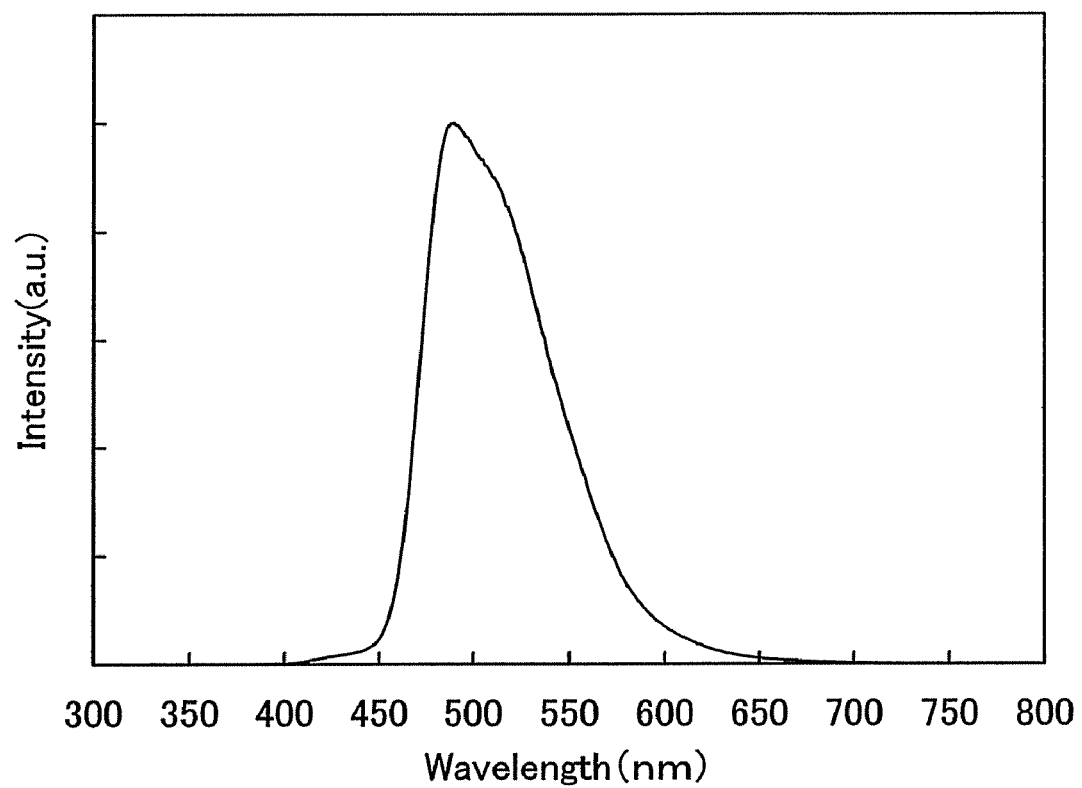
FIG. 38 is a graph showing an emission spectrum of the light-emitting element 3.

Current density-luminance characteristics, voltage-luminance characteristics, luminance-current efficiency characteristics, and luminance-external quantum efficiency characteristics of the light-emitting element 3 are shown in FIGS. 34, 35, 36, and 37, respectively. Also, the emission spectrum which was obtained at a current of 1 mA is shown in FIG. 38. As shown in FIG. 38, the emission of the light-emitting element 3 found to be emission from 2DPAPPA. A CIE chromaticity coordinate of the light-emitting element 3 at luminance of 800 cd/m$^2$ was (x=0.23, y=0.51), and light emission from the light-emitting element was bluish green. It can be concluded from FIG. 37 that the light-emitting element 3 exhibits high external quantum efficiency. Thus, the light-emitting element 3 has high luminous efficiency.

EXAMPLE 9

Example 9 will specifically describe a synthesis method of N-[4-(9,10-diphenyl-2-anthryl)phenyl]-N,N',N'-triphenyl-benzidine (abbreviation 2DPBAPPA), which is an anthracene derivative of the present invention represented by the structural formula (114).

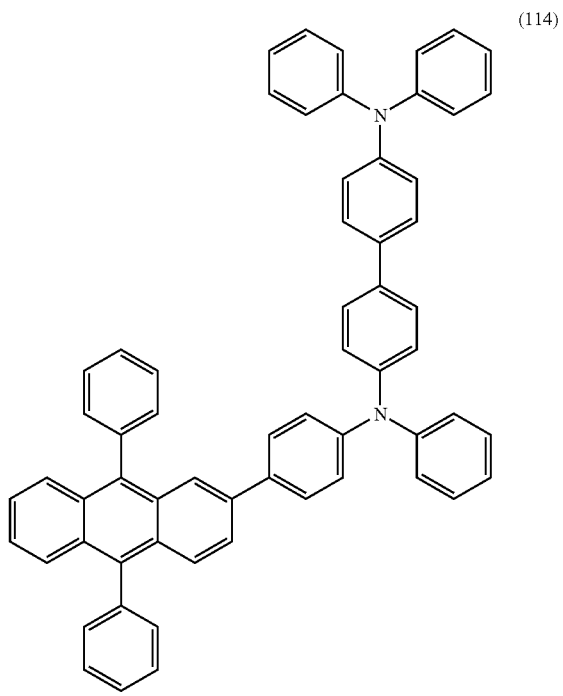

(114)

[Step 1] Synthesis of triphenylamine-4-boronic acid

A synthesis scheme of triphenylamine-4-boronic acid is shown in (H-1).

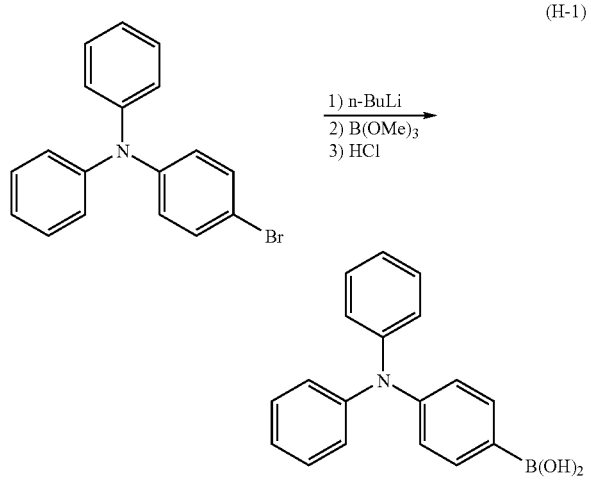

(H-1)

10 g (31 mmol) of 4-bromotriphenylamine was put into a 500 mL three-neck flask and the atmosphere in the flask was substituted by nitrogen. 150 mL of tetrahydrofuran (THF) was added thereto and cooled to −80° C. Into this solution, 20 mL (32 mmol) of n-butyllithium (1.58 mol/L hexane solution) wad dropped with a syringe. After dropping, the solution was stirred at the same temperature for one hour. 3.8 mL (34 mmol) of trimethyl borate was added into this solution, and while the temperature of the solution was being increased to room temperature, the solution was stirred for about 15 hours. After stirring, about 150 mL (1.0 mol/L) of dilute hydrochloric acid was added into this solution and stirred for one hour. After stirring, an aqueous layer of the mixture was extracted with ethyl acetate and the extracted solution and an organic layer were washed together with a saturated sodium hydrogen carbonate aqueous solution. The organic layer was dried with magnesium sulfate, the mixture was filtrated, and the filtrate was concentrated to obtain an oily light-brown substance. About 20 mL of chloroform was added into this oily substance, and further about 50 mL of hexane was added thereto. Then the mixture was left for one hour, so that a white solid substance was precipitated. This solid substance was collected by suction filtration, so that 5.2 g of the white solid substance was obtained in 58% yield.

[Step 2] Synthesis of N,N',N'-triphenylbenzidine (abbreviation: DPBA)

A synthesis scheme of N,N',N'-triphenylbenzidine (abbreviation: DPBA) is shown in (H-2).

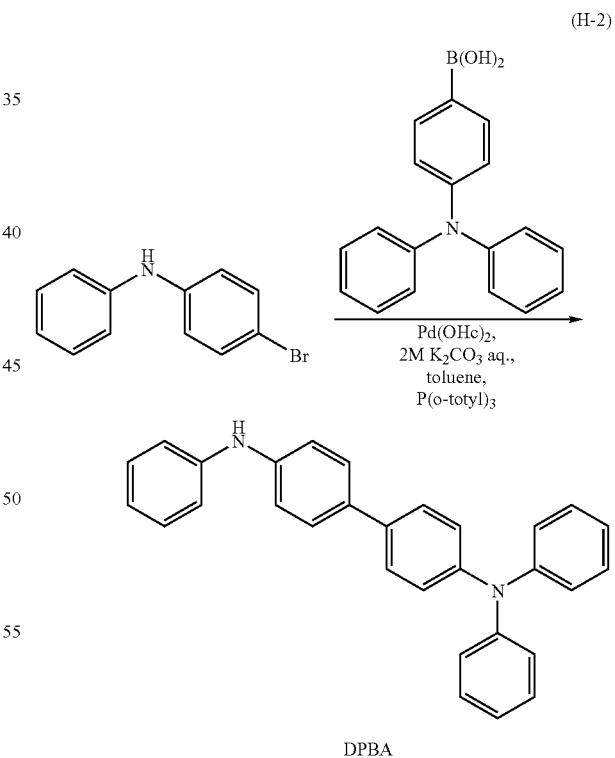

(H-2)

4.3 g (17 mmol) of 4-bromodiphenylamine, 5 g (17 mmol) of triphenylamine-4-boronic acid, and 532 mg of tri(o-tolyl)phosphine were put into a 500 mL three-neck flask, and the atmosphere in the flask was substituted by nitrogen. 60 mL of toluene, 40 mL of ethanol, and 14 ml of a potassium carbonate aqueous solution (0.2 mol/L) were added into this mixture.

The mixture was deaerated while being stirred under reduced pressure, and after deaeration, 75 mg (0.35 mmol) of palladium(II) acetate was added. This mixture was refluxed at 100° C. for 10.5 hours. An aqueous layer of the mixture was extracted with toluene. The extracted solution and an organic layer were washed together with saturated brine, and magnesium sulfate was added thereto for drying. This mixture was filtrated and the filtrate was concentrated to obtain an oily light-brown substance. The oily substance was dissolved in about 50 mL of toluene, and was subjected to suction filtration through Celite (manufactured by Celite Co., Ltd.), alumina, and Florisil (manufactured by Floridin Company). A solid substance obtained by concentrating the filtrate was purified by a silica gel column chromatography (developing solvent was a mixed solvent of hexane:toluene=4:6) to obtain a white solid substance. The obtained white solid substance was recrystallized with chloroform/hexane, so that 3.5 g of an white substance was obtained in yield 49%.

[Step 3] Synthesis of 2DPBAPPA

A synthesis scheme of 2DPBAPPA is shown in (H-3).

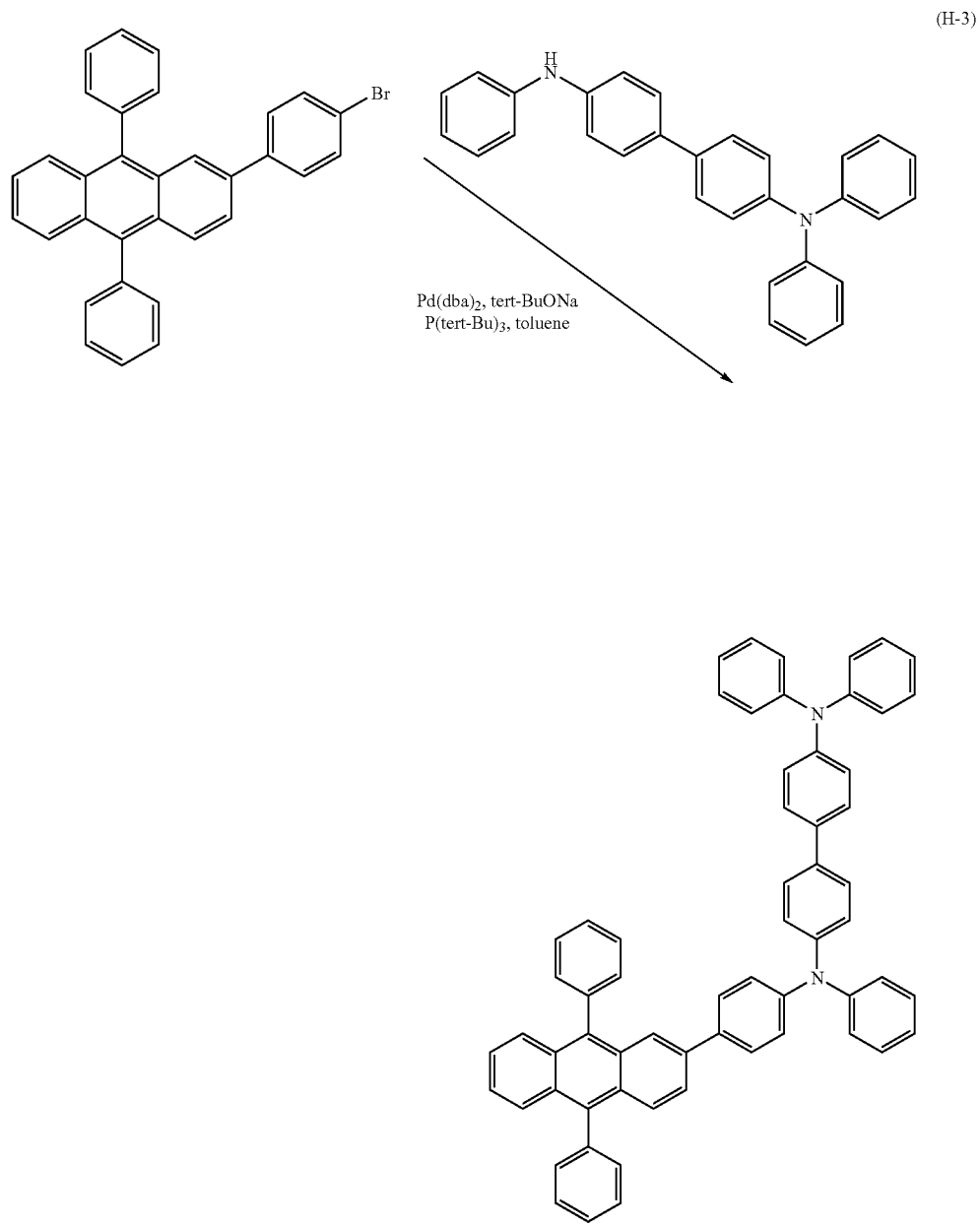

0.70 g (1.4 mmol) of 2-(4-bromophenyl)-9,10-diphenylanthracene, 0.60 g (1.4 mmol) of N,N',N'-triphenylbenzidine (abbreviation: DPBA), and 1.0 g (10 mmol) of sodium tert-butoxide were put into a 100 mL three-neck flask, and the atmosphere in the flask was substituted by nitrogen. 10 mL of toluene and 0.10 mL of tri(tert-butyl)phosphine 10 wt % hexane solution were added into this mixture. While the mixture was stirred to be deaerated under reduced pressure, and after deaeration, 58 mg (0.10 mmol) of bis(dibenzylideneacetone)palladium(0) was added. This mixture was stirred at 80° C. for three hours. This mixture was cooled to room temperature, and about 20 mL of toluene was added thereto and filtrated through Florisil (manufactured by Floridin Company), Celite (manufactured by Celite Co., Ltd.), and alumina. The obtained filtrate was concentrated to obtain a light-yellow solid substance. This light-yellow solid substance was purified by a silica gel column chromatography (developing solvent was a mixed solvent of hexane:toluene=3:2) to obtain a yellow solid substance. The obtained yellow solid substance was recrystallized with toluene/hexane, so that 0.82 g of the yellow powdered solid substance was obtained in yield 70%.

0.75 g of the obtained light-yellow powdered solid substance was purified by train sublimation. Under the sublimation conditions of the pressure of 6.0 Pa and the argon gas flow rate of 3.0 mL/min, the material was heated at 350° C. After sublimation, 0.63 g of the light-yellow solid substance was obtained in yield 83%.

By a nuclear magnetic resonance measurement (NMR), this compound was proved to be N-[4-(9,10-diphenyl-2-anthryl)phenyl]-N,N',N'-triphenylbenzidine (abbreviation: 2DPBAPPA).

Figure 42A:
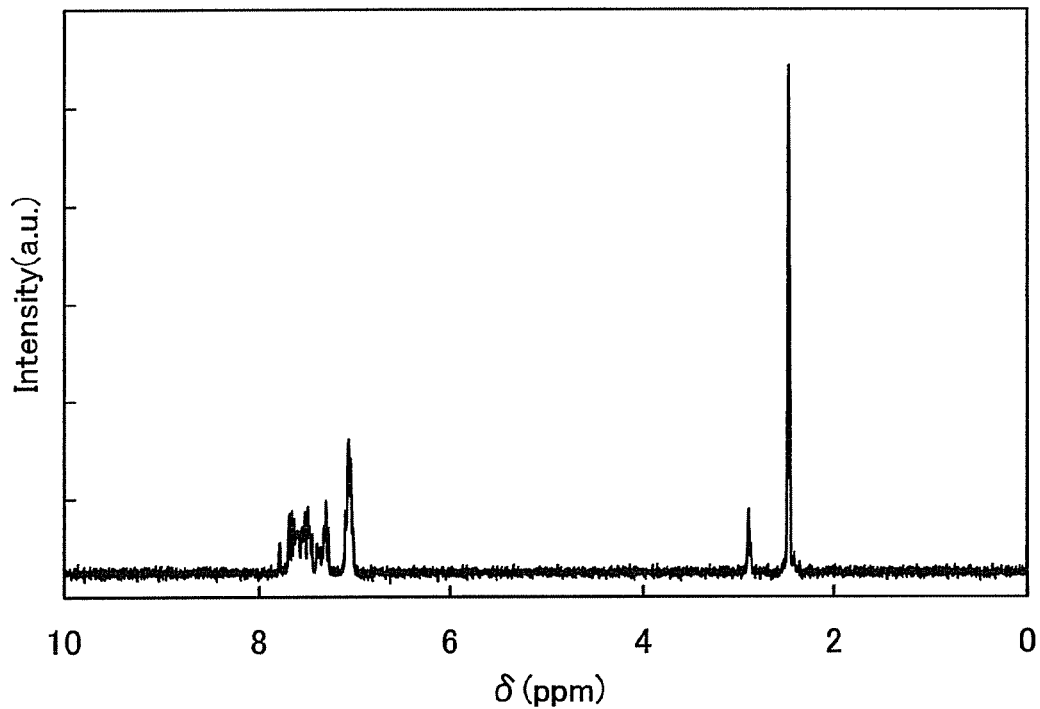
FIGS. 42A and 42B are each a $^1$H NMR chart of N-[4-(9,10-diphenyl-2-anthryl)phenyl]-N,N',N'-triphenylbenzidine (abbreviation 2DPBAPPA)
Figure 42B:
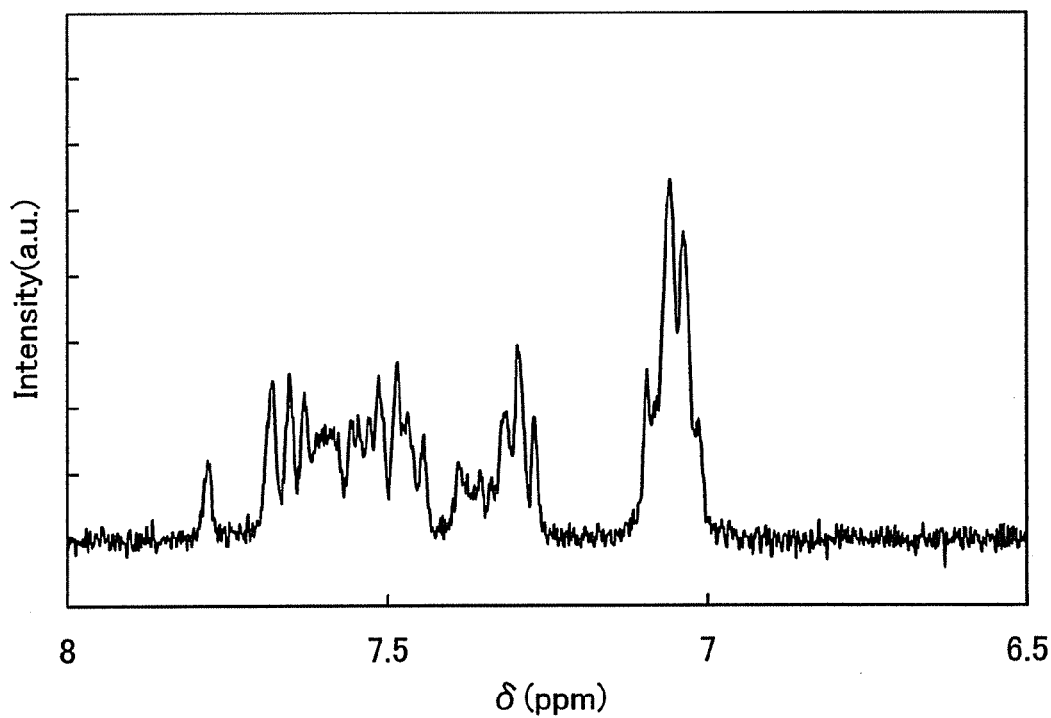

$^1$H NMR data of the obtained compound is shown below. $^1$H NMR (DMSO-d$_6$, 300 MHz): δ=7.04-7.10 (m, 15H), 7.27-7.31 (m, 8H), 7.39-7.68 (m, 20H), 7.78 (br, 1H). $^1$H NMR charts are shown in FIGS. 42A and 42B. Note that FIG. 42B is a chart in which the range of 6.5 ppm to 8.0 ppm in FIG. 42A is enlarged.

Figure 43:
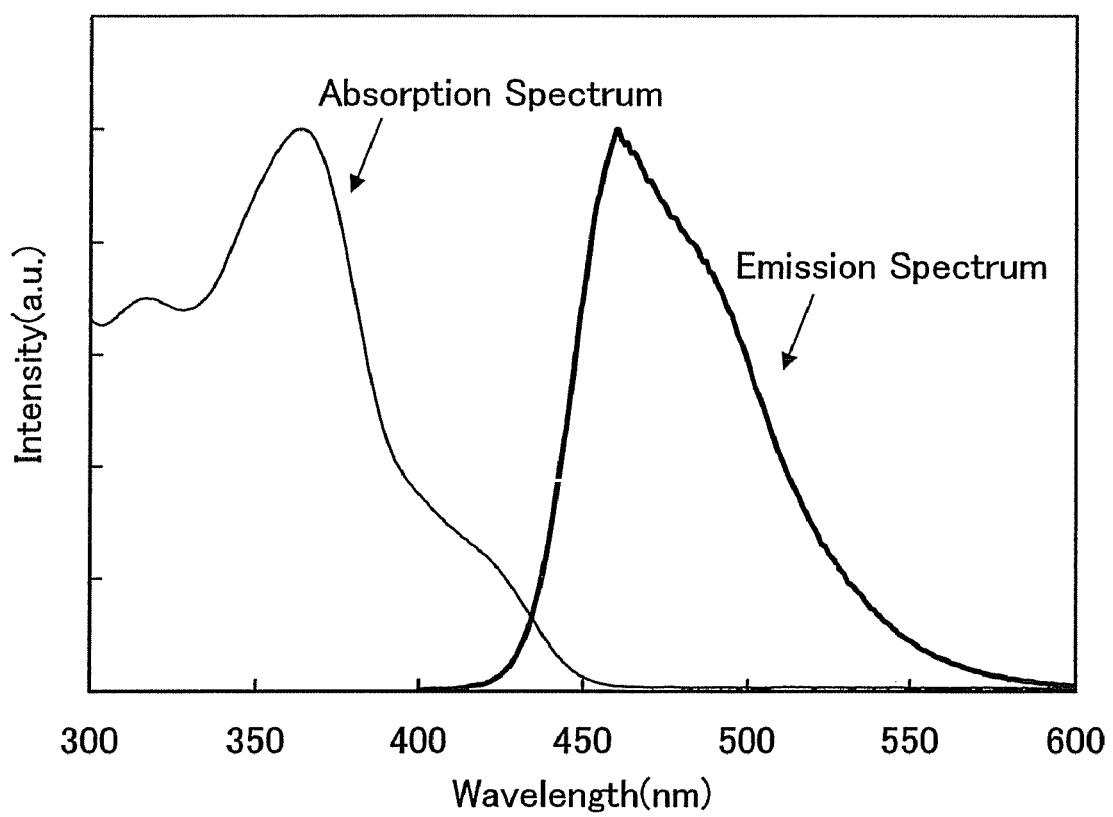
FIG. 43 is a graph showing an absorption spectrum and an emission spectrum of N-[4-(9,10-diphenyl-2-anthryl)phenyl]-N,N',N'-triphenylbenzidine (abbreviation 2DPBAPPA)

FIG. 43 shows absorption spectrum and emission spectrum in a toluene solution of 2DPBAPPA. An ultraviolet-visible spectrophotometer (V550, manufactured by Japan Spectroscopy Corporation) was used for measurement. The solution was put in a quartz cell and the absorption spectrum of the solution and the quartz cell was measured. The absorption spectrum of the solution which was obtained by subtracting the absorption spectrum of the quartz cell from the absorption spectrum of the solution and the quartz cell is shown in FIG. 43. In FIG. 43, the horizontal axis shows wavelength (nm) and the vertical axis shows absorption intensity (an arbitrary unit). In the case of the toluene solution, absorptions were observed at around 315 nm, 361 nm, and 421 nm. In the case of the toluene solution, the maximum emission wavelength was 460 nm (excitation wavelength of 370 nm).

Thermogravimetric/differential thermal analysis (TG-DTA) of 2DPBAPPA was carried out. In measuring, a high vacuum differential type differential thermal balance (TG-DTA2410SA, manufactured by Bruker AXS K.K.) was used. The rising temperature was set 10° C./min, and the temperature was increased under normal pressure. 5% weight reduction was seen at 460° C., which is indicative of high thermal stability of 2DPBAPPA.

EXAMPLE 10

Example 10 will specifically describe a synthesis method of 4-[4-(9H-carbazol-9-yl)phenyl]-4'-(9,10-diphenyl-2-anthryl)triphenylamine (abbreviation: 2YGBAPPA), which is an anthracene derivative of the present invention represented by a structural formula (191).

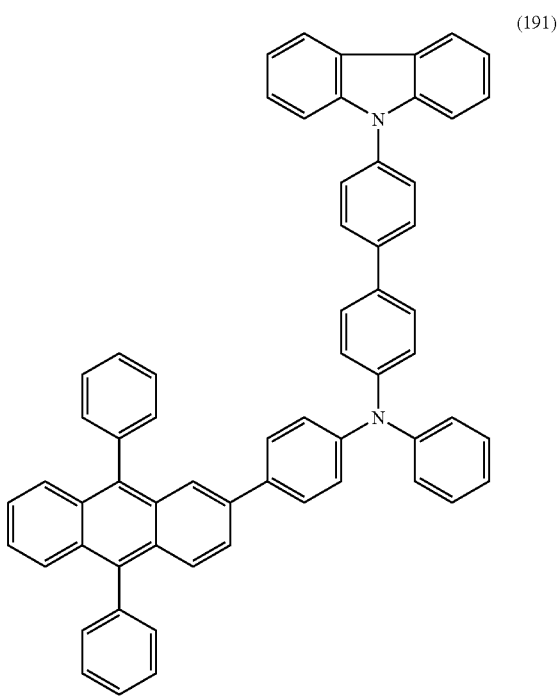

(191)

[Step 1] Synthesis of 4-(9H-carbazol-9-yl)phenylboronic acid

A synthesis scheme of 4-(9H-carbazol-9-yl)phenylboronic acid is shown in (J-1).

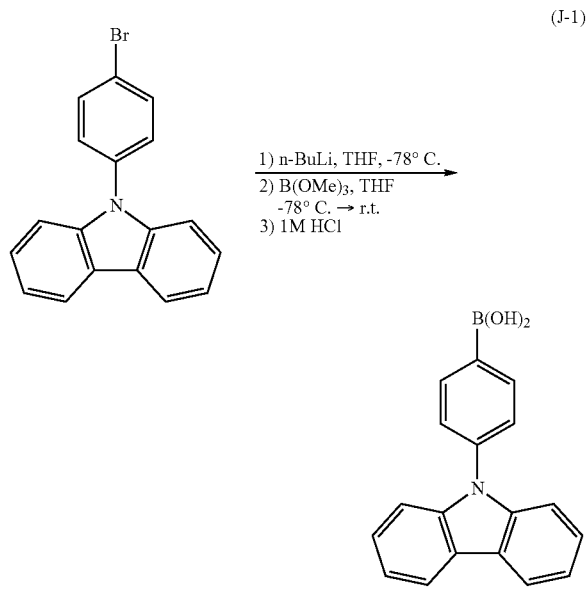

(J-1)

19.6 g (60.7 mmol) of N-(4-bromophenyl)carbazole synthesized in Step 1 of Example 3 was put into a 500 mL three-neck flask, and the atmosphere in the flask was substituted by nitrogen. 100 mL of tetrahydrofuran (THF) was added to the flask and cooled to −78° C. Into this solution, 66.8 mL (42.3 mmol) of n-butyllithium hexane solution (1.58 mol/L) wad dropped under a nitrogen gas flow, and the solution was stirred at the same temperature for three hours. Then, 13.5 mL (140 mmol) of trimethyl borate was added into this solution at the same temperature, and while the temperature of the solution was being increased to room temperature, the solution was stirred for about 24 hours. About 200 mL of 2.0 mol/L hydrochloric acid was added into this solution and stirred at room temperature for one hour. This solution was extracted with ethyl acetate and the extracted solution and an organic layer were washed together with a saturated brine and dried with magnesium sulfate. The mixture was filtrated, and the filtrate was concentrate to obtain a solid substance. The obtained solid substance was recrystallized with a mixed solvent of chloroform and hexane, so that 10.2 g of the white powder of 4(9H-carbazol-9-yl)phenylboronic acid was obtained in yield 58%.

[Step 2]
4-[4-(9H-carbazol-9-yl)phenyl]diphenylamine
(abbreviation: YGBA)

A synthesis scheme of 4-[4-(9H-carbazol-9-yl)phenyl] diphenylamine (abbreviation: YGBA) is shown in (J-2).

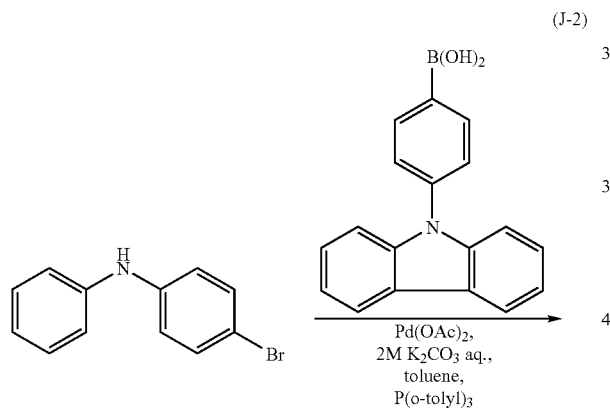

(J-2)

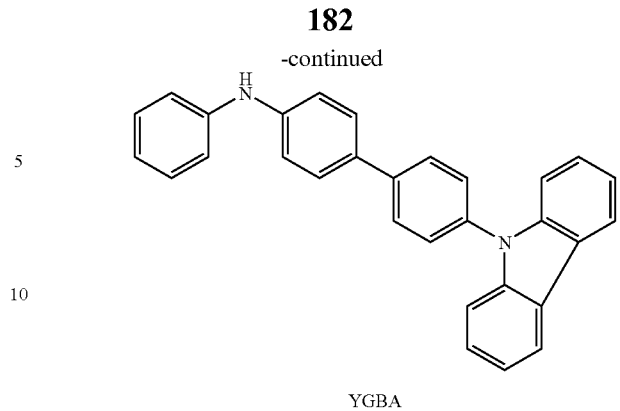

YGBA 2.2 g (8.8 mmol) of 4-bromodiphenylamine, 2.5 g (8.8 mmol) of 4-(9H-carbazol-9-yl)phenylboronic acid, 398 mg (1.3 mmol) of tri(o-tolyl)phosphine were put in a 200 mL three-neck flask, and the atmosphere in the flask was substituted by nitrogen. 30 mL of toluene, 20 mL of ethanol and 14 mL of potassium carbonate aqueous solution (0.2 mol/L) were added into this mixture. This mixture was deaerated under reduced pressure while being stirred, and 59 mg (0.26 mmol) of palladium(II) acetate was added thereto. The mixture was refluxed at 100° C. for 6.5 hours. This mixture was left to be cooled for about 15 hours, so that a gray solid substance was precipitated. The gray solid substance was collected by suction filtration, so that the gray solid substance was obtained in 70% yield.

[Step 4] Synthesis of 2YGBAPPA

A synthesis scheme of 2YGBAPPA is shown in (J-3).

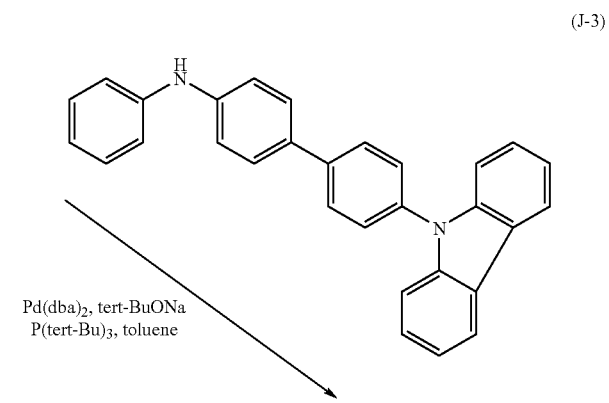

(J-3)

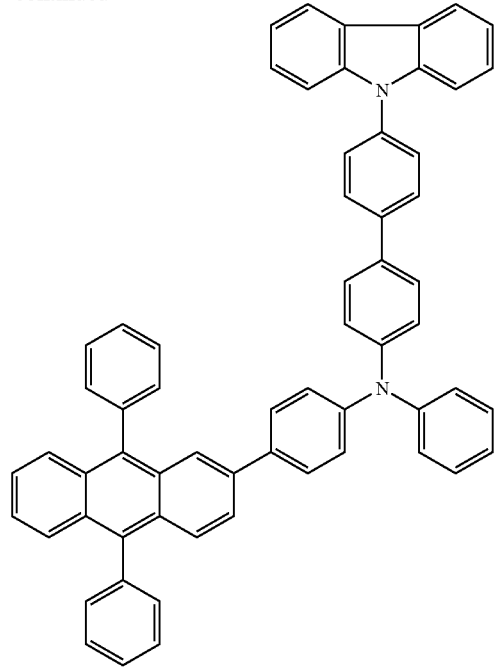

0.76 g (1.6 mmol) of 2-(4-bromophenyl)-9,10-diphenylanthracene, 0.64 g (1.6 mmol) of 4-[4-(9H-carbazol-9-yl)phenyl]diphenylamine (abbreviation: YGBA), and 1.0 g (10 mmol) of sodium tert-butoxide were put into a 100 mL three-neck flask, and the atmosphere in the flask was substituted by nitrogen. 10 mL of toluene and 0.10 mL of tri(tert-butyl)phosphine (10 wt % hexane solution) were added into this mixture. This mixture was deaerated under reduced pressure while being stirred, and then 58 mg (0.10 mmol) of bis(dibenzylideneacetone)palladium(0) acetate was added thereto. The mixture was refluxed at 80° C. for three hours. This mixture was cooled to room temperature, about 20 mL of toluene was added, and then filtrated through Florisil (manufactured by Floridin Company), Celite (manufactured by Celite Co., Ltd.), and alumina. The obtained filtrate was concentrated to obtain a light yellow solid substance. The solid substance was purified by a silica gel column chromatography (developing solvent was a mixed solvent of hexane:toluene=3:2) to obtain a yellow solid substance. The obtained yellow solid substance was recrystallized with toluene/hexane, so that 0.62 g of the yellow powdered solid substance was obtained in yield 48%.

0.60 g of the obtained light-yellow powdered solid substance was purified by train sublimation. The sublimation was conducted under conditions of a low pressure of 6.0 Pa, the argon gas flow rate of 3.0 mL/min, heating at 360° C. 0.53 g of the light-yellow solid substance, which is a material, was obtained in yield 89%.

By a nuclear magnetic resonance measurement (NMR), this compound was found to be 4-[4-(9H-carbazol-9-yl)phenyl]-4'-(9,10-diphenyl-2-anthryl)triphenylamine (abbreviation: 2YGBAPPA).

$^1$H NMR data of the obtained compound is shown below.
$^1$H NMR (DMSO-d$_6$, 300 MHz): δ=7.12-7.16 (m, 6H), 7.29-7.80 (m, 32H), 7.94 (d, J=7.8 Hz, 2H), 8.27 (d, J=7.2 Hz, 2H).

Figure 44A:
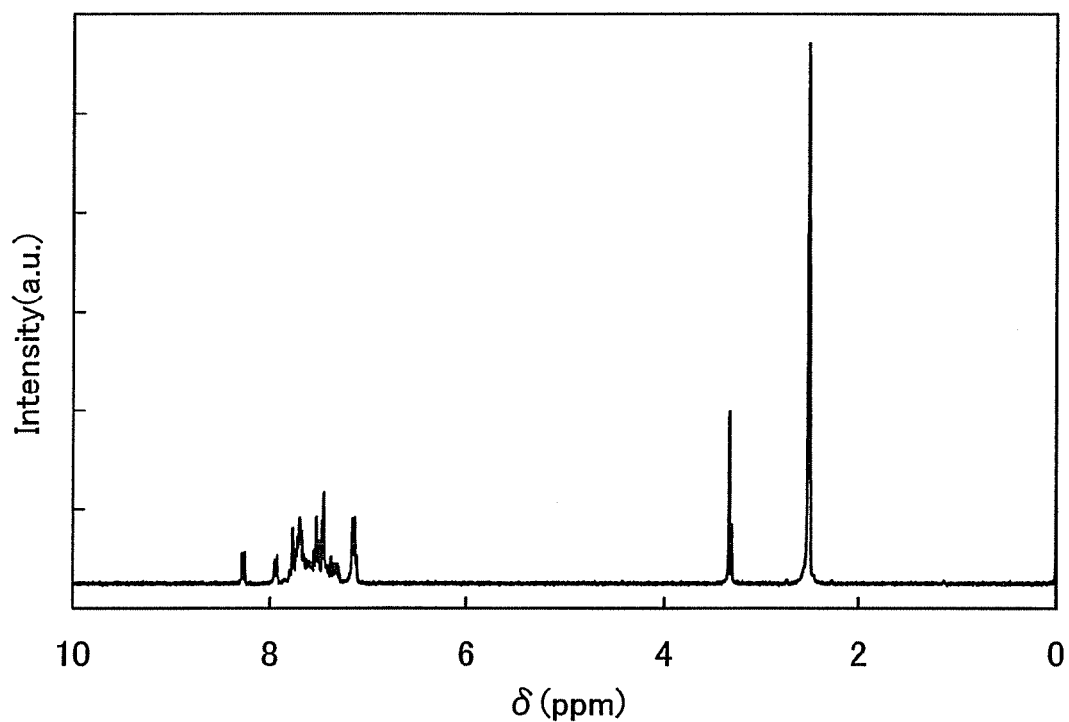
FIGS. 44A and 44B are each a $^1$H NMR chart of 4-[4-(9H-carbazol-9-yl)phenyl]-4'-(9,10-diphenyl-2-anthryl)triphenylamine (abbreviation: 2YGBAPPA)
Figure 44B:
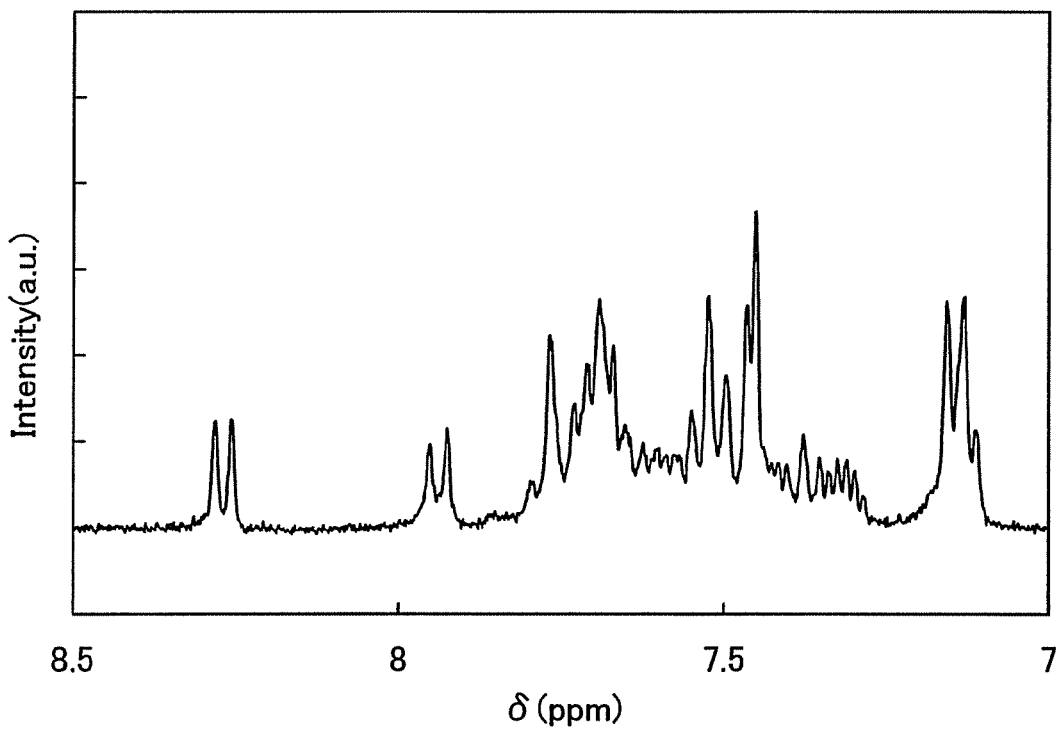

FIGS. 44A and 44B show $^1$H NMR charts. Note that FIG. 44B is a chart in which the range of 7.0 ppm to 8.5 ppm in FIG. 44A is enlarged.

Figure 45:
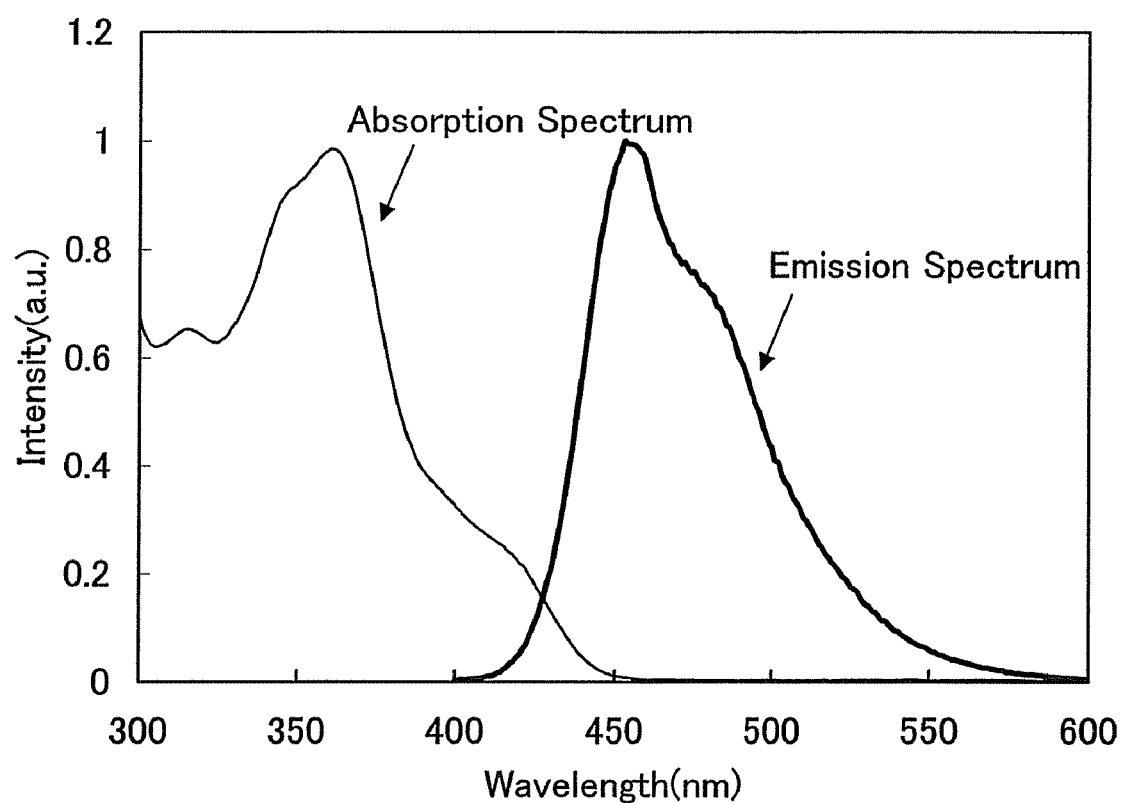
FIG. 45 is a graph showing an absorption spectrum and an emission spectrum of 4-[4-(9H-carbazol-9-yl)phenyl]-4'-(9,10-diphenyl-2-anthryl)triphenylamine (abbreviation: 2YGBAPPA).

FIG. 45 shows absorption spectrum and emission spectrum in a toluene solution of 2YGBAPPA. An ultraviolet-visible spectrophotometer (V550, manufactured by Japan Spectroscopy Corporation) was used for measurement. The solution was put in a quartz cell and the absorption spectrum of the solution and the quartz cell was measured. The absorption spectrum of the solution which was obtained by subtracting the absorption spectrum of the quartz cell from the absorption spectrum of the solution and the quartz cell is shown in FIG. 45. In FIG. 45, the horizontal axis shows wavelength (nm) and the vertical axis shows absorption intensity (an arbitrary unit). In the case of the toluene solution, absorptions were observed at around 313 nm, 358 nm, and 415 nm. In the case of the toluene solution, the maximum emission wavelength was 457 nm (excitation wavelength of 370 nm).

Thermogravimetric/differential thermal analysis (TG-DTA) of 2YGBAPPA was carried out. In measuring, a high vacuum differential type differential thermal balance (DTA2410SA, manufactured by Bruker AXS K.K) was used. The rising temperature was set 10° C./min, and the temperature was increased under normal pressure. 5% weight reduction was not seen at 500° C., which is indicative of high thermal stability of 2YGBAPPA.

This application is based on Japanese Patent Application serial no. 2006-355196 filed in Japan Patent Office on Dec. 28, 2006, the entire contents of which are hereby incorporated by reference.

What is claimed is:

1. An anthracene derivative represented by the structure:

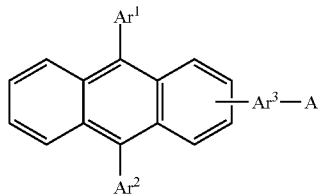

wherein $Ar^1$ and $Ar^2$ each represent an aryl group having 6 to 25 carbon atoms, $Ar^3$ represents an arylene group having 6 to 25 carbon atoms, and wherein A is selected from:

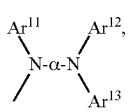 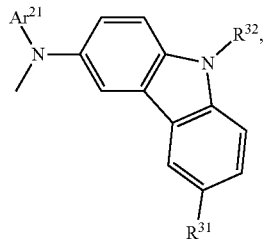

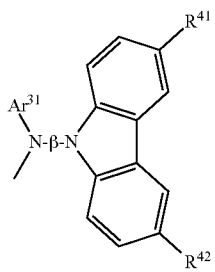

$Ar^{11}$ to $Ar^{13}$ each represent an aryl group having 6 to 25 carbon atoms;

α represents an arylene group having 6 to 25 carbon atoms;

$Ar^{21}$ represents an aryl group having 6 to 25 carbon atoms;

$R^{31}$ represents a hydrogen atom, an alkyl group having 1 to 4 carbon atoms, an aryl group having 6 to 25 carbon atoms, a halogen atom, or a haloalkyl group having 1 to 4 carbon atoms;

$R^{32}$ represents an alkyl group having 1 to 4 carbon atoms, an aryl group having 6 to 25 carbon atoms, or a haloalkyl group having 1 to 4 carbon atoms;

$Ar^{31}$ represents an aryl group having 6 to 25 carbon atoms;

β represents an arylene group having 6 to 25 carbon atoms; and $R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

2. An anthracene derivative according to claim 1, wherein A is selected from:

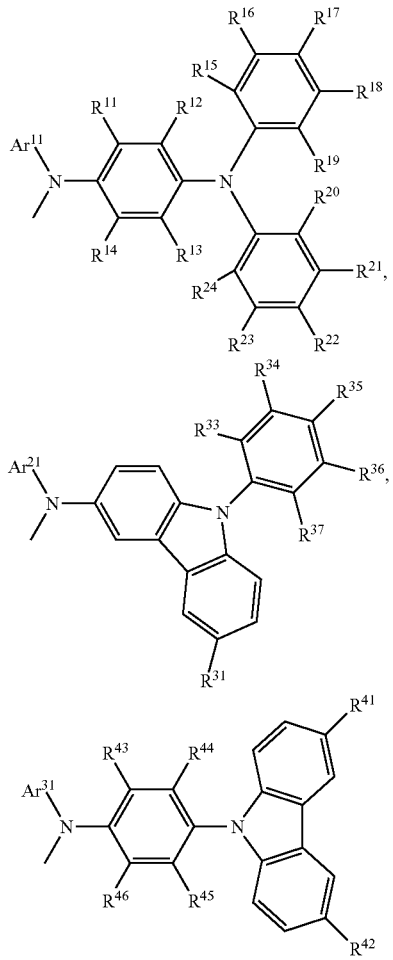

$Ar^{11}$ represents an aryl group having 6 to 25 carbon atoms;

$R^{11}$ to $R^{24}$ each represent a hydrogen atom, an alkyl group having 1 to 4 carbon atoms, an aryl group having 6 to 15 carbon atoms, a halogen atom, or a haloalkyl group having 1 to 4 carbon atoms;

$Ar^{21}$ represents an aryl group having 6 to 25 carbon atoms;

$R^{31}$ represents a hydrogen atom, an alkyl group having 1 to 4 carbon atoms, an aryl group having 6 to 25 carbon atoms, a halogen atom, or a haloalkyl group having 1 to 4 carbon atoms;

$R^{33}$ to $R^{37}$ each represent a hydrogen atom, an alkyl group having 1 to 4 carbon atoms, an aryl group having 6 to 15 carbon atoms, a halogen atom, or a haloalkyl group having 1 to 4 carbon atoms;

$Ar^{31}$ represents an aryl group having 6 to 25 carbon atoms;

$R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms; and $R^{43}$ to $R^{46}$ each represent a hydrogen atom, an alkyl group having 1 to 4 carbon atoms, an aryl group having 6 to 15 carbon atoms, a halogen atom, or a haloalkyl group having 1 to 4 carbon atoms.

3. An anthracene derivative according to claim 1, wherein A is selected from:

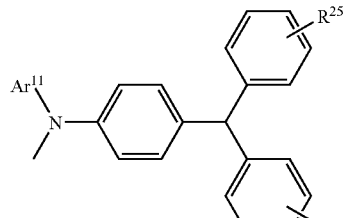

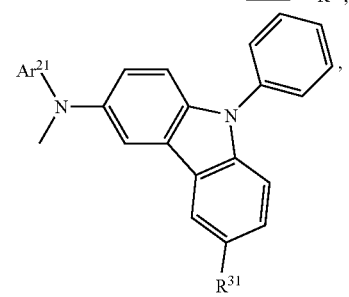

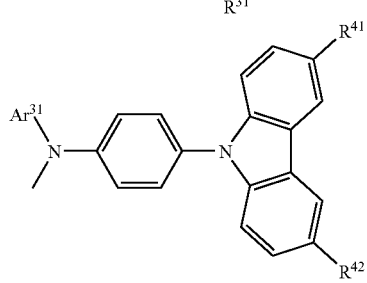

Ar$^{11}$ represents an aryl group having 6 to 25 carbon atoms;
R$^{25}$ and R$^{26}$ each represent a hydrogen atom, an alkyl group having 1 to 4 carbon atoms, an aryl group having 6 to 15 carbon atoms, a halogen atom, or a haloalkyl group having 1 to 4 carbon atoms;
Ar$^{21}$ represents an aryl group having 6 to 25 carbon atoms;
R$^{31}$ represents a hydrogen atom, an alkyl group having 1 to 4 carbon atoms, an aryl group having 6 to 25 carbon atoms, a halogen atom, or a haloalkcyl group having 1 to 4 carbon atoms;
Ar$^{31}$ represents an aryl group having 6 to 25 carbon atoms; and
R$^{41}$ and R$^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

4. An anthracene derivative according to claim 1, wherein A is selected from:

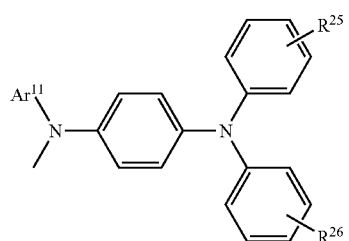

-continued

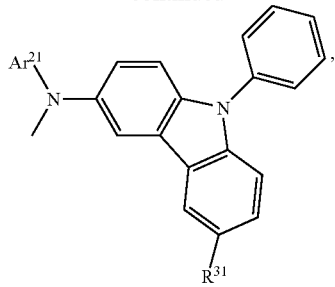

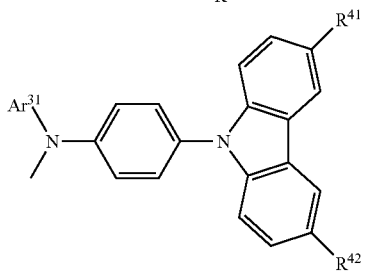

Ar$^{11}$ represents a phenyl group, a 1-naphthyl group or a 2-naphthyl group;
R$^{25}$ and R$^{26}$ each represent a hydrogen atom, an alkyl group having 1 to 4 carbon atoms, or an aryl group having 6 to 15 carbon atoms;
Ar$^{21}$ represents a phenyl group, a 1-naphthyl group or a 2-naphthyl group;
R$^{31}$ represents a hydrogen atom, an alkyl group having 1 to 4 carbon atoms, or an aryl group having 6 to 25 carbon atoms;
Ar$^{31}$ represents a phenyl group, a 1-naphthyl group or a 2-naphthyl group; and
R$^{41}$ and R$^{42}$ each represent a hydrogen atom, an alkyl group having 1 to 4 carbon atoms, or an aryl group having 6 to 25 carbon atoms.

5. An anthracene derivative according to claim 1, wherein Ar$^1$ and Ar$^2$ each are a substituent represented by the structure:

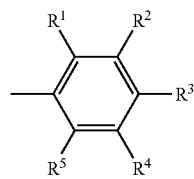

R$^1$ to R$^5$ each represent a hydrogen atom, an alkyl group having 1 to 4 carbon atoms, a haloalkyl group having 1 to 4 carbon atoms, or an aryl group having 6 to 15 carbon atoms.

6. An anthracene derivative according to claim 1, wherein Ar$^3$ is selected from:

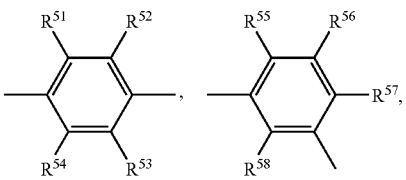

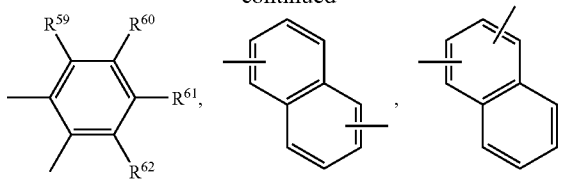

wherein $R^{51}$ to $R^{62}$ each represent a hydrogen atom, an alkyl group having 1 to 4 carbon atoms, an aryl group having 6 to 15 carbon atoms, a halogen atom, or a haloalkyl group having 1 to 4 carbon atoms.

7. An anthracene derivative represented by the structure:

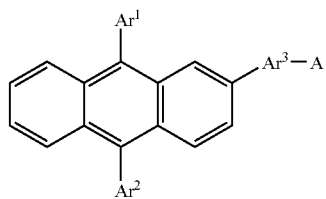

wherein $Ar^1$ and $Ar^2$ each represent an aryl group having 6 to 25 carbon atoms, $Ar^3$ represents an arylene group having 6 to 25 carbon atoms, and wherein A is selected from:

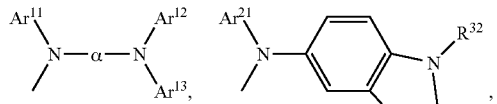

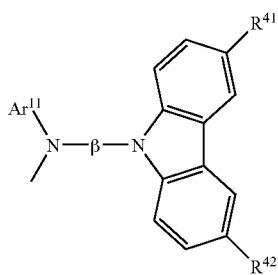

$Ar^{11}$ to $Ar^{13}$ each represent an aryl group having 6 to 25 carbon atoms;
α represents an arylene group having 6 to 25 carbon atoms;
$Ar^{21}$ represents an aryl group having 6 to 25 carbon atoms;
$R^{31}$ represents a hydrogen atom, an alkyl group having 1 to 4 carbon atoms, an aryl group having 6 to 25 carbon atoms, a halogen atom, or a haloallcyl group having 1 to 4 carbon atoms;
$R^{32}$ represents an alkyl group having 1 to 4 carbon atoms, an aryl group having 6 to 25 carbon atoms, or a haloalkyl group having 1 to 4 carbon atoms;
$Ar^{31}$ represents an aryl group having 6 to 25 carbon atoms;
β represents an arylene group having 6 to 25 carbon atoms; and
$R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

8. An anthracene derivative according to claim 7, wherein A is selected from:

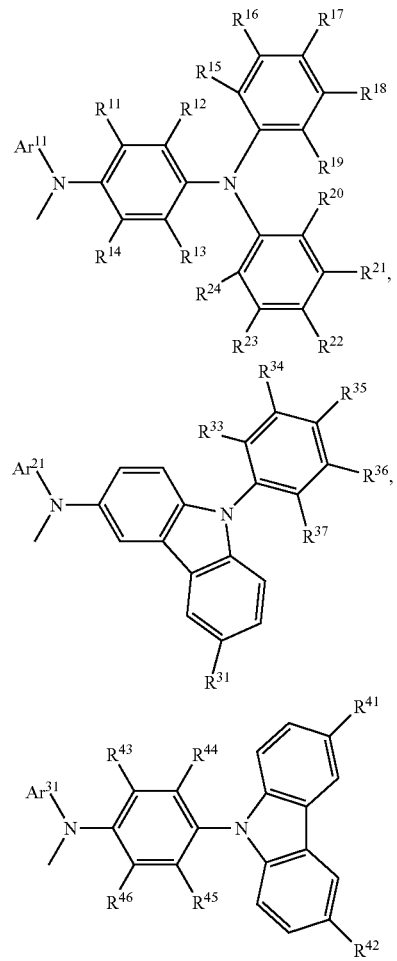

$Ar^{11}$ represents an aryl group having 6 to 25 carbon atoms;
$R^{11}$ to $R^{24}$ each represent a hydrogen atom, an alkyl group having 1 to 4 carbon atoms, an aryl group having 6 to 15 carbon atoms, a halogen atom, or a haloalkyl group having 1 to 4 carbon toms;
$Ar^{21}$ represents an aryl group having 6 to 25 carbon atoms;
$R^{31}$ represents a hydrogen atom, an alkyl group having 1 to 4 carbon atoms, an aryl group having 6 to 25 carbon atoms, a halogen atom, or a haloalkyl group having 1 to 4 carbon atoms;
$R^{33}$ to $R^{37}$ each represent a hydrogen atom, an alkyl group having 1 to 4 carbon atoms, an aryl group having 6 to 15 carbon atoms, a halogen atom, or a haloalkyl group having 1 to 4 carbon toms;
$Ar^{31}$ represents an aryl group having 6 to 25 carbon atoms;
$R^{41}$ and $R^{42}$ each represent a hydrogen atom, an alkyl group having 1 to 4 carbon atoms, an aryl group having 6 to 25 carbon atoms, a halogen atom, or a haloallcyl group having 1 to 4 carbon atoms; and
$R^{43}$ to $R^{46}$ each represent a hydrogen atom, an alkyl group having 1 to 4 carbon atoms, an aryl group having 6 to 15 carbon atoms, a halogen atom, or a haloalkyl group having 1 to 4 carbon atoms.

9. An anthracene derivative according to claim 7, wherein A is selected from:

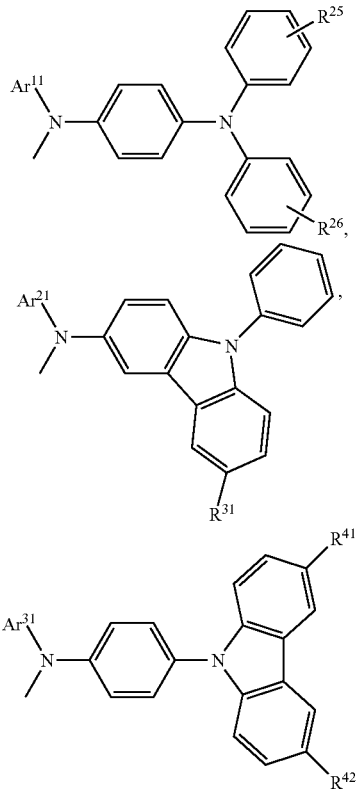

Ar¹¹ represents an aryl group having 6 to 25 carbon atoms;
$R^{25}$ and $R^{26}$ each represent a hydrogen atom, an alkyl group having 1 to 4 carbon atoms, an aryl group having 6 to 15 carbon atoms, a halogen atom, or a haloalkyl group having 1 to 4 carbon atoms;
$A^{21}$ represents an aryl group having 6 to 25 carbon atoms;
$R^{31}$ represents a hydrogen atom, an alkyl group having 1 to 4 carbon atoms, an aryl group having 6 to 25 carbon atoms, a halogen atom, or a haloalkyl group having 1 to 4 carbon atoms;
$Ar^{31}$ represents an aryl group having 6 to 25 carbon atoms; and
$R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

10. An anthracene derivative according to claim 7, wherein A is selected from:

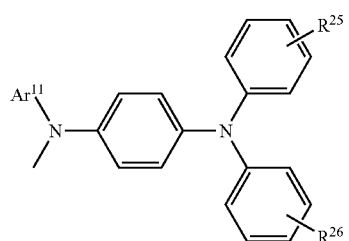

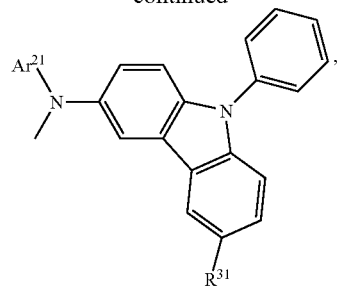

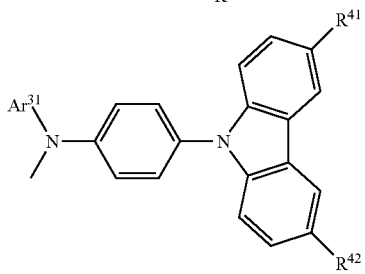

$Ar^{11}$ represents a phenyl group, a 1-naphthyl group or a 2-naphthyl group;
$R^{25}$ and $R^{26}$ each represent a hydrogen atom, an alkyl group having 1 to 4 carbon atoms, or an aryl group having 6 to 15 carbon atoms;
$Ar^{21}$ represents a phenyl group, a 1-naphthyl group or a 2-naphthyl group;
$R^{31}$ represents a hydrogen atom, an alkyl group having 1 to 4 carbon atoms, or an aryl group having 6 to 25 carbon atoms;
$Ar^{31}$ represents a phenyl group, a 1-naphthyl group or a 2-naphthyl group; and
$Ar^{41}$ and $R^{42}$ each represent a hydrogen atom, an alkyl group having 1 to 4 carbon atoms, or an aryl group having 6 to 25 carbon atoms.

11. An anthracene derivative according to claim 7, wherein $Ar^1$ and $Ar^2$ each are a substituent represented by the structure:

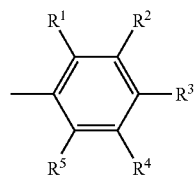

$R^1$ to $R^5$ each represent a hydrogen atom, an alkyl group having 1 to 4 carbon atoms, a haloalkyl group having 1 to 4 carbon atoms, or an aryl group having 6 to 15 carbon atoms.

12. An anthracene derivative according to claim 7, wherein $Ar^3$ is selected from:

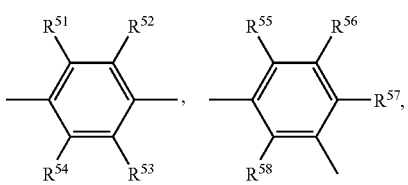

-continued

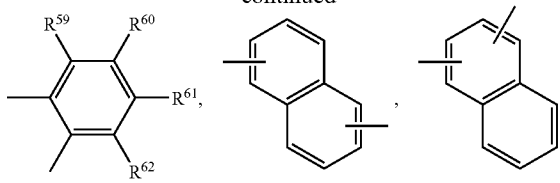

wherein $R^{51}$ to $R^{62}$ each represent a hydrogen atom, an alkyl group having 1 to 4 carbon atoms, an aryl group having 6 to 15 carbon atoms, a halogen atom, or a haloalkyl group having 1 to 4 carbon atoms.

13. A light-emitting device comprising a light-emitting element which comprises an anthracene derivative between a pair of electrodes,
wherein the anthracene derivative is represented by the structure:

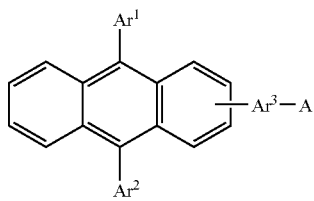

wherein $Ar^1$ and $Ar^2$ each represent an aryl group having 6 to 25 carbon atoms, $Ar^3$ represents an arylene group having 6 to 25 carbon atoms, and wherein A is selected from:

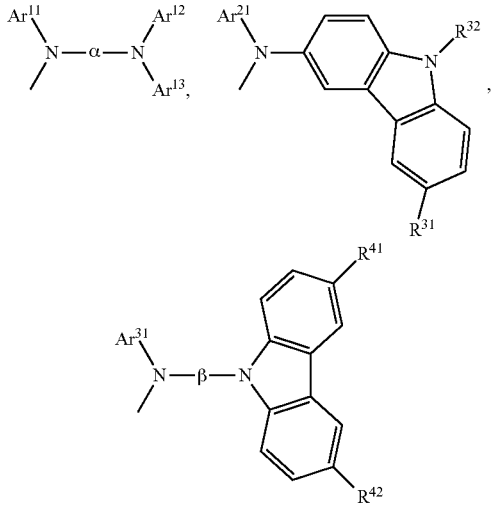

$Ar^{11}$ to $Ar^{13}$ each represent an aryl group having 6 to 25 carbon atoms;
α represents an arylene group having 6 to 25 carbon atoms;
$Ar^{21}$ represents an aryl group having 6 to 25 carbon atoms;
$R^{31}$ represents a hydrogen atom, an alkyl group having 1 to 4 carbon atoms, an aryl group having 6 to 25 carbon atoms, a halogen atom, or a haloalkyl group having 1 to 4 carbon atoms;
$R^{32}$ represents an alkyl group having 1 to 4 carbon atoms, an aryl group having 6 to 25 carbon atoms, or a haloalkyl group having 1 to 4 carbon atoms;

$Ar^{31}$ represents an aryl group having 6 to 25 carbon atoms;
β represents an arylene group having 6 to 25 carbon atoms; and
$R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

14. A light-emitting device according to claim 13, wherein A is selected from:

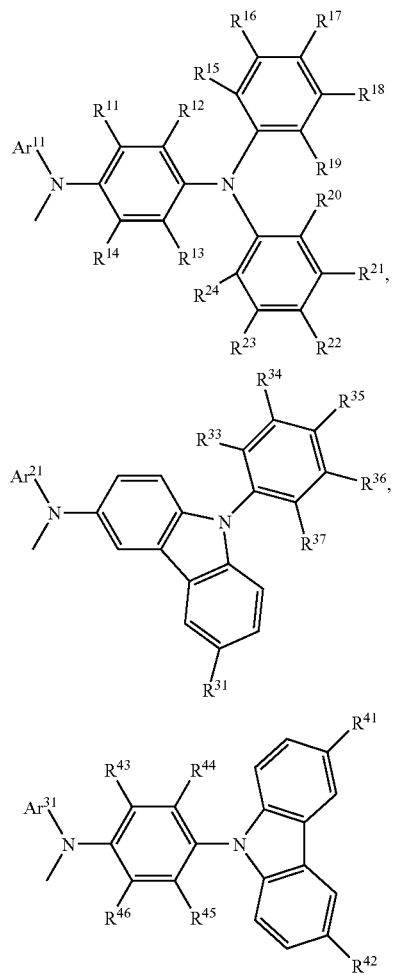

$Ar^{11}$ represents an aryl group having 6 to 25 carbon atoms;
$R^{11}$ to $R^{24}$ each represent a hydrogen atom, an alkyl group having 1 to 4 carbon atoms, an aryl group having 6 to 15 carbon atoms, a halogen atom, or a haloalkyl group having 1 to 4 carbon atoms;
$Ar^{21}$ represents an aryl group having 6 to 25 carbon atoms;
$R^{31}$ represents a hydrogen atom, an alkyl group having 1 to 4 carbon atoms, an aryl group having 6 to 25 carbon atoms, a halogen atom, or a haloalkyl group having 1 to 4 carbon atoms;
$R^{33}$ to $R^{37}$ each represent a hydrogen atom, an alkyl group having 1 to 4 carbon atoms, an aryl group having 6 to 15 carbon atoms, a halogen atom, or a haloalkyl group having 1 to 4 carbon atoms;

$Ar^{31}$ represents an aryl group having 6 to 25 carbon atoms;

$R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms; and $R^{43}$ to $R^{46}$ each represent a hydrogen atom, an alkyl group having 1 to 4 carbon atoms, an aryl group having 6 to 15 carbon atoms, a halogen atom, or a haloalkyl group having 1 to 4 carbon atoms.

15. A light-emitting device according to claim 13, wherein A is selected from:

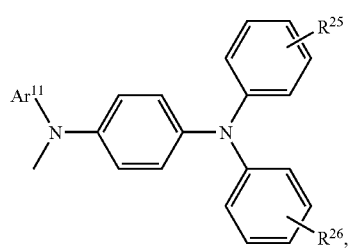

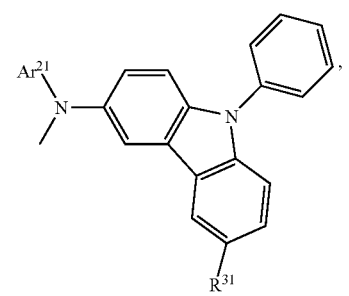

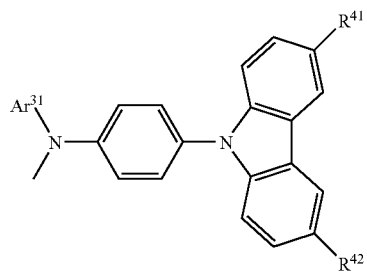

$Ar^{11}$ represents an aryl group having 6 to 25 carbon atoms;

$R^{25}$ and $R^{26}$ each represent a hydrogen atom, an alkyl group having 1 to 4 carbon atoms, an aryl group having 6 to 15 carbon atoms, a halogen atom, or a haloalkyl group having 1 to 4 carbon atoms;

$Ar^{21}$ represents an aryl group having 6 to 25 carbon atoms;

$R^{31}$ represents a hydrogen atom, an alkyl group having 1 to 4 carbon atoms, an aryl group having 6 to 25 carbon atoms, a halogen atom, or a haloalkyl group having 1 to 4 carbon atoms;

$Ar^{31}$ represents an aryl group having 6 to 25 carbon atoms; and $R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

16. A light-emitting device according to claim 13, wherein A is selected from:

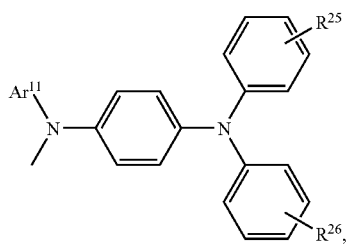

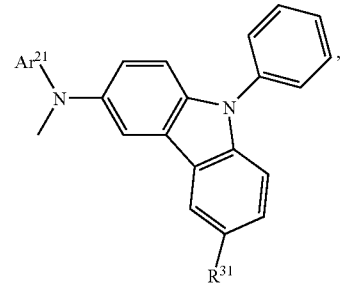

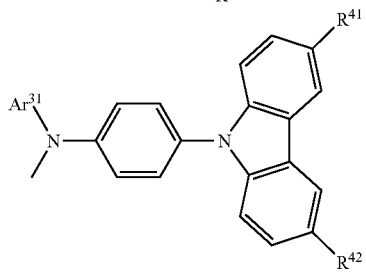

$Ar^{11}$ represents a phenyl group, a 1-naphthyl group or a 2-naphthyl group;

$R^{25}$ and $R^{26}$ each represent a hydrogen atom, an alkyl group having 1 to 4 carbon atoms, or an aryl group having 6 to 15 carbon atoms;

$Ar^{21}$ represents a phenyl group, a 1-naphthyl group or a 2-naphthyl group;

$R^{31}$ represents a hydrogen atom, an alkyl group having 1 to 4 carbon atoms, or an aryl group having 6 to 25 carbon atoms;

$Ar^{31}$ represents a phenyl group, a 1-naphthyl group or a 2-naphthyl group; and $R^{41}$ and $R^{42}$ each represent a hydrogen atom, an alkyl group having 1 to 4 carbon atoms, or an aryl group having 6 to 25 carbon atoms.

17. A light-emitting device according to claim 13, wherein $Ar^1$ and $Ar^2$ each are a substituent represented by the structure:

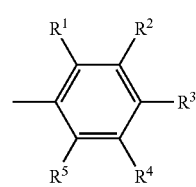

$R^1$ to $R^5$ each represent a hydrogen atom, an alkyl group having 1 to 4 carbon atoms, a haloaayl group having 1 to 4 carbon atoms, or an aryl group having 6 to 15 carbon atoms.

18. A light-emitting device according to claim 13, wherein $Ar^3$ is selected from:

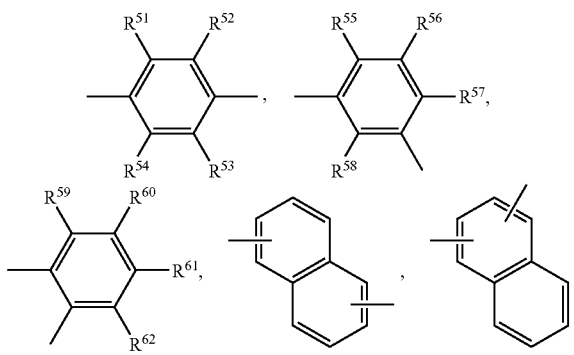

wherein $R^{51}$ to $R^{62}$ each represent a hydrogen atom, an alkyl group having 1 to 4 carbon atoms, an aryl group having 6 to 15 carbon atoms, a halogen atom, or a haloalkyl group having 1 to 4 carbon atoms.

19. An electronic device comprising a display portion which comprises a light-emitting device according to claim 13.

20. A light-emitting device comprising a light-emitting element which comprises an anthracene derivative between a pair of electrodes, wherein the anthracene derivative is represented by the structure:

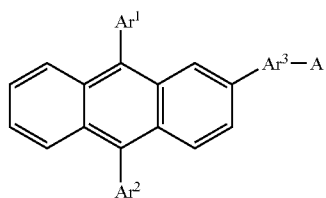

wherein $Ar^1$ and $Ar^2$ each represent an aryl group having 6 to 25 carbon atoms, $Ar^3$ represents an arylene group having 6 to 25 carbon atoms, and wherein A is selected from:

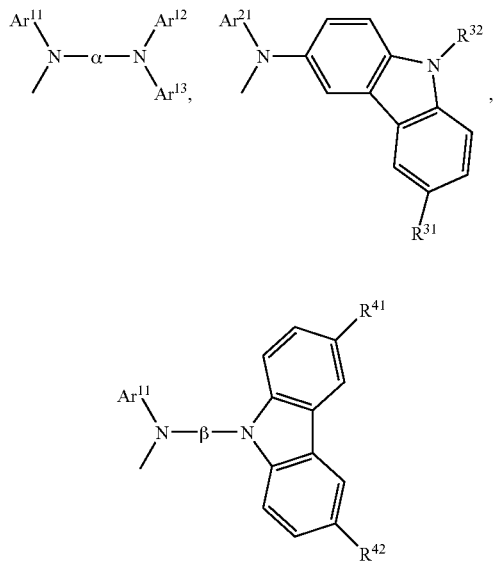

$Ar^{11}$ represents an aryl group having 6 to 25 carbon atoms;
$R^{11}$ to $R^{24}$ each represent a hydrogen atom, an alkyl group having 1 to 4 carbon atoms, an aryl group having 6 to 15 carbon atoms, a halogen atom, or a haloalkyl group having 1 to 4 carbon toms;
$Ar^{21}$ represents an aryl group having 6 to 25 carbon atoms;
$Ar^{11}$ to $Ar^{13}$ each represent an aryl group having 6 to 25 carbon atoms;
α represents an arylene group having 6 to 25 carbon atoms;
$Ar^{21}$ represents an aryl group having 6 to 25 carbon atoms;
$R^{31}$ represents a hydrogen atom, an alkyl group having 1 to 4 carbon atoms, an aryl group having 6 to 25 carbon atoms, a halogen atom, or a haloalkyl group having 1 to 4 carbon atoms;
$R^{32}$ represents an alkyl group having 1 to 4 carbon atoms, an aryl group having 6 to 25 carbon atoms, or a haloalkyl group having 1 to 4 carbon atoms;
$Ar^{31}$ represents an aryl group having 6 to 25 carbon atoms;
β represents an arylene group having 6 to 25 carbon atoms; and
$R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

21. A light-emitting device according to claim 20, wherein A is selected from:

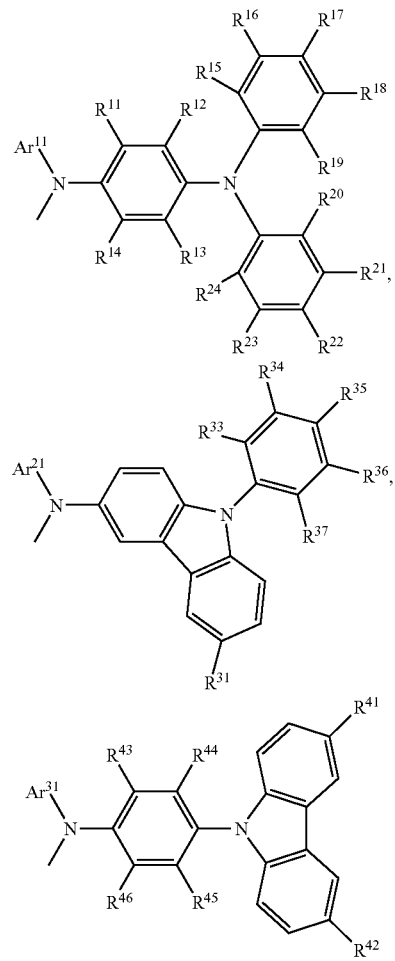

$R^{31}$ represents a hydrogen atom, an alkyl group having 1 to 4 carbon atoms, an aryl group having 6 to 25 carbon atoms, a halogen atom, or a haloalkyl group having 1 to 4 carbon atoms;

$R^{33}$ to $R^{37}$ each represent a hydrogen atom, an alkyl group having 1 to 4 carbon atoms, an aryl group having 6 to 15 carbon atoms, a halogen atom, or a haloalkyl group having 1 to 4 carbon atoms;

$Ar^{31}$ represents an aryl group having 6 to 25 carbon atoms;

$R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms; and $R^{43}$ to $R^{46}$ each represent a hydrogen atom, an alkyl group having 1 to 4 carbon atoms, an aryl group having 6 to 15 carbon atoms, a halogen atom, or a haloalkyl group having 1 to 4 carbon atoms.

22. A light-emitting device according to claim 20, wherein A is selected from:

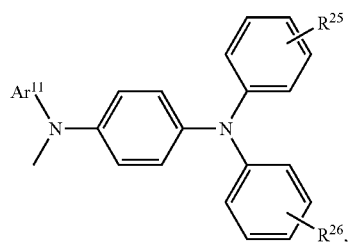

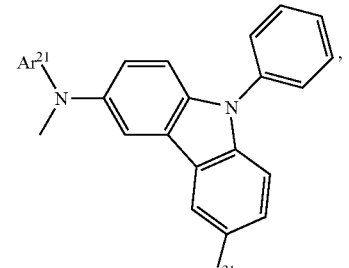

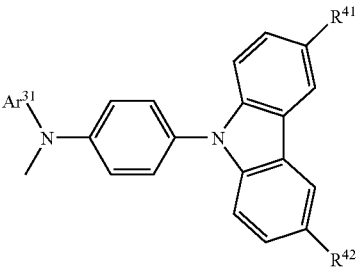

$Ar^{11}$ represents an aryl group having 6 to 25 carbon atoms;

$R^{25}$ and $R^{26}$ each represent a hydrogen atom, an alkyl group having 1 to 4 carbon atoms, an aryl group having 6 to 15 carbon atoms, a halogen atom, or a haloalkyl group having 1 to 4 carbon atoms;

$Ar^{21}$ represents an aryl group having 6 to 25 carbon atoms;

$R^{31}$ represents a hydrogen atom, an alkyl group having 1 to 4 carbon atoms, an aryl group having 6 to 25 carbon atoms, a halogen atom, or a haloalkyl group having 1 to 4 carbon atoms;

$Ar^{31}$ represents an aryl group having 6 to 25 carbon atoms; and $R^{41}$ and $R^{42}$ each represent a hydrogen atom, an alkyl group having 1 to 4 carbon atoms, an aryl group having 6 to 25 carbon atoms, a halogen atom, or a haloalkyl group having 1 to 4 carbon atoms.

23. A light-emitting device according to claim 20, wherein A is selected from:

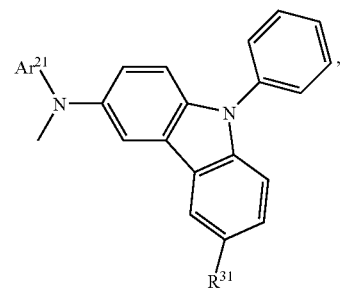

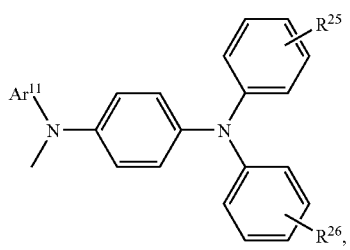

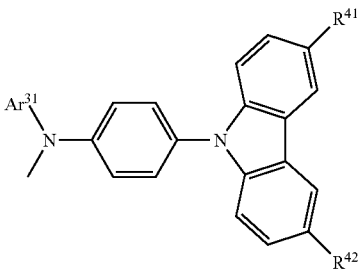

$Ar^{11}$ represents a phenyl group, a 1-naphthyl group or a 2-naphthyl group;

$R^{25}$ and $R^{26}$ each represent a hydrogen atom, an alkyl group having 1 to 4 carbon atoms, or an aryl group having 6 to 15 carbon atoms;

$Ar^{21}$ represents a phenyl group, a 1-naphthyl group or a 2-naphthyl group;

$R^{31}$ represents a hydrogen atom, an alkyl group having 1 to 4 carbon atoms, or an aryl group having 6 to 25 carbon atoms;

$Ar^{31}$ represents a phenyl group, a 1-naphthyl group or a 2-naphthyl group; and $R^{41}$ and $R^{42}$ each represent a hydrogen atom, an alkyl group having 1 to 4 carbon atoms, or an aryl group having 6 to 25 carbon atoms.

24. A light-emitting device according to claim 20, wherein $Ar^1$ and $Ar^2$ each are a substituent represented by the structure:

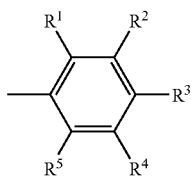

$R^1$ to $R^5$ each represent a hydrogen atom, an alkyl group having 1 to 4 carbon atoms, a haloalkyl group having 1 to 4 carbon atoms, or an aryl group having 6 to 15 carbon atoms.

25. A light-emitting device according to claim 20, wherein $Ar^3$ is selected from:

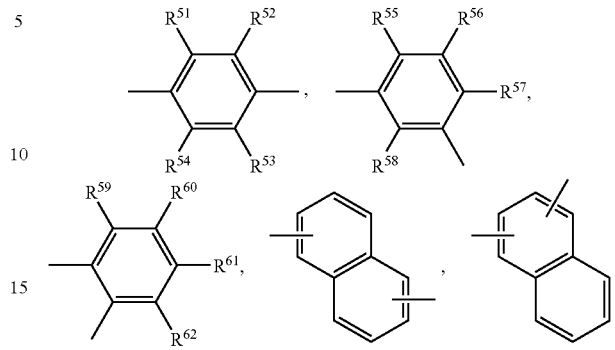

wherein $R^{51}$ to $R^{62}$ each represent a hydrogen atom, an alkyl group having 1 to 4 carbon atoms, an aryl group having 6 to 15 carbon atoms, a halogen atom, or a haloalkyl group having 1 to 4 carbon atoms.

26. An electronic device comprising a display portion which comprises a light-emitting device according to claim 20.

* * * * *

UNITED STATES PATENT AND TRADEMARK OFFICE
CERTIFICATE OF CORRECTION

PATENT NO. : 8,288,012 B2
APPLICATION NO. : 11/962509
DATED : October 16, 2012
INVENTOR(S) : Hiroko Nomura et al.

It is certified that error appears in the above-identified patent and that said Letters Patent is hereby corrected as shown below:

In the Specification:

Column 8, Line 40; Change "a represents" to --α represents--.

Column 8, Line 49; Change "6 represents" to --β represents--.

Column 17, Line 2; Change "a represents" to --α represents--.

Column 64, Lines 44; Change "represented by," to --represented by--.

Column 66, Line 39; Change "R to $R^{62}$" to --$R^{51}$ to $R^{62}$--.

Column 67, Line 28; Change "a represents" to --α represents--.

Column 67, Line 29; Change "$Ar^1$" to --$Ar^{21}$--.

Column 168, Line 9; Change "6=7.33-7.36" to --δ=7.33-7.36--.

Column 170, Line 3; Change "around 366 nM," to --around 366 nm,--.

Column 174, Line 30; Change "1000 cd/m)" to --1000 $cd/m^2$--.

Column 187, Line 45; Change "a haloallcyl group" to --a haloalkyl group--.

Column 189, Line 58; Change "a haloallcyl group" to --a haloalkyl group--.

Column 190, Line 62; Change "a haloallcyl group" to --a haloalkyl group--.

Column 192, Line 36; Change "$Ar^{41}$ and $R^{42}$" to --$R^{41}$ and $R^{42}$--.

Column 196, Line 65; Change "a haloaayl group" to --a haloalkyl group--.

Signed and Sealed this
Twenty-second Day of January, 2013

David J. Kappos
*Director of the United States Patent and Trademark Office*